United States Patent
Wakefield et al.

(10) Patent No.: US 11,879,125 B2
(45) Date of Patent: Jan. 23, 2024

(54) GALNAC COMPOSITIONS FOR IMPROVING SIRNA BIOAVAILABILITY

(71) Applicant: EMPIRICO INC., San Diego, CA (US)

(72) Inventors: Darren H. Wakefield, Fitchburg, WI (US); David Rozema, Cross Plains, WI (US); Omri Gottesman, San Diego, CA (US)

(73) Assignee: EMPIRICO INC., San Diego, CA (US)

( * ) Notice: Subject to any disclaimer, the term of this patent is extended or adjusted under 35 U.S.C. 154(b) by 0 days.

(21) Appl. No.: 18/184,528

(22) Filed: Mar. 15, 2023

(65) Prior Publication Data

US 2023/0295630 A1 Sep. 21, 2023

Related U.S. Application Data

(60) Provisional application No. 63/320,431, filed on Mar. 16, 2022, provisional application No. 63/354,359, filed on Jun. 22, 2022, provisional application No. 63/430,542, filed on Dec. 6, 2022.

(51) Int. Cl.
*C12N 15/113* (2010.01)
*C07H 15/18* (2006.01)

(52) U.S. Cl.
CPC ........... *C12N 15/113* (2013.01); *C07H 15/18* (2013.01); *C12N 2310/14* (2013.01); *C12N 2310/315* (2013.01); *C12N 2310/32* (2013.01)

(58) Field of Classification Search
None
See application file for complete search history.

(56) References Cited

U.S. PATENT DOCUMENTS

| | | |
|---|---|---|
| 5,846,514 A | 12/1998 | Foster et al. |
| 6,057,431 A | 5/2000 | Ishihara et al. |
| 6,334,997 B1 | 1/2002 | Foster et al. |
| 6,906,182 B2 | 6/2005 | Ts'o et al. |
| 7,399,845 B2 | 7/2008 | Seth et al. |
| 7,427,675 B2 | 9/2008 | Capaldi et al. |
| 7,579,451 B2 | 8/2009 | Manoharan et al. |
| 7,615,618 B2 | 11/2009 | Manoharan et al. |
| 7,626,014 B2 | 12/2009 | Manoharan et al. |
| 7,632,932 B2 | 12/2009 | Manoharan et al. |
| 7,674,778 B2 | 3/2010 | Manoharan et al. |
| 7,691,997 B2 | 4/2010 | Khvorova et al. |
| 7,723,512 B2 | 5/2010 | Manoharan et al. |
| 7,772,387 B2 | 8/2010 | Manoharan et al. |
| 7,893,224 B2 | 2/2011 | Manoharan et al. |
| 7,919,472 B2 | 4/2011 | Monia et al. |
| 7,928,217 B2 | 4/2011 | Vornlocher et al. |
| 8,013,136 B2 | 9/2011 | Manoharan et al. |
| 8,268,980 B2 | 9/2012 | Seth et al. |
| 8,278,425 B2 | 10/2012 | Prakash et al. |
| 8,334,373 B2 | 12/2012 | Vornlocher et al. |
| 8,394,947 B2 | 3/2013 | Bhat et al. |
| 8,470,988 B2 | 6/2013 | Manoharan et al. |
| 8,501,703 B2 | 8/2013 | Bennett et al. |
| 8,501,805 B2 | 8/2013 | Seth et al. |
| 8,637,478 B2 | 1/2014 | Bennett |
| 8,790,919 B2 | 7/2014 | Migawa et al. |
| 8,828,956 B2 | 9/2014 | Manoharan et al. |
| 8,846,639 B2 | 9/2014 | Swayze et al. |
| 8,877,439 B2 | 11/2014 | Butora et al. |
| 8,883,752 B2 | 11/2014 | Swayze et al. |
| 8,927,513 B2 | 1/2015 | Manoharan et al. |
| 8,957,223 B2 | 2/2015 | Manoharan et al. |
| 8,962,580 B2 | 2/2015 | Manoharan et al. |
| 8,975,389 B2 | 3/2015 | Manoharan et al. |
| 8,987,435 B2 | 3/2015 | Swayze et al. |
| 8,993,738 B2 | 3/2015 | Prakash et al. |
| 8,993,746 B2 | 3/2015 | Vornlocher et al. |
| 9,012,421 B2 | 4/2015 | Migawa et al. |
| 9,045,754 B2 | 6/2015 | Bhanot et al. |
| 9,102,938 B2 | 8/2015 | Rajeev et al. |
| 9,127,033 B2 | 9/2015 | Prakash et al. |
| 9,127,272 B2 | 9/2015 | Esau et al. |
| 9,156,873 B2 | 10/2015 | Prakash et al. |
| 9,157,081 B2 | 10/2015 | Bennett et al. |
| 9,181,549 B2 | 11/2015 | Prakash et al. |
| 9,243,246 B2 | 1/2016 | Lim et al. |
| 9,260,471 B2 | 2/2016 | Cancilla et al. |

(Continued)

FOREIGN PATENT DOCUMENTS

| | | |
|---|---|---|
| EP | 2906255 A4 | 7/2016 |
| EP | 2321414 B1 | 1/2018 |

(Continued)

OTHER PUBLICATIONS

Boeroeczky et al.: Cluster analysis as selection and dereplication tool for the identification of new natural compounds from large sample sets. Chemistry & Biodiversity. 3(6):622-634 (2006).

Cheng et al.: Stem-loop RT-PCR quantification of siRNAs in vitro and in vivo. Oligonucleotides 19:203-208 (S2009).

Chiaberge et al.: Amides in Bio-oil by Hydrothermal Liquifaction of Organic Wastes: A Mass Spectrometric Study of the Thermochemical Reaction Products of Binary Mixtures of Amino Acids and Fatty Acids. Energy & Fuels. 27(9):5287-5297 (2013).

Croce et al.: A Model Study to Unravel the Complexity of Bio-Oil from Organic Wastes. ChemSusChem. 10(1):171-181 (2017).

(Continued)

*Primary Examiner* — Traviss C McIntosh, III

(74) *Attorney, Agent, or Firm* — Wilson Sonsini Goodrich & Rosati

(57) ABSTRACT

Provided herein, are compositions comprising GalNAc moieties that may be conjugated to an oligonucleotide. The oligonucleotide may be a small interfering RNA or an antisense oligonucleotide. Also provided herein are methods of treatment that include administering the composition to a subject.

20 Claims, No Drawings

Specification includes a Sequence Listing.

(56) References Cited

U.S. PATENT DOCUMENTS

| | | |
|---|---|---|
| 9,290,534 B2 | 3/2016 | Seth et al. |
| 9,290,760 B2 | 3/2016 | Rajeev et al. |
| 9,321,799 B2 | 4/2016 | Prakash et al. |
| 9,352,048 B2 | 5/2016 | Manoharan et al. |
| 9,453,043 B2 | 9/2016 | Manoharan et al. |
| 9,453,222 B2 | 9/2016 | Manoharan et al. |
| 9,512,164 B2 | 12/2016 | Manoharan et al. |
| 9,518,259 B2 | 12/2016 | Rigo et al. |
| 9,550,988 B2 | 1/2017 | Swayze |
| 9,598,693 B2 | 3/2017 | Esau et al. |
| 9,617,540 B2 | 4/2017 | Bhanot et al. |
| 9,708,607 B2 | 7/2017 | Rajeev et al. |
| 9,725,479 B2 | 8/2017 | Manoharan et al. |
| 9,738,895 B2 | 8/2017 | Swayze et al. |
| 9,896,688 B2 | 2/2018 | Chang et al. |
| 9,914,922 B2 | 3/2018 | Freier et al. |
| 9,943,604 B2 | 4/2018 | Seth et al. |
| 9,970,005 B2 | 5/2018 | Cancilla et al. |
| 9,976,138 B2 | 5/2018 | Prakash et al. |
| 10,023,861 B2 | 7/2018 | Prakash et al. |
| 10,036,019 B2 | 7/2018 | Seth et al. |
| 10,087,210 B2 | 10/2018 | Prakash et al. |
| 10,131,908 B2 | 11/2018 | Manoharan et al. |
| 10,233,448 B2 | 3/2019 | Maier et al. |
| 10,337,007 B2 | 7/2019 | Freier et al. |
| 10,370,659 B2 | 8/2019 | Liang et al. |
| 10,385,337 B2 | 8/2019 | Manoharan et al. |
| 10,493,092 B2 | 12/2019 | Swayze |
| 10,570,169 B2 | 2/2020 | Seth et al. |
| 10,584,335 B2 | 3/2020 | Lim et al. |
| 10,668,170 B2 | 6/2020 | Rajeev et al. |
| 10,676,738 B2 | 6/2020 | Prakash et al. |
| 10,689,648 B2 | 6/2020 | Carr et al. |
| 10,806,791 B2 | 10/2020 | Manoharan et al. |
| 10,995,336 B2 * | 5/2021 | Schlegel ............... A61P 43/00 |
| 11,015,198 B2 | 5/2021 | Hauptmann et al. |
| 11,377,658 B2 | 7/2022 | Gottesman et al. |
| 11,400,161 B2 | 8/2022 | Cedillo et al. |
| 11,597,932 B2 | 3/2023 | Manoharan et al. |
| 2012/0035115 A1 | 2/2012 | Manoharan et al. |
| 2017/0349896 A1 | 12/2017 | Albaek et al. |
| 2018/0256729 A1 | 9/2018 | Seth et al. |
| 2018/0362977 A1 | 12/2018 | Cancilla et al. |
| 2018/0371005 A1 | 12/2018 | Prakash et al. |
| 2019/0136234 A1 | 5/2019 | Prakash et al. |
| 2019/0202855 A1 | 7/2019 | Sakamuri et al. |
| 2019/0270990 A1 | 9/2019 | Kordasiewicz et al. |
| 2019/0321387 A1 | 10/2019 | Prakash et al. |
| 2020/0063133 A1 | 2/2020 | Hauptmann et al. |
| 2020/0157548 A1 | 5/2020 | Prakash et al. |
| 2020/0190132 A1 | 6/2020 | Barnes-Seeman et al. |
| 2020/0239881 A1 | 7/2020 | Oestergaard et al. |
| 2020/0276221 A1 | 9/2020 | Swayze |
| 2020/0297853 A1 | 9/2020 | Manoharan et al. |
| 2020/0353097 A1 | 11/2020 | Rajeev et al. |
| 2020/0385722 A1 | 12/2020 | Prakash et al. |
| 2020/0392493 A1 | 12/2020 | Freier et al. |
| 2020/0392495 A1 | 12/2020 | Bethge et al. |
| 2020/0392499 A1 | 12/2020 | Carr et al. |
| 2020/0392509 A1 | 12/2020 | Oestergaard et al. |
| 2020/0407724 A1 | 12/2020 | Heyes et al. |
| 2021/0017513 A1 | 1/2021 | Seth et al. |
| 2021/0017519 A1 | 1/2021 | Maier et al. |
| 2021/0155926 A1 | 5/2021 | Bethge et al. |
| 2021/0169917 A1 | 6/2021 | Viney et al. |
| 2021/0238594 A1 | 8/2021 | Parmar et al. |
| 2021/0238595 A1 | 8/2021 | Matsuda et al. |

FOREIGN PATENT DOCUMENTS

| | | |
|---|---|---|
| WO | WO-2006119619 A1 | 11/2006 |
| WO | WO-2014059341 A2 | 4/2014 |
| WO | WO-2015069932 A1 | 5/2015 |
| WO | WO-2015188197 A2 | 12/2015 |
| WO | WO-2016055601 A1 | 4/2016 |
| WO | WO-2018044350 A1 | 3/2018 |
| WO | WO-2019053661 A2 | 3/2019 |
| WO | WO-2019217527 A1 | 11/2019 |
| WO | WO-2020072883 A1 | 4/2020 |
| WO | WO-2020072887 A1 | 4/2020 |
| WO | WO-2020097044 A1 | 5/2020 |
| WO | WO-2020173845 A1 | 9/2020 |
| WO | WO-2020236600 A1 | 11/2020 |
| WO | WO-2022140365 A1 | 6/2022 |

OTHER PUBLICATIONS

Dallagnol et al.: Flavonoids and Phenylethylamides are Pivotal Factors Affecting the Antimicrobial Properties of Stingless Bee Honey. Journal of Agricultural and Food Chemistry. 70(39):12596-12603 (2022).

Di Fabio et al.: Discovery of novel anti-HIV active G-quadruplex-forming oligonucleotides. Chemical Communications. 47(8):2363-2365 (2011).

Evans et al.: Synthesis of radiolabeled compounds. J. Radioanal. Chem. 64(1-2):9-32 (1981).

Kabalka et al.: The Synthesis of Radiolabeled Compounds via Organometallic Intermediates. Tetrahedron. 45(21):6601-6621 (1989).

Lukhtanov, E. CDPI3 MGB-Oligonucleotide conjugates and their applications. The Glen Report 29(1):1-16 (2017).

Matayeva et al.: Elucidation of reaction pathways of nitrogenous species by hydrothermal liquefaction process of model compounds. Fuel. 240:169-178 (2019).

PCT/US2020/063824 International Preliminary Report on Patentability dated Jun. 23, 2022.

PCT/US2021/064581 International Invitation to Pay Additional Fees dated Mar. 8, 2022.

PCT/US2021/064581 International Search Report and Written Opinion dated May 5, 2022.

PCT/US2023/064384 Invitation to Pay Additional Fees dated Jun. 5, 2023.

Pongs et al.: Affinity labeling of ribosomes. II. Synthesis of a chemically reactive analog of the initiation codon. Its reaction with ribosomes of *Escherichia coli*. Hoppe-Seyler's nZeitschrift Physiologische Chemis. 356(4):449-458 (1975).

Proschak et al.: Cytotoxic Fatty Acid Amides from Xenorhabdus. ChemBioChem. 12(13):2011-2015 (2011).

Romanucci et al.: Kinetic ESI-MS studies of potent anti-HIV aptamers based on the G-quadruplex forming sequence d(TGG-GAG). ACS Medicinal Chemistry Letters. 7(3):256-260: (2016).

Romanucci et al.: New findings on the d(TGGGAG) sequence: Surprising anti-HIV-1 activity. European Journal of Medicinal Chemistry. 145:425-430 (2018).

Shiono et al.: N-Phenethylhexadecanamide from the edible mushroom Laetiporus sulphureus. Natural Product Research. 19(4):363-366 (2005).

U.S. Appl. No. 17/476,317 Office Action dated Dec. 10, 2021.

Vandevoorde et al.: Modifications of the Ethanolamine Head in N-Palmitoylethanolamine: Synthesis and Evaluation of New Agents Interfering with the Metabolism of Anandamide. Journal of Medicinal Chemistry. 46(8):1440-1448 (2003).

Wang et al.: Constituents of Microsorum insigne. Chemistry of Natural Compounds. 53(4):789-790 (2017).

Wang et al.: Eco-Friendly Production of Fatty Amides Using 1-Monoacylglycerols as Acy Donors. ACS Sustainable Chemistry & Engineering. 8(25):9589-9596 (2020).

* cited by examiner

GALNAC COMPOSITIONS FOR IMPROVING SIRNA BIOAVAILABILITY

CROSS-REFERENCE

This application claims the benefit of U.S. Provisional Application No. 63/320,431, filed Mar. 16, 2022, U.S. Provisional Application No. 63/354,359, filed Jun. 22, 2022, and U.S. Provisional Application No. 63/430,542, filed Dec. 6, 2022, which applications are incorporated herein by reference.

INCORPORATION BY REFERENCE OF A SEQUENCE LISTING

The present application is being filed along with a Sequence Listing in electronic format. The Sequence Listing is provided as a file entitled 54462-735201_US.xml, created Mar. 13, 2023, which is 922,453 bytes in size. The information in the electronic format of the Sequence Listing is incorporated by reference in its entirety.

BACKGROUND

Cardiovascular, metabolic, and liver-related disorders are abundant, and may affect a wide variety of persons. Improved therapeutics are needed for treating these disorders.

SUMMARY

Disclosed Herein is a Compound Represented by Formula (I) or (11.1):

(I)

(II)

or a salt thereof; wherein

J is an oligonucleotide;

each w is independently selected from any value from 1 to 20;

each v is independently selected from any value from 1 to 20;

n is selected from any value from 1 to 20;

m is selected from any value from 1 to 20;

z is selected from any value from 1 to 3, wherein
  if z is 3, Y is C
  if z is 2, Y is $CR^6$, or
  if z is 1, Y is $C(R^6)_2$;

Q is selected from:
  $C_{3-10}$ carbocycle optionally substituted with one or more substituents independently selected from halogen, —CN, —$NO_2$, —$OR^7$, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, —$S(O)R^7$, and $C_{1-6}$ alkyl, wherein the $C_{1-6}$ alkyl, is optionally substituted with one or more substituents independently selected from halogen, —CN, —OH, —SH, —$NO_2$, and —$NH_2$;

$R^1$ is a linker selected from;
  —O—, —S—, —$N(R^7)$, —C(O)—, —$C(O)N(R^7)$—, —$N(R^7)C(O)$—, —$N(R^7)C(O)N(R^7)$—, —$OC(O)N(R^7)$—, —$N(R^7)C(O)O$—, —C(O)O—, —OC(O)—, —S(O)—, —$S(O)_2$—, —$OS(O)_2$—, —$OP(O)(OR^7)O$—, —$SP(O)(OR^7)O$—, —$OP(S)(OR^7)O$—, —$OP(O)(SR^7)O$—, —$OP(O)(OR^7)S$—, —OP(O)(O)O—, —SP(O)(O)O—, —OP(S)(O)O—, —OP(O)(S)O—, —$OP(O)(O)S$—, —$OP(O)(OR^7)NR^7$—, —$OP(O)(N(R^7)_2)NR^7$—, —$OP(OR^7)O$—, —$OP(N(R^7)_2)O$—, —$OP(OR^7)N(R^7)$—, and —$OPN(R^7)_2NR^7$— each $R^2$ is independently selected from:
  $C_{1-6}$ alkyl optionally substituted with one or more substituents independently selected from halogen, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, $T(R^7)C(O)OR^7$, —C(O)OR—$OC(O)R^7$, and —$S(O)R^7$;

$R^3$ and $R^4$ are each independently selected from:
  —$OR^7$, —$SR^7$, —$N(R^7)_2$, —$C(O)R^7$, —$C(O)N(R^7)_2$, —$N(R^7)C(O)R^7$, —$N(R^7)C(O)N(R)_2$, —$OC(O)N(R^7)_2$, —$N(R^7)C(O)OR^7$, —$C(O)OR^7$, —$OC(O)R^7$, and —$S(O)R^7$;

each $R^5$ is independently selected from:
  —$OC(O)R^7$, —$OC(O)N(R^7)_2$, —$N(R^7)C(O)R^7$, —$N(R^7)C(O)N(R^7)_2$; —$N(R^7)C(O)OR^7$, —$C(O)R^7$, —$C(O)OR^7$, and —$C(O)N(R^7)_2$;

each $R^6$ is independently selected from:
  hydrogen;
  halogen, —CN. —$NO_2$, —$SR^7$, —$N(R^7)_2$, —$C(O)R^7$, —$C(O)N(R^7)_2$, —$N(R)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, and —$S(O)R^7$; and
  $C_{1-4}$ alkyl optionally substituted with one or more substituents independently selected from halogen, —CN, —$NO_2$, —$OR^7$, —$SR^7$, —$N(R^7)_2$, —$C(O)R^7$, —C(O)

$N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, and —$S(O)R^7$;

each $R^7$ is independently selected from:

hydrogen; $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, —O—$C_{1-4}$ alkyl, —S—$C_{1-6}$ alkyl, —$N(C_{1-6}$ alkyl$)_2$, —$NH(C_{1-6}$ alkyl), $C_{1-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O =S, —O—$C_{1-6}$ alkyl, —S—$C_{1-6}$ alkyl, —$N(C_{1-6}$ alkyl$)_2$, —$NH(C_{1-6}$ alkyl), $C_{1-6}$ alkyl, $C_{2-6}$alkenyl, $C_{2-6}$ alkynyl, $C_{3-10}$ carbocycic, 3- to 10-membered heterocycle, and $C_{1-6}$haloalkyl.

In some embodiments, each w is independently selected from any value from 1 to 10. In some embodiments, each w is independently selected from any value from 1 to 5. In some embodiments, each w is 1. In some embodiments, each v is independently selected from any value from 1 to 10. In some embodiments, each v is independently selected from any value from 1 to 5. In some embodiments, each v is 1. In some embodiments, n is selected from any value from 1 to 10. In some embodiments, n is selected from any value from 1 to 5. In some embodiments, n is 2. In some embodiments, in is selected from any value from 1 to 10. In some embodiments, m is selected from any value from 1 to 5. In some embodiments, m is selected from 1 and 2. In some embodiments, z is 3 and Y is C. In some embodiments, Q is selected from $C_{5-6}$ carbocycle optionally substituted with one or more substituents independently selected from halogen. —CN, —$NO_2$, —$OR^7$, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$(R^7)C(O)OR^7$. —$C(O)OR^7$, —$OC(O)R^7$, and —$S(O)R^7$. In some embodiments, Q is selected from $C_{4-6}$ carbocycle optionally substituted with one or more substituents independently selected from halogen, —CN, —OH, —SH, —$NO_2$, and —$NH_2$. In some embodiments, Q is selected from phenyl and cyclohexyl, each of which is optionally substituted with one or more substituents independently selected from halogen, —CN, —OH, —SH, —$NO_2$, and —$NH_2$. In some embodiments, Q is selected from phenyl. In some embodiments, Q is selected from cyclohexyl. In some embodiments, $R^1$ is selected from —$OP(O)(OR^7)O$—, —$SP(O)(OR^7)O$—, —$OP(S)(OR^7)O$—, —$OP(O)(SR^7)O$—, —$OP(O)(OR^7)S$—, —$OP(O)(O$—$)O$—, —$SP(O)(O$—$)O$—, —$OP(S)(O$—$)O$—, —$OP(O)(S$—$)O$—, —$OP(O)(O$—$)S$—, —$OP(O)(OR^7)NR^7$—, —$OP(O)(N(R^1)_2)NR^7$—, —$OP(OR^7)O$—, —$OP(N(R^7)_2)O$—, —$OP(OR^7)N(R^7)$—, and —$OPN(R^7)_2NR^7$. In some embodiments, $R^2$ is selected from —$OP(O)(OR^7)O$—, —$SP(O)(OR^7)O$—, —$OP(S)(OR^7)O$—, —$OP(O)(SR^7)O$—, —$OP(O)(OR^7)S$—, —$OP(O)(O$—$)O$—, —$SP(O)(O$—$)O$—, —$OP(S)(O$—$)O$—, —$OP(O)(S$—$)O$—, —$OP(O)(O$—$)S$—, and —$OP(OR^7)O$—. In some embodiments, $R^1$ is selected from —$OP(O)(OR^7)O$—, —$OP(S)(OR^7)O$—, —$OP(O)(O)O$—, —$OP(S)(O$—$)O$—, —$OP(O)(S$—$)O$—, and —$OP(OR^7)O$—. In some embodiments. $R^1$ is selected from —$OP(O)(OR^7)O$— and —$OP(OR^7)O$—. In some embodiments, $R^2$ is selected from $C_{1-3}$ alkyl substituted with one or more substituents independently selected from halogen, —$OR^7$, —$OC(O)R^7$, —$SR^7$, —$N(R^7)_2$, —$C(O)R^7$, and —$S(O)R^7$, in some embodiments, $R^2$ is selected from $C_{1-3}$ alkyl substituted with one or more substituents independently selected from —OR, —$OC(O)R^7$, —$SR^7$, and —$N(R^7)_2$. In some embodiments, $R^2$ is selected from $C_{1-3}$ alkyl substituted with one or more substituents independently selected from —$OR^7$ and —$OC(O)R^7$. In some embodiments, $R^2$ is selected from halogen, —$OR^7$, —$SR^7$, —$N(R^7)_2$, —$C(O)R^7$, —$OC(O)R^7$, and —$S(O)R^7$, In some embodiments, $R^3$ is selected from —$OR^7$—$SR^7$, —$OC(O)OR^7$, and —$N(R^7)_2$. In some embodiments, $R^3$ is selected from —$OR^7$— and —$OC(O)R^7$. In some embodiments, $R^4$ is selected from halogen, —$OR^7$, —S—$N(R^7)_2$, —$C(O)R^7$, —$OC(O)R^7$, and —$S(O)R^7$. In some embodiments, $R^4$ is selected from —$OR^7$—$SR^7$, —$OC(O)R^7$, and —$N(R^7)_2$. In some embodiments, $R^4$ is selected from —$OR^7$— and —$OC(O)R^7$. In some embodiments, $R^5$ is selected from —$O(O)R^7$, —$OC(O)N(R^7)_2$, —$N(R^7)C(O)R^7$, —$N(R^7)C(O)N(R^7)_2$, and —$N(R^7)C(O)OR^7$. In some embodiments, $R^2$ is selected from —$OC(O)R^7$ and —$N(R^7)C(O)R^7$, In some embodiments, each $R^7$ is independently selected from: hydrogen; and $C_{1-6}$ alkyl optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-6}$ $C_{3-10}$ carbocycle, or 3- to 10-membered heterocycle. In some embodiments, each $R^7$ is independently selected from $C_{4-6}$ alkyl optionally substituted with one or more substituents independently selected from halogen, —CN, —OH, —SH, —$NO_2$, —$NH_2$, =O. =S, —O—$C_{1-6}$ alkyl, —S—$C_{1-4}$ alkyl, —$N(C_{1-6}$ alkyl$)_2$, and —$NH(C_{1-6}$ alkyl). In some embodiments, each $R^7$ is independently selected from Go alkyl optionally substituted with one or more substituents independently selected from halogen, —CN, —OH, and —SH. In some embodiments, w is 1; v is 1, n is 2, m is 1 or 2; z is 3 and is Q is phenyl or cyclohexyl, each of which is optionally substituted with one or more substituents independently selected from halogen, —CN, —OH, —SH, —$NO_2$, —$NH_2$, and $C_{1-3}$ alkyl; $R^7$ is selected from —$OP(O)(OR^7)O$—, —$OP(S)(OR^7)O$—, —$OP(O)(O$—$)O$—, —$OP(S)(O$—$)O$—, —$OP(O)(S$—$)O$—, and —$OP(OR^7)O$—; $R^2$ is $C_1$ alkyl substituted with —OH or —$OC(O)CH_3$; $R^3$ is —OH or —$OC(O)CH_3$; $R^4$ is —OH or —$OC(O)CH_3$; and $R^5$ is —$NH(O)CH_3$. In some embodiments, the compound comprises:

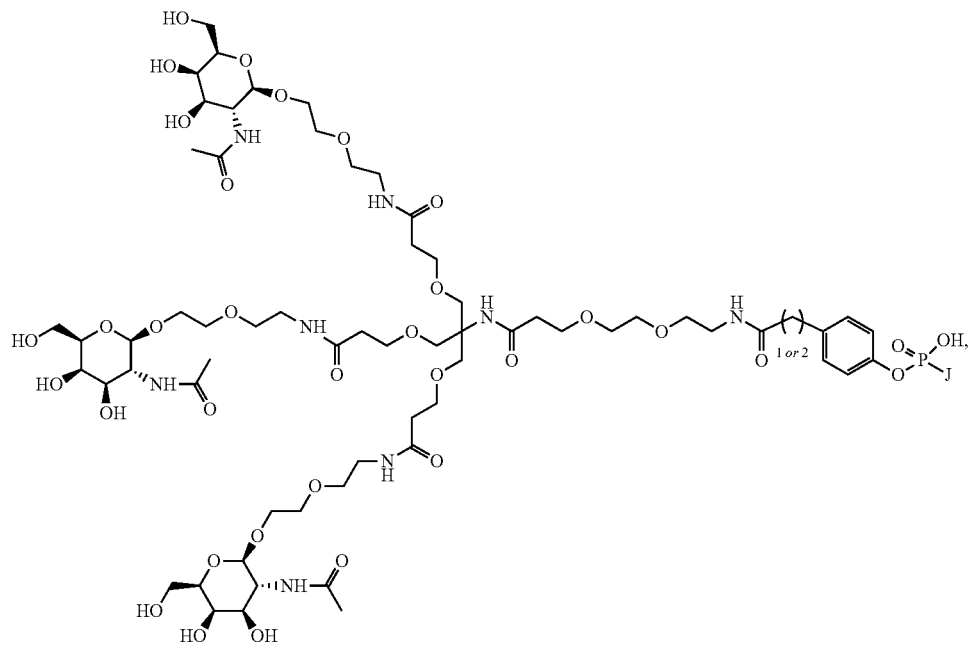
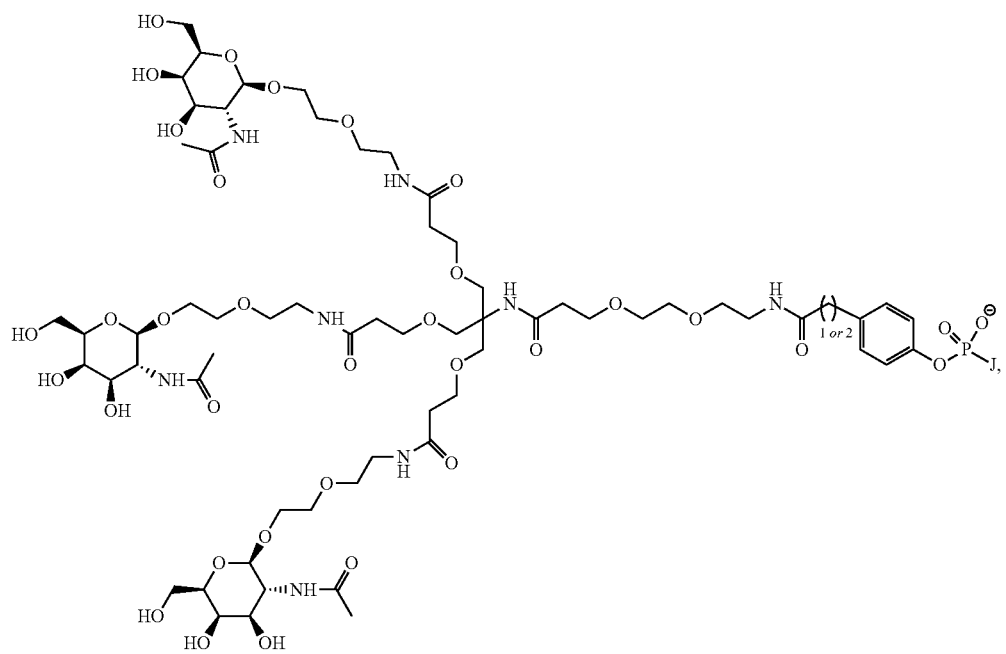

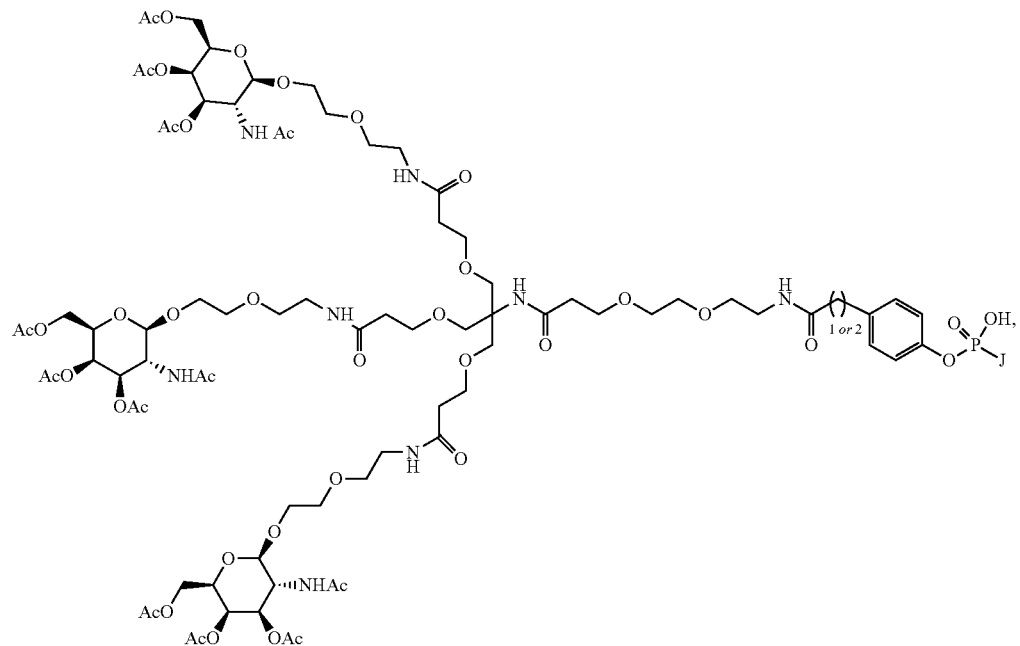
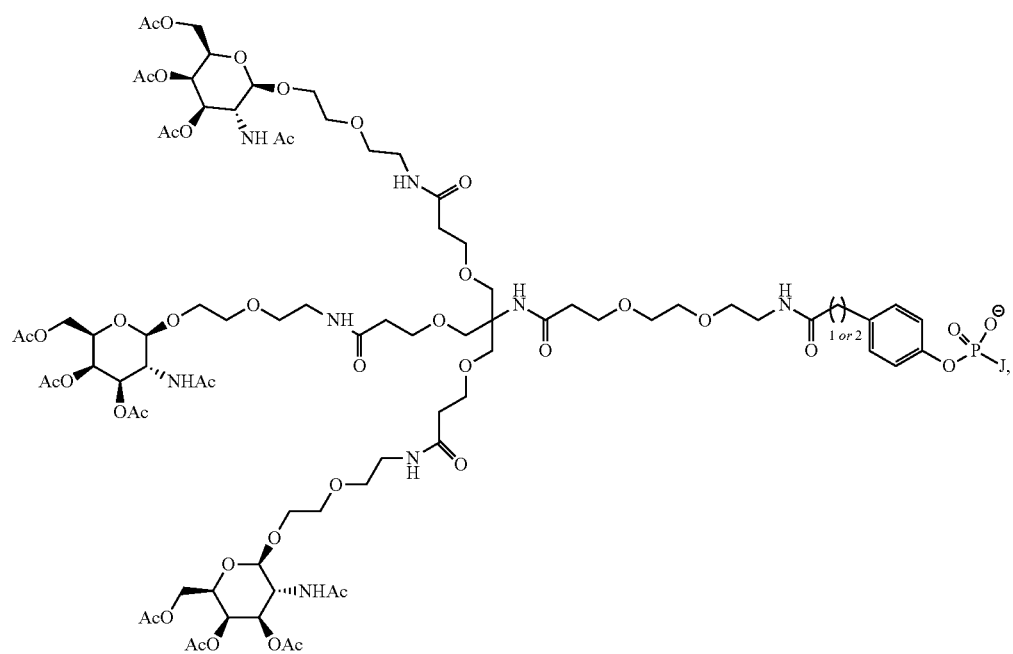

-continued
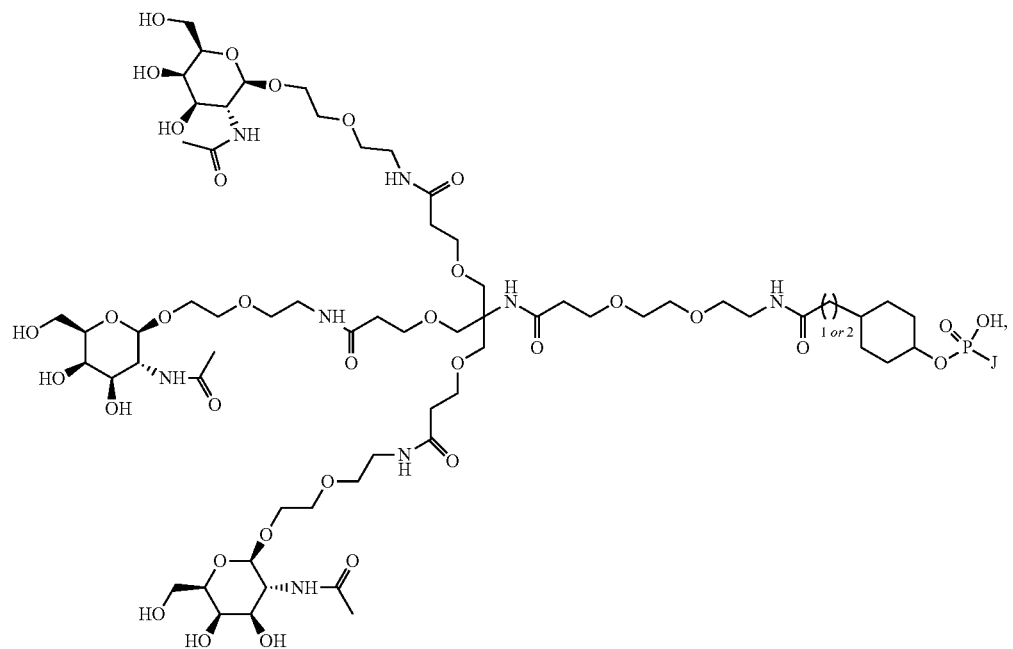
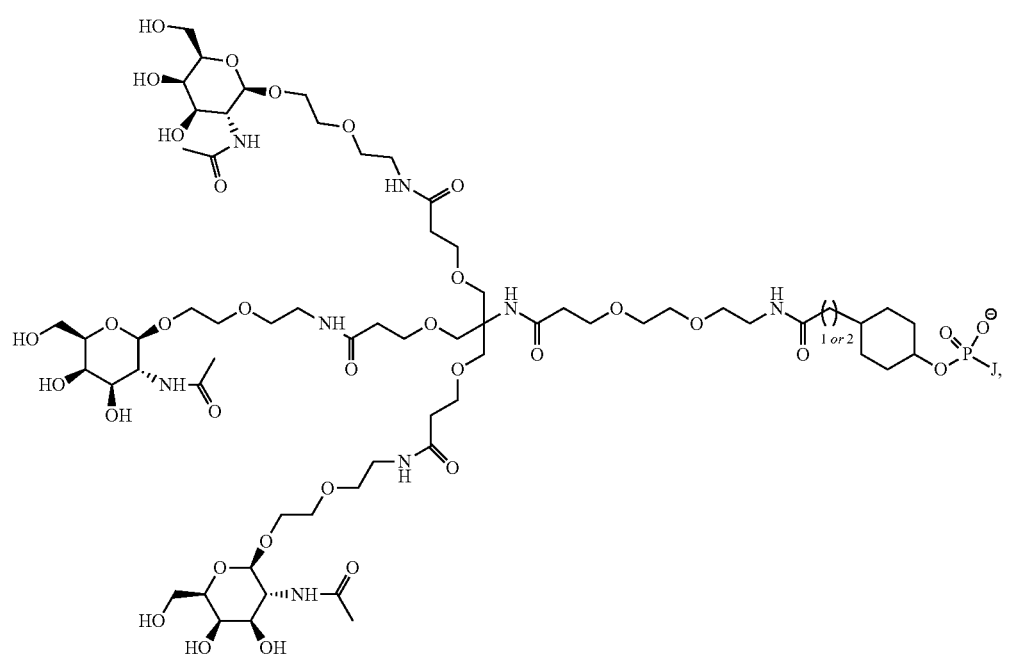

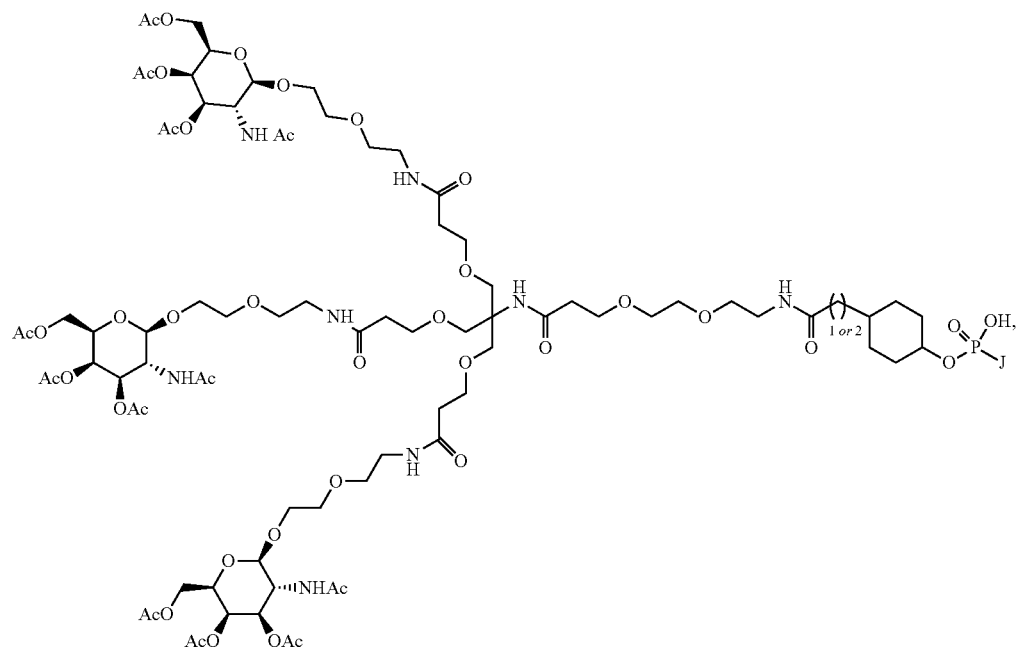
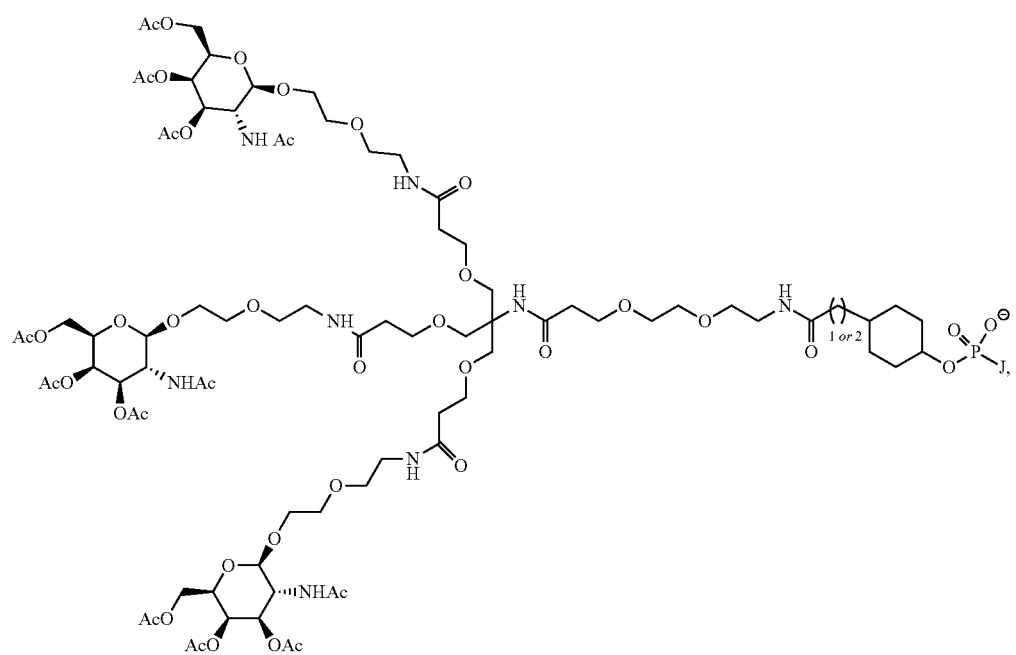

-continued
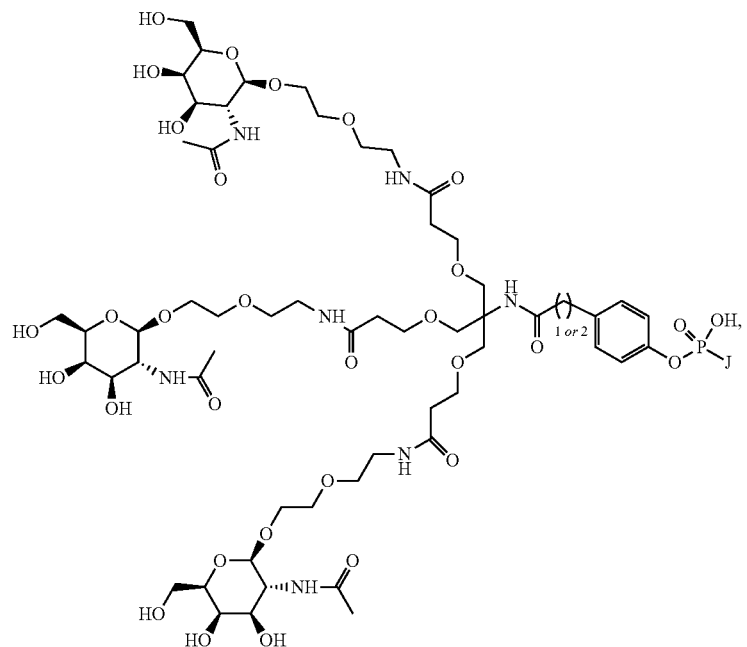
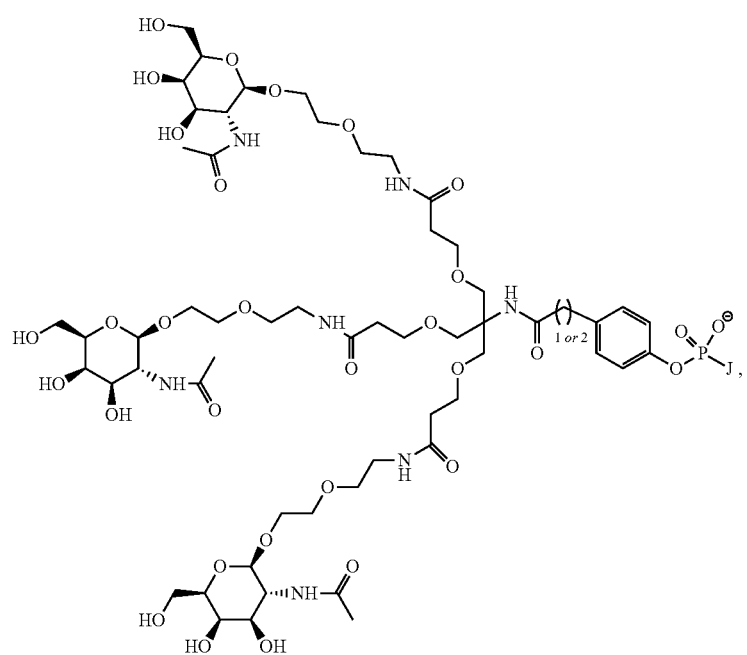

-continued
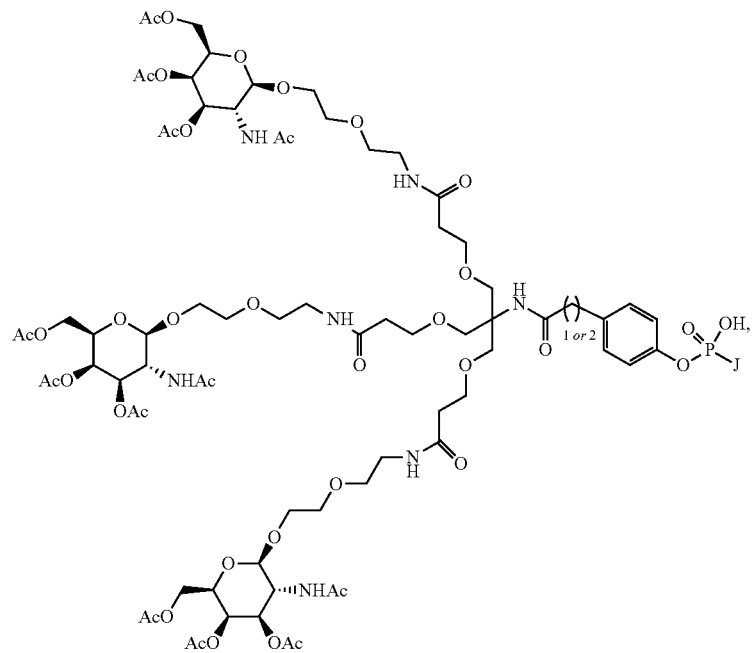
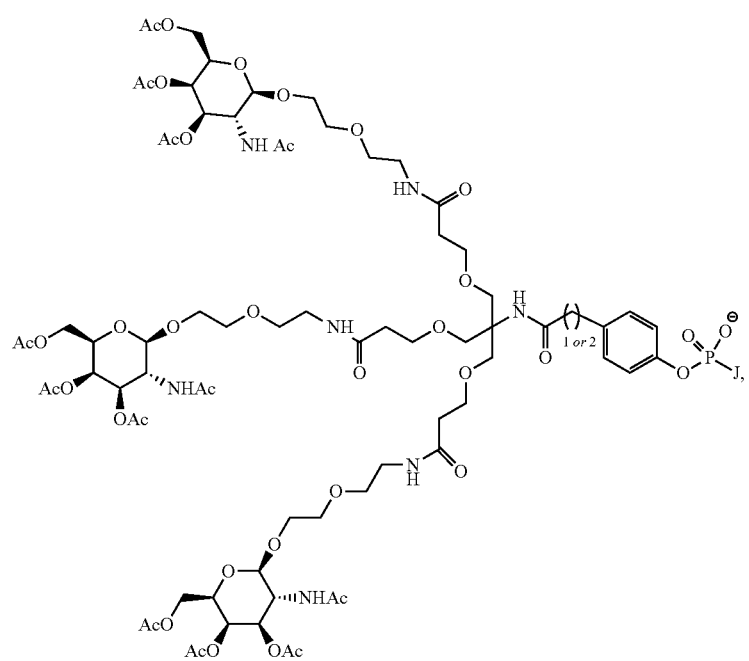

-continued
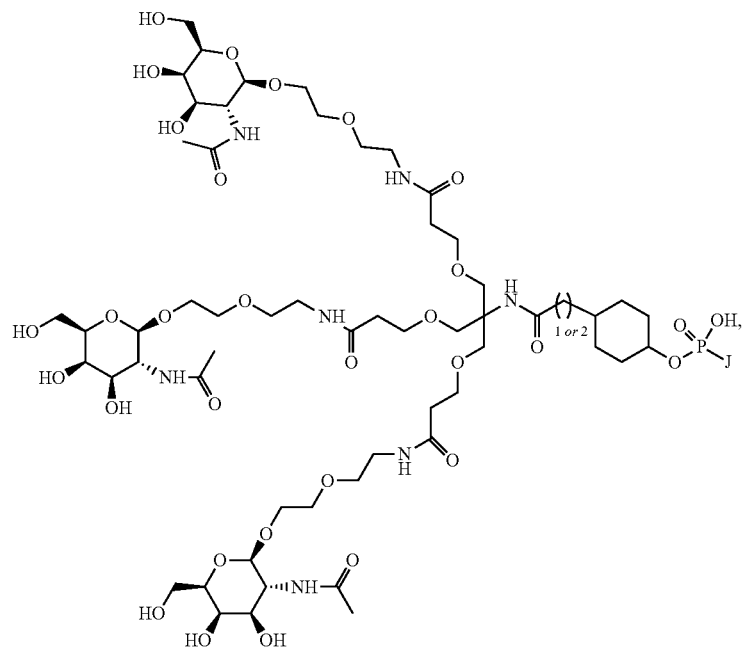
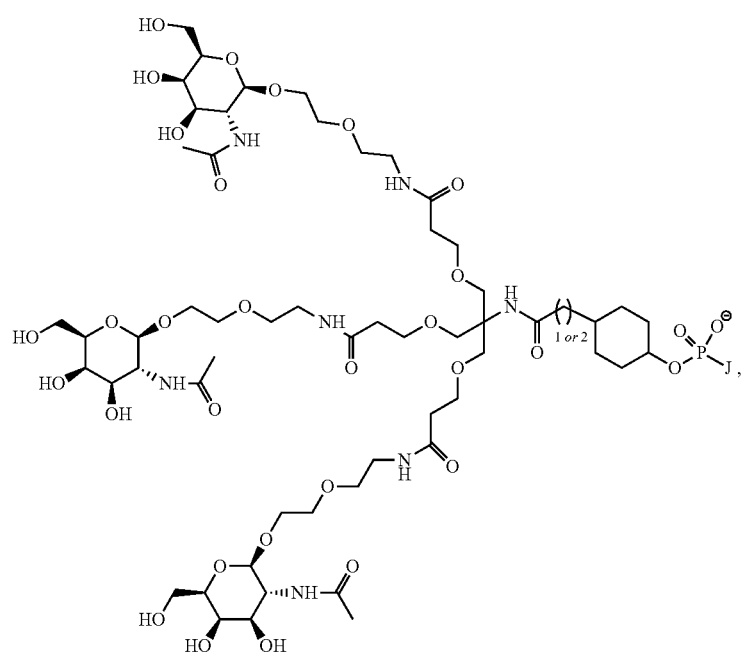

-continued
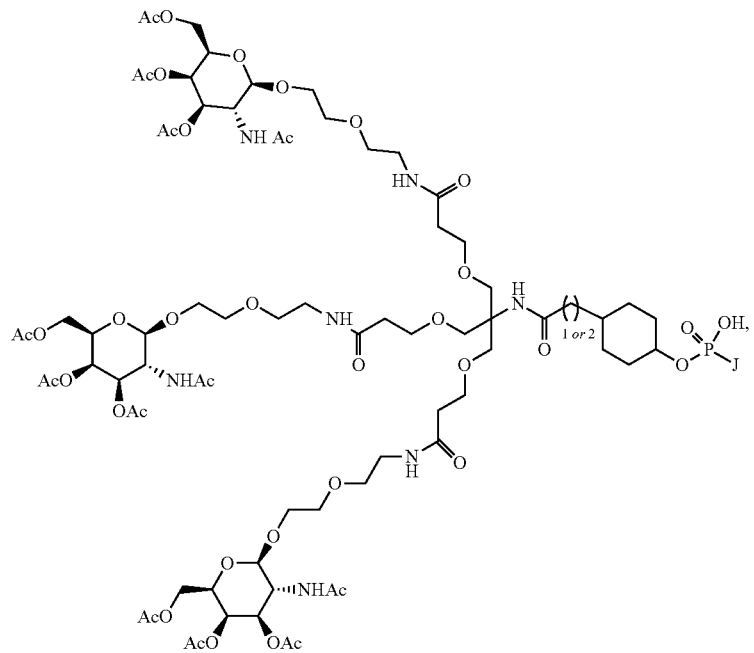
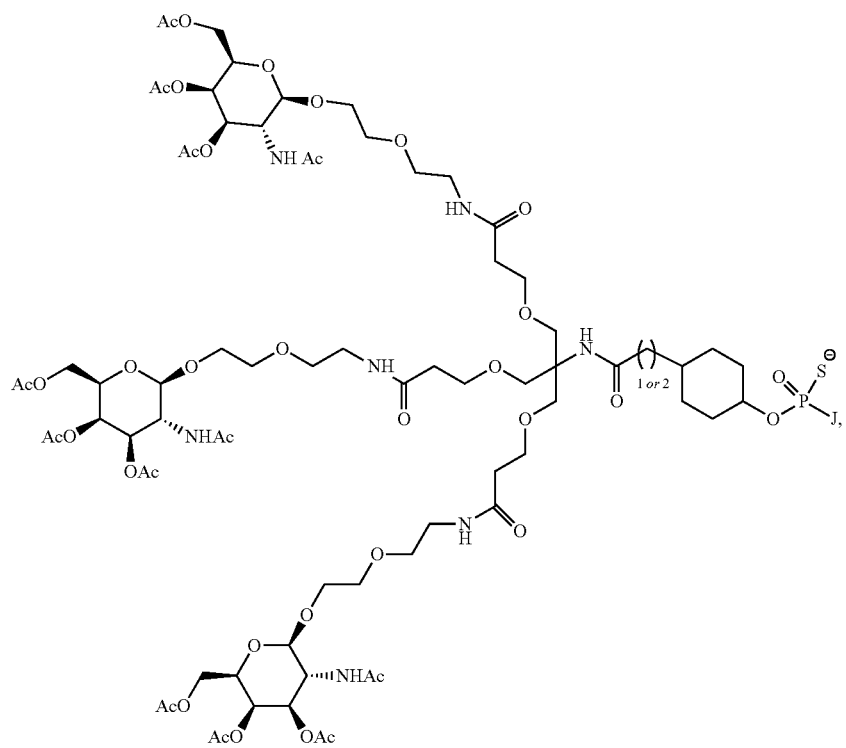

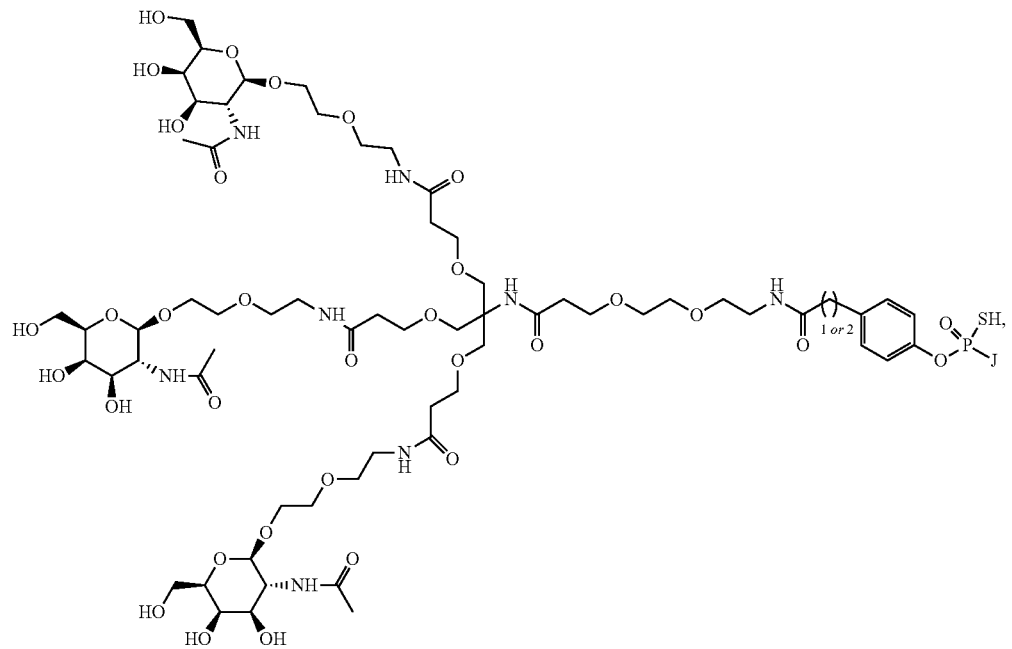
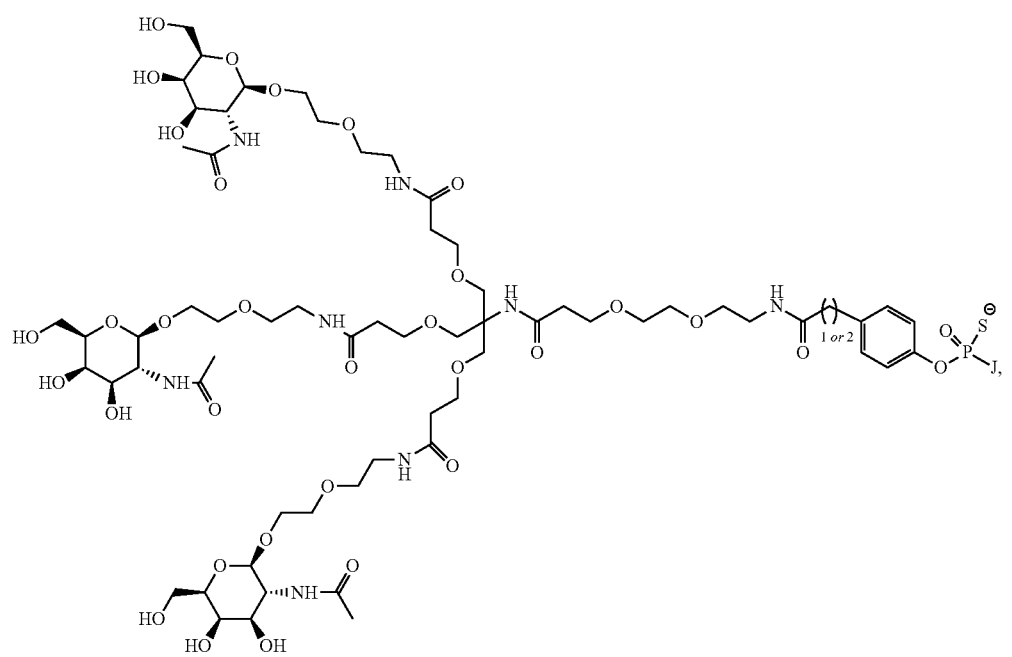

-continued
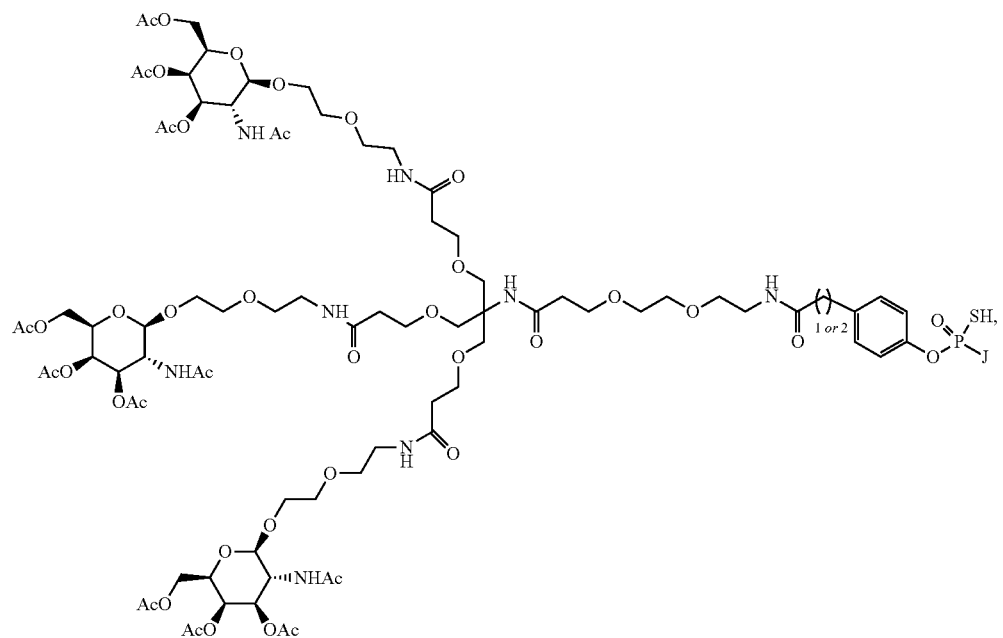
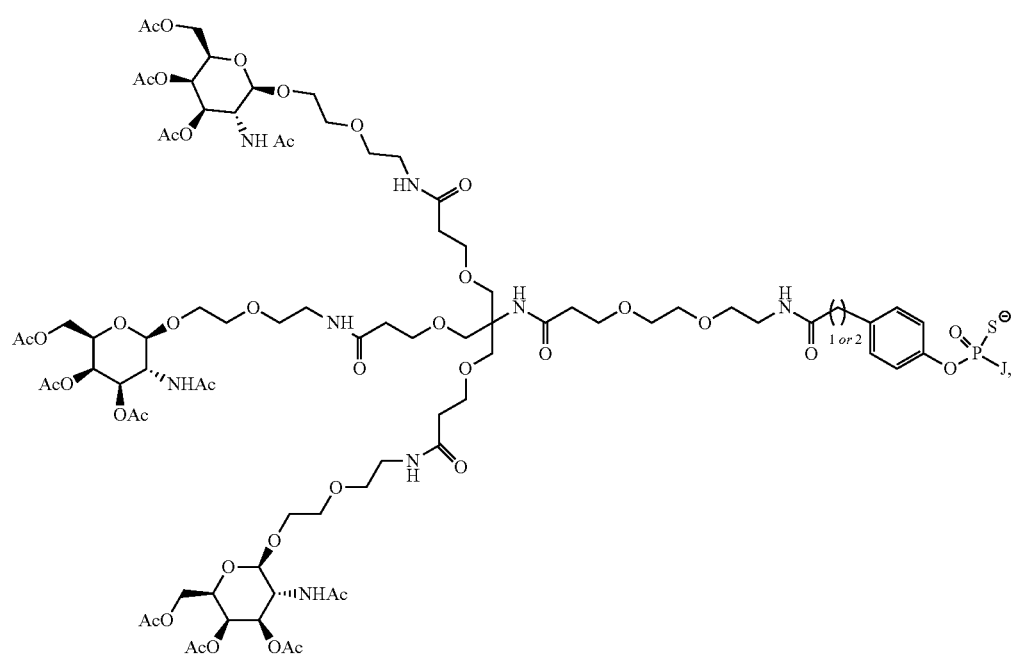

-continued
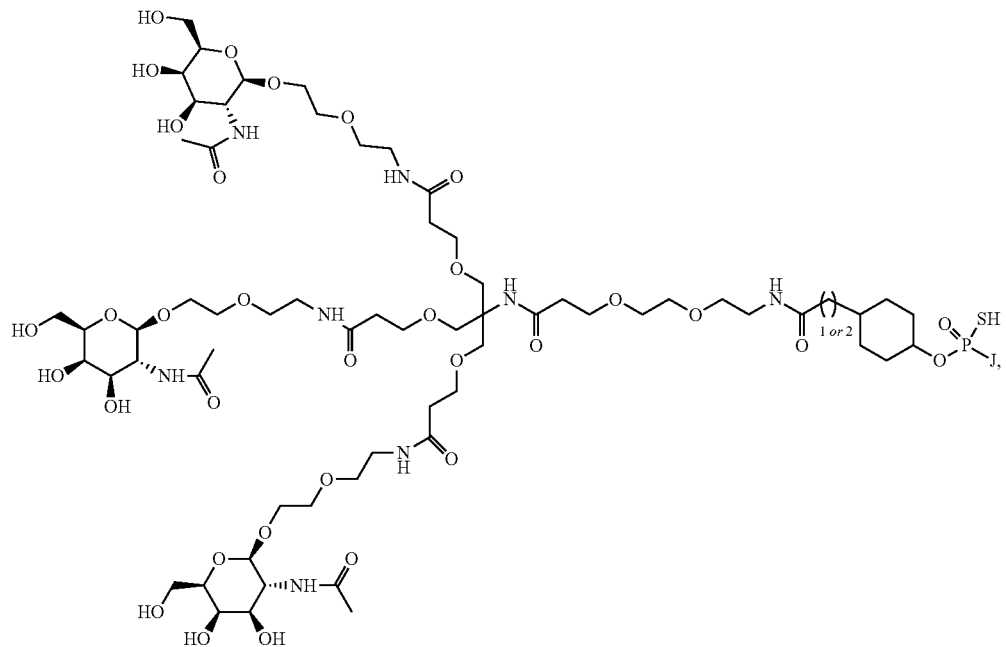
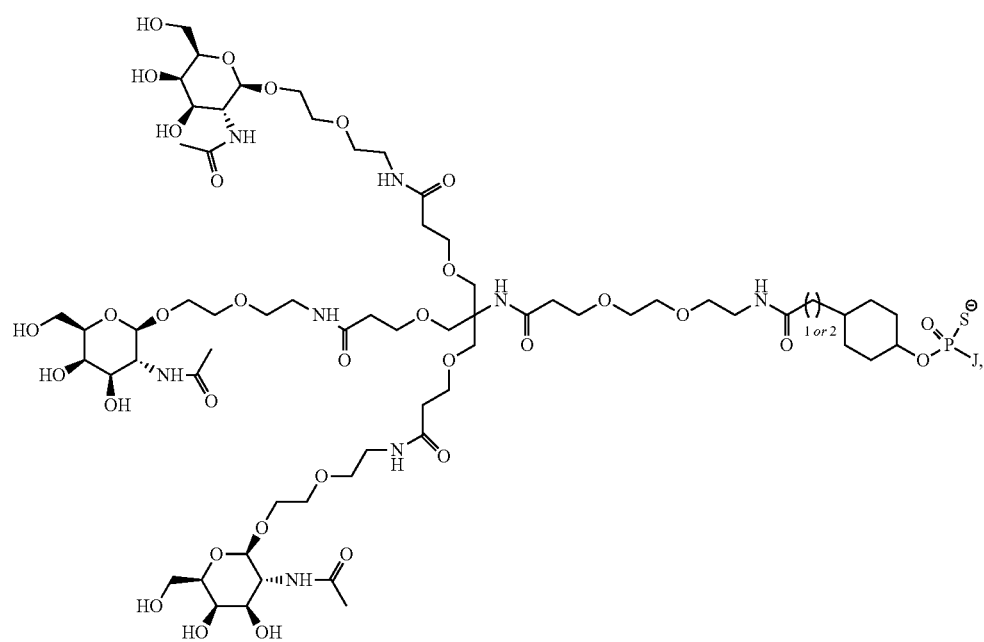

-continued
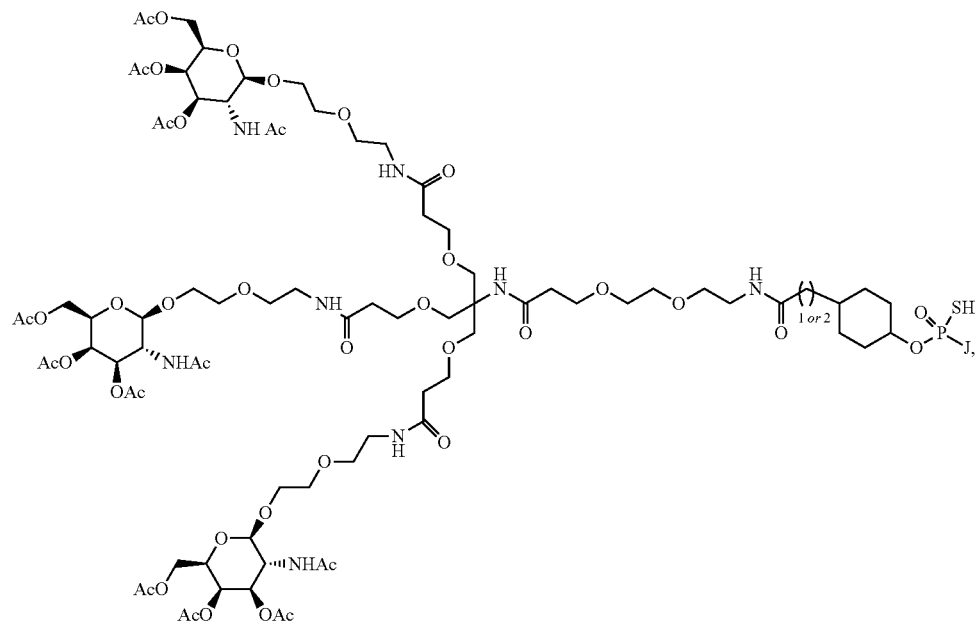
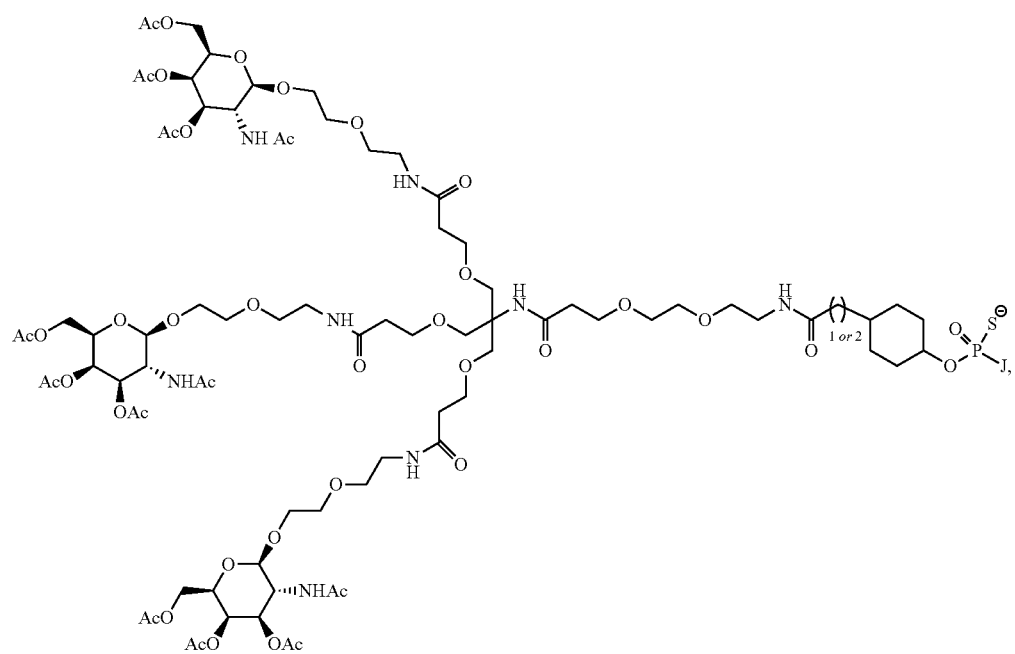

-continued
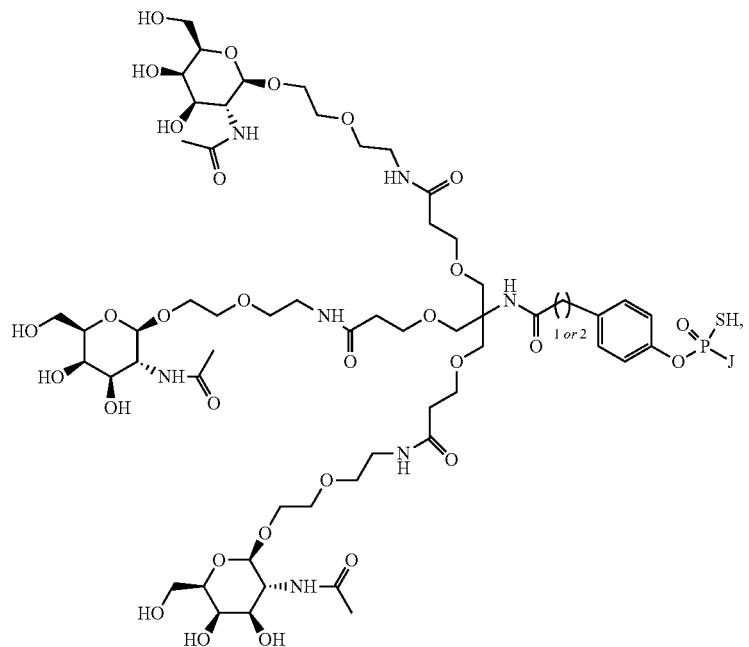
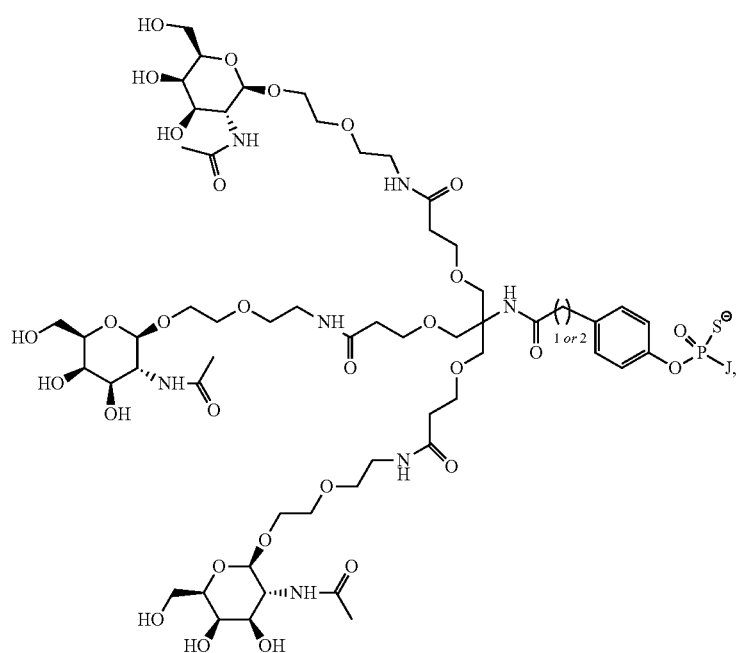

-continued
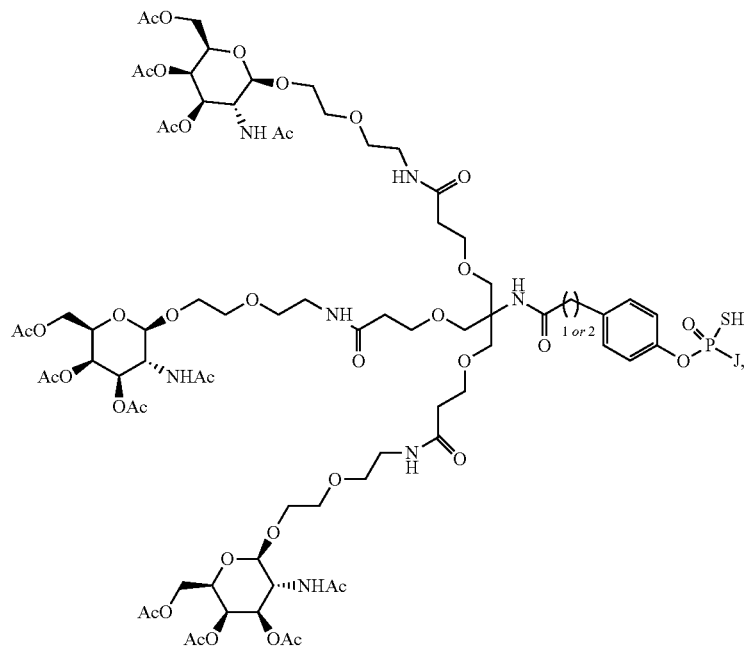
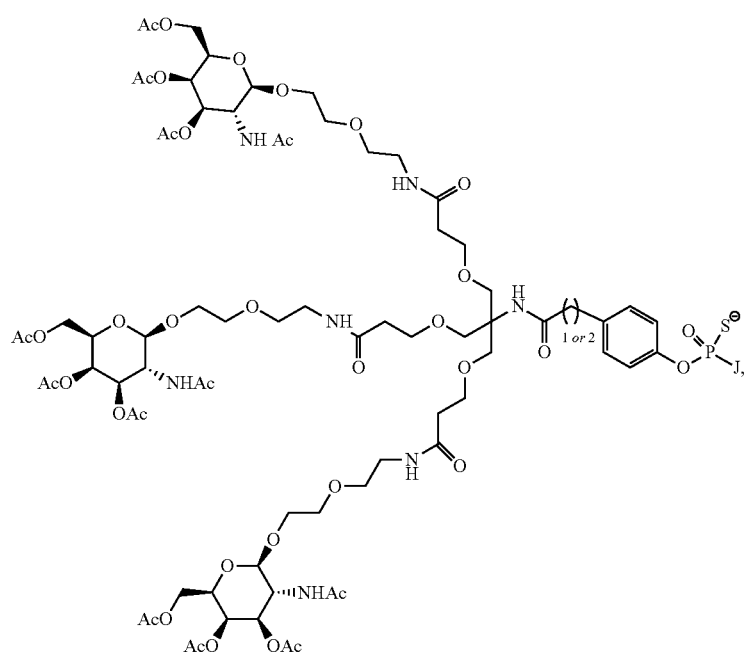

-continued
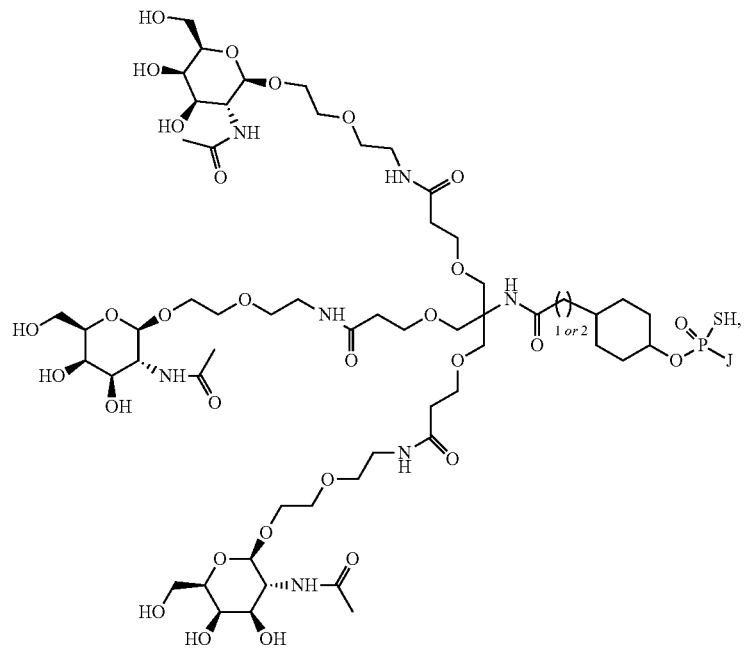
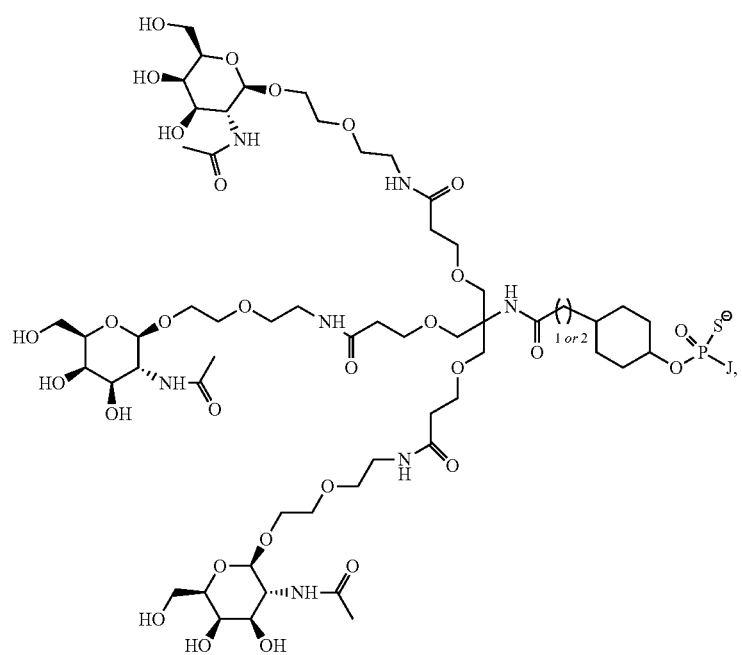

-continued

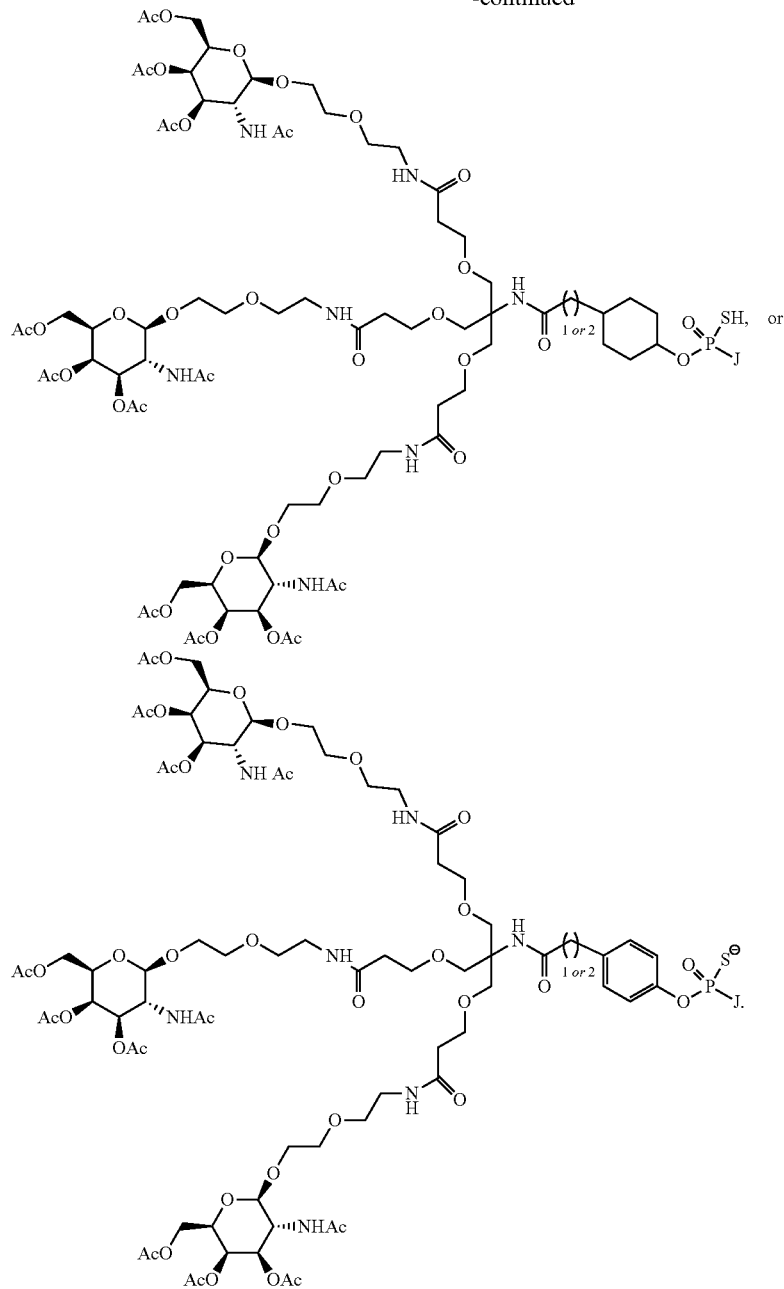

In some embodiments, the oligonucleotide (J) is attached at a 5' end or a 3' end of the oligonucleotide. In some embodiments, the oligonucleotide comprises DNA. In some embodiments, the oligonucleotide comprises RNA. In some embodiments, the oligonucleotide comprises one or more modified internucleoside linkages. In some embodiments, the one or more modified internucleoside linkages comprise alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the oligonucleotide comprises 1, 2, 3, 4, 5, 6, 7, 8, 9, 10, 11, 12, 13, 14, 15, 16, 17, 18, 19, or 20 modified internucleoside linkages. In some embodiments, the oligonucleotide comprises one or more modified nucleosides. In some embodiments, the one or more modified nucleosides comprise a locked nucleic acid (LNA), hexitol nucleic acid (FILA), cyclohexene nucleic acid (CeNA), 2'-methoxyethyl, 2c-O-alkyl, 2c-fluoro, car 2'-deoxy, or a combination thereof. In some embodiments, the one or more modified nucleosides comprise a 2',4' constrained ethyl nucleoside, a 2'-O-methyl nucleoside, 21-deoxyfluoro nucleoside. 2?-O—N-methylacetamido (2'-O-NMA) nucleoside, a 2'-O-dimethylaminoethoxyethyl (2'-O-DMAEOE) nucleoside, 2'-O-aminopropyl (2'-O-AP) nucleoside. 2'-ara-F, 2' fluoro, or 2' O-alkyl, or a combination thereof. In some embodiments, the oligonucleotide comprises 1, 2, 3, 4, 5, 6, 7, 8, 9, 10, 11, 12, 13, 14, 15, 16, 17, 18, 19, 20, 21, m more modified nucleosides. In some embodiments, the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenovl, mvristvl, pahnityl stearyk or α-tocopherol, or a combination thereof. In some embodiments, the oligonucleotide comprises an arginine-glycine-aspartic acid (ROD) peptide attached at a 3' or 5' terminus of the oligonucleotide. In some embodiments, the ROD peptide comprises Cyclo(-Arg-Gly-Asp-D-Phe-Cys), Cyclo(-Arg-Gly-Asp-D-Phe-Lys), Cyclo(-Arg-Gly-Asp-D-Phe-azido), an amino benzoic acid derived ROD, or a combination thereof. In some embodiments, the oligonucleotide comprises a small interfering RNA (siRNA) comprising a sense strand and an antisense strand. In some embodiments, the sense strand is 12-30 nucleosides in length. In some embodiments, the antisense strand is 12-30 nucleosides in length. In some embodiments, the sense strand and the antisense strand form a double-stranded RNA duplex. In some embodiments, a first base pair of the double-stranded RNA duplex is an AU base pair. In some embodiments, the sense strand or the antisense strand comprises a 3' overhang. In some embodiments, the 3' overhang comprises 1, 2, or more nucleosides. In some embodiments, the sense strand comprises any one of modification patterns 1S to 6S, or 1S#2 to 6S#2. In some embodiments, the antisense strand comprises any one of modification patterns 1AS to 9AS. In some embodiments, the oligonucleotide comprises an antisense oligonucleotide (ASO). In some embodiments, the ASO is 12-30 nucleosides in length. In some embodiments, the ASO comprises modification pattern ASO1. In some embodiments, the compound binds to an asialoglycoprotein receptor. In some embodiments, the compound targets a hepatocyte.

Disclosed herein is a pharmaceutical composition comprising the compound of any one of the compounds described herein, and a pharmaceutically acceptable carrier, excipient, or diluent. In some embodiments, the pharmaceutical composition is sterile. In some embodiments, the pharmaceutical composition comprises a pharmaceutically acceptable carrier. In some embodiments, the pharmaceutically acceptable carrier comprises water, a buffer, or a saline solution. In some embodiments, the oligonucleotide targets a target mRNA and when administered to a subject in an effective amount decreases the target mRNA or a target protein by at least 10%.

Disclosed herein is a method of decreasing a target mRNA or target protein in a subject in need thereof, comprising administering an effective amount of the pharmaceutical composition of any one of the compounds described herein. In some embodiments, the effective amount decreases a measurement of the target mRNA or target protein in the subject; relative to a baseline target mRNA or target protein measurement. In some embodiments, the effective amount treats a disorder in the subject. In some embodiments, the effective amount decreases a measurement of a symptom or parameter related to the disorder in the subject, relative to a baseline symptom or parameter measurement. In some embodiments, the measurement of the symptom or the parameter related to the disorder in the subject is decreased for at least 10 days. In some embodiments, the measurement of the symptom or the parameter related to the disorder in the subject is decreased for at least 100 days. In some embodiments, the disorder comprises a metabolic disorder. In some embodiments, the disorder comprises a liver disorder.

Disclosed herein is a compound represented by Formula (A) or (B):

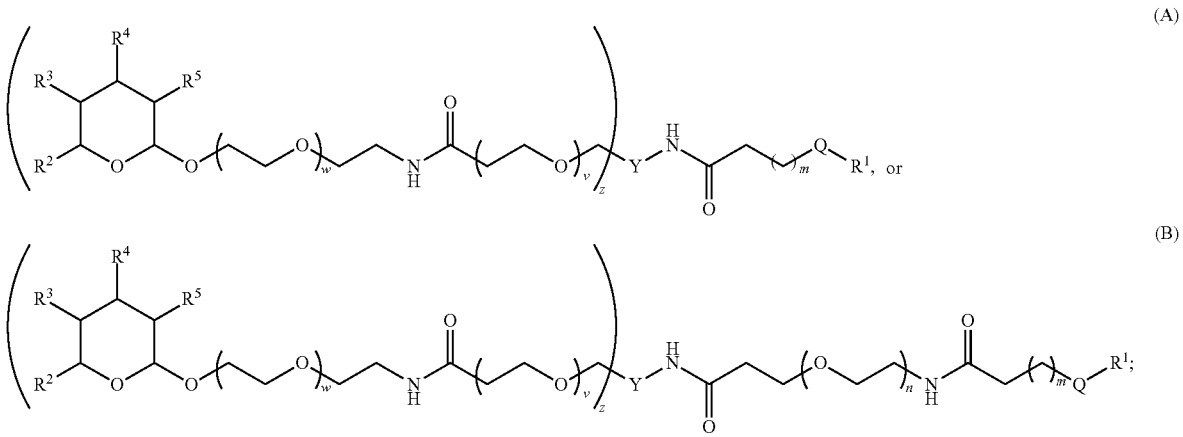

or a salt thereof, wherein
each w is independently selected from any value from 1 to 20,
each v is independently selected from any value from 1 to 20;
n is selected from any value from 1 to 20;
m is selected from any value from 1 to 20;
z is selected from any value from 1 to 3, wherein
  if z is 3, Y is C
  if z is 2, Y is CR', or
  if z is 1, Y is C(R$^6$)$_2$;
Q is selected from:
  C$_{3\text{-}10}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$—N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, and C$_{1\text{-}6}$ wherein the C$_{1\text{-}6}$ alkyl, is optionally substituted with one or more substituents independently selected from halogen, —CN, —OH, —SH, —NO$_2$, and —NH$_2$;
R$^1$ is selected from:
  —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, —S(O)$_2$R$^7$, —OS(O)$_2$R$^7$, —OP(O)(OR$^7$)$_2$, —OP(S)(OR$^7$)$_2$, —SP(O)(OR$^7$)$_2$, —OP(O)(SR$^7$)(OR$^7$), —OP(O)(OR$^7$)N(R$^7$)$_2$, —OP(S)(OR$^7$)N(R$^7$)$_2$, —SP(O)(OR$^7$)N(R$^7$)$_2$, —OP(O)(SR$^7$)N(R$^7$)$_2$, —OP(O)(N(R$^7$)$_2$)$_2$, —OP(S)(N(R$^7$)$_2$)$_2$, —SP(O)(N(R$^7$)$_2$)$_2$, —OP(OR$^7$)$_2$, —SP(OR$^7$)$_2$, —OP(OR$^7$)(SR$^7$), —OP(OR$^7$)N(OR$^7$), —OP(SR$^7$)N(R$^7$)$_2$, —SP(OR$^7$)N(R$^7$)$_2$, —OP(N(R$^7$)$_2$)$_2$, and —SP(N(R$^7$)$_2$)$_2$;

each R$^2$ is independently selected from:

C$_{1-6}$ alkyl optionally substituted with one or more substituents independently selected from halogen, —OR$^7$, —SR$^7$, —N(R$^7$)$_2$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$;

R$^3$ and R$^4$ are each independently selected from:

—OR$^7$, —SR$^7$, —N(R$^7$)$_2$, —C(O)R$^7$, —CO)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$;

each R$^5$ is independently selected from:

—OC(O)R$^7$, —OC(O)N(R$^7$)$_2$, —N(R$^7$)C(O)R$^7$, —N(R$^7$)C(O)N(R$^7$)$_2$, —N(R$^7$)C(O)OR$^7$, —C(O)R$^7$, —C(O)OR$^7$, and —C(O)N(R$^7$)$_2$;

each R$^6$ is independently selected from:

hydrogen;

halogen, —CN; —NO$_2$, —SR, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$; and C$_{1-6}$ alkyl optionally substituted with one or more substituents independently selected from halogen, —CN, —NO$_2$, —S—N(R$^7$)$_2$, —C(O)R$^7$, —C(O)N(R$^7$)$_2$, —N(R$^7$)C(O)R$^7$, —N(R$^7$)C(O)N(R)$_2$, —OC(O)N(R$^7$)$_2$, —N(R$^7$)C(O)OR$^7$, —C(O)OR$^7$; —OC(O)R$^7$, and —S(O)R$^7$;

each R$^7$ is independently selected from:

hydrogen;

C$_{1-6}$ alkyl, C$_{2-6}$ alkenyl, and C$_{2-6}$ alkynyl, each of which is optionally substituted with one or more substituents independently selected from halogen. —CN, —OH, —SH, —NO$_2$, —NH$_2$, =O, =S, —O—C$_{1-6}$ alkyl, —S—C$_{16}$ alkyl, —N(C$_{1-6}$ alkyl)$_2$, —NH(C$_{1-6}$ alkyl), C$_{3-10}$ carbocycle, and 3- to 10-membered heterocycle; and C$_{3-10}$ carbocycle, and 3- to 10-membered heterocycle, each of which is optionally substituted with one or more substituents independently selected from halogen. —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl. C$_{5-10}$ carbocycle, 3- to 10-membered heterocycle, and C$_{1-6}$ haloalkyl.

In some embodiments, each w is independently selected from airs, value from 1 to 10. In some embodiments, each w is independently selected from any value from 1 to 5. In some embodiments, each w is 1. In some embodiments, each v is independently selected from any value from 1 to 10, In some embodiments, each v is independently selected from any value from 1 to 5. In some embodiments, each v is 1. In some embodiments, n is selected from any value from 1 to 10. In some embodiments, n is selected from any value from 1 to 5. In some embodiments, n is 2. In some embodiments, m is selected from any value from 1 to 10. In some embodiments, m is selected from any value from 1 to 5. In some embodiments, m is selected from 1 and 2. In some embodiments, z is 3 and Y is C. In some embodiments, Q is selected from C$_{5-6}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$, In some embodiments, Q is selected from C$_{5-6}$ carbocycle optionally substituted with one or more substituents independently selected from halogen, —CN, —OH, —SH, —NO$_2$, and —NH$_2$. In some embodiments, Q is selected from phenyl and cyclohexyl, each of which is optionally substituted with one or more substituents independently selected from halogen, —CN, —OH, —SH. —NO$_2$, and —NH$_2$, In some embodiments, Q is selected from phenyl. In some embodiments, Q is selected from cyclohexyl. In some embodiments, R$^1$ is selected from —OP(O)(OR$^7$)$_2$, —OP(O)(OR$^7$)N(R$^7$)$_2$, —OP(O)(N(R$^7$)$_2$)$_2$, —OP(OR$^7$)$_2$, —OP(OR)N(R$^2$)$_2$, and —OP((NR$^7$)$_2$)$_2$. In some embodiments, R is selected from —OP(O)(OR$^7$)$_2$ and —OP(OR$^7$)N(R$^7$)$_2$. In some embodiments, R$^1$ is selected from —OP(O)(OCH$_2$CH$_3$)OH and —OP(OCH$_2$CH$_2$CN)N(CH(CH$_3$)$_2$)$_2$. In some embodiments, R$^1$ is —OP(OCH$_2$CH$_2$CN)N(CH(CH$_3$)$_2$)$_2$. In some embodiments. R$^2$ is selected from C$_{1-3}$ alkyl substituted with one or more substituents independently selected from halogen, —OR$^7$, —OC(O)R$^7$, —SR$^7$, —N(R$^7$)$_2$, —C(O)R$^7$, and —S(O)R$^7$. In some embodiments, R$^2$ is selected from C$_{1-3}$ alkyl substituted with one or more substituents independently selected from —OR$^7$, —OC(O)R$^7$, —SR$^7$, and —N(R$^7$)$_2$. In some embodiments, R$^2$ is selected from C$_{1-3}$ alkyl substituted with one or more substituents independently selected from —OR$^7$ and —OC(O)R$^7$. In some embodiments, R$^3$ is selected from halogen, —OR$^7$, —SR$^7$, —N(R$^7$)$_2$, —C(O)R$^7$, —OC(O)R$^2$, and —S(O)R$^7$. In some embodiments, R$^3$ is selected from —OR$^7$, —SR$^7$, —OC(O)R$^7$, and —N(R$^7$)$_2$. In some embodiments, R$^3$ is selected from —OR$^7$— and —OC(O)R$^7$. In some embodiments, R$^2$ is selected from halogen, —OR$^7$, —SR$^7$, —N(R$^2$)$_2$, —C(O)R$^7$, —OC(O)R$^7$, and —S(O)R$^7$. In some embodiments. R$^4$ is selected from —OR$^7$, —SR$^7$, —OC(O)R$^7$, and —N(R$^7$)$_2$, In some embodiments, R$^4$ is selected from —OR$^7$— and —OC(O)R$^7$. In some embodiments, R$^5$ is selected from —OC(O)R$^7$, —OC(O)N(R$^7$)$_2$, —N(R)C(O)R$^7$, —N(R$^7$)(O)N(R$^7$)$_2$, and —N(R$^7$)C(O)OR$^7$. In some embodiments, R$^5$ is selected from —OC(O)R$^7$ and —N(R$^7$)C(O)R$^7$. In some embodiments, each R$^7$ is independently selected from: hydrogen; and alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-4}$ alkyl)$_2$, —NH(C$_{1-6}$ alkyl), C$_{5-10}$ carbocycle, or 3- to 10-membered heterocycle. In some embodiments, each R$^7$ is independently selected from C$_{1-4}$ alkyl optionally substituted with one or more substituents independently selected from halogen, —CN, —OH, —SH, —NO$_2$, —NH$_2$, =O, =S, —O—C$_{1-6}$ alkyl, —N(C$_{1-6}$ alkyl)$_2$, and —NH(C$_{1-6}$ alkyl). In some embodiments, each R$^7$ is independently selected from C$_{1-6}$ alkyl optionally substituted with one or more substituents independently selected from halogen. —CN, —OH, and —SH. In some embodiments, w is 1; v is 1; n is 2: m is 1 or 2; z is 3 and Y is C; Q is phenyl or cyclohexyl, each of which is optionally substituted with one or more substituents independently selected from halogen, —CN, —OH, —SH, —NO$_2$, —NH$_2$, and C$_{1-3}$ alkyl; R$^1$ is selected from —OP(O)(OR$^7$)$_2$ and —OP(OR)N(R$^7$)$_2$, R$^2$ is C$_1$ alkyl substituted with —OH or —OC(O)CH$_3$; R$^3$ is —OH or —OC(O)CH$_2$; R$^4$ is —OH or —OC(O)CH$_3$; and R$^5$ is —NH(O)CH$_3$. In some embodiments, the compound comprises:

41
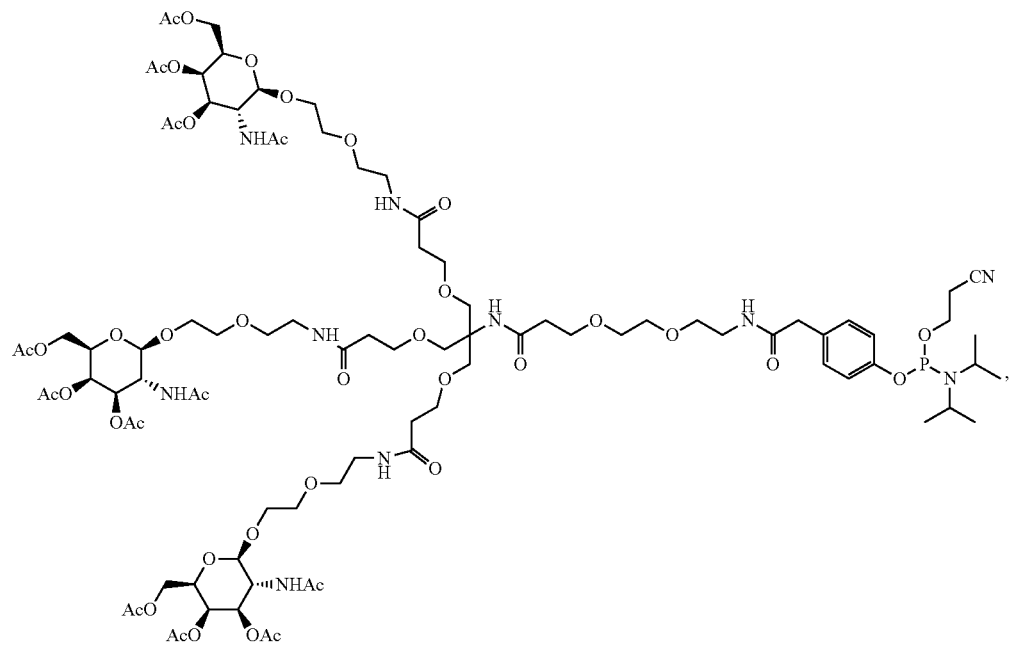
42
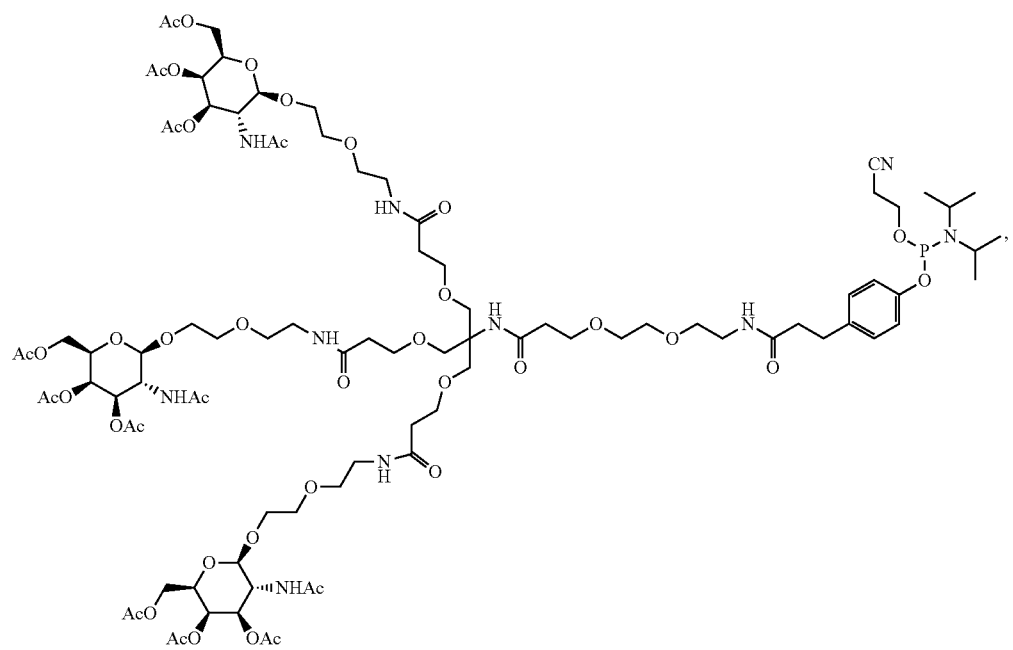

-continued
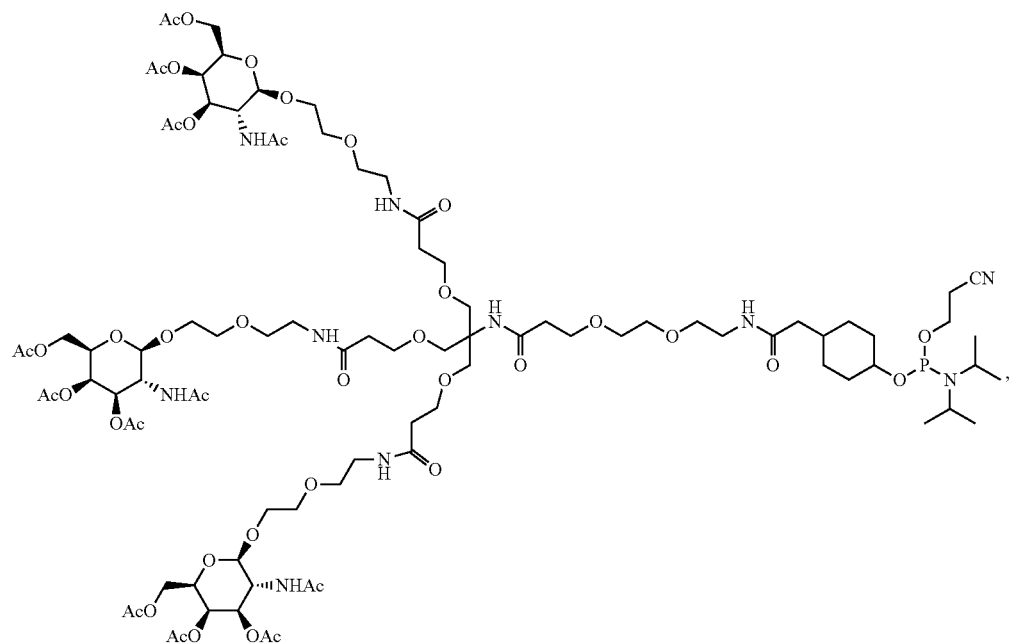
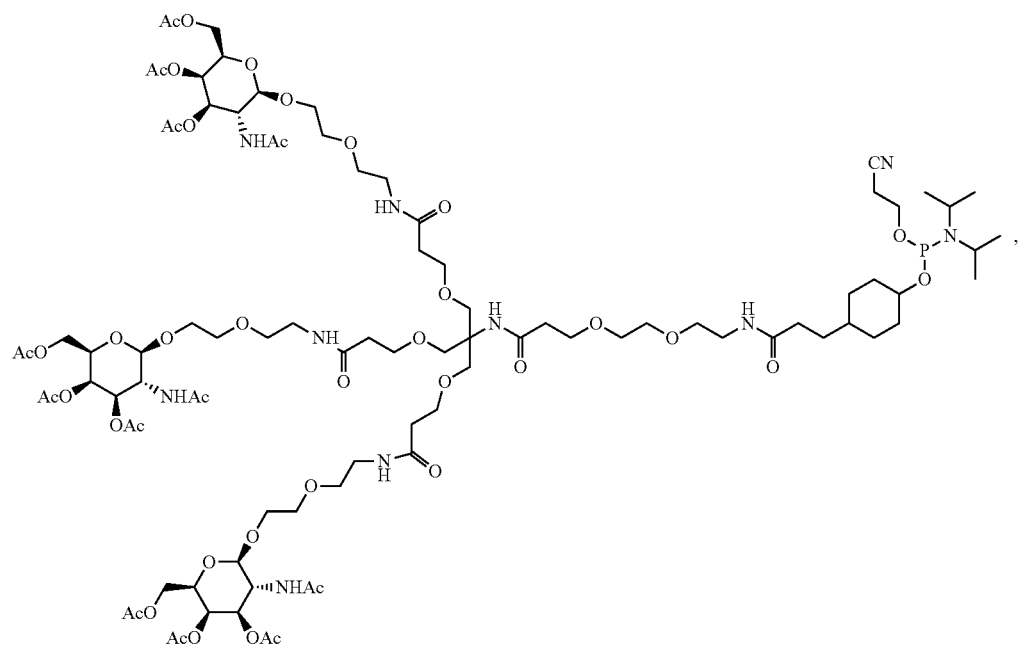

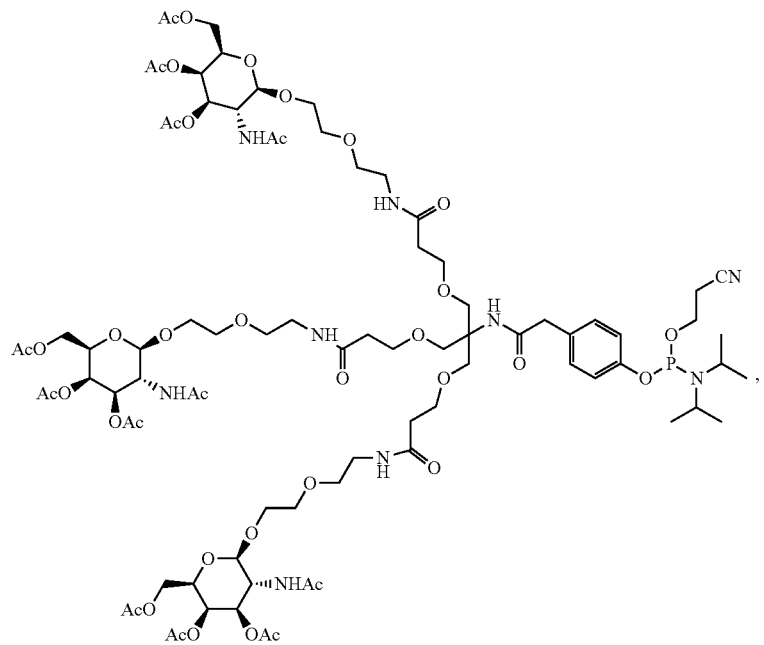
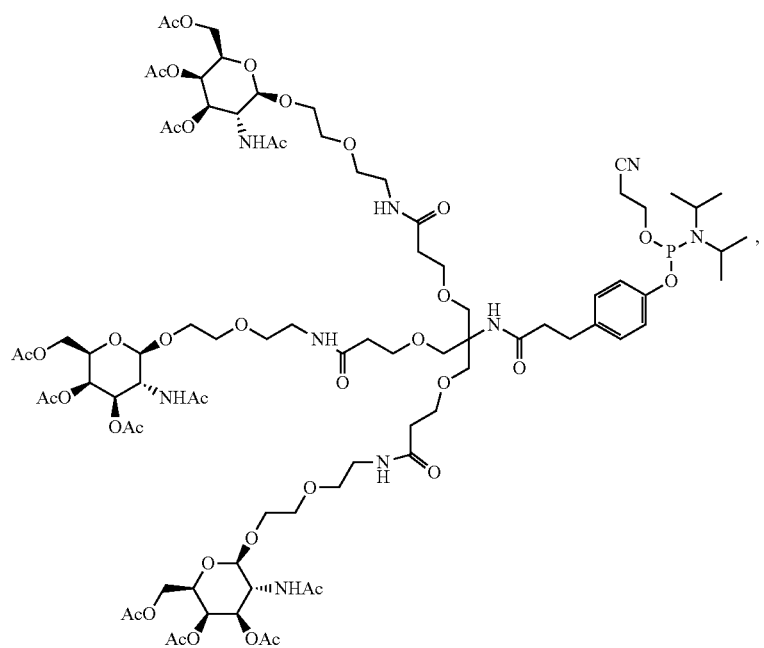

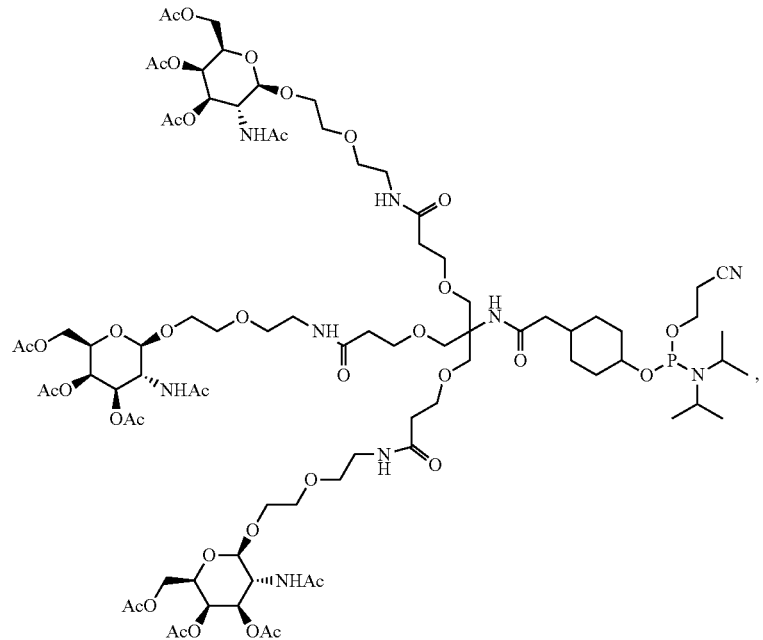
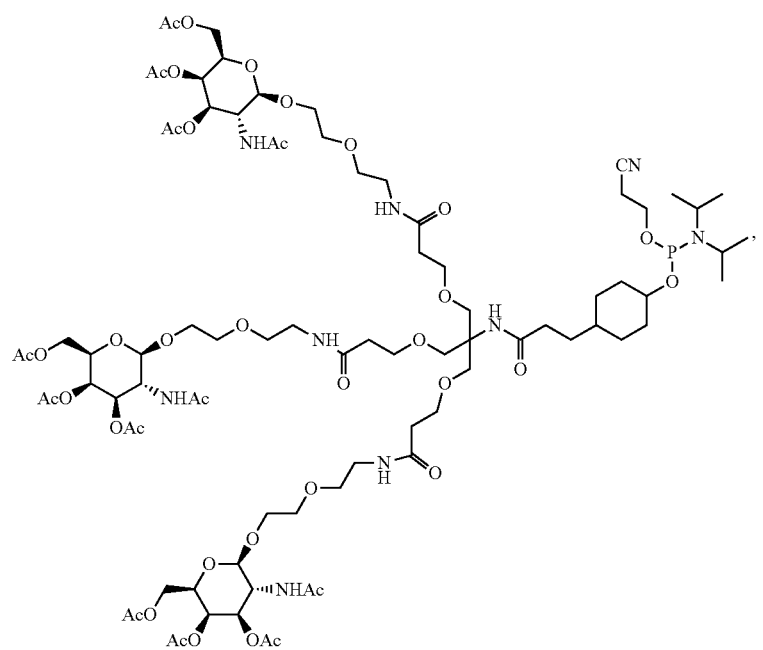

-continued
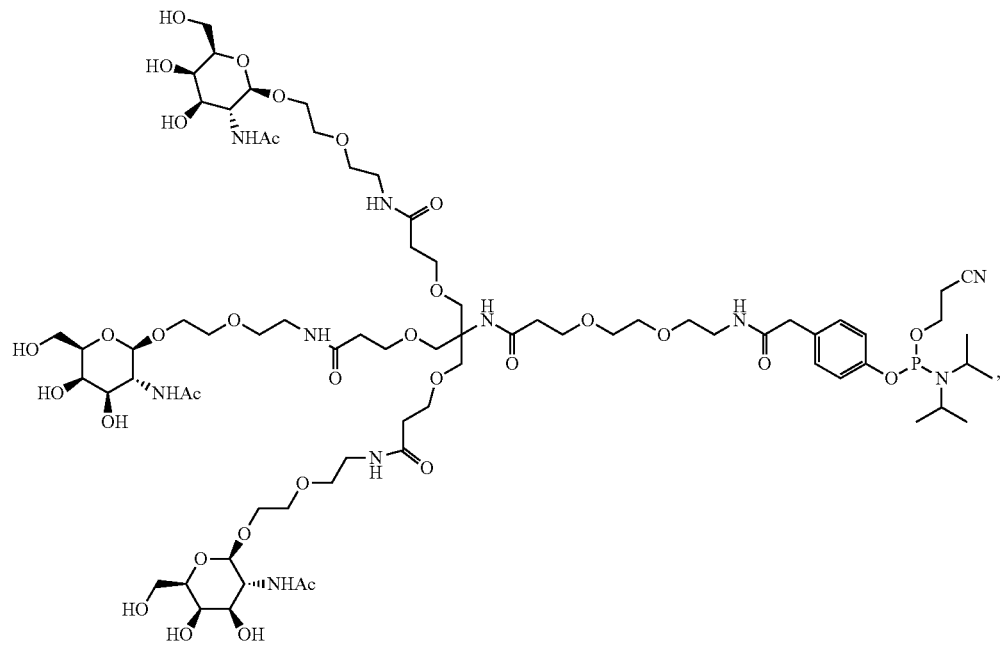
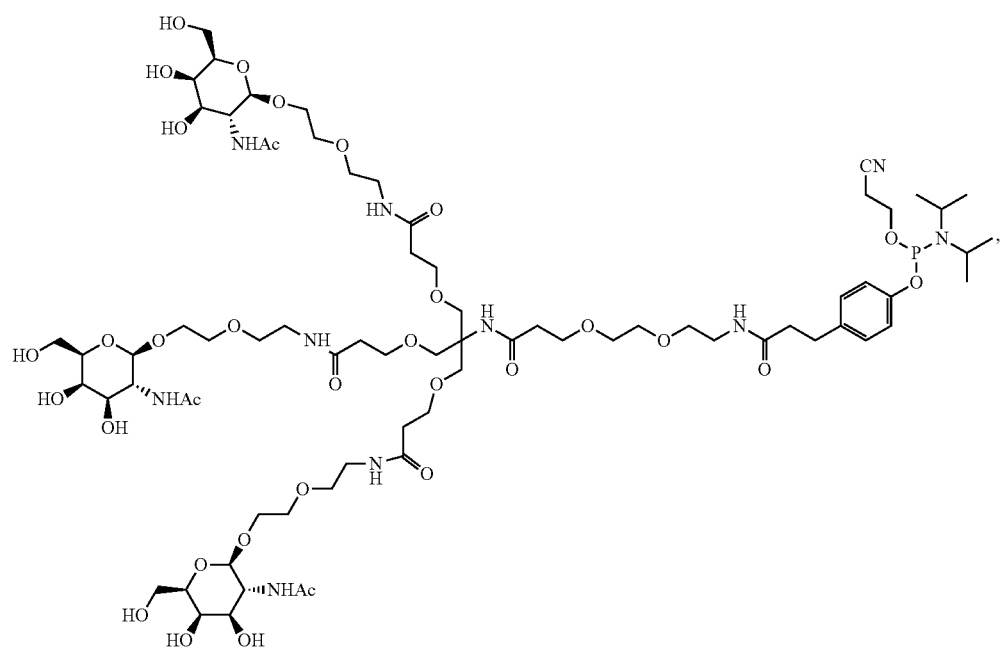

-continued
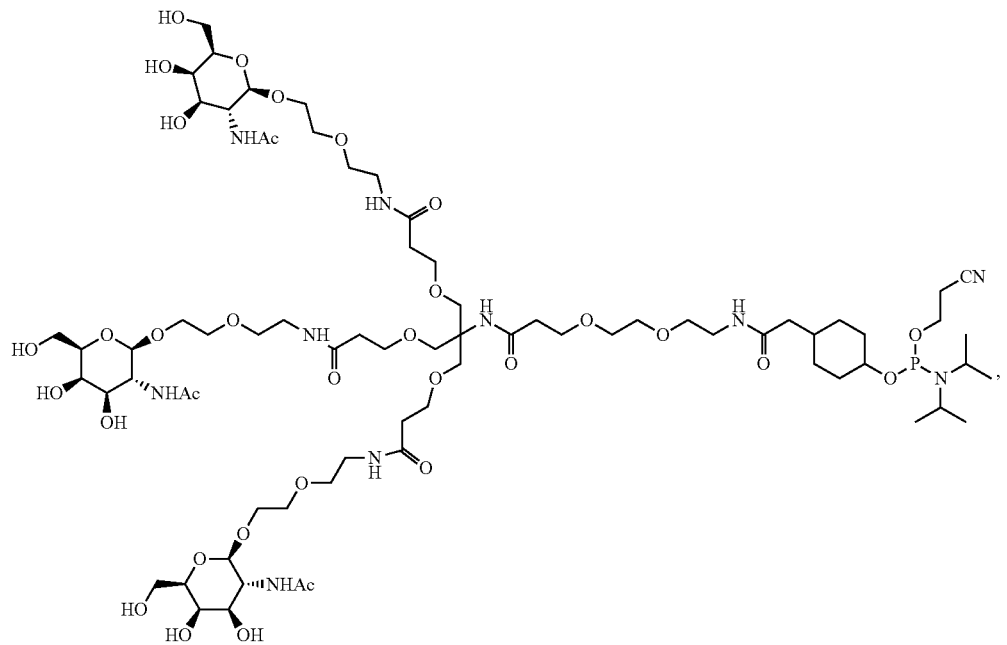
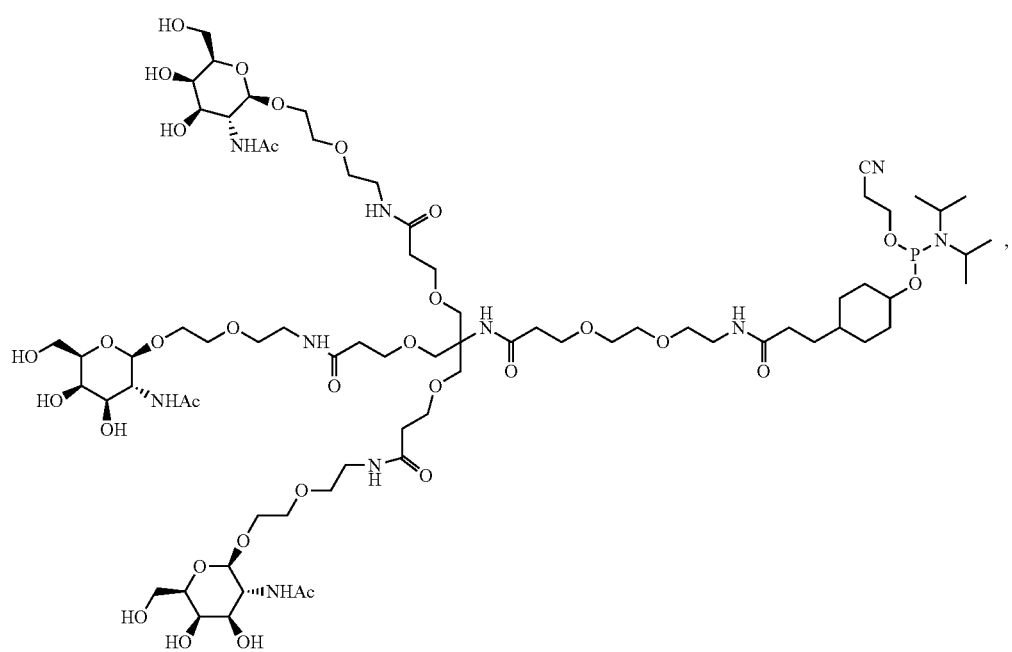

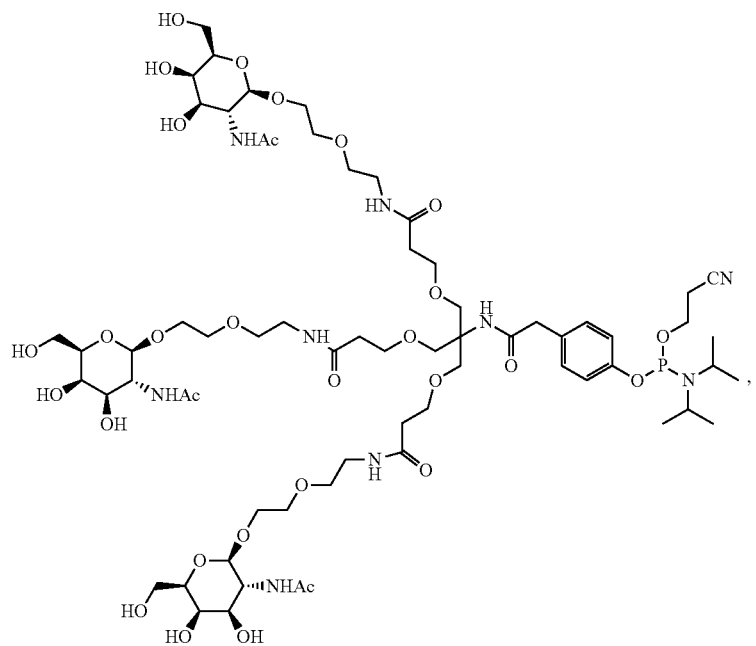
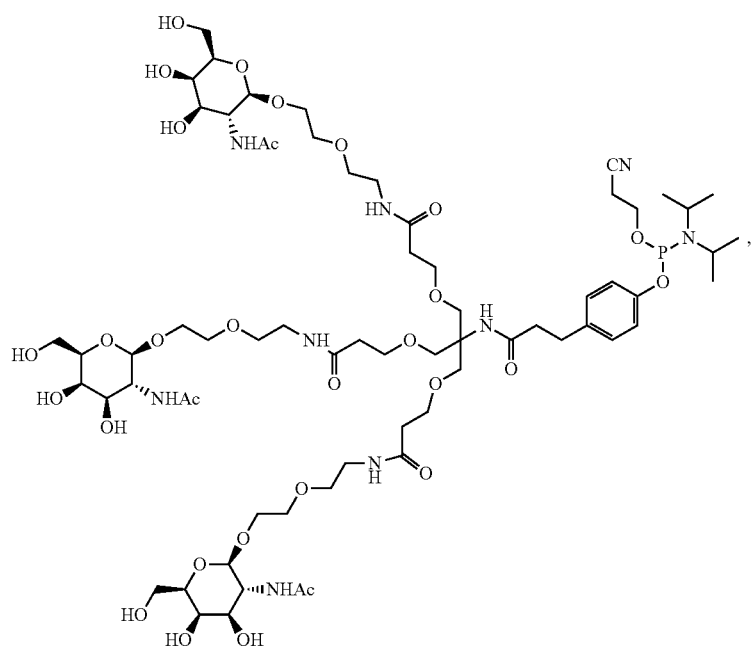

-continued

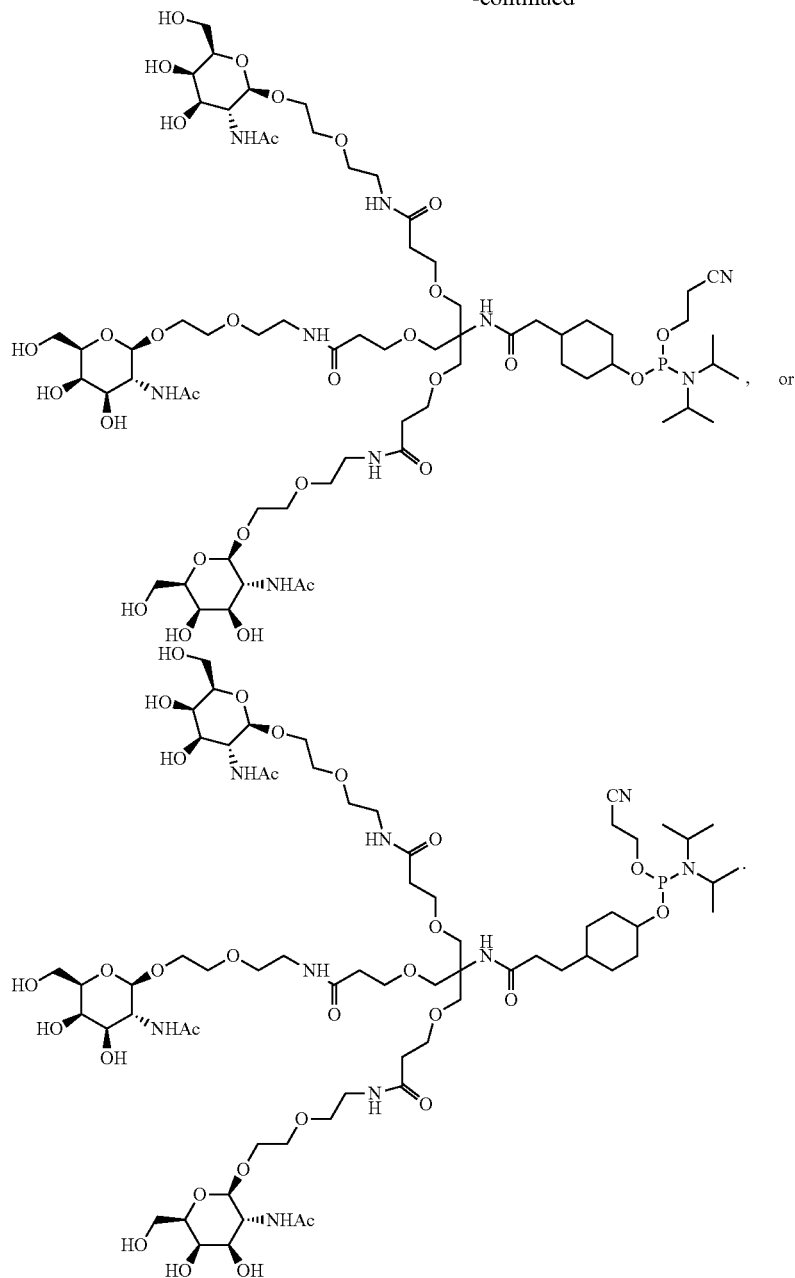

DETAILED DESCRIPTION

N-Acetylgalactosamine (GalNAc), is an amino sugar derivative of galactose. GalNAc and GalNAc-containing moieties may bind lectins such as asialoglycoprotein receptors. These receptors may be included on hepatocytes. Thus, GalNAc may target air oligonucleotide to a hepatocyte or to the liver.

Provided herein, are GalNAc moieties. These GalNAc moieties may be conjugated to an oligonucleotide such as a small interfering RNA (siRNA) or antisense oligonucleotide (ASO). The oligonucleotide conjugated to the GalNAc moiety may be administered to a subject, targeted to a liver or hepatocyte, or used to treat a liver related disorder in the subject.

I. Compositions

Provided herein, in some embodiments, are compositions comprising an oligonucleotide and an N-Acetylgalactosamine (GalNAc) moiety. In some embodiments, the composition comprises an oligonucleotide. The oligonucleotide may inhibit a target gene or oligonucleotide. The oligonucleotide may bind a target oligonucleotide. In some embodiments, the composition is used in a method described herein.

Provided herein, in some embodiments, are compounds comprising an oligonucleotide and a GalNAc moiety. In some embodiments, the compound comprises an oligonucleotide. The oligonucleotide may bind to a target oligonucleotide. In some embodiments, the compound is used in a method described herein. In some embodiments, the compound is included in a composition described herein.

The oligonucleotide of the compound or composition described herein may comprise a small interfering RNA (siRNA) or an antisense oligonucleotide (ASO).

Some embodiments include a composition comprising a GalNAc moiety, and an oligonucleotide that when administered to a subject in an effective amount decreases a target mRNA or protein level in a cell, fluid or tissue of the subject. Some embodiments include a composition comprising a GalNAc moiety, and an oligonucleotide that when administered to a subject in an effective amount decreases a target mRNA or protein level in liver tissue or in a hepatocyte. In some embodiments, the composition comprises a GalNAc moiety, and an oligonucleotide that when administered to a subject in an effective amount decreases levels of a target e.g. mRNA in a cell or tissue. In some embodiments, the cell is a hepatocyte. In some embodiments, the tissue is liver tissue. Some embodiments include a composition comprising a GalNAc moiety, and an oligonucleotide that when administered to a subject in an effective amount decreases a target mRNA level in liver tissue. Some embodiments include a composition comprising a GalNAc moiety, and an oligonucleotide that when administered to a subject in an effective amount decreases a target mRNA level in a hepatocyte.

In some embodiments, the decrease in the target oligonucleotide level is specific to a hepatocyte in relation to another cell type. In some embodiments, the decrease in the target RNA level is specific to a hepatocyte in relation to another cell type. In some embodiments, the decrease in the target mRNA level is specific to a hepatocyte in relation to another cell type. In some embodiments, the decrease in the target protein level is specific to a hepatocyte in relation to another cell type. In some embodiments, the decrease in the target oligonucleotide level is specific to liver tissue in relation to another tissue type. In some embodiments, the decrease in the target RNA level is specific to liver in relation to another tissue type. In some embodiments, the decrease in the target mRNA level is specific to liver in relation to another tissue type. In some embodiments, the decrease in the target protein level is specific to liver in relation to another tissue type.

In some embodiments, the composition comprises a GalNAc moiety, and an oligonucleotide that binds to a target oligonucleotide, which when administered to a subject in an effective amount decreases the target oligonucleotide levels in a cell or tissue. In some embodiments, the target oligonucleotide levels are decreased by about 2.5% or more, about 5% or more, or about 7.5% or more, as compared to prior to administration. In some embodiments, the target oligonucleotide levels are decreased by about 10% or more, as compared to prior to administration. In some embodiments, the target oligonucleotide levels are decreased by about 20% or more, about 30% or more, about 40% or more, about 50% or more, about 60% or more, about 70% or more, about 80% or more, about 90% or more, or about 100%, as compared to prior to administration. In some embodiments, the target oligonucleotide levels are decreased by no more than about 2.5%, no more than about 5%, or no more than about 7.5%, as compared to prior to administration. In some embodiments, the target oligonucleotide levels are decreased by no more than about 10%, as compared to prior to administration. In some embodiments, the target oligonucleotide levels are decreased by no more than about 20%, no more than about 30%, no more than about 40%, no more than about 50%, no more than about 60%, no inure than about 70%, no more than about 80% no more than about 90%, or no more than about 100% as compared to prior to administration. In some embodiments, the target oligonucleotide levels are decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises a GalNAc moiety, and an oligonucleotide that binds to a target mRNA, which when administered to a subject in an effective amount decreases the target mRNA levels in a cell or tissue. In some embodiments, the target mRNA levels are decreased by about 2.5% or more, about 5% or more, or about 7.5% or more, as compared to prior to administration. In some embodiments, the target mRNA levels are decreased by about 10% or more, as compared to prior to administration. In some embodiments, the target mRNA levels are decreased by about 20% or more, about 30% or more, about 40% or more, about 50% or more, about 60% or more, about 70% or more, about 80% or more, about 90% or more, or about 100%, as compared to prior to administration. In some embodiments, the target mRNA levels are decreased by no inure than about 2.5%, no more than about 5%, or no more than about 7.5%, as compared to prior to administration. In some embodiments, the target mRNA levels are decreased by no more than about 10%, as compared to prior to administration. In Soiree embodiments, the target mRNA levels are decreased by no more than about 20%, no more than about 30%, no more than about 40%, no more than about 50%, no more than about 60%, no more than about 70%, no more than about 80%, no more than about 90%, or no more than about 100%, as compared to prior to administration. In some embodiments, the target mRNA levels are decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises a GalNAc moiety, and an oligonucleotide that binds to an oligonucleotide encoding a target protein, which when the composition is administered to a subject in an effective amount decreases the target protein levels in a cell or tissue. In some embodiments, the cell is a hepatocyte. In some embodiments, the tissue is liver tissue. In some embodiments, the target protein levels are decreased by about 2.5% or more, about 5% or more, or about 7.5% or more, as compared to prior to administration. In some embodiments, the target protein levels are decreased by about 10% or more, as compared to prior to administration. In some embodiments, the target protein levels are decreased by about 20% or more, about 30% or more, about 40% or more, about 50% or more, about 60% or more, about 70% or more, about 80% or more, about 90% or more, or about 100%, as compared to prior to administration. In some embodiments, the target protein levels are decreased by no more than about 2.5%, no more than about 5%, or no more than about 7.5%, as compared to prior to administration. In some embodiments, the target protein levels are decreased by no more than about 10%, as compared to prior to administration. In some embodiments, the target protein levels are decreased by no more than about 20%, no more than about 30%, no more than about 40%, no more than about 50%, no more than about 60%, no more than about 70%, no more than about 80%, no more than about 90%, or no more than about 100%, as compared to prior to administration, in some embodiments, the target protein levels are decreased by 2.5%, 5%, 7.5%, 10%, 15%, 20%, 25%, 30%, 33%, 40%, 45%, 50%, 55%, 60%, 65%, 70%, 75%, 80%, 85%, 90%, 95%, or 100%, or by a range defined by any of the two aforementioned percentages.

In some embodiments, the composition comprises a GalNAc moiety, and an oligonucleotide that binds to a target oligonucleotide (e.g. mRNA) and when administered to a subject in an effective amount decreases an adverse phenotype (e.g. a symptom of a disorder associated with the target oligonucleotide). In some embodiments, the adverse phenotype is decreased by about 2.3% or more, about 3% or more, or about 7.5% or more, as compared to prior to administration. In some embodiments, the adverse phenotype is decreased by about 10% or more, as compared to prior to administration. In some embodiments, the adverse phenotype is decreased by about 20% or more, about 30% or more, about 40% or more, about 50% or more, about 60% or more, about 70% or more, about 80% or more, about 90% or more, or about 100%, as compared to prior to administration. In some embodiments, the adverse phenotype is decreased by no more than about 2.5%, no more than about 5%, or no more than about 7.5%, as compared to prior to administration. In some embodiments, the adverse phenotype is decreased by no more than about 10%, as compared to prior to administration. In some embodiments, the adverse phenotype is decreased by no more than about 20%, no more than about 30%, no more than about 40%, no more than about 50%, no more than about 60%, no more than about 70%, no more than about 80%, no more than about 90%, or no more than about 100%, as compared to prior to administration. In some embodiments, the adverse phenotype is decreased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or by a range defined by any of the two aforementioned percentages.

In some embodiments, the composition comprises a GalNAc moiety, and an oligonucleotide that binds to a target oligonucleotide (e.g. mRNA) and when administered to a subject in an effective amount increases a protective phenotype (e.g. protective against a disorder). In some embodiments, the protective phenotype is increased by about 2.5% or more, about 5% or more, or about 7.3% or more, as compared to prior to administration. In some embodiments, the protective phenotype is increased by about 10% or more, as compared to prior to administration. In some embodiments, the protective phenotype is increased by about 20% or more, about 30% or more, about 40% or more, about 50% or more, about 60% or more, about 70% or more, about 80% or more, about 90% or more, or about 100% or more, as compared to prior to administration. In some embodiments, the protective phenotype is increased by about 200% or more, about 300% or more, about 400% or more, about 500% or more, about 600% or more, about 700% or more, about 800% or more, about 900% or more, or about 1000% or more, as compared to prior to administration. In some embodiments, the protective phenotype is increased by no more than about 2.5%, no more than about 5%, or no more than about 7.5%, as compared to prior to administration. In some embodiments, the protective phenotype is increased by no more than about 10%, as compared to prior to administration. In some embodiments, the protective phenotype is increased by no more than about 20%, no more than about 30%, no more than about 40%, no more than about 50%, no more than about 60%, no more than about 70%, no more than about 80%, no more than about 90%, or no more than about 100%, as compared to prior to administration. In some embodiments, the protective phenotype is increased by no more than about 200%, no more than about 300%, no more than about 400%, no more than about 500%, no more than about 600%, no more than about 700%, no more than about 800%, no more than about 900%, or no more than about 1000%, as compared to prior to administration. In some embodiments, the protective phenotype is increased by 2.5%, 5%, 7.5%, 10%, 15%, 20%, 25%, 30%, 35%, 40%, 45%, 50%, 55%, 60%, 65%, 70%, 75%, 80%, 85%, 90%, 95%, 100%, 150%, 200%, 250%, 300%, 400%, 500%, 600%, 700%, 800%, 900%, or 1000%, or by a range defined by any of the two aforementioned percentages.

A. GalNAc moieties and compounds

Provided herein, in some embodiments, are compositions comprising a GalNAc moiety. Provided herein, in some embodiments, are compositions comprising a GalNAc moiety and an oligonucleotide. In some embodiments, a composition comprising GalNAc moiety and an oligonucleotide is described by a compound of Formula (I) or Formula (II). In Kale embodiments the oligonucleotide of Formula (I) or Formula (11), is J. In some embodiments the GalNAc moiety of Formula (I) or Formula (II) is the molecular moiety bound to J. The oligonucleotide may comprise a small interfering RNA (siRNA) or an antisense oligonucleotide (ASO).

Provided herein, in some embodiments, is a compound represented by Formula (I) or (II):

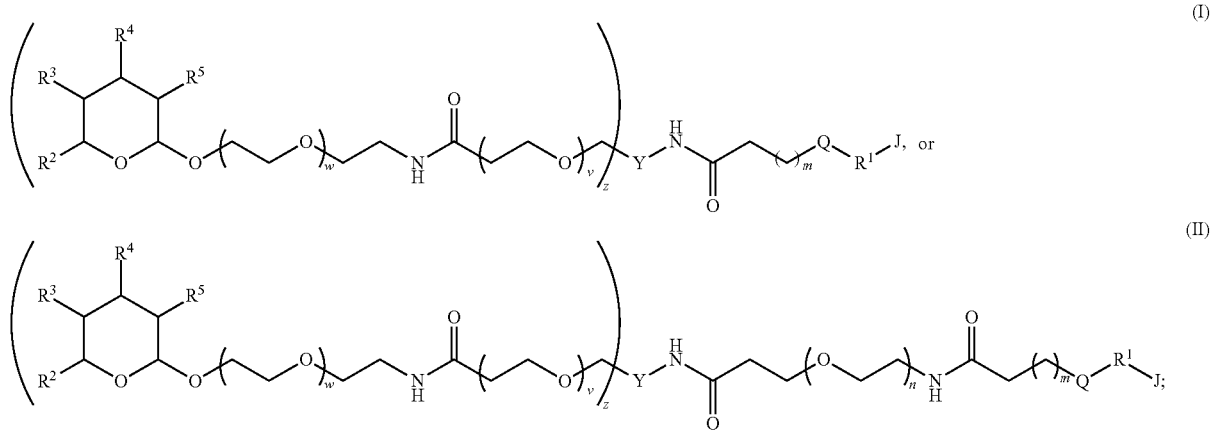

or a salt thereof, wherein

J is an oligonucleotide;

each w is independently selected from any value from 1 to 20;

each v is independently selected from any value from 1 to 20;

n is selected from any value from 1 to 20;

m is selected from any value from 1 to 20;

z is selected from any value from 1 to 3, wherein
  if z is 3, Y is C
  if z is 2, Y is $CR^6$, or
  if z is 1, Y is $C(R^6)_2$;

Q is selected from:
  $C_{3-10}$ carbocycle optionally substituted with one or more substituents independently selected from halogen, —CN, —$NO_2$, —$OR^7$, —$SR^7$, —$N(R^7)_2$, —$C(O)R^7$, —$C(O)N(R^7)_2$, —$N(R^7)C(O)R^7$, —$N(R)C(O)N(R^7)_2$, —$OC(O)N(R^7)_2$, —$N(R^7)C(O)OR^7$, —$C(O)OR^7$, —$OC(O)R^7$, —$S(O)R^7$, and $C_{1-6}$ alkyl, wherein the $C_{1-6}$ alkyl, is optionally substituted with one or more substituents independently selected from halogen, —CN, —OH, —SH, —$NO_2$, and —$NH_2$;

$R^1$ is a linker selected from:
  —O—, —S—, —C(O)—, —$C(O)N(R^7)$—, —$N(R^7)C(O)$—, —$N(R^7)C(O)N(R^7)$—, —$OC(O)N(R^7)$—, —$N(R^7)C(O)O$—, —C(O)O—, —OC(O)—, —S(O)—, —$S(O)_2$—, —$OS(O)_2$—, —$OP(O)(OR^7)O$—, —$SP(O)(OR^7)O$—, —$OP(S)(OR^7)O$—, —$OP(O)(SR^7)O$—, —$OP(O)(OR^7)S$—, —$OP(O)(O)O$—, —$SP(O)(O)O$—, —$OP(S)(O)O$—, $OP(O)(S)O$—, —$OP(O)(O)S$—, —$OP(O)(O)S$—, —$OP(O)(OR^7)NR^7$—, —$OP(O)(N(R^7)_2)NR^7$—, —$OP(OR^7)O$—, —$OP(N(R^7)_2)O$—, —$OP(OR^7)N(R^7)$—, and —$OPN(R^7)_2NR^7$—;

each $R^2$ is independently selected from:
  $C_{1-6}$ alkyl optionally substituted with one or more substituents independently selected from halogen, —$OR^7$, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, and —$S(O)R^7$;

$R^3$ and $R^4$ are each independently selected from:
  —$SR^7$, —$N(R^7)_2$, —$C(O)R^7$, —$C(O)N(R^7)_2$, —$N(R^7)C(O)R^7$, —$N(R^7)C(O)$—$N(R^7)_2$, —$OC(O)N(R^7)_2$, —$N(R^7)C(O)OR^7$, —$C(O)OR^7$, —$OC(O)R^7$, and —$S(O)R^7$, each $R^5$ is independently selected from:
  —$OC(O)R^7$, —$OC(O)N(R^7)_2$, —$N(R^7)C(O)R^7$, —$N(R^7)C(O)N(R^7)_2$, —$N(R^7)C(O)OR^7$, —$C(O)R^7$, —$C(O)OR^7$, and —$C(O)N(R^7)_2$;

each $R^6$ is independently selected from:
  hydrogen;
  halogen, —CN, —$NO_2$, —$SR^7$, —$N(R^1)_2$, —$C(O)R^7$, —$C(O)N(R^1)_2$, —$N(R^7)C(O)R^7$, —$N(R^7)C(O)N(R^7)_2$, —$OC(O)N(R^7)_2$, —$N(R^7)O(O)OR^7$, —$C(O)OR^7$, —$OC(O)R^7$, and —$S(O)R^7$; and
  $C_{1-6}$ alkyl optionally substituted with one or more substituents independently selected from halogen, —CN, —$NO_2$, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, and —$S(O)R^7$;

each $R^7$ is independently selected from:
  hydrogen;
  $C_{1-6}$ alkyl, $C_{2-6}$ alkenyl, and $C_{2-6}$ alkynyl, each of which is optionally substituted with one or more substituents independently selected from halogen, —CN, —OH, —SH, —$NO_2$, —$NH_2$, =O, =S, alkyl, —S—$C_{1-6}$ alkyl, —$N(C_{1-6}$ alkyl$)_2$, —$NH(C_{1-6}$ alkyl), $C_{2-10}$ carbocycle, and 3- to 10-membered heterocycle; and $C_{3-10}$ carbocycle, and 3- to 10-membered heterocycle, each of which is optionally substituted with one or more substituents independently selected from halogen, —CN, —OH, —SH, —$NO_2$, —$NH_2$, =O, =S, —O—$C_{1-6}$ alkyl, —S—$C_{1-6}$ alkyl, —$N(C_{1-6}$ alkyl$)_2$, —$NH(C_{1-4}$ alkyl), $C_{1-6}$ alkyl, $C_{2-6}$ alkenyl, $C_{2-6}$ alkynyl, $C_{3-10}$ carbocycle, 3- to 10-membered heterocycle, and $C_{1-6}$ haloalkyl.

In some embodiments, each w is independently selected from any value from 1 to 20. In some embodiments, each w is independently selected from any value from 1 to 15. In some embodiments, each w is independently selected from any value from 1 to 10. In some embodiments, each w is independently selected from any value from 1 to 5. In some embodiments, each w is independently selected from any value from 1 to 4. In some embodiments, each w is independently selected from any value from 1 to 3. In some embodiments, each w is independently selected from any value from 1 to 2. In some embodiments, each w is independently 1. In some embodiments, w is 1, 2, 3, 4, 5, 6, 7, 8, 9, 10, 11, 12, 13, 14, 15, 16, 17, 18, 19, or 20.

In some embodiments, each v is independently selected from any value from 1 to 20. In some embodiments, each v is independently selected from any value from 1 to 15. In some embodiments, each v is independently selected from any value from 1 to 10. In some embodiments, each v is independently selected from any value from 1 to 5. In some embodiments, each v is independently selected from any value from 1 to 4. In some embodiments, each v is independently selected from any value from 1 to 3. In some embodiments, each v is independently selected from any value from 1 to 2. In some embodiments, each v is independently 1. In some embodiments, v is 1, 2, 3, 4, 5, 6, 7, 8, 9, 10, II, 12, 13, 14, 15, 16, 17, 18, 19, or 20.

In some embodiments, n is selected from any value from 1 to 20. In some embodiments, n is selected from any value from 1 to 15, In some embodiments, n is selected from any value from 1 to 10. In some embodiments, n is selected from any value from 1 to 9. In some embodiments, n is selected from any value from 1 to 8. In some embodiments, n is selected from any value from 1 to 7. In some embodiments, n is selected from any value from 1 to 6. In some embodiments, n is selected from any value from 1 to 5. In some embodiments; n is selected from any value from 1 to 4. In some embodiments, n is selected from any value from 2 to 4. In some embodiments, n is selected from any value from 1 to 3. In some embodiments, n is 2 or 3. In some embodiments, n is 3. In some embodiments, n is selected from any value from 1 to 2. In some embodiments, n is 2. In some embodiments, n is 1. In some embodiments, n is 1, 2, 3, 4, 5, 6, 7, 8, 9, 10, 11 12, 13, 14, 15, 16, 17, 18, 19, or 20.

In some embodiments, m is selected from any value from 1 to 20. In some embodiments, m is selected from any value from 1 to 15. In some embodiments, m is selected from any value from 1 to 10. In some embodiments, m is selected from any value from 1 to 9. In some embodiments, in is selected from any value from 1 to 8. In Kale embodiments, in is selected from any value from 1 to 7. In some embodiments, in is selected from any value from 3 to 7. In some embodiments, m is selected from any value from 1 to 6. In some embodiments, m is selected from any value from 2 to 6. In some embodiments, m is selected from any value from 3 to 6. In some embodiments, in is selected from any value from 4 to 6. In some embodiments, in is 6. In some embodiments, m is selected from any value from 1 to 5. In some embodiments, m is selected from any value from 3 to 5. In some embodiments, m is 5. In some embodiments, m is 4 or 5. In some embodiments, m is selected from any value from 1 to 4. In some embodiments, m is 4. In some embodiments, m is 3 or 4. In some embodiments, m is selected from any value from 2 to 4. In some embodiments, m is selected from any value from 1 to 3. In some embodiments, in is 3. In some embodiments, m is selected from any value from 1 to 2, In some embodiments, m is 2. In some embodiments, m is 1. In some embodiments, m is 1, 2, 3, 4, 5, 6, 7, 8, 9, 10, 11, 12, 13, 14, 15, 16, 17, 18, 19, or 20.

In some embodiments, z is selected from any value from 1 to 3. In some embodiments, z is 3 and Y is C. In some embodiments, z is 2 and Y is $CR^6$. In some embodiments, z is 1 and Y is $C(R^6)_2$.

In some embodiments, Q is selected from $C_{3-10}$ carbocycle optionally substituted with one or more substituents independently selected from halogen, —CN, —NO$_2$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, and $C_{1-6}$ alkyl, wherein the $C_{1-6}$ alkyl, is optionally substituted with one or more substituents independently selected from halogen, —CN, —OH, —SH, —NO$_2$, and —NH$_2$. In some embodiments, Q is selected from $C_{3-4}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$), —N(R$^7$)C(O)R$^7$, —N(R$^7$)C(O)N(R$^7$)$_2$, —OC(O)N(R$^7$)$_2$, —NR$^7$C(O)OR$^7$, —C(O)OR$^7$, —OC(O)R$^7$, —S(O)R$^7$, and $C_{1-6}$ alkyl, wherein the $C_{1-6}$ alkyl, is optionally substituted with one or more substituents independently selected from halogen, —CN, —OH, —SH, —NO$_2$, and —NH$_2$. In some embodiments, Q is selected from $C_{5-6}$ carbocycle optionally substituted with one or more substituents independently selected from halogen, —CN, —NO$_2$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, Q is selected from $C_{5-6}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R and —S(O)R$^7$. In some embodiments, Q is selected from $C_5$ carbocycle optionally substituted with one or more substituents independently selected from halogen. —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$ and —S(O)R$^7$. In some embodiments, Q is selected from $C_{5-6}$ carbocycle optionally substituted with one or more substituents independently selected from halogen, —CN, —OH, —SH, —NO$_2$, and —NH$_2$ in some embodiments, Q is selected from phenyl, cyclohexyl, cyclopentadiene, and cyclopentyl, each of which is optionally substituted with one or more substituents independently selected from halogen, —CN, —OH, —NO$_2$, and —NH$_2$. In some embodiments, Q is selected from phenyl and cyclohexyl, each of which is optionally substituted with one or more substituents independently selected from halogen, —CN, —OH, —SH, —NO$_2$, and —NH$_2$. In some embodiments, Q is selected from phenyl and cyclohexyl. In some embodiments, Q is phenyl. In some embodiments, Q is cyclohexyl.

In some embodiments, $R^1$ is a linker selected from —O—, —S—, —N(R$^7$)—, —C(O)—, —C(O)N(R$^7$)—, —N(R$^7$)C(O)—, —N(R$^7$)C(O)N(R$^7$)—, —OC(O)N(R$^7$)—, —N(R$^7$)C(O)O—, —C(O)O—, —OC(O)—, —S(O)—, —S(O)$_2$—, —OS(O)$_2$—, —OP(O)(OR$^7$)O—, —SP(O)(OR$^7$)O—, —OP(S)(OR$^7$)O—, —OP(O)(SR$^7$)O—, —OP(O)(OR$^7$)S—, —OP(O)(OR$^7$)S—, —OP(O)(OR$^7$)NR$^7$—, —OP(O)(N(R$^7$)$_2$)NR$^7$—, —OP(OR$^7$)O—, —OP(N(R$^7$)$_2$)O—, —OP(OR$^7$)(R$^7$)—, and —OPN(R$^7$)$_2$NR$^7$—. In some embodiments, $R^1$ is a linker selected from —O—, —S—, —N(R$^7$)—, —C(O)—, —C(O)N(R$^7$)—, —N(R$^7$)C(O)—, —N(R$^7$)C(O)N(R$^7$)—, —OC(O)N(R$^7$)—, —N(R$^7$)C(O)O—, —C(O)O—, —OC(O)—, —S(O)—, —S(O)$_2$—, —OS(O)$_2$—, OP(O)(OR—SP(O)(OR$^7$)O—, —SP(O)(OR$^7$))—, —OP(S)(OR$^7$)O—, —OP(O)(SR$^7$)O—, —OP(O)(OR$^7$)S—, —OP(O)(O—)O—, —SP(O)(O—) O—, —OP(S)(O—)O—, —OP(O)(S—)O—, —OP(O)(O—)S—, —OP(O)(OR$^7$)NR$^7$—, —OP(O)(N(R$^7$)$_2$)NR$^7$—, —OP(OR$^7$)O—, OP(N(R$^7$)$_2$)O—, —OP(OR$^7$)N(R$^7$)—, and —OPN(R$^7$)$_2$NR$^7$—. In some embodiments, $R^1$ is selected from —OP(O)(OR$^7$)O—, —SP(O)(OR$^7$)O—, —OP(S)(OR$^7$)O—, —OP(O)(SR$^7$)O—, —OP(O)(OR$^7$)S—, —OP(O)(O—)O—, —SP(O)(O—)O—, —OP(S)(O—)O—, —OP(O)(S—)O—, —OP(O)(O—)S—, —OP(O)(OR$^7$)NR$^7$—, —OP(O)(N(R$^7$)$_2$)NR$^7$—, —OP(OR)O—, —OP(N(R$^7$)$_2$)O—, —OP(OR$^7$)N(R$^7$)—, and —OPN(R$^7$)$_2$NR$^7$. In some embodiments, $R^1$ is selected from —OP(O)(OR$^7$)O—, —SP(O)(OR$^7$)O—, —OP(S)(OR$^7$)O—, —OP(O)(SR$^7$)O—, —OP(O)(OR$^7$)S—, —OP(O)(O)O—, —SP(O)(O—) O—, —OP(S)(O—)O—, —OP(O)(S—)O—, —OP(O)(O—)S—, and —OP(OR$^7$)O—. In some embodiments, $R^1$ is selected from —OP(O)(OR$^1$)O—, —OP(S)(OR$^7$)O—, —OP(O)(O)O—, —OP(S)(O—)O—, —OP(O)(S—)O—, and —OP(OR$^7$)O—. In some embodiments, $R^1$ is selected from —OP(O)(OR$^7$)O— and —OP(OR$^7$)O—. In some embodiments, $R^1$ is a linker selected from —OP(O)(OH)O—, —SP(O)(OH)O—, —OP(S)(OH)O—, —OP(O)(SH)O—, —OP(O)(OH)S—, —OP(O)(O—)O—SP(O)(O—)O—, —OP(S)(O—)O—, —OP(O)(S—)O—, and —OP(O)(O—)S—. In some embodiments, $R^1$ is a selected from —OP(O)(OR$^7$)O—, —OP(O)(OR$^7$)NR$^7$—, —OP(O)(N(R$^7$)$_2$)NR$^7$—, —OP(OR)O—, —OP(N(R$^7$)$_2$)O—, —OP(OR$^7$)N(R$^7$)—, and —OPN(R$^7$)$_2$NR$^7$—. In some embodiments, $R^1$ is selected from —S—, —S(O)—, —S(O)$_2$—, —OS(O)$_2$, —SP(O)(OR$^7$)O—, —OP(S)(OR$^7$)O—, —OP(O)(SR$^7$)O—, —OP(O)(OR$^7$)S—, —SP(O)(O—)O—, —OP(S)(O—)O—, —OP(O)(S—)O—, and —OP(O)(O—)S—. In some embodiments, R' is selected from —S—, —S(O)—, —S(O)$_2$—, —OS(O)$_2$, —SP(O)(OR$^7$)O—, OP(S)(OR$^1$)O—, —OP(O)(SR$^7$)O—, and —OP(O)(OR$^7$)S—, In some embodiments, $R^1$ is selected from —OP(S)(OR$^7$)O—, —OP(O)(SR$^7$)O—, and —OP(O)(OR$^7$)S—. In some embodiments, $R^1$ is selected from —OP(S)(OR$^7$)O—, —OP(O)(SR$^7$)O—, —OP(S)(O)O—, and —OP(O)(S—)O—. In some embodiments, $R^1$ is selected from —OP(S)(OR$^7$)O— and —OP(O)(SR$^7$)O—. In some embodiments, $R^1$ is selected from —OP(O)(OR$^7$)O—, —OP(OR$^7$)N(R$^7$)—, and —OPN(R$^7$)$_2$O—. In some embodiments, $R^1$ is —OP(O)(OH)O—, —OP(O)(OCH$_2$CH$_3$)O—, OP(OCH$_2$CH$_2$CN)N(CH(CH$_3$)$_2$)—, or —OPN(CH(CH$_3$)$_2$)$_2$O—. In some embodiments, $R^1$ is selected from —OP(O)(OH)O— and OP(O)(O—)O—. In some embodiments, $R^1$ comprises —O— or —S—. In some embodiments, $R^1$ comprises —O—. In some embodiments, $R^1$ comprises —S—. In some embodiments, $R^1$ is a linker selected from —O— or —S—. In some embodiments, $R^1$ is —O—. In some embodiments, $R^1$ is —S—.

In some embodiments, each $R^2$ is independently selected from $C_{1-6}$ alkyl optionally substituted with one or more substituents independently selected from halogen, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^2$, —OC(O)R$^7$, and —S(O)R$^7$. In some embodiments, each $R^2$ is independently selected from $C_{1-3}$ alkyl substituted with one or more substituents independently selected from halogen, —OR$^7$, —OC(O)R$^7$, —SR$^7$, —N(R$^7$)$_2$, —C(O)R$^7$, and —S(O)R$^2$. In some embodiments, each R$^2$ is independently selected from C$_{1-3}$ alkyl substituted with one or more substituents independently selected from —OR$^7$, —OC(O)R$^7$, —SR$^7$, and —N(R$^7$)$_2$. In some embodiments, each R$^2$ is independently selected from C$_1$ alkyl substituted with one or more substituents independently selected from —OR$^7$ and —OC(O)R$^7$. In some embodiments, each R$^2$ is independently selected from —CH$_2$OH and —CH$_2$OC(O)CH$_3$.

In some embodiments, each R$^3$ is independently selected from —OR$^7$, —S—N(R$^7$)$_2$, —C(O)R$^7$, —C(O)N(R$^2$)$_2$, —N(R$^7$)C(O)R$^2$, —N(R$^7$)C(O)N(R$^2$)$_2$, —OC(O)N(R$^2$)$_2$, —N(R$^7$)O(O)OR$^7$, —C(O)OR$^7$, —OC(O)R$^7$, and —S(O)R$^7$. In some embodiments, each R$^3$ is independently selected from halogen, —OR$^7$, —N(R$^7$)$_2$, —C(O)R$^7$, —OC(O)R$^7$, and —S(O)R$^2$. In some embodiments, each R$^3$ is independently selected from —OR$^7$, —OC(O)R$^7$, —SR$^7$, and —N(K)$_2$, in some embodiments, each R$^3$ is independently selected from —OR$^7$ and —OC(O)R$^7$. In some embodiments, R$^3$ is independently selected from —OH and —OC(O)CH$_3$.

In some embodiments, each R$^4$ is independently selected from —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, each R$^4$ is independently selected from halogen, —OR$^7$, —SR$^7$, —N(R$^7$)$_2$, —C(O)R$^7$, —OC(O)R$^7$, and —S(O)R$^7$. In some embodiments, each R$^4$ is independently selected from —OR$^7$, —OC(O)R$^7$, —SR$^7$, and —N(R$^7$)$_2$. In some embodiments, each R$^4$ is independently selected from —OR$^7$ and —OC(O)R$^7$. In some embodiments, R$^4$ is independently selected from —OH and —OC(O)CH$_3$.

In some embodiments, each R$^2$ is independently selected from —OC(O)R$^7$, —OC(O)N(R$^7$)$_2$, —N(R$^7$)C(O)R$^7$, —N(R$^7$)C(O)N(R$^7$)$_2$, —N(R$^7$)C(O)OR$^7$, —C(O)R$^7$, —C(O)OR$^7$, and —C(O)N(R$^7$)$_2$. In some embodiments, each R$^5$ is selected from —OC(O)R$^7$, —OC(O)N(R$^7$)$_2$, —N(R$^7$)C(O)R$^7$, —N(R$^7$)C(O)N(R$^1$)$_2$, and —N(R$^2$)C(O)OR$^7$. In some embodiments, each R$^5$ is independently selected from —OC(O)R$^7$ and —N(R$^7$)C(O)R$^7$. In some embodiments, each R$^5$ is independently selected from —N(H)C(O)CH$_3$.

In some embodiments, each R$^6$ is independently selected from hydrogen, halogen, —CN, —OR$^7$, —SR$^7$, —N(R)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$; and C$_{1-6}$ alkyl optionally substituted with one or more substituents independently selected from halogen, —CN, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^1$. In some embodiments, each R$^5$ is independently selected from hydrogen, halogen, —CN— OR$^7$, —SR$^7$, —N(R$^7$)$_2$, and C$_{1-6}$ alkyl optionally substituted with one or more substituents independently selected from halogen, —OR$^7$, —SR$^7$, and —N(R$^7$)$_2$. In some embodiments, each R$^7$ is independently selected from hydrogen, halogen, —CN, —OH, —SH, and —NH$_2$.

In some embodiments, each R$^7$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$, =O, =S, —O—C$_{7-6}$ alkyl, —S—C$_{1-6}$ alkyl, —N(C$_{1-6}$ alkyl)$_2$, —NH(C$_{1-6}$ alkyl), C$_{3-10}$ carbocycle, and 3- to 10-membered heterocycle; and C$_{3-10}$ carbocycle, and 3- to 10-membered heterocycle; each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$ haloalkyl. In some embodiments, each R$^7$ is independently selected from: hydrogen; and Go alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, 3- to 10-membered heterocycle. In some embodiments, each R$^7$ is independently selected from C$_{1-6}$ alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, —N(C$_{1-6}$ alkyl)$_2$, and —NH(C$_{1-6}$ alkyl). In some embodiments, R$^7$ is independently selected from C$_{1-6}$ alkyl optionally substituted with one or more substituents independently selected from halogen, —CN, —OH, and —SR. In some embodiments, each R$^7$ is independently selected from hydrogen. In some embodiments, each R$^7$ is independently selected from C$_{1-3}$ alkyl optionally substituted with one or more substituents independently selected from halogen, —CN, —OH, —SH, —NO$_2$, —NH$_2$, —O—C$_{1-6}$ alkyl, —S—C$_{1-6}$ alkyl, —N(C$_{1-6}$ alkyl)$_2$, and —NH(C$_{1-6}$ alkyl).

In some embodiments, w is 1; v is 1; n is 2; m is 1 or 2; z is 3 and Y is C; Q is phenyl or cyclohexyl, each of which is optionally substituted with one or more substituents independently selected from halogen, —CN, —OH, —SH, —NO$_2$, —NH$_2$, and C$_{1-3}$ alkyl; R$^1$ is selected from —OP(O)(OR$^7$)O—, —OP(S)(OR$^7$)O—, —OP(O)(O—) O—, —OP(S)(O—)O—, —OP(O)(S—)O—, and —OP(OR$^7$) O—; R$^2$ is C$_1$ alkyl substituted with —OH or —OC(O)C$_{1-13}$; R$^3$ is —OH or —O(O)CH$_3$; R$^4$ is —OH or —OC(O)CH$_3$; and R$^5$ is —NH(O)CH$_3$.

In some embodiments, w is 1; v is 1; n is 2; m is 1 or 2; z is 3 and Y is C; Q is phenyl or cyclohexyl, each of which is optionally substituted with one or more substituents independently selected from halogen, —CN, —OH, —SH, —NO$_2$, —NH$_2$, and C$_{1-3}$ alkyl; R$^1$ is selected from —OP(O)(OH)O—, —OP(S)(OH)O—, —OP(O)(O)O—, —OP(S)(O)O—, —OP(O)(S—)O—, and —OP(OH)O—; R$^2$ is C alkyl substituted with —OH or —OC(O)CH$_3$; R$^3$ is —OH or —OC(O)CH$_3$; R$^4$ is —OH or —OC(O)CH$_3$; and R$^5$ is —NH(O)CH$_3$. In some embodiments, w is 1; v is 1; a is 2; in is 1 or 2; z is 3 and Y is C; Q is phenyl or cyclohexyl; each of which is optionally substituted with one or more substituents independently selected from halogen, —CN, —OH, —SH, —NO$_2$, —NH$_2$, and C$_{1-3}$ alkyl, R$^1$ is selected from —OP(O)(OH)O—, —OP(S)(OH)O—, and —OP(OH)O—; R$^2$ is C$_1$ alkyl substituted with —OH or —OC(O)CH$_3$; R$^3$ is —OH or —OC(O)CH$_3$; R$^4$ is —OH or —OC(O)CH$_3$; and R$^5$ is —NH(O)CH$_3$.

In some, embodiments, a compound of Formula (I) is selected from:

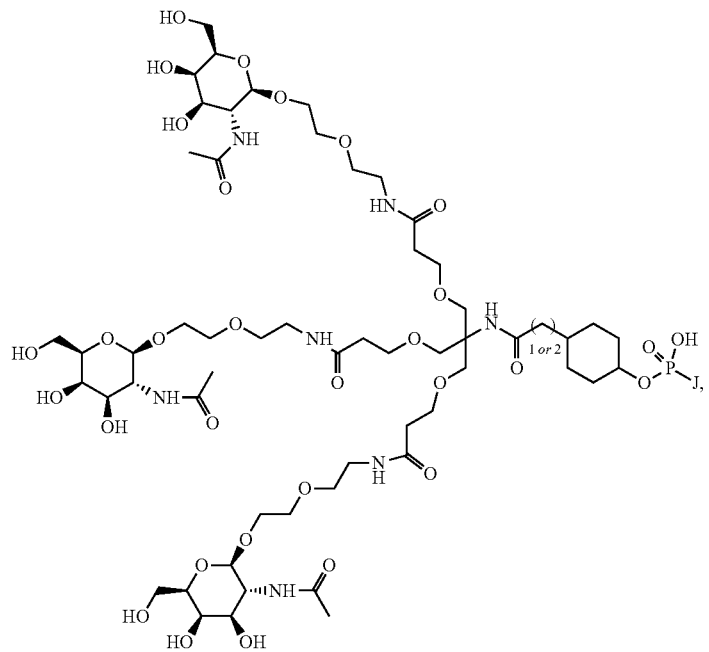
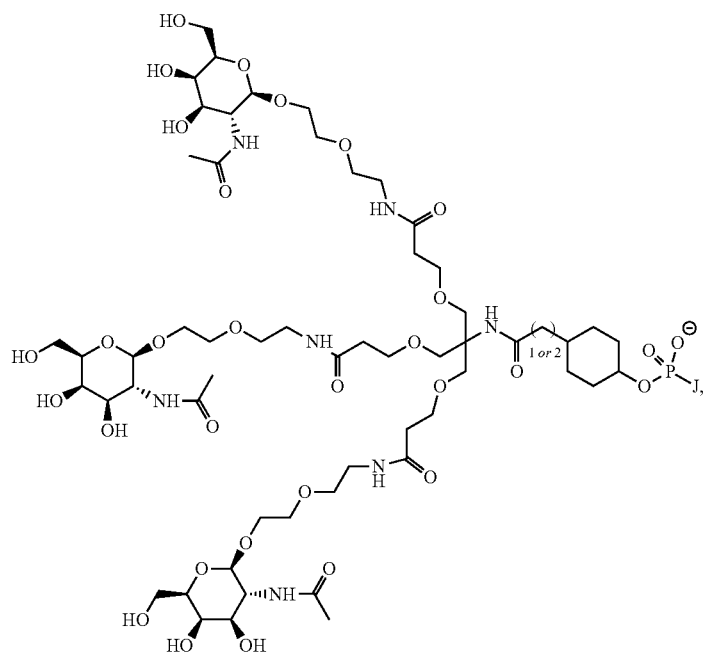

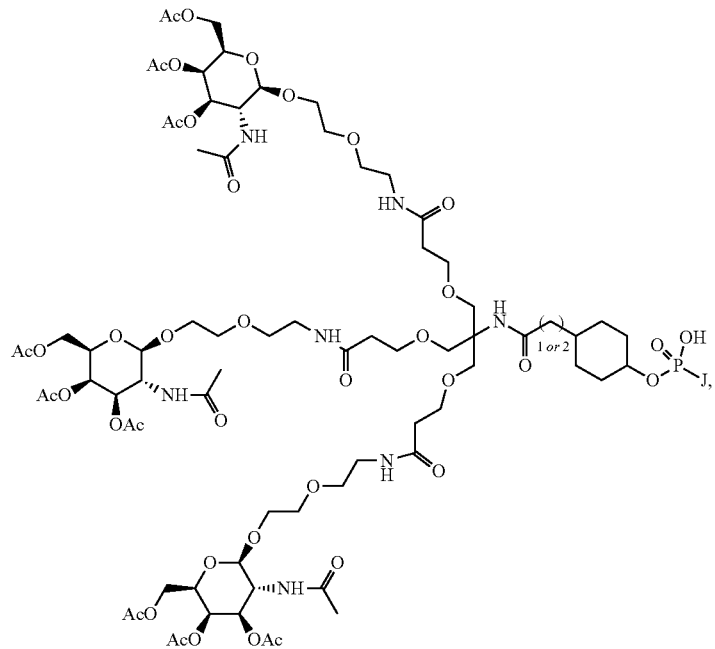
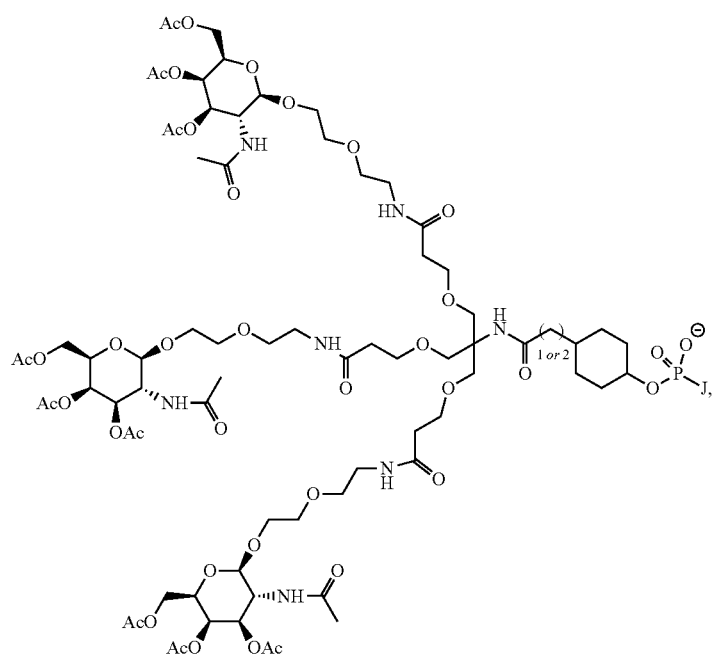

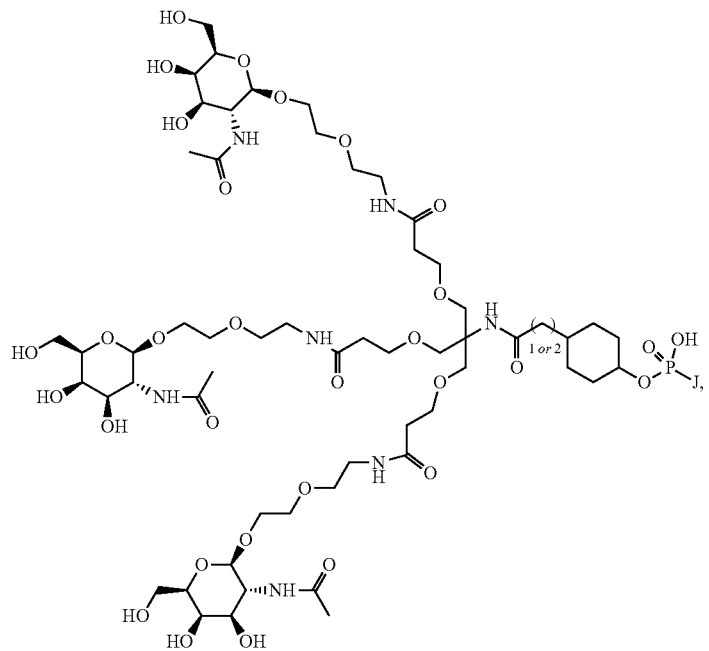
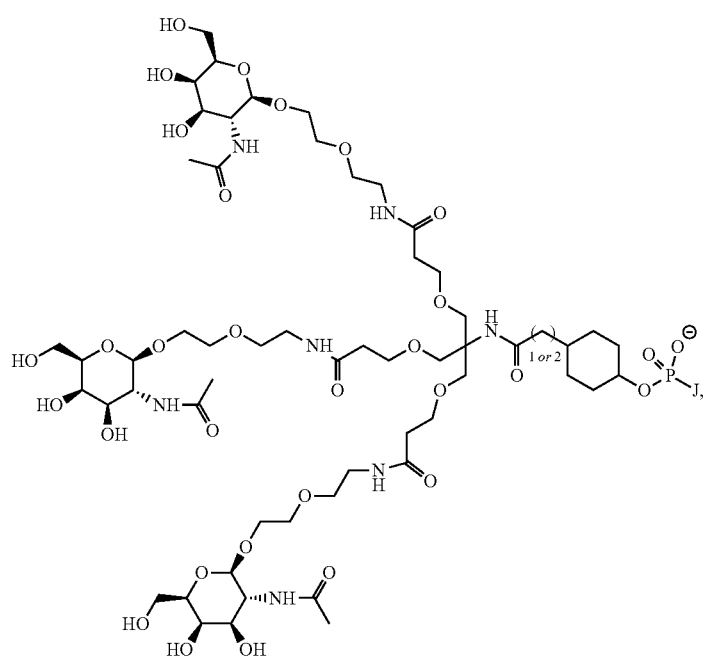

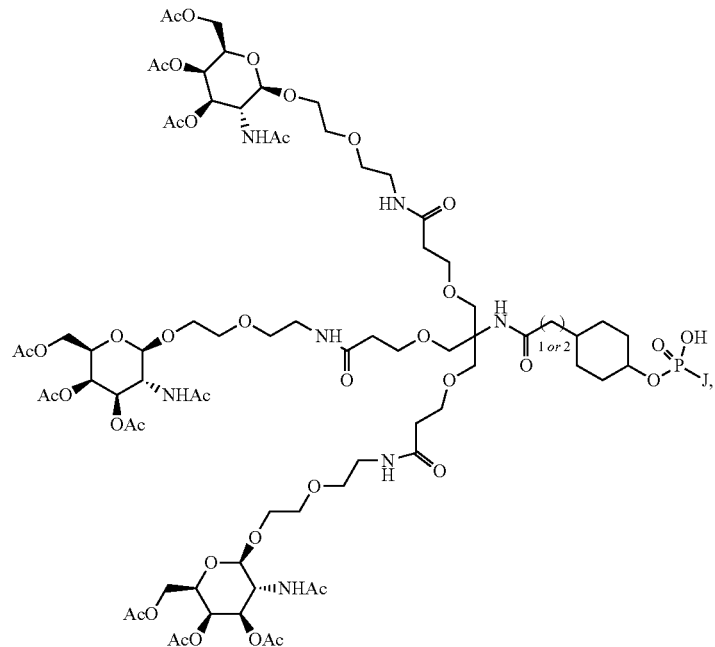
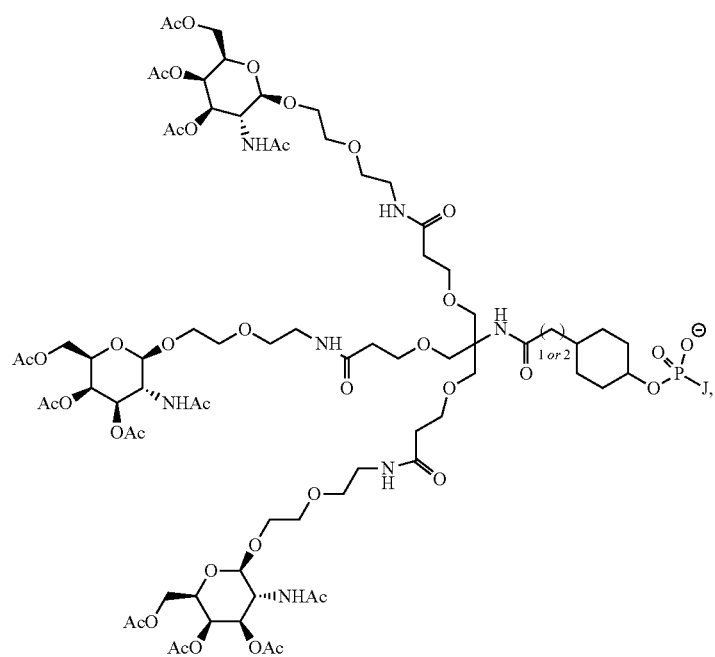

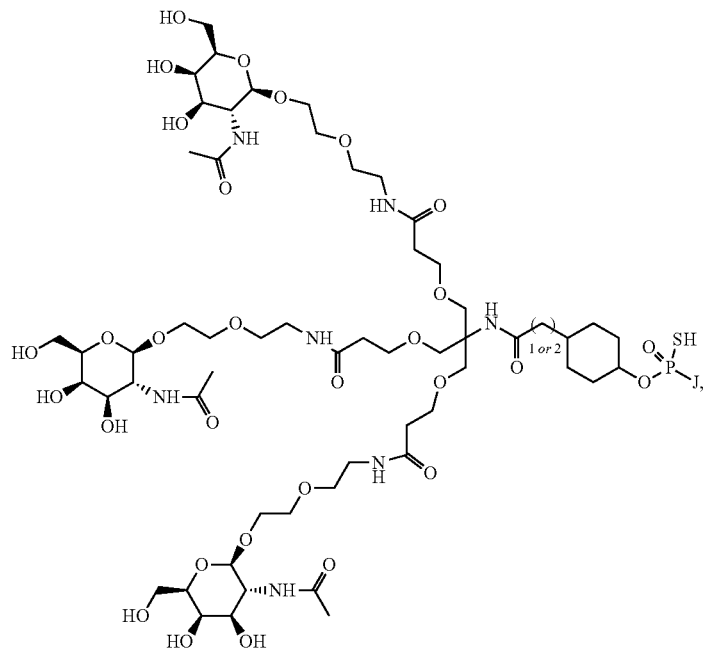
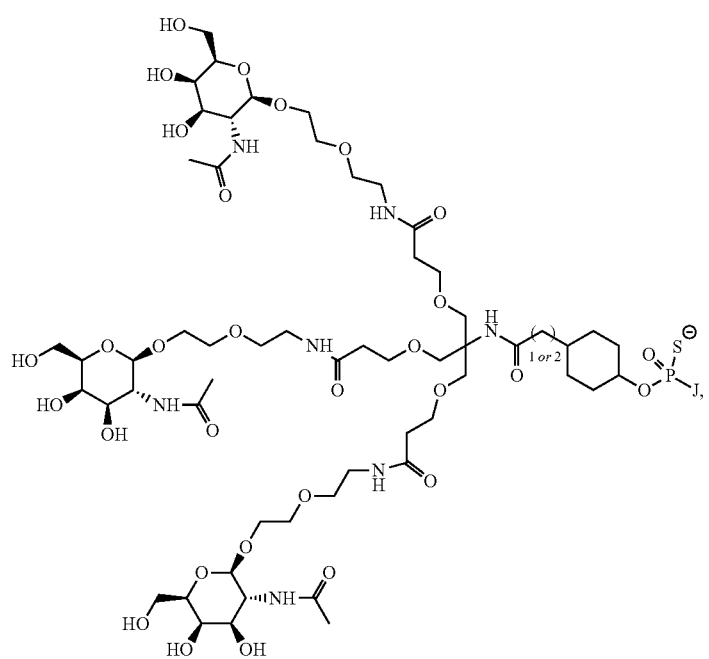

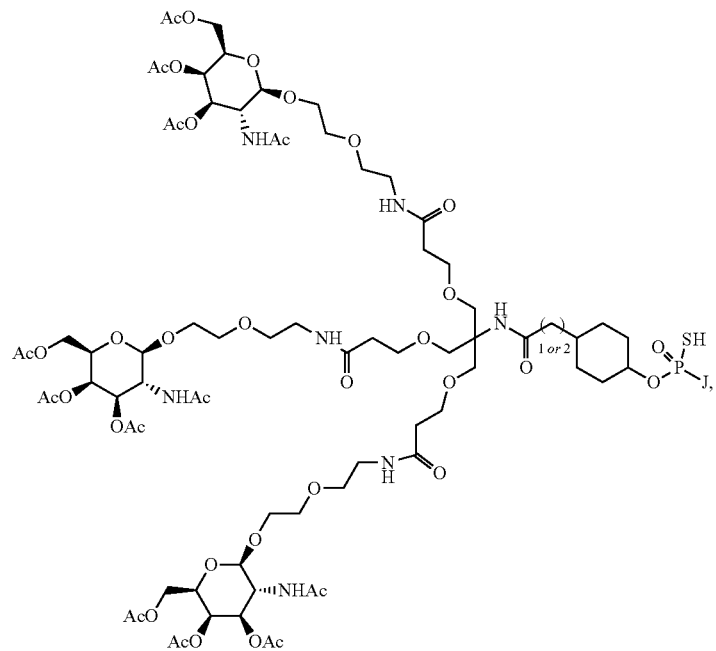
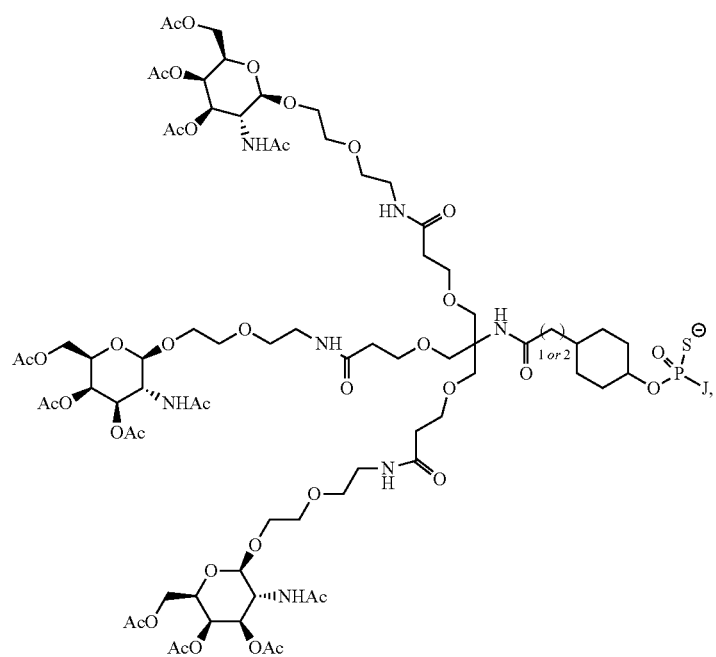

-continued
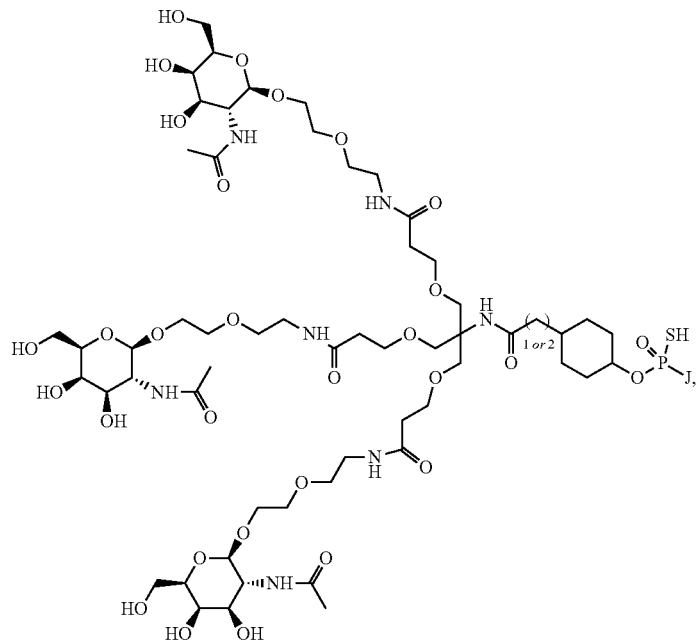
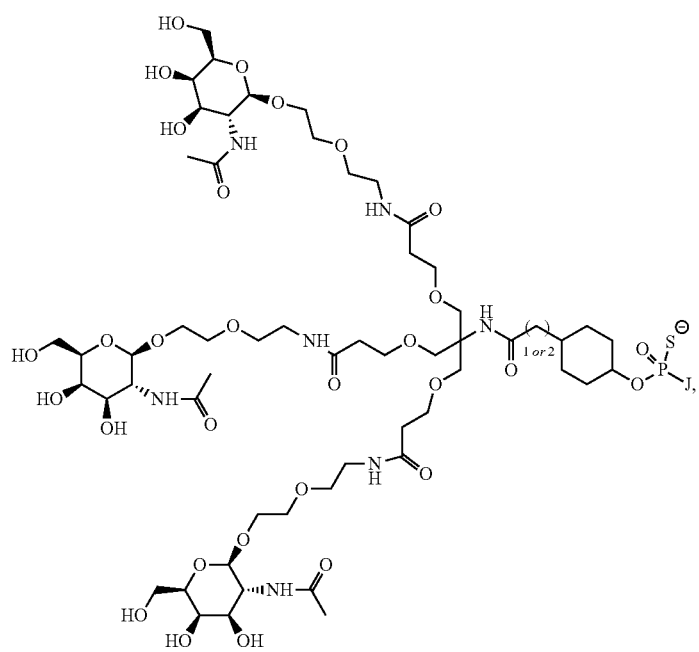

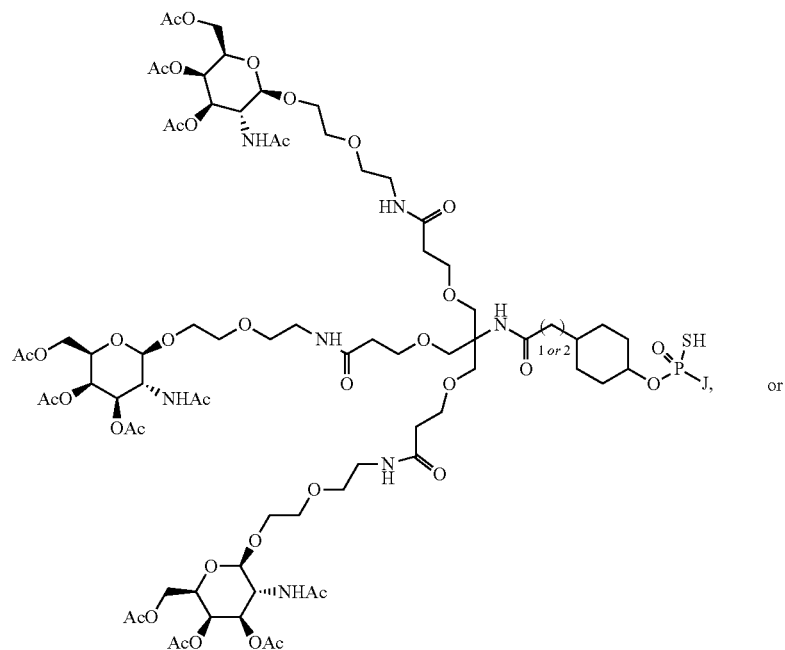
or
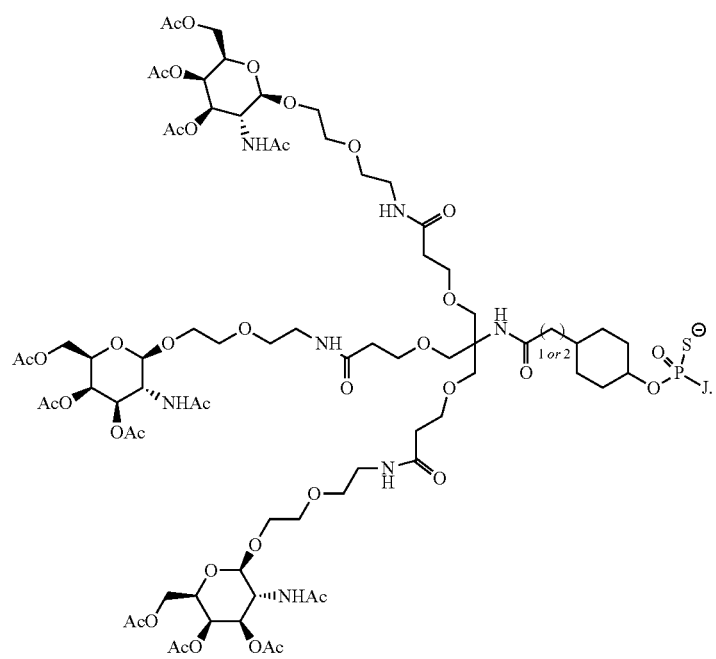

In some embodiments, a compound of Formula (II) is selected from:
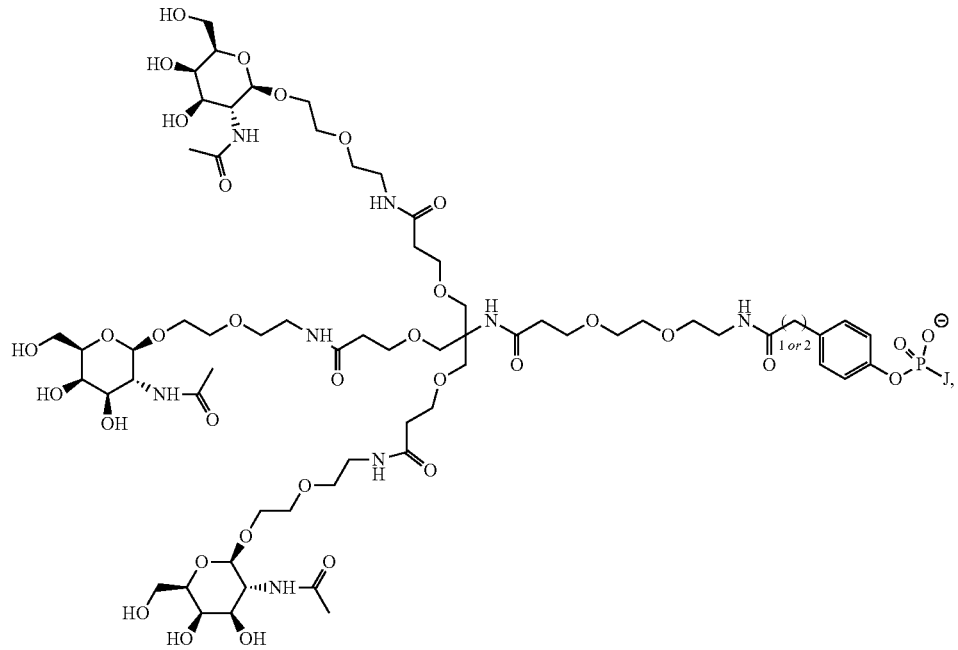
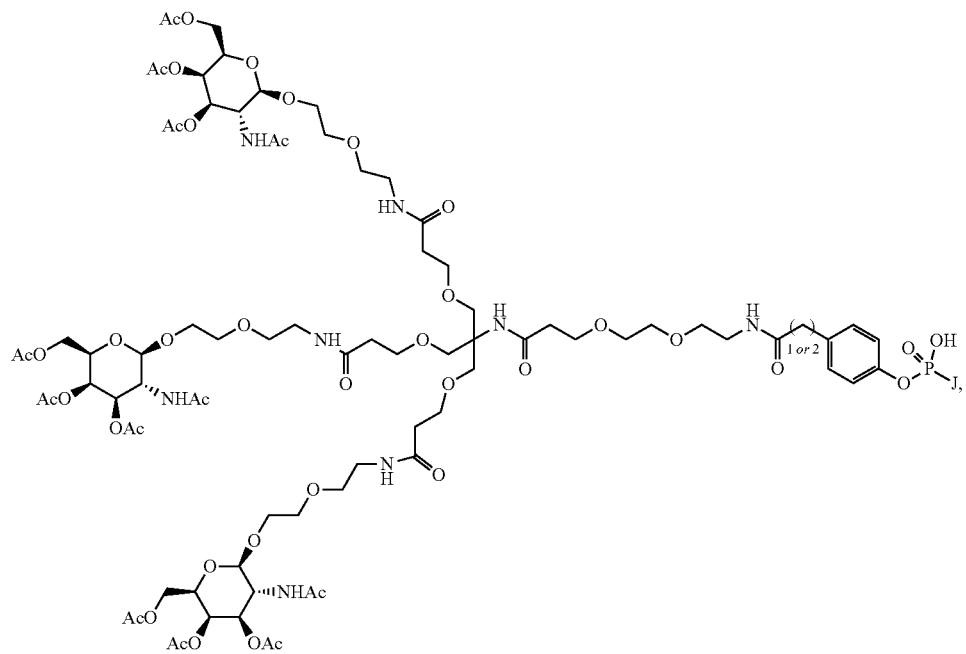

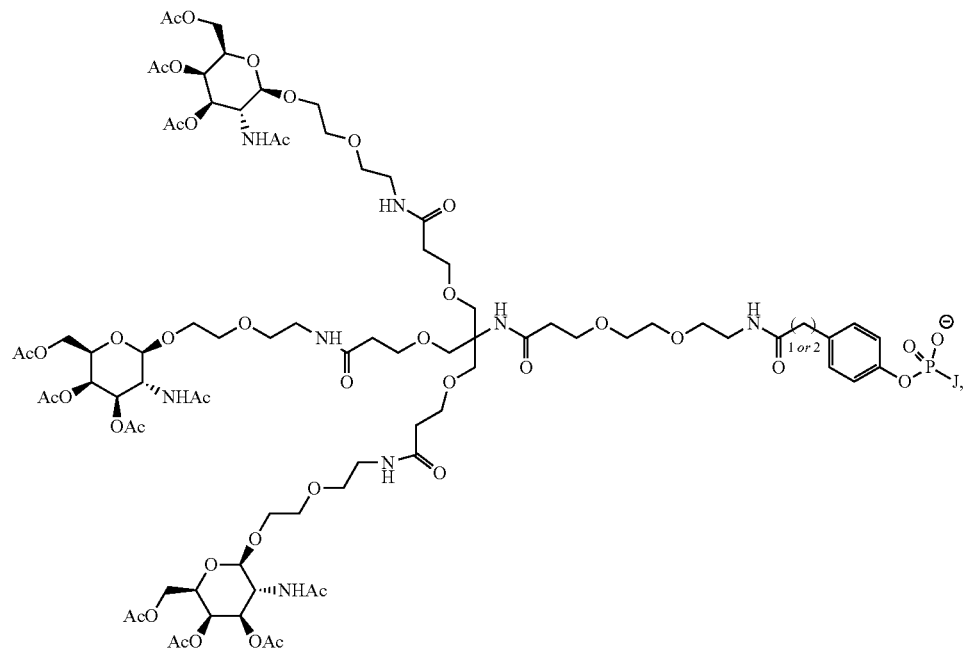
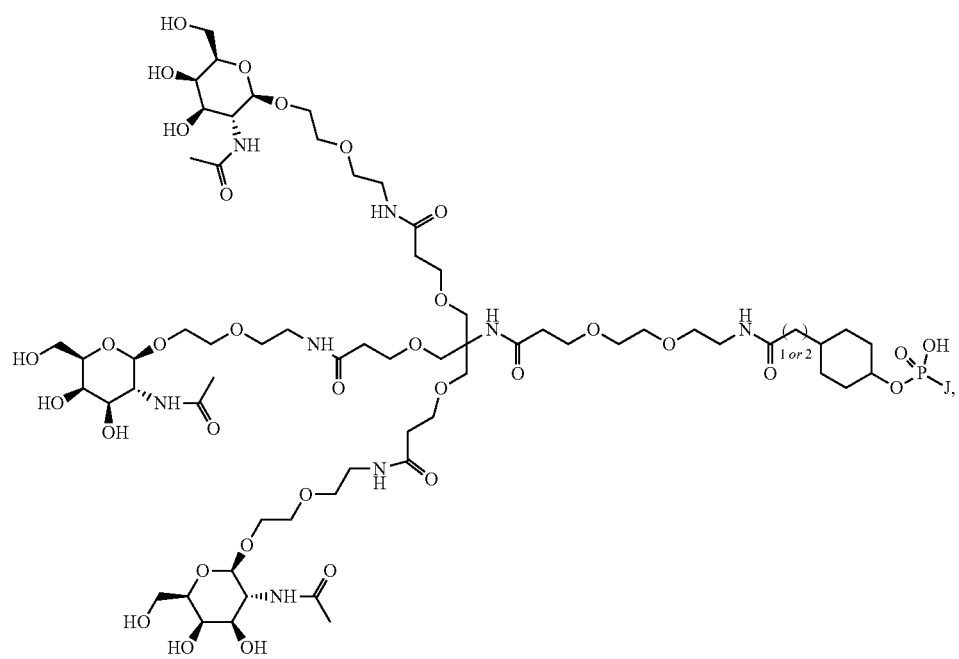

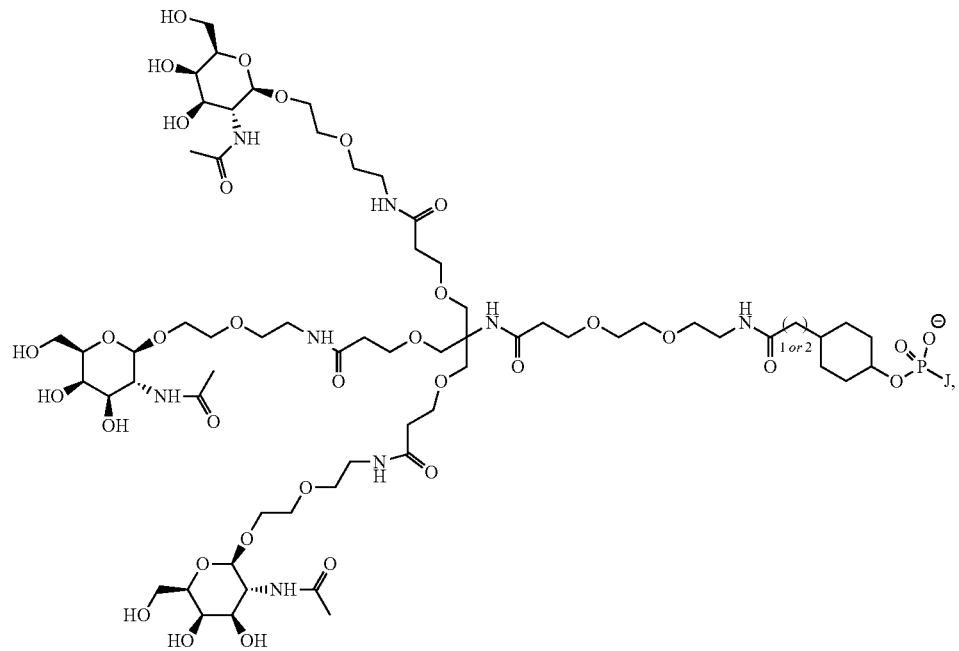
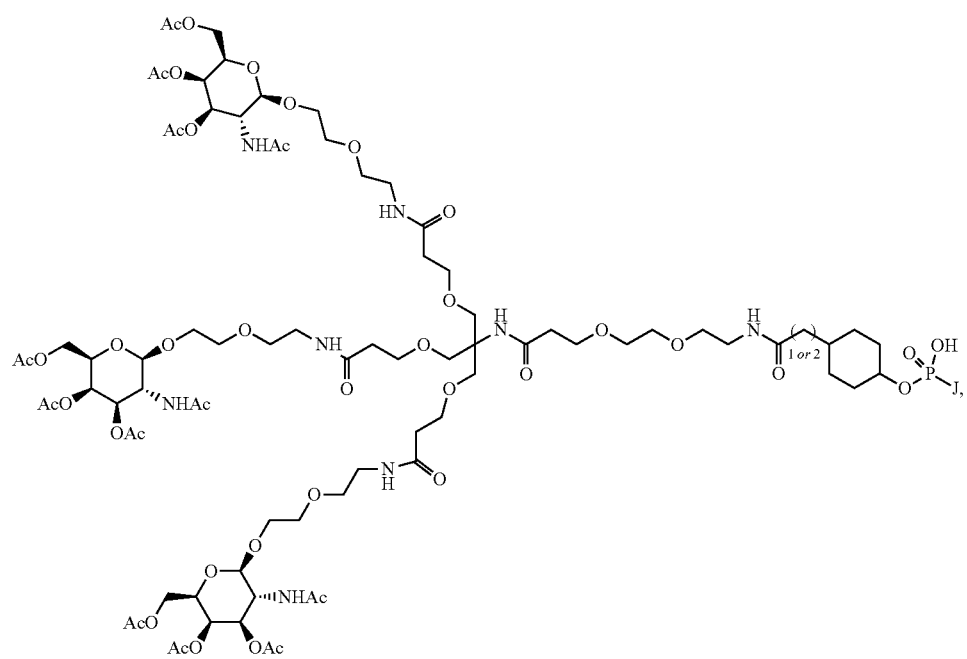

-continued
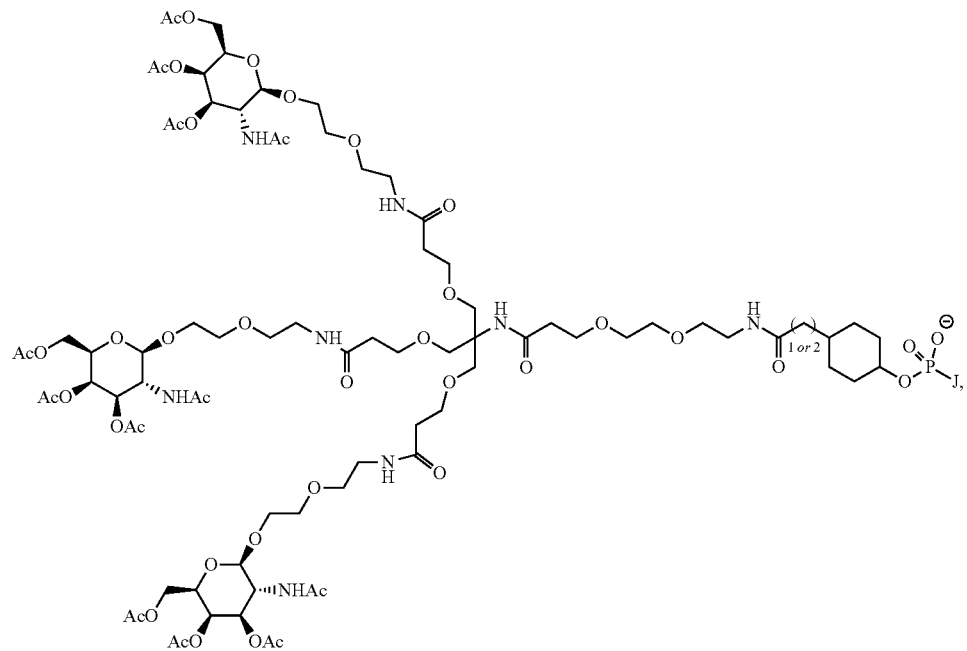
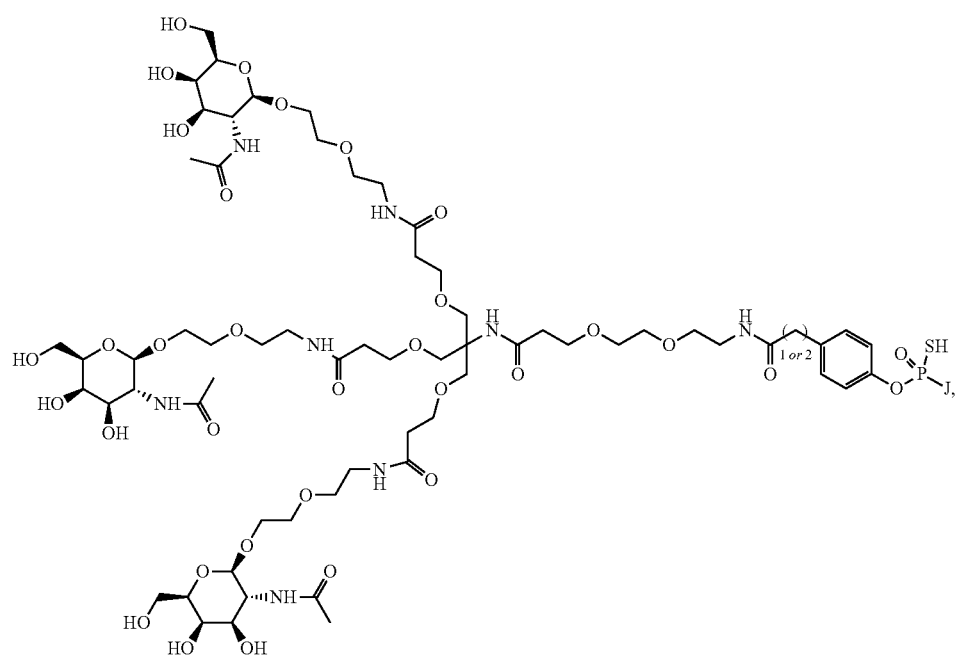

-continued
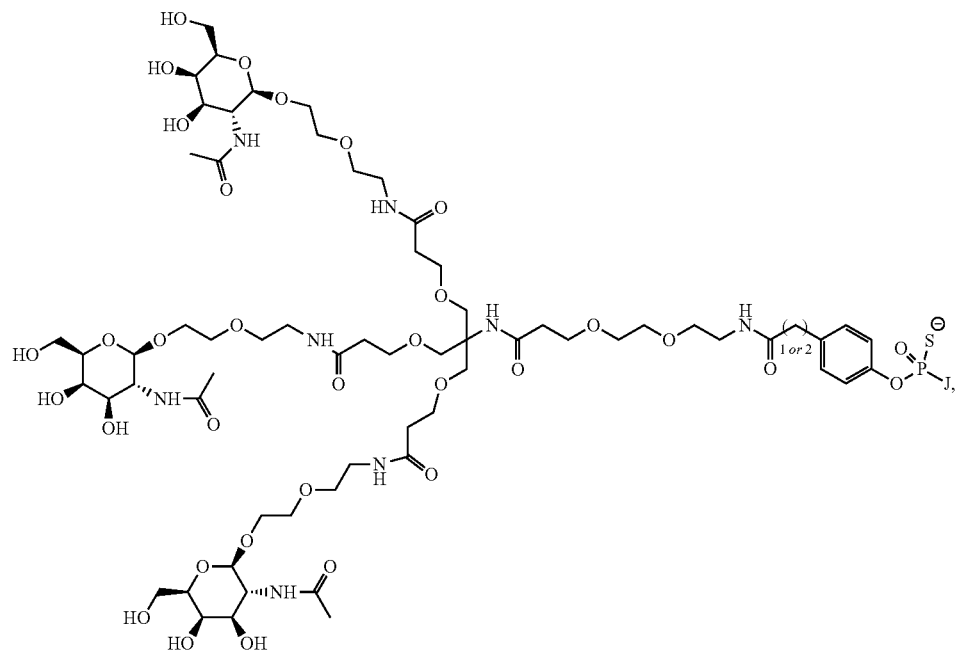
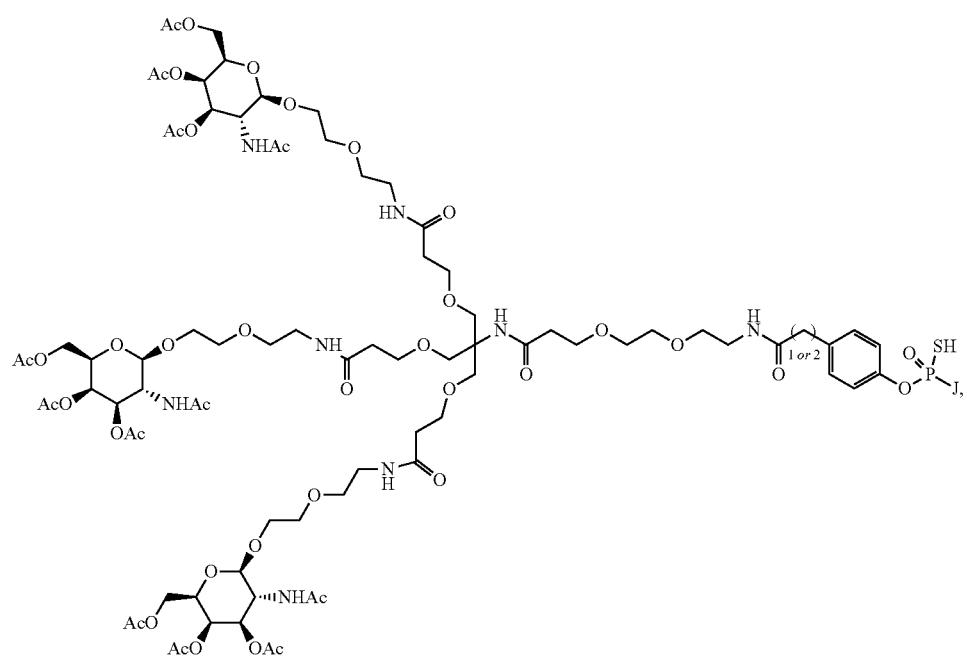

-continued
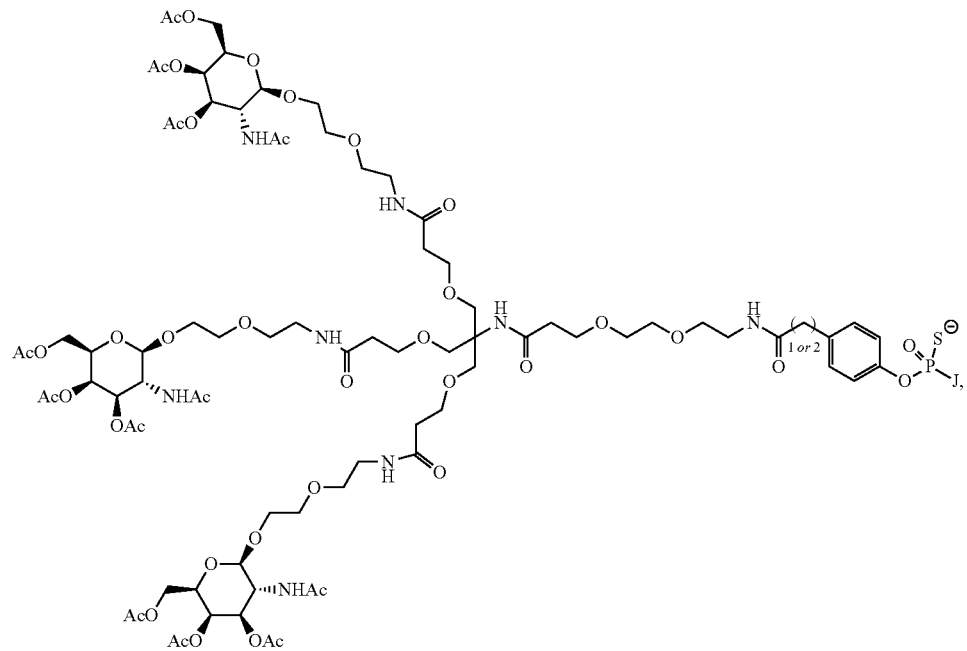
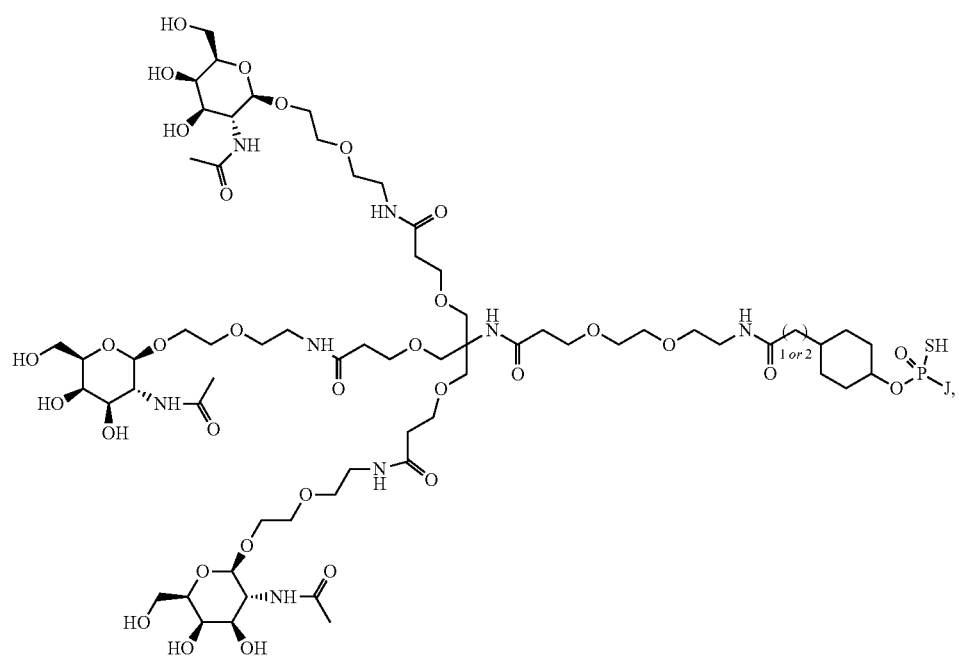

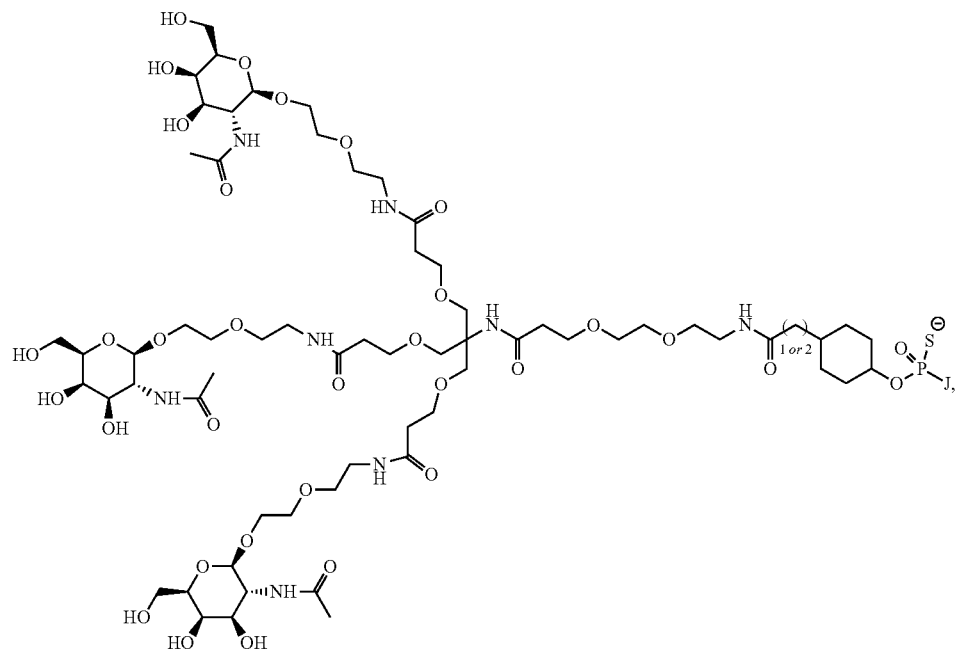
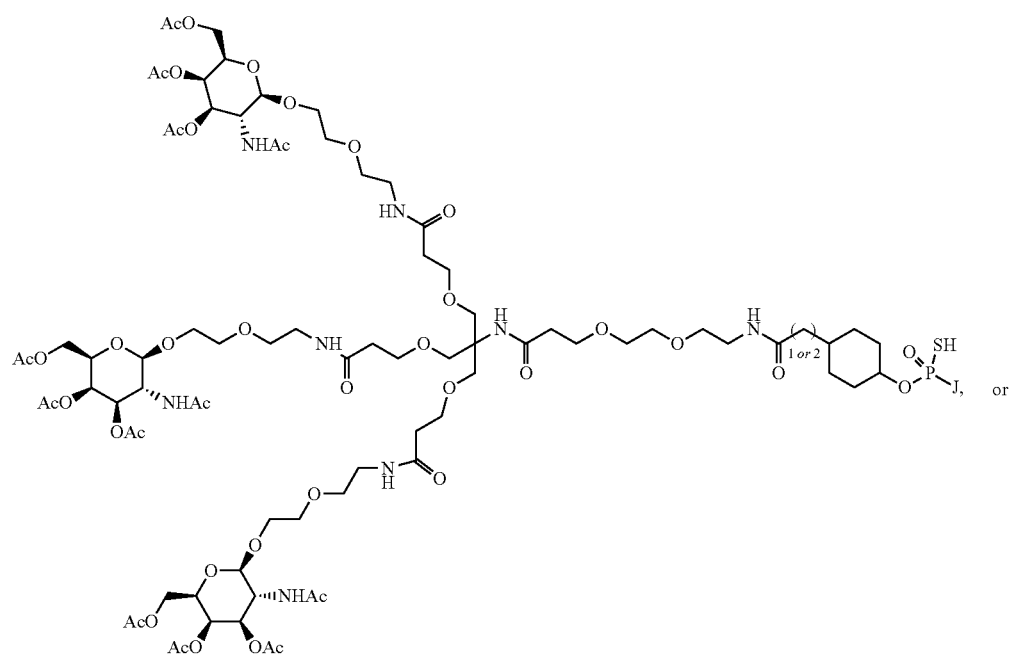 or

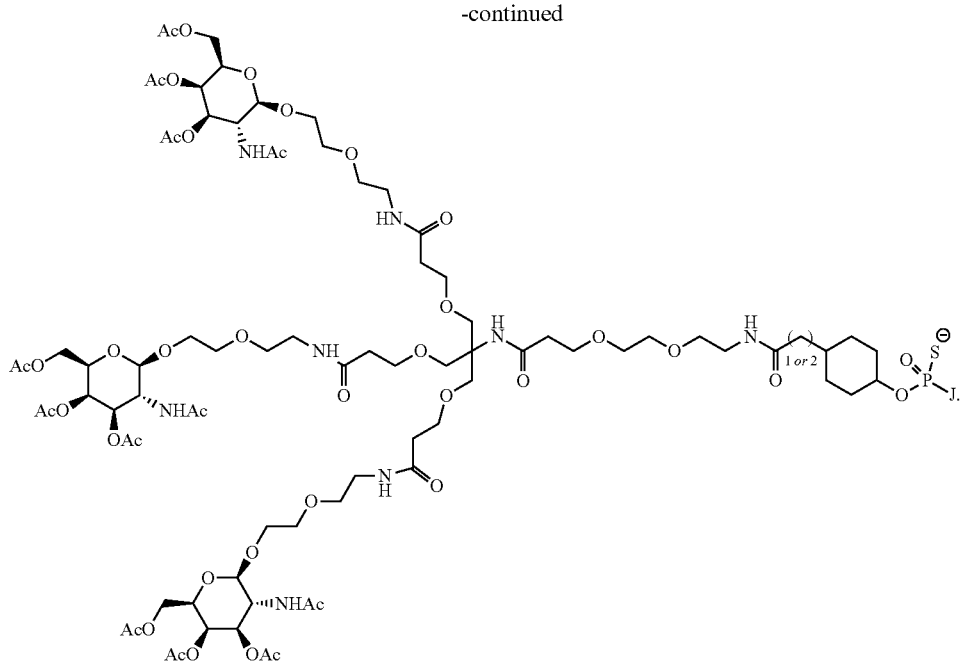

In some embodiments, the compound of Formula (I), (II), or (III) binds to a lectin. In some embodiments, the compound binds to an asialoglycoprotein receptor. In some embodiments, the compound binds to a liver cell receptor. In some embodiments, the compound binds to a hepatoc:site receptor. In some embodiments, the compound targets a liver cell.

Provided herein, in some embodiments, compositions described herein comprise a GalNAc compound. In some embodiments, a GalNAc compound describes a compound of Formula (A) or Formula (B):

if z is 3, Y is C
if z is 2, Y is $CR^6$, or
if z is 1, Y is $C(R^6)_2$;

Q is selected from:

$C_{3-10}$ carbocycle optionally substituted with one or more substituents independently selected from halogen, —CN, —$NO_2$, —$OR^7$, —$SR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, —$S(O)R^7$, and $C_{1-6}$ alkyl, wherein the $C_{1-6}$ alkyl, is optionally

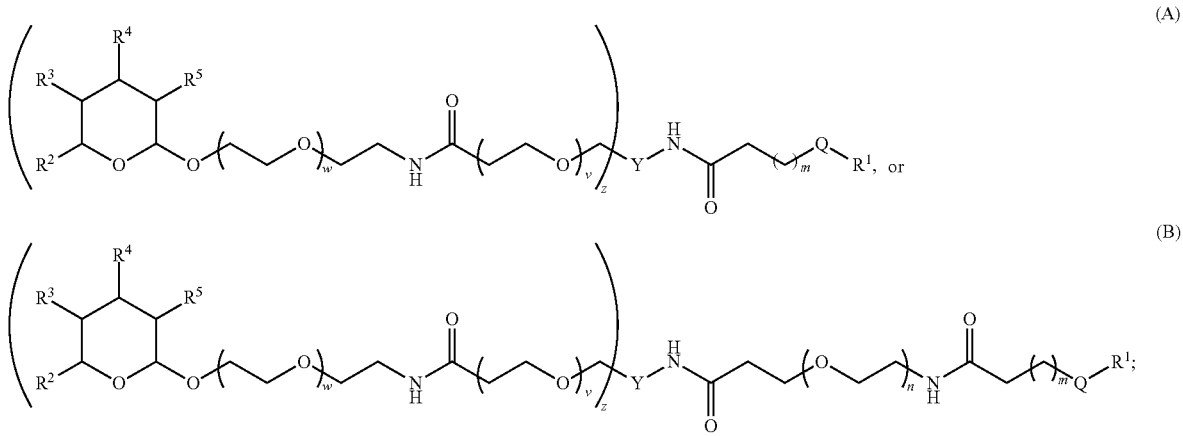

or a salt thereof, wherein
each w is independently selected from any value from 1 to 20;
each v is independently selected from any value from 1 to 20;
n is selected from any value from 1 to 20;
in is selected from any value from 1 to 20;
z is selected from any value from 1 to 3, wherein substituted with one or more substituents independently selected from halogen, —CN, —OH, —SH, —$NO_2$, and —$NH_2$;

$R^1$ is selected from:
—$OR^7$, —$SR^7$, —$N(R^7)_2$, —$C(O)R^7$, —$C(O)N(R^7)_2$, —$N(R^7)C(O)R^7$, —$N(R^7)C(O)N(R^7)_2$, $OC(O)N(R^7)_2$, —$N(R^7)C(O)OR^7$, —$C(O)OR^7$, —$OC(O)R^7$, —$S(O)R^7$, —$S(O)_2R^7$, —$OS(O)_2R^7$, —$OP(O)(OR^7)_2$, —$OP(S)(OR^7)_2$, —SP(O)(OR$^7$)$_2$, —OP(O)(SR$^7$)(OR$^7$), —OP(O)(OR$^7$)N(R$^7$)$_2$, —OP(S)(OR$^7$)N(R$^7$)$_2$, SP(O)(OR$^7$)N(R$^7$)$_2$, —OP(O)(SR$^7$)N(R$^7$)$_2$, —OP(O)(NR$^7$)$_2$)$_2$, —OP(S)(N(R$^7$)$_2$)$_2$, —SP(O)(N(R$^7$)$_2$)$_2$, —OP(OR$^7$)$_2$, —SP(OR$^7$)$_2$, —OP(OR$^7$)(SR$^7$), —OP(OR$^7$)N(R$^7$)$_2$, —OP(SR$^7$)N(R$^7$)$_2$, —SP(OR$^7$)N(R$^7$)$_2$, OP(N(R$^7$)$_2$)$_2$, and —SP(N(R$^7$)$_2$)$_2$;

each R$^2$ is independently selected from:

C$_{1-6}$ alkyl optionally substituted with one or more substituents independently selected from halogen, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)O(O)OR$^7$, —C(O)OR$^7$, —OC(O)R$^7$, and —S(O)R$^7$;

R$^3$ and R$^4$ are each independently selected from:

—OR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$;

each R$^3$ is independently selected from:

—OC(O)R$^7$, —O(O)N(R$^7$)$_2$, —N(R$^7$)C(O)R$^7$, —N(R$^7$)C(O)N(R$^7$)$_2$, —N(R$^7$)C(O)OR$^7$, —C(O)R$^7$, —C(O)OR$^7$, and —C(O)N(R$^7$)$_2$;

each R$^7$ is independently selected from:

hydrogen;

halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$; and C$_{1-6}$ alkyl optionally substituted with one or more substituents independently selected from halogen, —CN, —NO$_2$, —OR$^7$, —S—N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$;

each R$^7$ is independently selected from:

hydrogen;

alkyl, C$_{2-6}$ alkenyl, and C$_{2-6}$ alkynyl, each of which is optionally substituted with one or more substituents independently selected from halogen, —CN, —OH, —SH, —NO$_2$, =O, =S, —O—C$_{1-6}$ alkyl, —S—C$_{1-6}$ alkyl, —N(C$_{1-6}$ alkyl), —NH(C$_{1-6}$ alkyl), C$_{3-10}$ carbocycle, and 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =5, —O—C$_{1-6}$ alkyl, —S—C$_{1-6}$ alkyl, —N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-membered heterocycle, and C$_{1-6}$haloalkyl.

In some embodiments, each w is independently selected from any value from 1 to 20. In some embodiments, each w is independently selected from any value from 1 to 15. In some embodiments, each w is independently selected from any value from 1 to 10. In some embodiments, each w is independently selected from any value from 1 to 5. In some embodiments, each w is independently selected from any value from 1 to 4. In some embodiments, each w is independently selected from any value from 1 to 3. In some embodiments, each w is independently selected from any value from 1 to 2. In some embodiments, W is 1. In some embodiments, w is 1, 2, 3, 4, 5, 6, 7, 8, 9, 10, 11, 12, 13, 14, 15, 16, 17, 18, 19, or 20.

In some embodiments, each v is independently selected from any value from 1 to 20. In some embodiments, each v is independently selected from any value from 1 to 15. In some embodiments, each v is independently selected from any value from 1 to 10. In some embodiments, each v is independently selected from any value from 1 to 5. In some embodiments, each vis independently selected from any value from 1 to 4. In some embodiments, each v is independently selected from any value from 1 to 3. In some embodiments, each v is independently selected from any value from 1 to 2. In some embodiments, each v is independently 1. In some embodiments, v is 1, 2, 3, 4, 5, 6, 7, 8, 9, 10, 11, 12, 13, 14, 15, 16, 17, 18, 19, or 20.

In some embodiments, n is selected from any value from 1 to 20. In some embodiments, n is selected from any value from 1 to 15. In some embodiments, n is selected from any value from 1 to 10. In some embodiments, n is selected from any value from 1 to 9. In some embodiments, n is selected from any value from 1 to 8, In some embodiments, n is selected from any value from 1 to 7. In some embodiments, n is selected from any value from 1 to 6. In some embodiments, n is selected from any value from 1 to 5. In some embodiments, n is selected from any value from 1 to 4. In some embodiments, ii is selected from any value from 2 to 4. In some embodiments, n is selected from any, value from 1 to 3. In some embodiments, n is 2 or 3. In some embodiments, n is 3. In some embodiments, n is selected from any value from 1 to 2, In some embodiments, n is 2. In some embodiments, n is 1. In some embodiments, n is 1, 2, 3, 4, 5, 6, 7, 8, 9, 10, 11, 12, 13, 14, 15, 16, 17, 18, 19, or 20.

In some embodiments, in is selected from any value from 1 to 20. In some embodiments, in is selected from any value from 1 to 15. In some embodiments, m is selected from any value from 1 to 10. In some embodiments, in is selected from any value from 1 to 9. In some embodiments, m is selected from any value from 1 to 8. In some embodiments, m is selected from any value from 1 to 7. In some embodiments, m is selected from any value from 3 to 7. In some embodiments, in is selected from any value from 1 to 6. In some embodiments, in is selected from any value from 2 to 6. In some embodiments, in is selected from any value from 3 to 6. In some embodiments, in is selected from any value from 4/to 6. In some embodiments, m is 6. In some embodiments, m is selected from any value from 1 to 5. In some embodiments, m is selected from any value from 3 to 5. In some embodiments, in is 5. In some embodiments, m is 4 or 5. In some embodiments, in is selected from any value from 1 to 4. In some embodiments, in is 4. In some embodiments, m is 3 or 4. In some embodiments, m is selected from any value from 2 to 4, In some embodiments, m is selected from any value from 1 to 3. In some embodiments, m is 3. In some embodiments, m is selected from any value from 1 to 2. In some embodiments, in is 2. In some embodiments, m is 1. In some embodiments, in is L 2, 3, 4, 5, 6, 7, 8, 9, 10, 11, 12, 13, 14, 15, 16, 17, 18, 19, or 20.

In some embodiments, z is selected from any value from 1 to 3, In some embodiments, z is 3 and Y is C. In some embodiments, z is 2 and Y is CR'. In some embodiments, z is 1 and Y is C(R$^6$)$_2$.

In some embodiments. Q is selected from C$_{3-10}$ carbocycle optionally substituted with one or more substituents independently selected from halogen, —CN, —NO$_2$, —OR$^7$, —S—N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, and C$_{1-6}$ alkyl, wherein the C$_{1-6}$ alkyl, is optionally substituted with one or more substituents independent's, selected from halogen, —CN, —OH, —SH, —NO$_2$, and —NH$_2$. In some embodiments, Q is selected from C$_{1-6}$ carbocycle optionally substituted with one or more substituents independently selected from halogen, —CN, —NO$_2$, —OR$^7$, —N(R$^7$)$_2$, —C(O)R$^1$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, and C$_{1-6}$alkyl, wherein the C$_{1-6}$alkyl, is optionally substituted with one or more substituents independently selected from halogen, —CN, —OH, —SH, —NO$_2$, and NH$_2$. In some embodiments, Q is selected from C$_{5-6}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —NO(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, Q is selected from C$_6$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, Q is selected from C$_{5-6}$ carbocycle optionally substituted with one or more substituents independently selected from halogen, —CN, —NO$_2$, —OR$^7$, —SR$^7$, —N(R$^7$)$_2$, —C(O)R$^7$, —C(O)N(R$^7$)$_2$, —N(R$^7$)C(O)R$^7$, —N(R)C(O)N(R$^7$)$_2$, —OC(O)N(R$^7$)$_2$, —N(R$^7$)C(O)OR$^7$, —C(O)OR$^7$, —OC(O)R and —S(O)R$^7$, In some embodiments, Q is selected from C$_{5-6}$ carbocycle optionally substituted with one or more substituents independently selected from halogen, —CN, —OH, —SH, —NO$_2$, and —NH$_2$. In some embodiments, Q is selected from phenyl, cyclohexyl, cyclopentadiene, and cyclopentyl, each of which is optionally substituted with one or more substituents independently selected from halogen, —CN, —OH, —SH, —NO$_2$, and —NH$_2$. In some embodiments. Q is selected from phenyl and cyclohexyl, each of which is optionally substituted with one or more substituents independently selected from halogen, —CN, —OH, —SH, —NO$_2$, and —NH$_2$. In some embodiments. Q is selected from phenyl and cyclohexyl. In some embodiments, Q is phenyl. In some embodiments, Q is cyclohexyl.

In some embodiments, R' is selected from —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —S(O)R$^7$, —S(O)$_2$R$^7$, —OS(O)$_2$R$^7$, —OP(O)(OR$^7$)$_2$, —OP(S)(OR$^7$)$_2$, —SP(O)(OR$^7$)$_2$, —OP(O)(SR$^7$)(OR$^7$), —OP(O)(OR$^7$)N(R$^7$)$_2$, —OP(S)(OR$^7$)N(R$^7$)$_2$, —SP(O)(OR$^7$)N(R$^7$)$_2$, —OP(O)(SR$^7$)N(R$^7$)$_2$, —OP(O)(N(R$^7$)$_2$)$_2$, —OP(S)(N(R$^7$)$_2$)$_2$, —SP(O)(N(R$^7$)$_2$)$_2$, —OP(OR$^7$)$_2$, —SP(OR)$_2$, —OP(OR$^7$)(SR$^7$), —OP(OR$^7$)N(R$^7$)$_2$, —OP(SR$^7$)N(R$^7$)$_2$, —SP(OR$^7$)N(R$^7$)$_2$, and —SP(N(R$^7$)$_2$)$_2$. In some embodiments, R$^1$ is selected from —OR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, —OP(O)(OR$^7$)$_2$, —OP(O)(OR$^7$)N(R$^7$)$_2$, —OP(O)(N(R$^1$)$_2$)$_2$, —OP(OR$^7$)$_2$, OP(OR$^7$)N(R$^7$)$_2$, and —OP(N(R$^7$)$_2$)$_2$. In some embodiments, R$^1$ is selected from —SR$^7$, —S(O)R$^7$, —S(O)$_2$R$^7$, —OS(O)$_2$R$^7$, —OP(S)(OR$^7$)$_2$, —SP(O)(OR")$_2$, —OP(O)(SR$^1$)(OR$^7$), —OP(S)(OR$^7$)N(R$^7$)$_2$, —SP(O)(OR$^7$)N(R$^7$)$_2$, —OP(O)(SR$^7$)N(R$^1$)$_2$, —OP(S)(N(R$^7$)$_2$)$_2$, —SP(O)(N(R$^7$)$_2$)$_2$, —SP(OR$^7$)$_2$, OP(OR$^7$)(SR), —OP(SR$^7$)N(R$^7$)$_2$, —SP(OR$^7$)N(R$^7$)$_2$, and —SP(N(R$^7$)$_2$)$_2$. In some embodiments. R$^1$ is selected from —OP(O)(OR$^7$)$_2$, —OP(S)(OR$^7$)$_2$, —SP(O)(OR$^7$)$_2$, —OP(O)(SR$^7$)(OR$^7$), —OP(O)(OR$^7$)N(R$^7$)$_2$, —OP(S)(OR$^7$)N(R$^7$)$_2$, —SP(O)(OR$^7$)N(R$^7$)$_2$, —OP(O)(SR)N(R$^7$)$_2$, —OP(O)(N(R$^7$)$_2$)$_2$, —OP(S)(N(R$^7$)$_2$)$_2$, —SP(O)(N (R$^7$)$_2$)$_2$, —OP(OR$^7$)$_2$, —SP(OR$^7$)$_2$, —OP(OR$^7$)(SR$^7$), —OP(OR$^7$)N(R$^7$)$_2$, —OP(SR$^7$)N(R$^7$)$_2$, —SP(OR$^7$)N(R$^7$)$_2$, —OP(N(R$^7$)$_2$)$_2$, and —SP(N(R$^7$)$_2$)$_2$. In some embodiments, R$^1$ is a selected from —OP(O)(OR$^7$)$_2$, —OP(O)(OR$^7$)N(R$^7$)$_2$, —OP(O)(N(R$^7$)$_2$)$_2$, —OP(OR$^7$)$_2$, —OP(OR$^7$)N(R$^7$)$_2$, and —OP((NR$^7$)$_2$)$_2$. In some embodiments, R$^1$ is a selected from —OP(O)(OR$^7$)$_2$ and —OP (OR$^7$)N(R$^7$)$_2$. In some embodiments, R$^1$ is selected from —OP(O)(OCH$_2$CH$_3$)OH and —OP(OCH$_2$CH$_2$CN)N(CH (CH$_3$)$_2$)$_2$, In some embodiments, R$^1$ is —OP(OCH$_2$CH$_2$CN) N(CH(CH$_3$)$_2$)$_2$.

In some embodiments, each IV is independently selected from C$_{1-6}$ alkyl optionally substituted with one or more substituents independently selected from halogen, —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, each R$^2$ is independently selected from C$_{1-3}$ alkyl substituted with one or more substituents independently selected from halogen. —OR$^7$, —OC(O)R$^7$, —SR$^7$, —N(R$^7$)$_2$, —C(O)R$^7$, and —S(O)R$^7$. In some embodiments, each R$^2$ is independently selected from C$_{1-3}$ alkyl substituted with one or more substituents independently selected from —OR$^7$, —OC(O)R$^7$, —SR$^7$, and —N(R$^7$)$_2$. In some embodiments, each R$^2$ is independently selected from C$_1$ alkyl substituted with one or more substituents independently selected from —OR$^7$ and —OC(O)R$^7$. In some embodiments, each R$^2$ is independently selected from —CH$_2$OH and —CH$_2$OC(O)CH$_3$.

In some embodiments, each R$^3$ is independently selected from —OR$^7$, —SR$^7$, —N(R$^7$)$_2$, —C(O)R$^7$, —C(Q)N(R$^7$)$_2$, —N(R)C(O)R$^7$, —N(R$^7$)C(O)N(R$^7$)$_2$, —OC(O)N(R$^7$)$_2$, —N(R$^7$)C(O)OR$^7$, —C(O)OR—OC(O)R$^7$, and —S(O)R$^7$. In some embodiments, each R$^3$ is independently selected from halogen. —OR$^7$, —SR$^7$, —N(R$^7$)$_2$, —C(O)R$^7$, —OC(O)R$^7$, and —S(O)R$^7$. In some embodiments, each R$^3$ is independently selected from —OR$^7$, —OC(O)R$^7$, —SR$^7$, and —N(R$^7$)$_2$. In some embodiments, each R$^3$ is independently selected from —OR$^7$ and —OC(O)R$^7$. In some embodiments, R$^3$ is independently selected from —OH and —OC(O)CH$_3$.

In some embodiments, each R$^4$ is independently selected from —OR$^7$, —SR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O)R$^7$, and —S(O)R$^7$. In some embodiments, each R$^4$ is independently selected from halogen, —OR$^7$, —SR$^7$, —N(R$^7$)$_2$, —C(O)R$^7$, —OC(O)R$^7$, and —S(O)R$^7$. In some embodiments, each R$^4$ is independently selected from —OR, —OC(O)R$^7$, —SR$^7$, and —N(R$^7$)$_2$. In some embodiments, each R$^4$ is independently selected from —OR$^7$ and —OC(O)R$^7$. In some embodiments, R$^4$ is independently selected from —OH and —OC(O)CH$_3$.

In some embodiments, each R$^5$ is independently selected from —OC(O)R$^7$, —OC(O)N(R$^7$)$_2$, N(R$^7$)C(O)R$^7$, —N(R$^7$)C(O)N(R$^7$)$_2$, —N(R$^7$)C(O)OR$^7$, —C(O)R$^7$, —C(O)OR$^7$, and —C(O)N(R$^7$)$_2$. In some embodiments, each R$^5$ is selected from —OC(O)R$^7$, —OC(O)N(R$^7$)$_2$, —N(R$^7$)C(O) R$^7$, —N(R$^7$)C(O)N(R$^7$)$_2$, and —N(R$^7$)C(O)OR$^7$, In some embodiments, each R$^5$ is independently selected from —OC(O)R$^7$ and —N(R$^7$)C(O)R$^7$. In some embodiments, each R$^5$ is independently selected from —N(H)C(O)CH$_3$.

In some embodiments, each R$^6$ is independently selected from hydrogen, halogen, —CN, —OR$^7$, —N(R$^7$)$_2$, —C(O)R$^7$, —C(O)N(R$^7$)$_2$, —N(R$^7$)C(O)R$^7$, —N(R$^7$)C(O)N(R$^7$)$_2$, —OC(O)N(R$^7$)$_2$, —N(R$^7$)C(O)OR$^7$, —C(O)OR$^7$, —OC(O) R$^7$, and —S(O)R$^7$; and C$_{1-6}$ alkyl optionally substituted with one or more substituents independently selected from halogen, —CN, —OR$^7$, —S—N(R$^7$)$_2$, —C(O)R$^7$, —C(O) N(R)$_2$, —N(R$^7$)C(O)R$^7$, —N(R$^7$)C(O)N(R$^7$)$_2$, —OC(O)N (R$^7$)$_2$, —N(R$^7$)C(O)OR$^7$, —C(O)OR$^7$, —OC(O)R$^7$, and —S(O)R$^7$. Ire some embodiments, each R$^6$ is independently selected from hydrogen, halogen, —CN—SR$^7$, —N(R$^7$)$_2$, and C$_{1-6}$ alkyl optionally substituted with one or more substituents independently selected from halogen. —OR$^7$, —SR$^7$, and —N(R)$_2$. In some embodiments, each R$^6$ is independently selected from hydrogen, halogen, —CN, —OH, —SH, and —NH$_2$.

In some embodiments, each R$^7$ is independently selected from: hydrogen; C$_{1-6}$ alkyl, C$_{2-6}$ alkenyl, and C$_{2-6}$ alkynyl, each of which is optionally substituted with one or more substituents independently selected from halogen, —CN, —OH, —SH, —NO$_2$, —NH$_2$; =O, =S, —O—C$_{1-6}$ alkyl, —S—C$_{1-6}$ alkyl, —N(C$_{1-6}$ alkyl)$_2$, —NH(C$_{1-6}$ alkyl), C$_{3-10}$ carbocycle, and 3- to 10-membered heterocycle; and C$_{3-10}$ carbocycle, and 3- to 10-membered heterocycle, each of which is optionally substituted with one or more substituents independently selected from halogen, —CN, —OH, —SH, —NO$_2$, —NH$_2$, =O, =S, —O—C$_{1-6}$ alkyl, —S—C$_{1-6}$—N(C$_{1-6}$ alkyl)$_2$, —NH(C$_{1-6}$ alkyl), C$_{1-6}$ alkyl, C$_{2-6}$ alkenyl, C$_{2-6}$ alkynyl, C$_{3-10}$ carbocycle, 3- to 10-Membered heterocycle, and C$_{1-6}$ haloalkyl. In some embodiments, each R$^7$ is independently selected from: hydrogen; and C$_{1-6}$ alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl, =N(C$_{1-6}$ alkyl)$_2$, —NH(C$_{1-6}$ alkyl), C$_{3-10}$ carbocycle, 3- to -10-membered heterocycle. In some embodiments, each R$^7$ is independently selected from C$_{1-6}$ alkyl optionally substituted with one or more substituents independently selected from halogen, —CN, —OH, —SH, —NO$_2$, —NH$_2$, =O, =S, —O—C$_{1-6}$ alkyl, —S—C$_{1-6}$ alkyl. —N(C$_{1-6}$ alkyl)$_2$, and —NH(C$_{1-6}$ alkyl). In some embodiments, each R$^7$ is independently selected from hydrogen. In some embodiments, each R$^7$ is independently selected from C$_{1-3}$ alkyl optionally substituted with one or more substituents independently selected from halogen, —CN, —OH, —SH, —NO$_2$, —NH$_2$, —O—C$_{1-6}$ alkyl, —S—C$_{1-6}$ alkyl, —N(C$_{1-6}$ alkyl)$_2$, and —NH(C$_{1-6}$ alkyl). In some embodiments, each R$^7$ is independently selected from C$_{1-6}$ alkyl optionally substituted with one or more substituents independently selected from halogen, —CN, —OH, and —SH.

In some embodiments, a compound of Formula (A) is selected from:

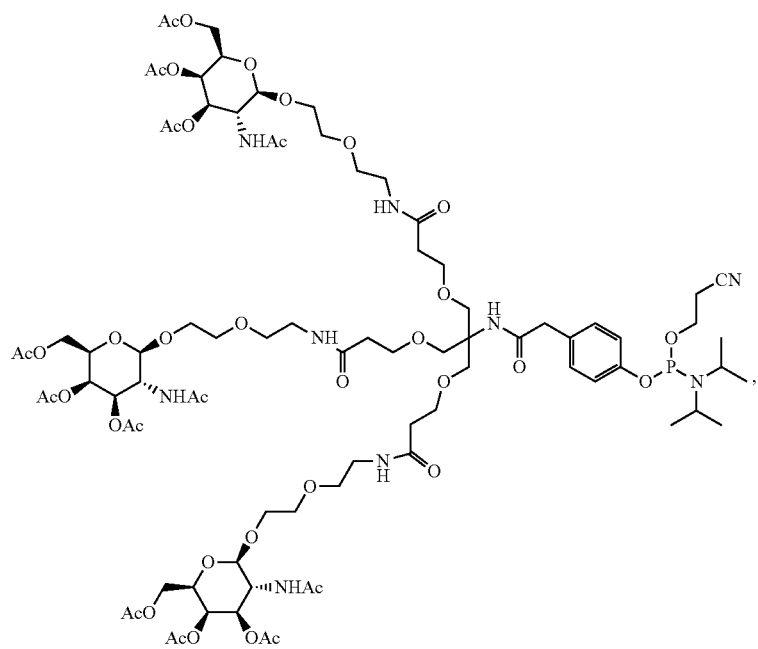

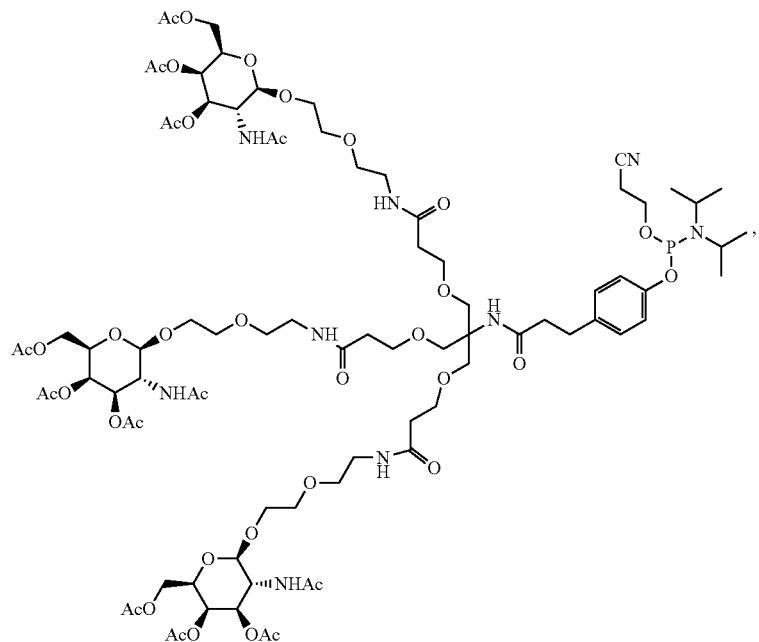
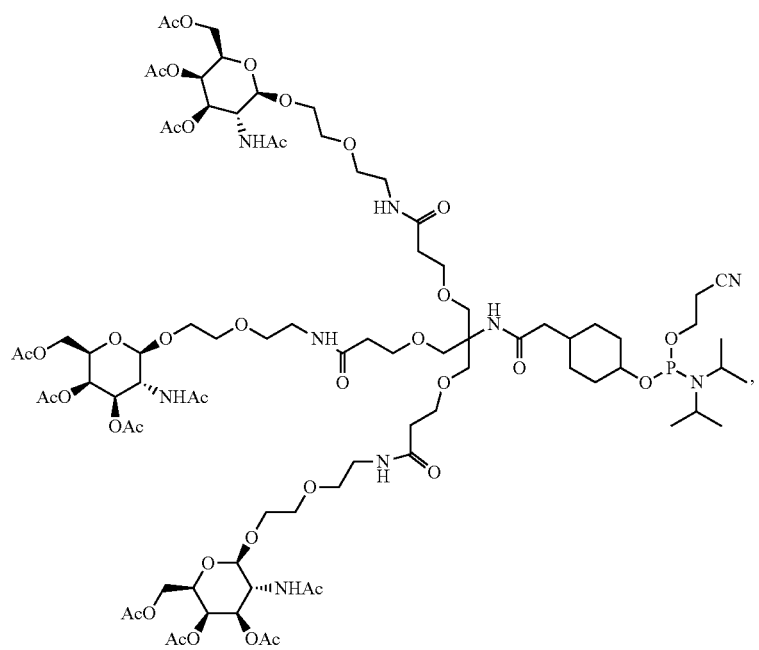

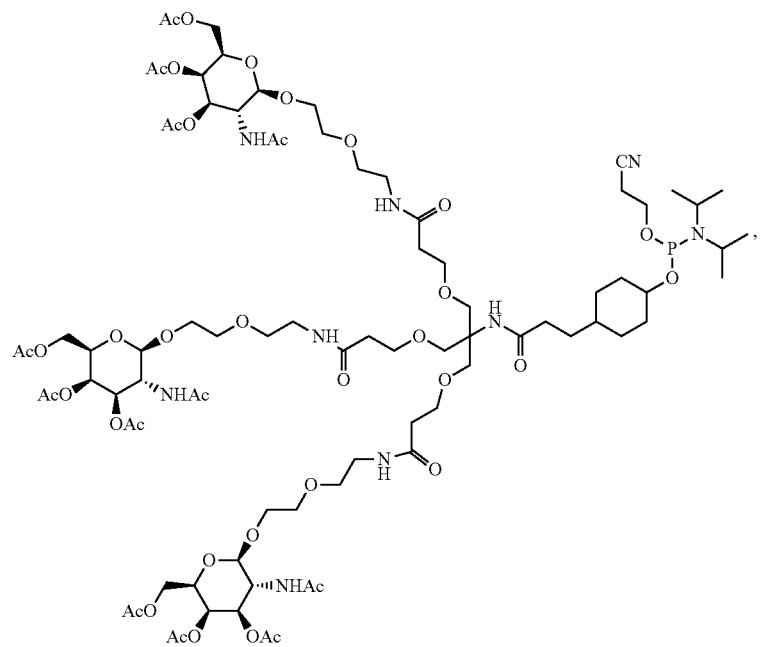
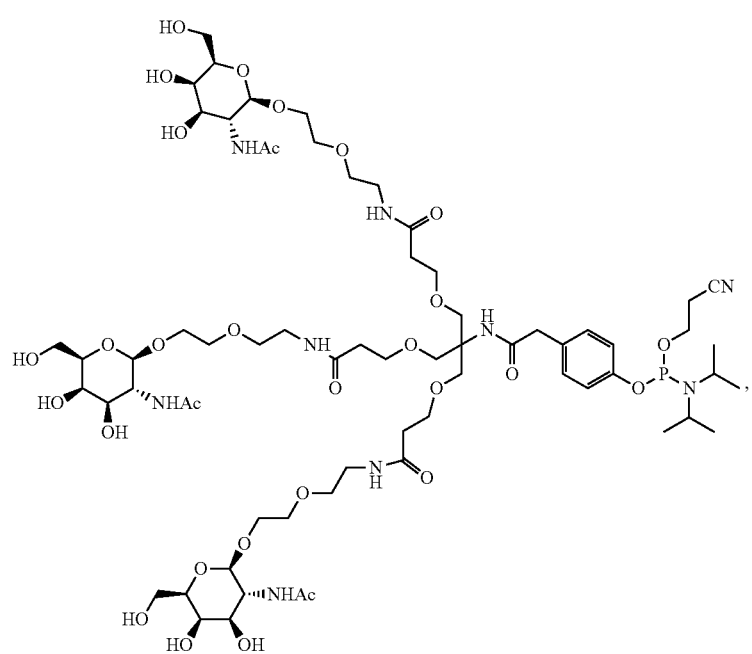

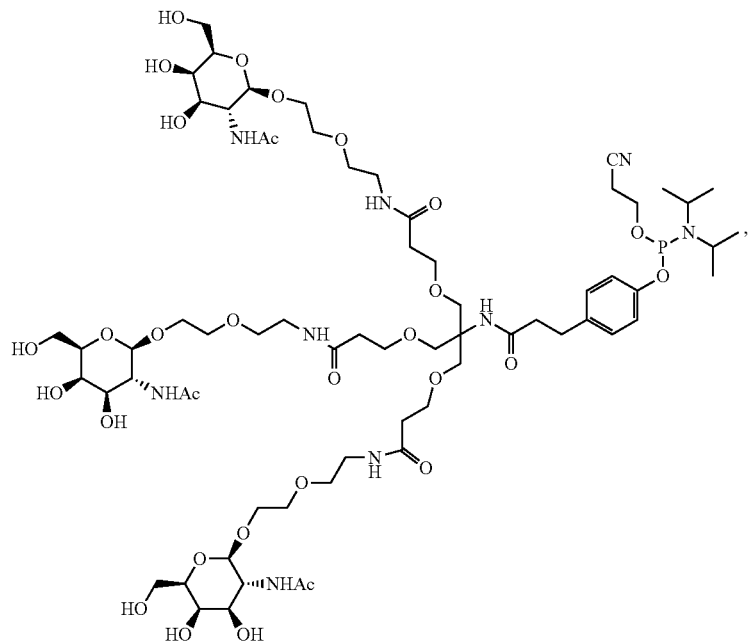
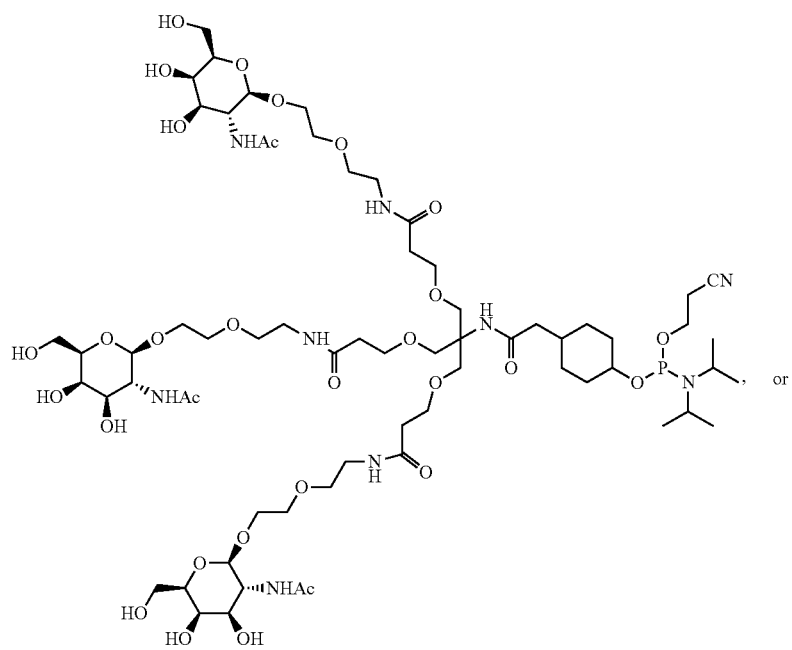
, or

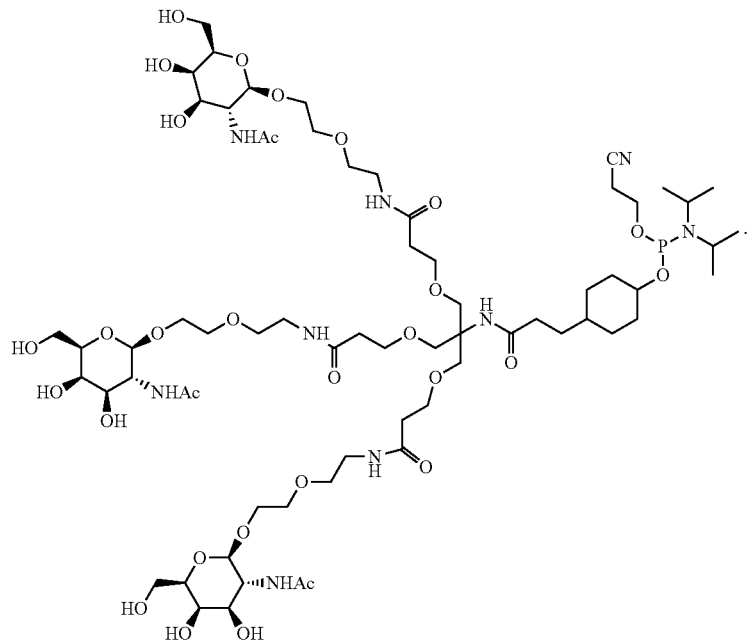
Provided herein, in some embodiments, is a compound represented by Formula (B):
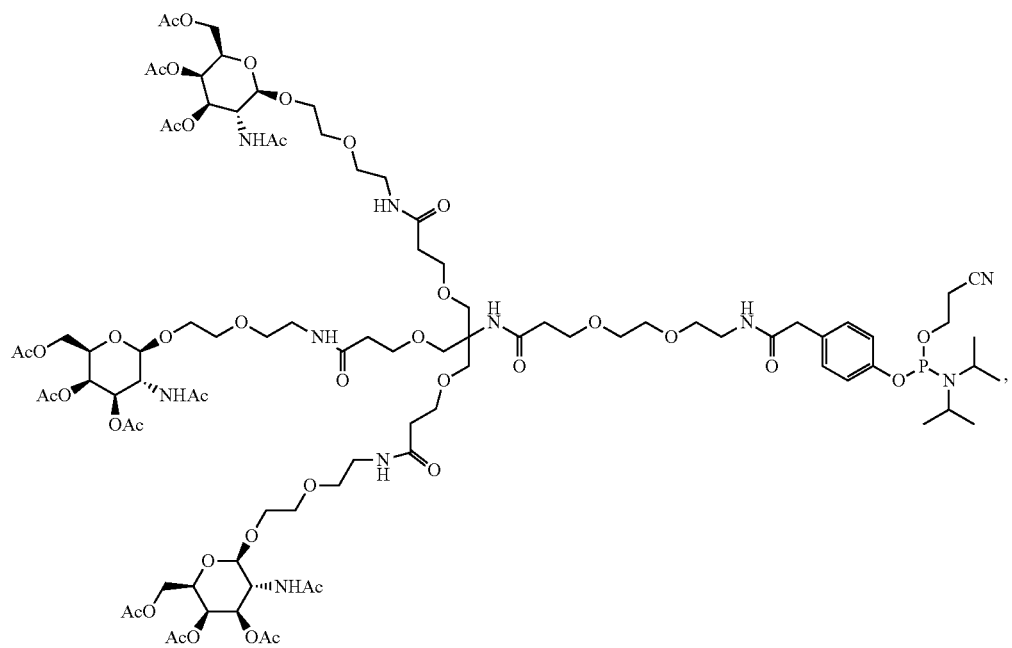

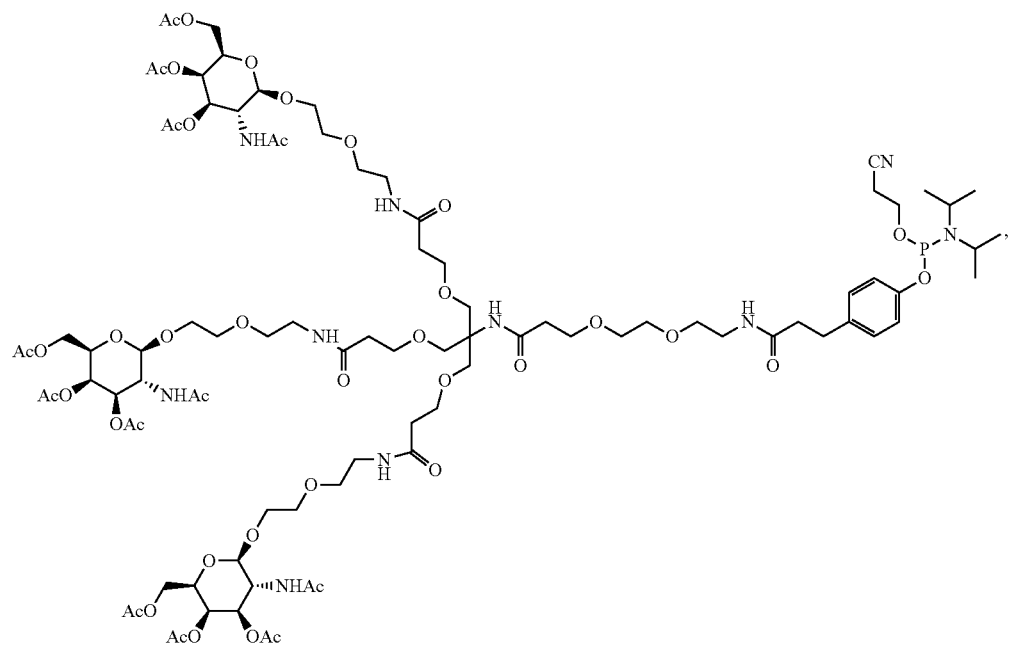
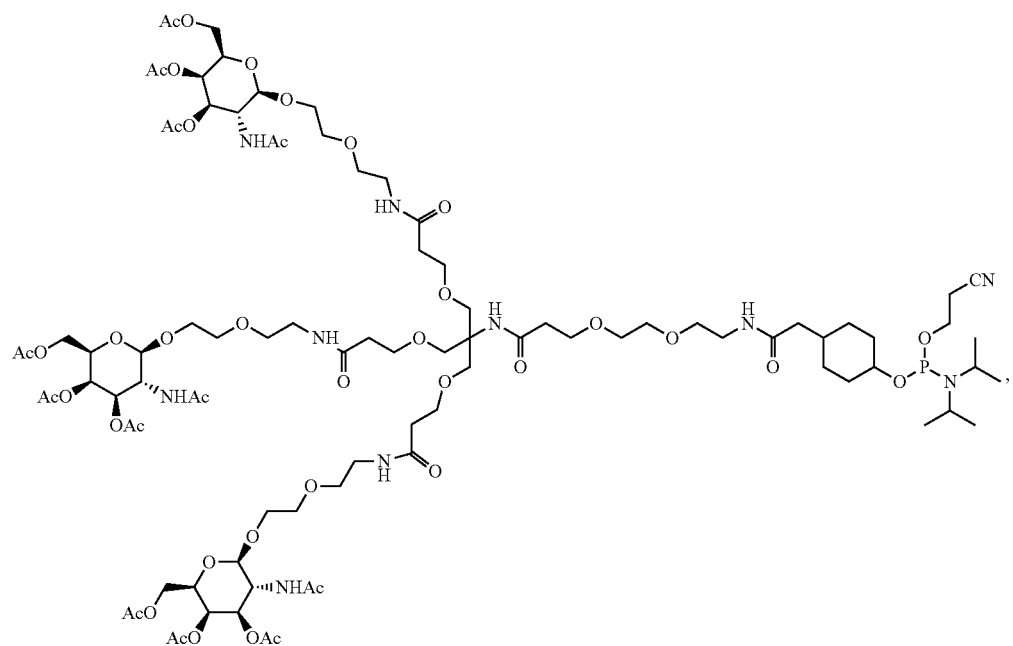

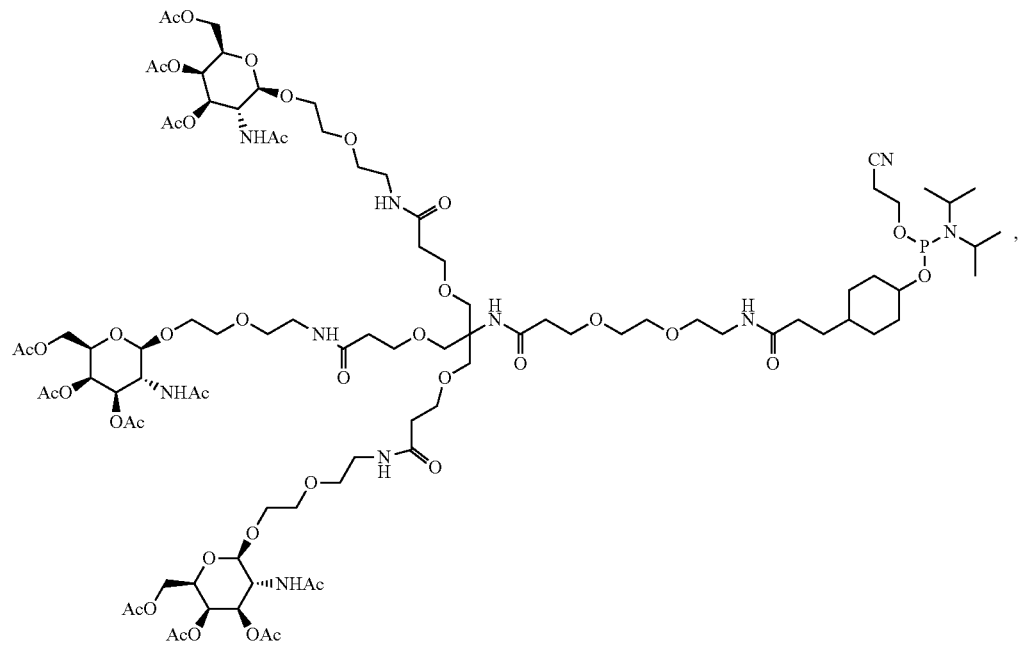
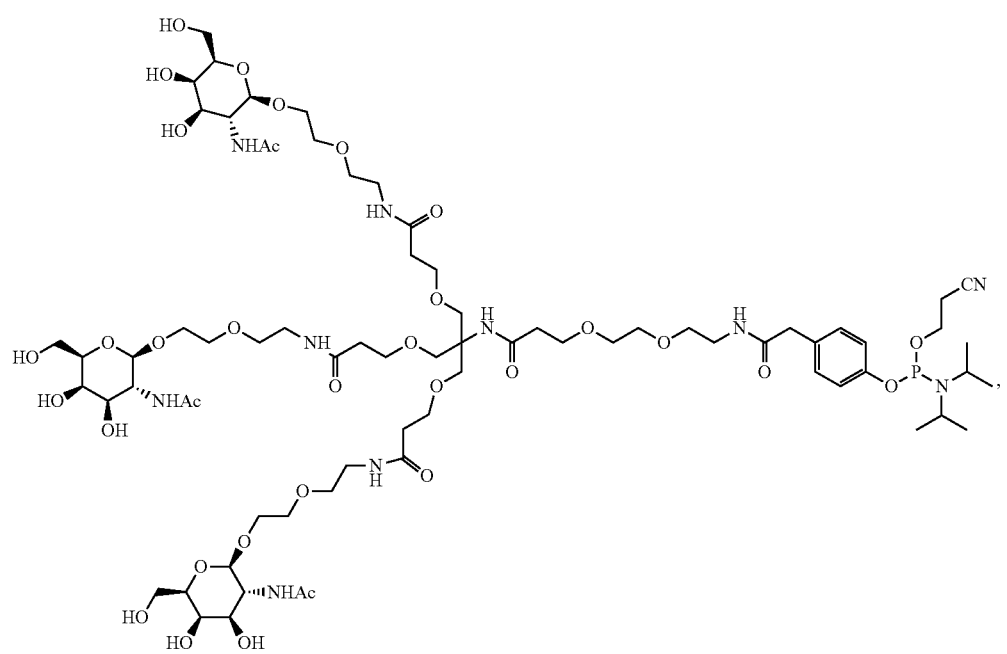

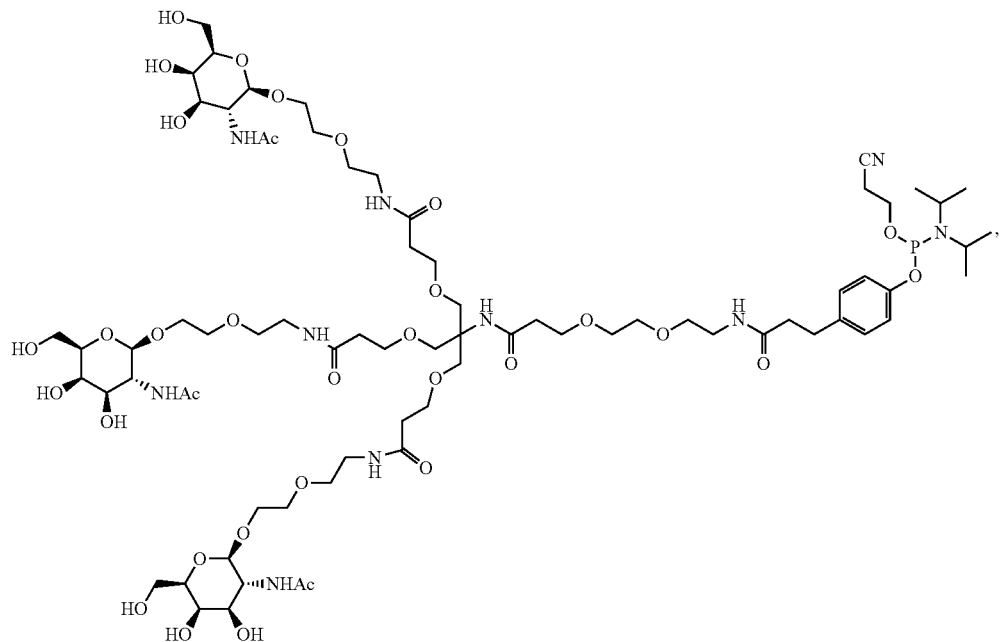
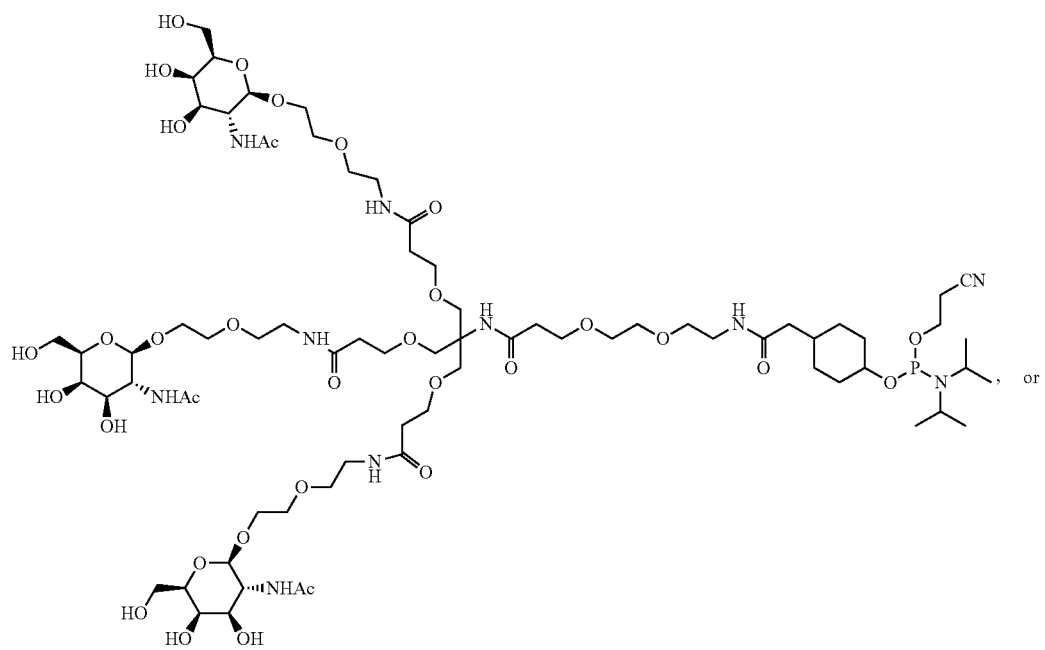

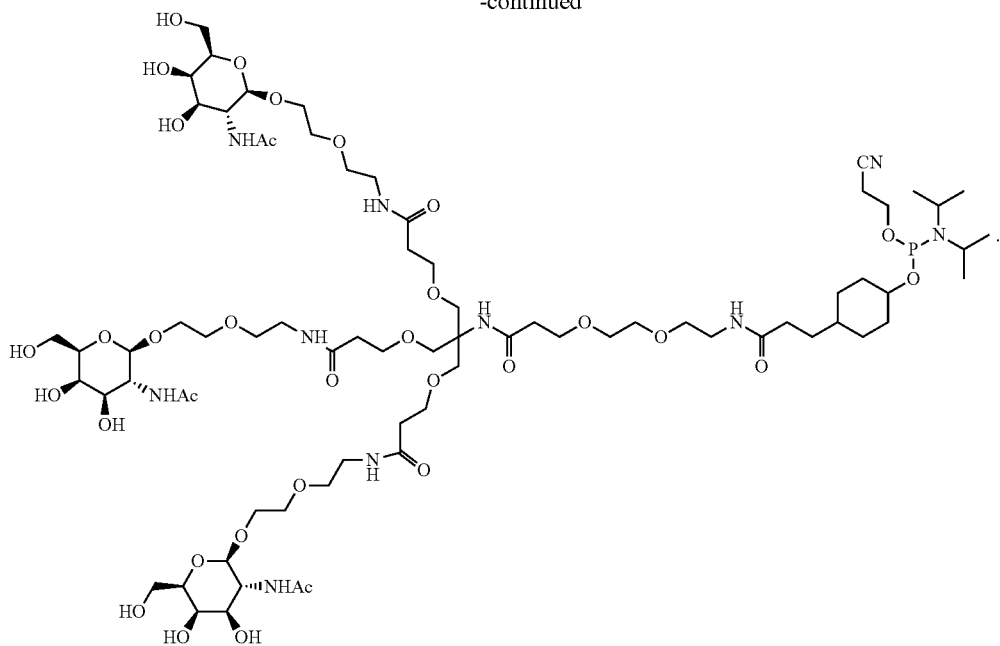

In some embodiments, the phosphate is deprotonated to form a salt of Formula (I), (II), (A), or (B). In some embodiments, the cation is a metal ion such as a metal cation. Non limiting examples of metal cations include Na+, K+, Mg2+, and Ca2+. In some embodiments, the metal cation comprises Na+. In some embodiments, the metal cation comprises K. In some embodiments, the metal cation comprises Mg'. In some embodiments, the metal cation comprises Ca'. In some embodiments, the cation is an organic or inorganic small molecule. In some embodiments wherein the compound is a deprotonated form of Formula (I) or (II), the cation is a positively charged nucleic acid present in the oligonucleotide.

Some embodiments include the following, where J is the oligonucleotide:

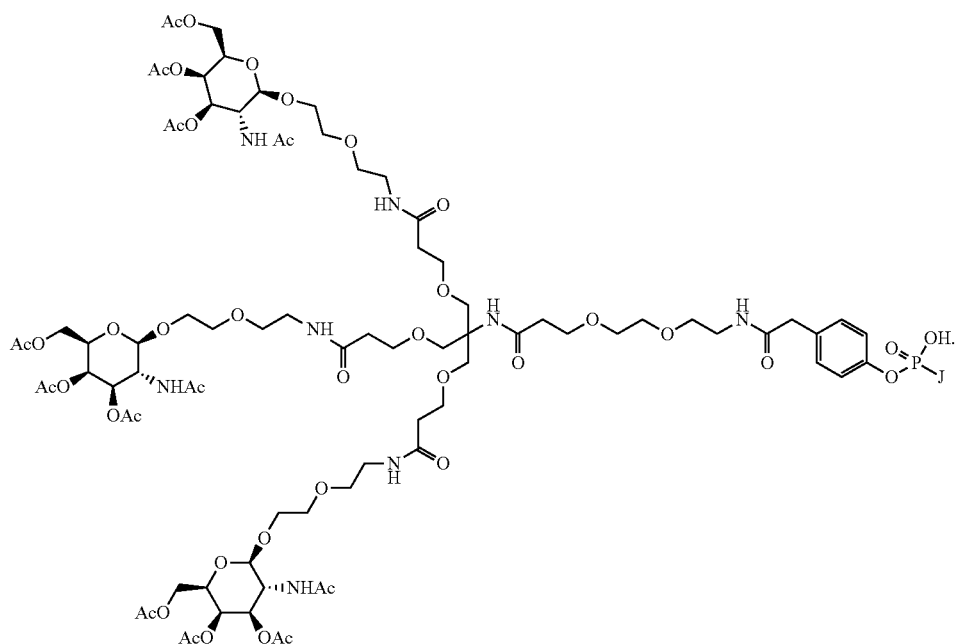

J may include one or more additional phosphates, or one or more phosphorothioates linking to the oligonucleotide. J may include one or more additional phosphates linking to the oligonucleotide. J may include one or more phosphorothioates linking to the oligonucleotide.

Some embodiments include the following, when J is the oligonucleotide:

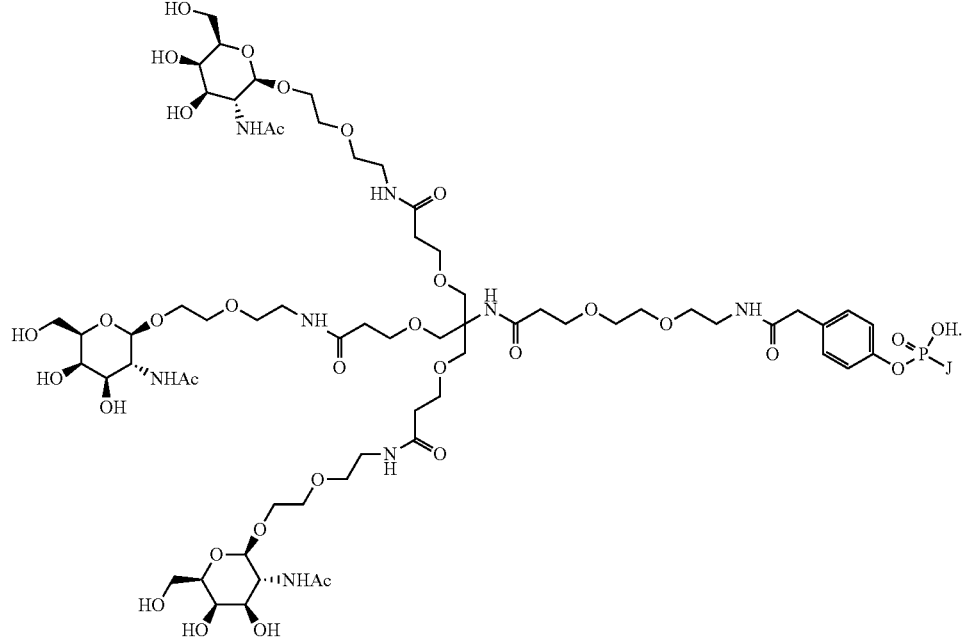

J may include one or more additional phosphates, or one or more phosphorothioates linking; to the oligonucleotide, include one or more additional phosphates linking to the oligonucleotide. J may include one or more phosphorothioates linking to the oligonucleotide.

Some embodiments include the following, where J is the oligonucleotide:

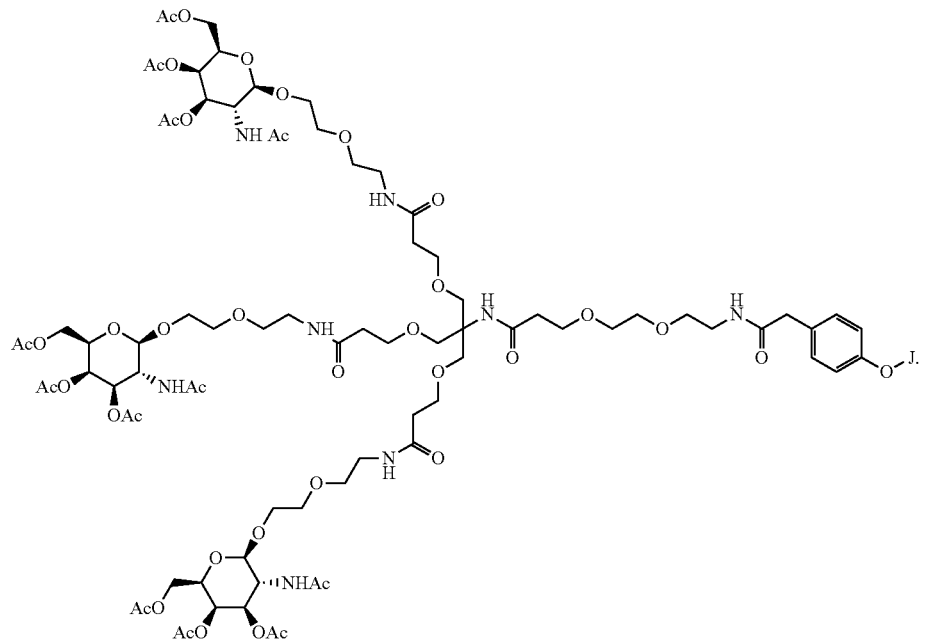

J may include one or more phosphates or phosphorothioates linking to the oligonucleotide. J may include one or more phosphates linking to the oligonucleotide. J may include a phosphate linking to the oligonucleotide. J may include one or more phosphorothioates linking to the oligonucleotide. J may include a phosphorothioate linking to the oligonucleotide.

Some embodiments include the following, where J is the oligonucleotide:

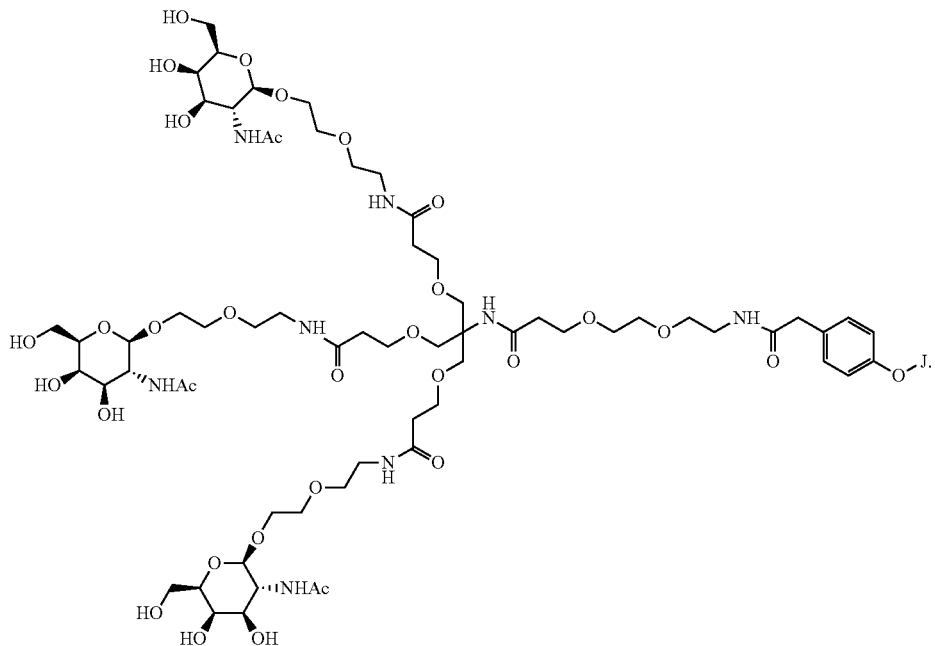

The structure in this compound attached to the oligonucleotide (J) is an example of a GalNAc moiety. J may include one or more phosphates or phosphorothioates linking to the oligonucleotide. J may include one or more phosphates linking to the oligonucleotide. J may include a phosphate linking to the oligonucleotide. J may include one or more phosphorothioates linking to the oligonucleotide. J may include a phosphorothioate linking to the oligonucleotide.

Some embodiments include the following, where J is the oligonucleotide:

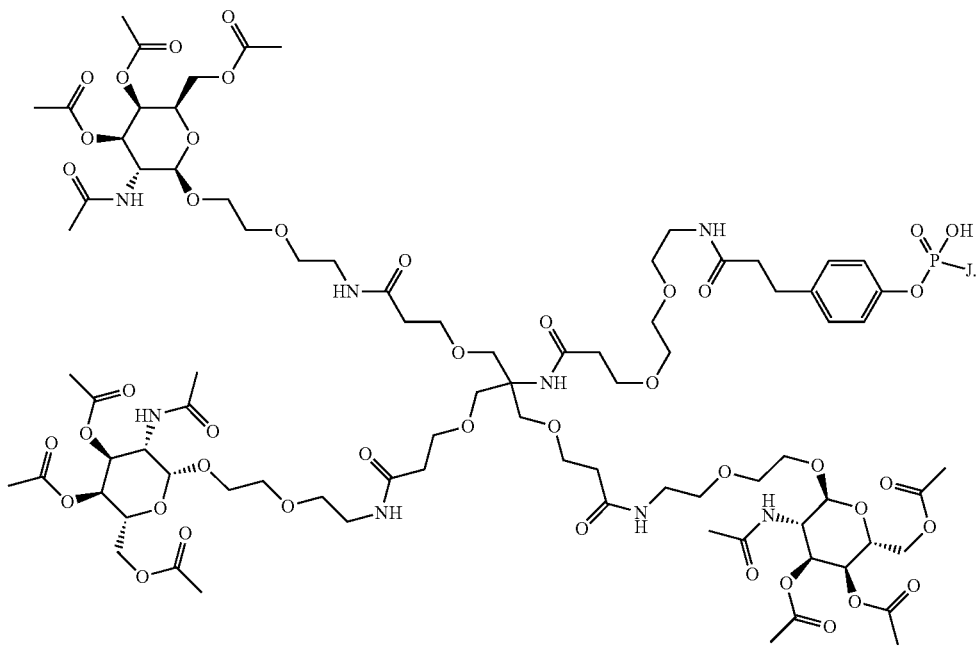

J may include one or more additional phosphates, or one or more phosphorothioates linking to the oligonucleotide. J may include one or more additional phosphates linking to the oligonucleotide. J may include one or more phosphorothioates linking to the oligonucleotide.

Some embodiments include the following, where J is the oligonucleotide:

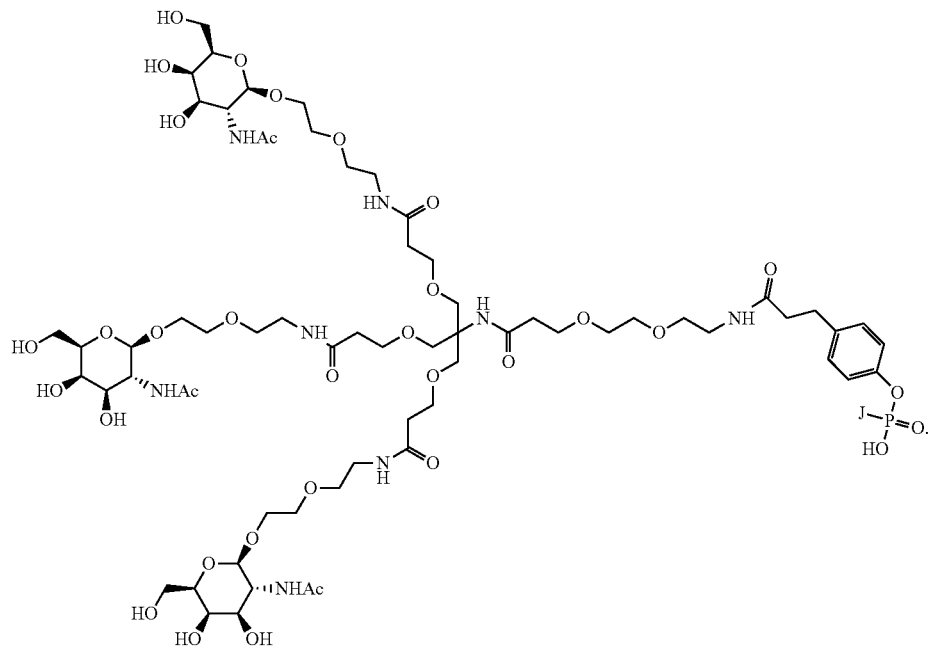

J include one or more additional phosphates, or one or more phosphorothioates linking to the oligonucleotide. J may include one or more additional phosphates linking to the oligonucleotide. J may include one or more phosphorothioates linking to the oligonucleotide.

Some embodiments include the following, where J is the oligonucleotide:

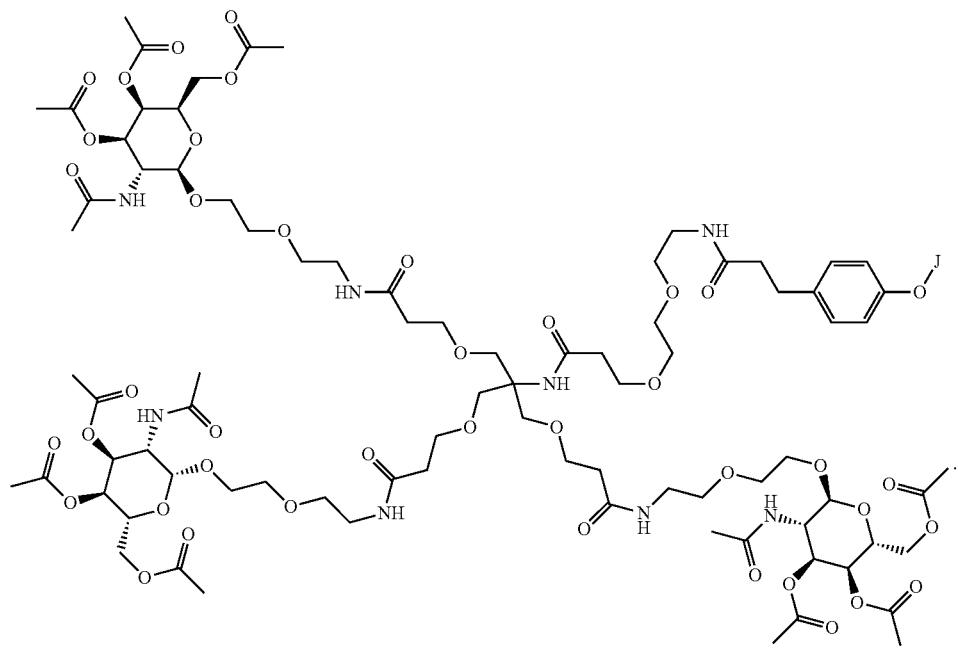

J may include one or more phosphates or phosphorothioates linking to the oligonucleotide. J may include one or more phosphates linking to the oligonucleotide. J may include a phosphate linking to the oligonucleotide. J may include one or more phosphorothioates linking to the oligonucleotide. J may include a phosphorothioate linking to the oligonucleotide.

The structure in this compound attached to the oligonucleotide (J) may be referred to as "ETL17," and is an example of a GalNAc moiety. J may include one or more phosphates or phosphorothioates linking to the oligonucleotide. J may include one or more phosphates linking to the oligonucleotide. J may include a phosphate linking to the oligonucleotide. J may include one or more phosphorothioates linking to the oligonucleotide. J may include a phosphorothioate linking to the oligonucleotide.

Some embodiments include the following, where J is the oligonucleotide:

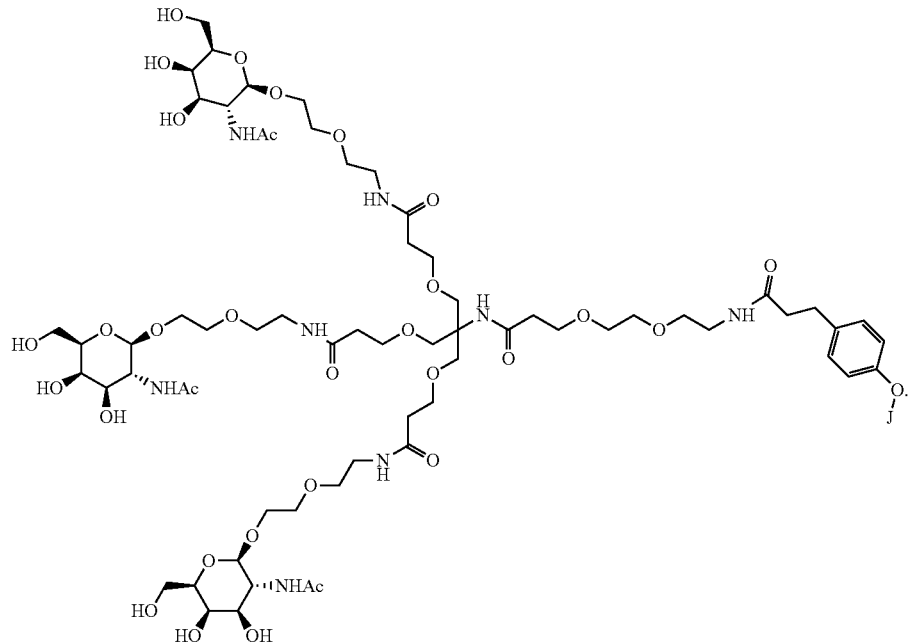

Some embodiments include the following, where J is the oligonucleotide:

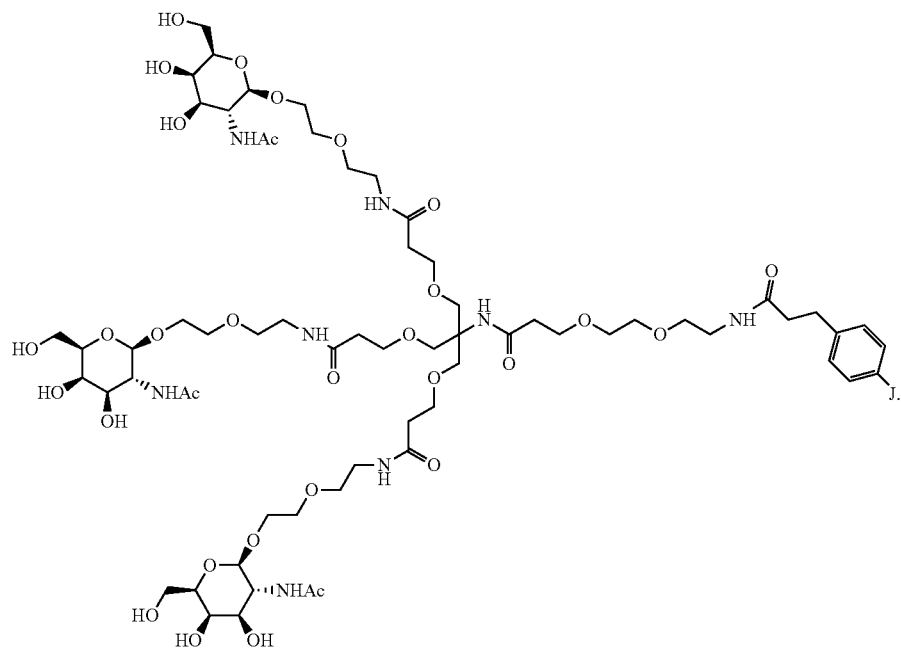

The structure in this compound attached to the oligonucleotide (J) is an example of a CialNAc moiety. J may include one or more phosphates or phosphorothioates linking to the oligonucleotide. J may include one or more phosphates linking to the oligonucleotide. J may include a phosphate linking to the oligonucleotide may include one or more phosphorothioates linking to the oligonucleotide. J may include a phosphorothioate linking to the oligonucleotide. In any embodiment, J may include an additional linker.

1. Analogues

Chemical entities having carbon-carbon double bonds or carbon-nitrogen double bonds may exist in Z- or E- form (or cis- or irons- form). Furthermore, some chemical entities may exist in various tautomeric forms. Unless otherwise specified, compounds described herein are intended to include all Z-. F- and tautomeric forms as well.

A "tautomer" refers to a molecule or moiety wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

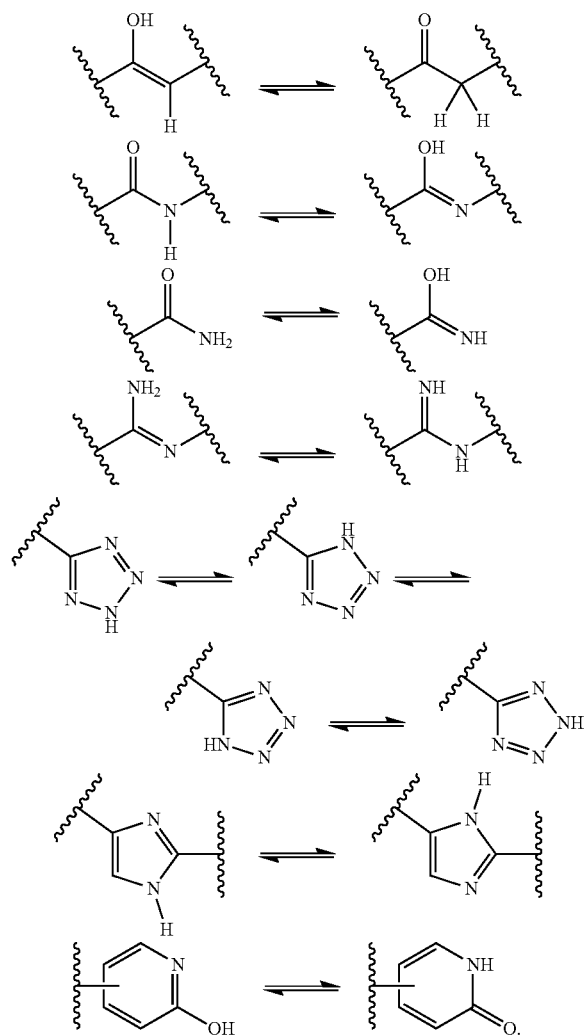

The compounds and moieties disclosed herein, in some embodiments, are used in different enriched isotopic forms, e.g., enriched in the content of $^2$H, $^3$H, $^{11}$C, $^{13}$C and/or In one particular embodiment, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, compounds described herein and moieties are intended to include compounds and moieties which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds and moieties of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, and $^{125}$I are all contemplated. All isotopic variations of the compounds and moieties of the present invention, whether radioactive or not, are encompassed within the scope of the present invention.

In certain embodiments, the compounds and moieties disclosed herein have some or all of the $^1$H atoms replaced with $^2$H atoms. The methods of synthesis for deuterium-containing compounds are known in the art and include, by way of non-limiting example only, the following synthetic methods.

Deuterium substituted compounds are synthesized using various methods such as described in: Dean, Dennis C.; Editor. Recent Advances in the Synthesis and Applications of Radiolabeled Compounds for Drug Discovery and Development. [In: Curr, Phann. Des., 2000; 6(10)]2000. 110 pp; George W.; Varma, Rajender S. The Synthesis of Radiolabeled Compounds via Organometallic intermediates, Tetrahedron, 1989, 45(21), 6601-21; and Evans, E. Anthony. Synthesis of radiolabeled compounds, J. Radioanal. Chem., 1981, 64(1-2), 9-32.

Deuterated starting materials are readily available and are subjected to the synthetic methods described herein to provide for the synthesis of deuterium-containing compounds. Large numbers of deuterium-containing reagents and building blocks are available commercially from chemical vendors, such as Aldrich Chemical Co.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. "Enantiomers, Racemates and Resolutions", John Wiley And Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated or solvated forms with pharmaceutically acceptable solvents such as Water, ethanol, and the like. The solvated forms of the compounds presented herein are also considered to be disclosed herein.

B. Oligonucleotides

Provided herein, in some embodiments, are compositions or compounds comprising an oligonucleotide. The oligonucleotide may be conjugated to a GalNAc moiety. The oligonucleotide may be directly connected to a linker connected to the GalNAc moiety. The oligonucleotide may be used in a method described herein.

In some embodiments, the oligonucleotide binds to a target oligonucleotide. Examples of target oligonucleotides include a target RNA or a target DNA. In some embodiments, the oligonucleotide binds to a target DNA. In some embodiments, the oligonucleotide binds to a target DNA, and inhibits RNA (e.g. mRNA) expression from the target DNA. In some embodiments, the oligonucleotide binds to a target RNA. The target RNA may include a target mRNA. In some embodiments, the oligonucleotide binds to a target mRNA. In some embodiments, the oligonucleotide inhibits the target mRNA such as by reducing an amount of the target mRNA, causing degradation of the target mRNA, or decreasing or preventing translation of the target mRNA. In some embodiments, the oligonucleotide reduces an amount of a target protein produced from the target mRNA, for example by inhibiting the target mRNA. The oligonucleotide may include a small interfering RNA (siRNA). The oligonucleotide may include an antisense oligonucleotide (ASO).

In some embodiments, the composition comprises an oligonucleotide that binds to a target oligonucleotide and inhibits expression of a target protein encoded by the target oligonucleotide. In some embodiments, the composition comprises an oligonucleotide that binds to a target RNA and inhibits expression of a target protein encoded by the target RNA. In some embodiments, the composition comprises an oligonucleotide that binds to a target mRNA and inhibits expression of a target protein encoded by the target mRNA.

In some embodiments, the composition comprises an oligonucleotide that binds to a target oligonucleotide and inhibits expression of a second oligonucleotide encoded by the target oligonucleotide. In some embodiments, the composition comprises an oligonucleotide that binds to a target DNA and inhibits expression of a target RNA encoded by the target DNA. In some embodiments, the composition comprises an oligonucleotide that binds to a target DNA and inhibits expression of a target mRNA encoded by the target DNA.

Target oligonucleotides may be identified by a variety of ways. In some instances, the target oligonucleotide comprises an mRNA that has expression levels that are associated with incidence of a disorder (e.g. a liver disorder). In some instances, the target oligonucleotide comprises an mRNA that is encoded by a gene that has a particular genotype associated with the disorder. Large-scale human genetic data can improve the success rate of pharmaceutical discovery and development. A Genome Wide Association Study (GWAS) may detect associations between genetic variants and traits in a population sample. A GWAS may enable better understanding of the biology of disease, and provide applicable treatments. A GWAS can utilize genotyping and/or sequencing data, and often involves an evaluation of millions of genetic variants that are relatively evenly distributed across the genome. The most common GWAS design is the case-control study, which involves comparing variant frequencies in cases versus controls. If a variant has a significantly different frequency in cases versus controls, that variant is said to be associated with disease. Association statistics that may be used in a GWAS are p-values, as a measure of statistical significance; odds ratios (OR), as a measure of effect size; or beta coefficients (beta), as a measure of effect size. Researchers often assume an additive genetic model and calculate an allelic odds ratio, which is the increased (or decreased) risk of disease conferred by each additional copy of an allele (compared to carrying no copies of that allele). An additional concept in design and interpretation of GWAS is that of linkage disequilibrium, which is the non-random association of alleles. The presence of linkage disequilibrium can obfuscate which variant is "causal."

Functional annotation of variants and/or wet lab experimentation can identify the causal genetic variant identified via GWAS, and in many cases may lead to the identification of disease-causing genes. In particular, understanding the functional effect of a causal genetic variant (for example, loss of protein function, gain of protein function, increase in gene expression, or decrease in gene expression) may allow that variant to be used as a proxy for therapeutic modulation of the target gene, or to gain insight into potential therapeutic efficacy and safety of a therapeutic that modulates that target.

Identification of such gene-disease associations has provided insights into disease biology and may be used to identify novel therapeutic targets for the pharmaceutical industry. In order to translate the therapeutic insights derived from human genetics, disease biology in patients may be exogenously 'programmed' into replicating the observation from human genetics. There are several potential options for therapeutic modalities that may be brought to bear in translating therapeutic targets identified via human genetics into novel medicines. These may include well established therapeutic modalities such as small molecules and monoclonal antibodies, maturing modalities such as oligonucleotides, and emerging modalities such as gene therapy and gene editing. The choice of therapeutic modality can depend on several factors including the location of a target (for example, intracellular, extracellular, or secreted), a relevant tissue (for example, liver) and a relevant indication. Such studies may be conducted to identify specific liver disorder-related targets for siRNA or ASO inhibition by a composition or compound described herein.

Some embodiments include a method of making an oligonucleotide or siRNA using a method disclosed herein. For example, any aspect of an Example herein that includes steps for synthesis may be used. Some embodiments include making a GalNAc moiety, or making an oligonucleotide with a GalNAc moiety.

L siRNA

In some embodiments, the composition comprises an oligonucleotide that binds to a target oligonucleotide (e.g.

mRNA), wherein the oligonucleotide comprises a small interfering RNA (siRNA.). In some embodiments, the composition comprises an oligonucleotide that binds to a target oligonucleotide (e.g. mRNA), wherein the oligonucleotide comprises an siRNA comprising a sense strand and an antisense strand. In some embodiments, the sense strand comprises RNA. In some embodiments, the antisense strand comprises RNA.

In some embodiments, the sense strand is 12-30 nucleosides in length. In some embodiments, the sense strand is 14-30 nucleosides in length. In some embodiments, the sense strand is at least about 10, 11, 12, 13, 14, 15, 16, 17, 18, 19, 20, 21, 22, 23, 24, 25, 26, 27, 28, 29, or 30 nucleosides in length. In some embodiments, the sense strand is at least 12 nucleotides in length. In some embodiments, the sense strand is at least 14 nucleotides in length. In some embodiments, the sense strand is at least 16 nucleotides in length. In some embodiments, the sense strand is at least 18 nucleotides in length. In some embodiments, the sense strand is at least 20 nucleotides in length. In some embodiments, the sense strand is at least 22 nucleotides in length. In some embodiments, the sense strand is at least 24 nucleotides in length. In some embodiments, the sense strand is at least 26 nucleotides in length. In some embodiments, the sense strand is at least 28 nucleotides in length. In some embodiments, the sense strand is at least 30 nucleotides in length. In some embodiments, the sense strand is no more than about 10, 11, 12, 13, 14, 15, 16, 17, 18, 19, 20, 21, 22, 23, 24, 25, 26, 27, 28, 29, or 30 nucleosides in length. In some embodiments, the sense strand is no more than 12 nucleotides in length. In some embodiments, the sense strand is no more than 14 nucleotides in length. In some embodiments, the sense strand is no more than 16 nucleotides in length. In some embodiments, the sense strand is no more than 18 nucleotides in length. In some embodiments, the sense strand is no more than 20 nucleotides in length. In some embodiments, the sense strand is no more than 22 nucleotides in length. In some embodiments, the sense strand is no more than 24 nucleotides in length. In some embodiments, the sense strand is no more than 26 nucleotides in length. In some embodiments, the sense strand is no more than 28 nucleotides in length. In some embodiments, the sense strand is no more than 30 nucleotides in length.

In some embodiments, the antisense strand is 12-30 nucleosides in length. In soiree embodiments, the antisense strand is 14-30 nucleosides in length. In some embodiments, the antisense strand is at least about 10, 11, 12, 13, 14, 15, 16, 17, 18, 19, 20, 21, 22, 23, 24, 25, 26, 27, 28, 29, or 30 nucleosides in length. In some embodiments, the antisense strand is at least 12 nucleotides in length. In some embodiments, the antisense strand is at least 14 nucleotides in length. In some embodiments, the antisense strand is at least 16 nucleotides in length. In some embodiments, the antisense strand is at least 18 nucleotides in length. In some embodiments, the antisense strand is at least 20 nucleotides in length. In some embodiments, the antisense strand is at least 22 nucleotides in length. In some embodiments, the antisense strand is at least 24 nucleotides in length. In some embodiments, the antisense strand is at least 26 nucleotides in length. In some embodiments, the antisense strand is at least 28 nucleotides in length. In some embodiments, the antisense strand is at least 30 nucleotides in length. In some embodiments, the antisense strand is no more than about 10, 11, 12, 13, 14, 15, 16, 17, 18, 19, 20, 21, 22, 23, 24, 25, 26, 27, 28, 29, or 30 nucleotides in length. In some embodiments, the antisense strand is no more than 12 nucleotides in length. In some embodiments, the antisense strand is no more than 14 nucleotides in length. In some embodiments, the antisense strand is no more than 16 nucleotides in length. In some embodiments, the antisense strand is no more than 18 nucleotides in length. In some embodiments, the antisense strand is no more than 20 nucleotides in length. In some embodiments, the antisense strand is no more than 22 nucleotides in length. In some embodiments, the antisense strand is no more than 24 nucleotides in length. In some embodiments, the antisense strand is no more than 26 nucleotides in length. In some embodiments, the antisense strand is no more than 28 nucleotides in length. In some embodiments, the antisense strand is no more than 30 nucleotides in length. In some embodiments, the antisense strand is the same length as the sense strand.

In some embodiments, the composition comprises an oligonucleotide that inhibits the expression of a target oligonucleotide (e.g. mRNA), wherein the oligonucleotide comprises an siRNA comprising a sense strand and an antisense strand, wherein the sense strand is 12-30 nucleosides in length. In some embodiments, the composition comprises a sense strange that is 10, 11, 12, 13, 14, 15, 16, 17, 18, 19, 20, 21, 2:2, 2:3, 24, 25, 26, 27, 28, 29, or 30 nucleosides in length, or a range defined by any of the two aforementioned numbers. In some embodiments, the composition comprises an antisense strand is 12-30 nucleosides in length. In some embodiments, the composition comprises an antisense strange that is 10, 11, 12, 13, 14, 15, 16, 17, 18, 19, 20, 21, 22, 23, 24, 25, 26, 27, 28, 29, or 30 nucleosides in length, or a range defined by any of the two aforementioned numbers.

In some embodiments, the composition comprises an oligonucleotide that inhibits the expression of a target oligonucleotide (e.g. mRNA), wherein the oligonucleotide comprises an siRNA comprising a sense strand and an antisense strand, each strand is independently about 14-30 nucleosides in length, and at least one of the sense strand and the antisense strand comprises a nucleoside sequence comprising about 12-30 contiguous nucleosides of a full-length human target mRNA sequence. In some embodiments, at least one of the sense strand and the antisense strand comprise a nucleoside sequence comprising at least about 10, 11, 12, 13, 14, 15, 16, 17, 18, 19, 20, 21, 22, 23, 24, 25, 26, 27, 28, 29, 30, or more contiguous nucleosides of one of the full-length human target mRNA sequence.

In some embodiments, the composition comprises an oligonucleotide that inhibits the expression of a target protein, wherein the oligonucleotide comprises an siRNA comprising a sense strand and an antisense strand, wherein the sense strand and the antisense strand form a double-stranded RNA duplex. In some embodiments, the first base pair of the double-stranded. RNA duplex is an AU base pair.

In some embodiments, the sense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the sense strand further comprises a 5' overhang. In some embodiments, the 5' overhang comprises 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the antisense strand further comprises a 3' overhang. In some embodiments, the 3' overhang comprises 1, 2, 3, 4, 5, 6, 7, 8, 9, or 10 nucleosides, or a range of nucleotides defined by any two of the aforementioned numbers. In some embodiments, the 3' overhang comprises 1, 2, or more nucleosides. In some embodiments, the 3' overhang comprises 2 nucleosides. In some embodiments, the antisense strand further comprises a 5' overhang. In some embodiments, the 5' overhang comprises 1, 2, 3, 4, 5, 6, 7, 8, 9, or 10 nucleosides, or a range of nucleotides defined by any two of the aforementioned numbers. In some embodiments, the 5' overhang comprises 1, 2, or more nucleosides. In some embodiments, the 5' overhang comprises 2 nucleosides.

In some embodiments, the composition comprises an oligonucleotide that inhibits the expression of a target protein, wherein the oligonucleotide comprises an siRNA comprising a sense strand and an antisense strand, wherein the siRNA binds with a 19mer in a human target mRNA encoding the target protein. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a human target mRNA.

In some embodiments, the composition comprises an oligonucleotide that inhibits the expression of a target protein, wherein the oligonucleotide comprises an siRNA comprising a sense strand and an antisense strand, wherein the siRNA binds with a 17mer in a non-human primate target mRNA encoding the target protein. In some embodiments, the siRNA binds with a 12mer, a 13mer, a 14mer, a 15mer, a 16mer, a 17mer, a 18mer, a 19mer, a 20mer, a 21mer, a 22mer, a 23mer, a 24mer, or a 25mer in a non-human primate target mRNA.

In some embodiments, the composition comprises an oligonucleotide that inhibits the expression of a target protein, wherein the oligonucleotide comprises an siRNA comprising a sense strand and an antisense strand, wherein the siRNA binds with a 19mer in a human target mRNA encoding the target protein, or a combination thereof. In some embodiments, the siRNA binds with a 12mer, a 13mer, a 14mer, a 15mer, a 16mer, a 17mer, and 18mer, a 19mer, a 20mer, a 21mer, a 22mer, a 23mer, a 24mer, or a 25mer in a human target mRNA.

2. ASOs

In some embodiments, the composition comprises an oligonucleotide that inhibits expression of a target oligonucleotide (e.g. mRNA), wherein the oligonucleotide comprises an antisense oligonucleotide (ASO). In some embodiments, the ASO is 12-30 nucleosides in length. In some embodiments, the ASO is 14-30 nucleosides in length. In some embodiments, the ASO is 10, 11, 12, 13, 14, 15, 16, 17, 18, 19, 20, 21, 22, 23, 24, 25, 26, 27, 28, 29, or 30 nucleosides in length, or a range defined by any of the two aforementioned numbers. In some embodiments, the ASO is 15-25 nucleosides in length. In some embodiments, the ASO is 20 nucleosides in length. In some embodiments, the ASO comprises DNA.

In some embodiments, the ASO is 12-30 nucleosides in length. In some embodiments, the ASO is 14-30 nucleosides in length. In some embodiments, the ASO is at least about 10, 11, 12, 13, 14, 15, 16, 17, 18, 19, 20, 21, 22, 23, 24, 25, 26, 27, 28, 29, or 30 nucleosides in length. In some, embodiments, the ASO is at least 12 nucleotides in length. In some embodiments, the ASO is at least 14 nucleotides m length. In some embodiments, the ASO is at least 16 nucleotides in length. In some embodiments, the ASO is at least 18 nucleotides in length. In some embodiments, the ASO is at least 20 nucleotides in length. In some embodiments, the ASO is at least 22 nucleotides in length. In some embodiments, the ASO is at least 24 nucleotides in length. In some embodiments, the ASO is at least 26 nucleotides in length. In some embodiments, the ASO is at least 28 nucleotides in length. In some embodiments, the ASO is at least 30 nucleotides in length. In some embodiments, time ASO is no more than about 10, 11, 12, 13, 14, 15, 16, 17, 18, 19, 20, 21, 22, 23, 24, 25, 26, 27, 28.29 or 30 nucleosides in length. In some embodiments, the ASO is no more than 12 nucleotides in length. In some embodiments, the ASO is no more than 14 nucleotides in length. In some embodiments, the ASO is no more than 16 nucleotides in length. In some embodiments, the ASO is no more than 18 nucleotides in length. In some embodiments, the ASO is no more than 20 nucleotides in length. In some embodiments, the ASO is no more than 22 nucleotides in length. In some embodiments, the ASO is no more than 24 nucleotides in length. In some embodiments, the ASO is no more than 26 nucleotides in length. In some embodiments, the ASO is no more than 28 nucleotides in length. In some embodiments, the ASO is no more than 30 nucleotides in length.

In some embodiments, the composition comprises an oligonucleotide that inhibits the expression of a target protein, wherein the oligonucleotide comprises an ASO about 12-30 nucleosides in length and comprising a nucleoside sequence complementary to about 12-30 contiguous nucleosides of a full-length human pre-mRNA target sequence encoding the target protein; wherein (r) the oligonucleotide comprises a modification comprising a modified nucleoside and/or a modified internucleoside linkage, and/or (ii) the composition comprises a pharmaceutically acceptable carrier.

In some embodiments, the composition comprises an oligonucleotide that inhibits the expression of a target protein, wherein the oligonucleotide comprises an ASO about 12-30 nucleosides in length and comprising a nucleoside sequence complementary to about 12-30 contiguous nucleosides of a full-length human target mRNA sequence encoding the target protein; wherein (i) the oligonucleotide comprises a modification comprising a modified nucleoside and/or a modified internucleoside linkage, and/or (ii) the composition comprises a pharmaceutically acceptable carrier.

1. Oligonucleotide modification patterns

In some embodiments, the composition comprises an oligonucleotide that binds to a target oligonucleotide, wherein the oligonucleotide comprises a modification comprising a modified nucleoside and/or a modified internucleoside linkage, and/or (ii) the composition comprises a pharmaceutically acceptable carrier. In some embodiments, the oligonucleotide comprises a modification comprising a modified nucleoside and/or a modified internucleoside linkage. In some embodiments, the oligonucleotide comprises a modified internucleoside linkage. In some embodiments, the modified internucleoside linkage comprises alkylphosphonate, phosphorothioate, methylphosphonate, phosphorodithioate, alkylphosphonothioate, phosphoramidate, carbamate, carbonate, phosphate triester, acetamidate, or carboxymethyl ester, or a combination thereof. In some embodiments, the modified internucleoside linkage comprises one or more phosphorothioate linkages. Benefits of the modified internucleoside linkage may include decreased toxicity or improved pharmacokinetics.

In some embodiments, the composition comprises an oligonucleotide that binds to a target oligonucleotide, wherein the oligonucleotide comprises a modified internucleoside linkage, wherein the oligonucleotide comprises 1, 2, 3, 4, 5, 6, 7, 8, 9, 10, 11, 12, 13, 14, 15, 16, 17, 18, 19, or 20 modified internucleoside linkages, or a range of modified internucleoside linkages defined by any two of the aforementioned numbers. In some embodiments, the oligonucleotide comprises no more than 18 modified internucleoside linkages. In some embodiments, the oligonucleotide comprises no more than 20 modified internucleoside linkages. In some embodiments, the oligonucleotide comprises 2 or more modified internucleoside linkages, 3 or more modified internucleoside linkages, 4 or more modified internucleoside linkages, 5 or more modified internucleoside linkages, 6 or more modified internucleoside linkages, 7 or more modified internucleoside linkages, 8 or more modified internucleoside linkages, 9 or more modified internucleoside linkages, 10 or more modified internucleoside linkages, 11 or more modified internucleoside linkages, 12 or more modified internucleoside linkages, 13 or more modified internucleoside linkages, 14 or more modified internucleoside linkages, 15 or more modified internucleoside linkages, 16 or more modified internucleoside linkages, 17 or more modified internucleoside linkages, 18 or more modified internucleoside linkages, 19 or more modified internucleoside linkages, or 20 or more modified internucleoside linkages.

In some embodiments, the composition comprises an oligonucleotide that binds to a target oligonucleotide, wherein the oligonucleotide comprises the modified nucleoside. In some embodiments, the modified nucleoside comprises a locked nucleic acid (LNA), hexitol nucleic acid (HLA), cyclohexane nucleic acid (CeNA), 2'-methoxyethyl, 2'-O-alkyl, 2'-O-allyl, 2'-fluoro, or 2'-deoxy, or a combination thereof. In some embodiments, the modified nucleoside comprises a LNA. In some embodiments, the modified nucleoside comprises a 2',4' constrained ethyl nucleic acid. In some embodiments, the modified nucleoside comprises HLA. In some embodiments, the modified nucleoside comprises CeNA. In some embodiments, the modified nucleoside comprises a 2'-methoxyethyl group. In some embodiments, the modified nucleoside comprises a 2'-O-alkyl group. In some embodiments, the modified nucleoside comprises a 2'-O-allyl group. In some embodiments, the modified nucleoside comprises a 2'-fluoro group. In some embodiments, the modified nucleoside comprises a 2'-deoxy group. In some embodiments, the modified nucleoside comprises a 2'-O-methyl nucleoside, T-deoxyfluoro nucleoside, 2'-O—N-methylacetamido (2'-O-NMA) nucleoside, a T-O-dimethylaminoethoxyethyl (2'-O-DMAEOE) nucleoside, 2'-O-aminopropyl (2'-O-AP) nucleoside, or 2'-am-F, or a combination thereof. In some embodiments, the modified nucleoside comprises a 2'-O-methyl nucleoside. In some embodiments, the modified nucleoside comprises a 2'-deoxyfluoro nucleoside. In some embodiments, the modified nucleoside comprises a 2c-O-NMA nucleoside. In some embodiments, the modified nucleoside comprises a 2'-O-DMAEOE nucleoside. In some embodiments, the modified nucleoside comprises a 2'-O-aminopropyl (2'-O-AP) nucleoside. In some embodiments, the modified nucleoside comprises 2'-ara-F. In some embodiments, the modified nucleoside comprises one or more 2' fluoro modified nucleosides. In some embodiments, the modified nucleoside comprises a 2' O-alkyl modified nucleoside. Benefits of the modified nucleoside may include decreased toxicity or improved pharmacokinetics.

In some embodiments, the oligonucleotide comprises 1, 2, 3, 4, 5, 6, 7, 8, 9, 10, 11, 12, 13, 14, 15, 16, 17, 18, 19, 20, or 21 modified nucleosides, or a range of nucleosides defined by any two of the aforementioned numbers. In some embodiments, the oligonucleotide comprises no more than 19 modified nucleosides. In some embodiments, the oligonucleotide comprises no more than 21 modified nucleosides. In some embodiments, the oligonucleotide comprises 2 or more modified nucleosides, 3 or more modified nucleosides, 4 or more modified nucleosides, 5 or more modified nucleosides, 6 or more modified nucleosides, 7 or more modified nucleosides, 8 or more modified nucleosides, 9 or more modified nucleosides, 10 or more modified nucleosides, 1.1 or more modified nucleosides, 12 or more modified nucleosides, 13 or more modified nucleosides, 14 or more modified nucleosides. 15 or more modified nucleosides, 16 or more modified nucleosides, 17 or more modified nucleosides, 18 or more modified nucleosides, 19 or more modified nucleosides, 20 or more modified nucleosides, or 21 or more modified nucleosides.

In some embodiments, the composition comprises an oligonucleotide that binds to a target oligonucleotide, wherein the oligonucleotide comprises a lipid attached at a 3' or 5' terminus of the oligonucleotide. In some embodiments, the lipid comprises cholesterol, myristoyl, palmitoyl, stearoyl, lithocholoyl, docosanoyl, docosahexaenoyl, myristyl, palmityl stearyl, or α-tocopherol, or a combination thereof.

In some embodiments, the composition comprises an oligonucleotide that inhibits the expression of a target mRNA, wherein the oligonucleotide comprises a sugar moiety. The sugar moiety may include an N-acetyl galactose moiety (e.g. an N-acetylgalactosamine (GalNAc) moiety), an —N-acetyl glucose moiety (e.g. an N-acetylglucosamine (GlcN-Ac) moiety), a fucose moiety, or a mannose moiety. The sugar moiety may include 1, 2, 3, or more sugar molecules. The sugar moiety may be attached at a 3' or 5' terminus of the oligonucleotide. The sugar moiety may include an N-acetyl galactose moiety. The sugar moiety may include as N-acetylgalactosamine (GalNAc) moiety. The sugar moiety may include an N-acetyl glucose moiety. The sugar moiety may include N-acetylglucosamine (GlcNAc) moiety. The sugar moiety may include a fucose moiety. The sugar moiety may include a mannose moiety. N-acetyl glucose, GlcNAc, fucose, or mannose may be useful for targeting macrophages since they may target or hind a mannose receptor such as CD206.

In some embodiments, the composition comprises an oligonucleotide that inhibits the expression of a target mRNA, wherein the oligonucleotide comprises an N-acetyl-galactosamine (GalNAc) moiety. GalNAc may be useful for hepatocyte targeting. In some embodiments, the composition comprises GalNAc. In some embodiments, the composition comprises a GalNAc derivative. The GalNAc moiety may include 1, 2, 3, or more GalNAc molecules. The GalNAc moiety may include a bivalent or trivalent branched linker. The oligo may be attached to 1, 2 or 3 GalNAcs through a bivalent or trivalent branched linker. The GalNAc moiety may be attached at a 3' or 5' terminus of the oligonucleotide.

The oligonucleotide may include purities. Examples of purines include adenine (A) or guanine (G), or modified versions thereof. The oligonucleotide may include pyrimidines. Examples of pyrimidines include cytosine (C), thymine (T), or uracil (U), or modified versions thereof.

In some embodiments, purines of the oligonucleotide comprise 2' fluoro modified purines. In some embodiments, purines of the oligonucleotide comprise 2s-O-methyl modified purines. In some embodiments, purines of the oligonucleotide comprise a mixture of 2' fluoro and 2'-O-methyl modified purines. In some embodiments, all purines of the oligonucleotide comprise 2' fluoro modified purines. In some embodiments, all purines of the oligonucleotide comprise 2'-O-methyl modified purines. In some embodiments, all purines of the oligonucleotide comprise a mixture of 2' fluoro and 2'-O-methyl modified purines. In some embodiments, 2'-O-methyl includes 2' O-methyl.

In some embodiments, pyrimidines of the oligonucleotide comprise 2' fluoro modified pyrimidines. In some embodiments, pyrimidines of the oligonucleotide comprise 2'-O-methyl modified pyrimidines. In some embodiments, pyrimidines of the oligonucleotide comprise a mixture of 2' fluoro and 2'-O-methyl modified pyrimidines. In some embodiments, all pyrimidines of the oligonucleotide comprise 2' fluoro modified pyrimidines. In some embodiments, all pyrimidines of the oligonucleotide comprise 2'O-methyl modified pyrimidines. In Kale embodiments, all pyrimidines of the oligonucleotide comprise a mixture of 2' fluoro and 2s-O-methyl modified pyrimidines.

In some embodiments, purines of the oligonucleotide comprise 2' fluoro modified purines, and pyrimidines of the oligonucleotide comprise a mixture of 2' fluoro and 2'-O-methyl modified pyrimidines. In some embodiments, purines of the oligonucleotide comprise 2s-O-methyl modified purines, and pyrimidines of the oligonucleotide comprise a mixture of 2' fluoro and 2'-O-methyl modified pyrimidines. In some embodiments, purines of the oligonucleotide comprise 2' fluoro modified purities, and pyrimidines of the oligonucleotide comprise 2'-O-methyl modified pyrimidines. In some embodiments, purines of the oligonucleotide comprise 2'-O-methyl modified purines, and pyrimidines of the oligonucleotide comprise 2' fluoro modified pyrimidines. In some embodiments, pyrimidines of the oligonucleotide comprise 2' fluoro modified pyrimidines, and purines of the oligonucleotide comprise a mixture of 2' fluoro and 2s-O-methyl modified purines. In some embodiments, pyrimidines of the oligonucleotide comprise 2%0-meth 71 modified pyrimidines, and purines of the oligonucleotide comprise a mixture of 2' fluoro and 2'-O-methyl modified purines. In some embodiments, pyrimidines of the oligonucleotide comprise 2' fluoro modified pyrimidines, and purines of the oligonucleotide comprise 2'-O-methyl modified purines. In some embodiments, pyrimidines of the oligonucleotide comprise 2'O-methyl modified pyrimidines, and purines of the oligonucleotide comprise 2' fluoro modified purities.

In some embodiments, all purines of the oligonucleotide comprise 2' fluoro modified purines, and all pyrimidines of the oligonucleotide comprise a mixture of 2' fluoro and 2'-O-methyl modified pyrimidines. In some embodiments, all purines of the oligonucleotide comprise 2'-O-methyl modified purines, and all pyrimidines of the oligonucleotide comprise a mixture of 2' fluoro and 2'O-methyl modified pyrimidines. In some embodiments, all purines of the oligonucleotide comprise 2' fluoro modified purines, and all pyrimidines of the oligonucleotide comprise 2'O-methyl modified pyrimidines. Iii some embodiments, all purines of the oligonucleotide comprise 2'-O-methyl modified purines, and all pyrimidines of the oligonucleotide comprise 2' fluoro modified pyrimidines. In some embodiments, all pyrimidines of the oligonucleotide comprise 2' fluoro modified pyrimidines, and all purines of the oligonucleotide comprise a mixture of 2' fluoro and 2'-O-methyl modified purines. In some embodiments, all pyrimidines of the oligonucleotide comprise 2'O-methyl modified pyrimidines, and all purines of the oligonucleotide comprise a mixture of 2' fluoro and 2'O-methyl modified purines. In some embodiments, all pyrimidines of the oligonucleotide comprise 2' fluoro modified pyrimidines, and all purines of the oligonucleotide comprise 2'-O-methyl modified purines. In some embodiments, all pyrimidines of the oligonucleotide comprise methyl modified pyrimidines, and all purines of the oligonucleotide comprise 2' fluoro modified purines, 2. siRNA modification patterns In some embodiments, the sense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, or 29 modified internucleoside linkages, or a range of modified internucleoside linkages defined by any two of the aforementioned integers. In some embodiments, the sense strand comprises 1-11 modified internucleoside linkages. In some embodiments, the sense strand comprises 2-6 modified internucleoside linkages. In some embodiments, the sense strand comprises 5 modified internucleoside linkages. In some embodiments, the sense strand comprises 4 modified internucleoside linkages.

In some embodiments, the antisense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, or 29 modified internucleoside linkages, or a range of modified internucleoside linkages defined by any two of the aforementioned integers. In some embodiments, the antisense strand comprises 1-11 modified internucleoside linkages. In some embodiments, the antisense strand comprises 2-6 modified internucleoside linkages. In some embodiments, the antisense strand comprises 5 modified internucleoside linkages. In some embodiments, the antisense strand comprises 4 modified internucleoside linkages.

In some embodiments, the sense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 modified nucleosides, or a range of modified nucleosides defined by any two of the aforementioned integers. In some embodiments, the sense strand comprises 12-19 modified nucleosides. In some embodiments, the sense strand comprises 12-21 modified nucleosides. In some embodiments, the sense strand comprises 19 modified nucleosides. In some embodiments, the sense strand comprises 21 modified nucleosides.

In some embodiments, the antisense strand comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 modified nucleosides, or a range of modified nucleosides defined by any two of the aforementioned integers. In some embodiments, the antisense strand comprises 12-19 modified nucleosides. In some embodiments, the antisense strand comprises 12-21 modified nucleosides. In some embodiments, the antisense strand comprises 19 modified nucleosides. In some embodiments, the antisense strand comprises 21 modified nucleosides.

In some embodiments, the sense strand or the antisense strand further comprises at least 2 additional nucleosides attached to a 3' terminus of the sense strand or the antisense strand. In some embodiments, the sense strand or the antisense strand comprises 2 additional nucleosides attached to a 3' terminus of the sense strand or the antisense strand. As part of the sense strand, the additional nucleosides may or may not be complementary to a target mRNA. The additional nucleosides of the antisense strand may include a uracil. The 2 additional nucleosides of the antisense strand may both include uracil.

In some embodiments, the sense strand or the sense strand further comprises at least 2 additional nucleosides attached to a 3' terminus of the sense strand or the sense strand. In some embodiments, the sense strand or the sense strand comprises 2 additional nucleosides attached to a 3' terminus of the sense strand or the sense strand. The additional nucleosides of the sense strand may include a uracil. The 2 additional nucleosides of the sense strand may both include uracil.

In some embodiments, the composition comprises an oligonucleotide that binds to a target oligonucleotide, wherein the oligonucleotide comprises an siRNA comprising a sense strand and an antisense strand, wherein the sense strand comprises a modification pattern. In some embodiments, the sense strand comprises modification pattern 1S: 5'-NfsnsNftiNfriNfNfNfNiiiNfriNfriNfnNfriNfsnsn-3', wherein "—Nf" is a 2' fluoro-modified nucleoside, "n" is a 2' O-methyl modified nucleoside, and "s" is a phosphorothioate linkage. In some embodiments, the sense strand comprises modification pattern 1S#2: 5'-NfriNfriNfiiNfMN-fiiNftiNftiNfiiNfriNfstisn-3', wherein "Ni" is a 2' fluoro-modified nucleoside, "n" is a 2' O-methyl modified nucleoside, and "s" is a phosphorothioate linkage. In some embodiments, the sense strand comprises modification pattern 2S: 5'-nsnsnnNfnNfNfNfnrinnininrinnsnsri-3' wherein "Nf" is a 2' fluoro-modified nucleoside, "n" is a 2' O-methyl modified nucleoside, and "s" is a phosphorothioate linkage. In some embodiments, the sense strand comprises modification pattern 2S #2: 5'-rinnriNfliNiNfNfiumnrinninmsnsn-3', wherein "NI" is a 2' fluoro-modified nucleoside, "n" is a 2' O-) methyl modified nucleoside, and "s" is a phosphorothioate linkage. In some embodiments, the sense strand comprises modification pattern 3S: 5'-nsnsnnNfriNfiiNfinninnnnininsnsn-3', wherein "NI" is a 2' fluoro-modified nucleoside, "n" is a 2' O-methyl modified nucleoside, and "s" is a phosphorothioate linkage. In some embodiments, the sense strand comprises modification pattern 3S#2: 5'-im-miNfriNfriNfnnimmtinniisnsn-3', wherein "NI" is a 2' fluoro-modified nucleoside, "n" is a 2' O-methyl modified nucleoside, and "s" is a phosphorothioate linkage. In some embodiments, the sense strand comprises modification pattern 4S: 5'-NfsnsNfriNfnNfNfNfnNfriNfliNfliNfliNfsnsliN-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 4S #2: 5'-NfnNfriNfiiNfNiNfnNfliNfliNfliNfliNfsn-siiN-3', wherein "NI" is a 2' fluoro-modified nucleoside, "n" is a 2' O-methyl modified nucleoside. "s" is a phosphorothioate linkage, and N comprises one or more nucleosides. In some embodiments, the sense strand comprises modification pattern 5S: 5'-nsitsrinNfnNfNfNfninumnrinniisiisnN-3', wherein "NI" is a 2' fluoro-modified nucleoside, "n" is a 2' o-methyl modified nucleoside, "s" is a phosphorothioate linkage, and N comprises one or inure nucleosides. In some embodiments, the sense strand comprises modification pattern 5S #2.: 5'-nnrinNfliNfNfNflihnniirinnniisnsnN-3', wherein "Nf" is a 2' fluoro-modified nucleoside. "n" is a 2' O-methyl modified nucleoside, "s" is a phosphorothioate linkage, and N comprises one or more nucleosides. In some embodiments, the sense strand comprises modification pattern 6S: 5'-NfsnsNfliNfliNfiiNfnNfnNfrNfnNfriNfiiNfsnsn-3', wherein "Nf" is a 2' fluoro-modified nucleoside, "n" is a 2' O-methyl modified nucleoside, "s" is a phosphorothioate linkage, and N comprises one or more nucleosides. In some embodiments, the sense strand comprises modification pattern 6S#2: 5'-NfriNfliNftiNftiNftiNfiiNfriNfnNfnNfsristi-3', wherein "NI" is a 2' fluoro-modified nucleoside, "n" is a 2' O-methyl modified nucleoside, "s" is a phosphorothioate linkage, and N comprises one or more nucleosides. In some embodiments, the sense strand comprises any one of modification patterns 1S, 2S, 3S, 4S, 5S, or 6S. In some embodiments, the sense strand comprises any one of modification patterns 1S #2, 2S#2, 3S#2, 4S #2, 5S#2, or 6S#2. In some embodiments, the sense strand comprises any one of modification patterns 1S, 3S, 4S, or 6S. In some embodiments, the sense strand comprises any one of modification patterns 1S #2, 3S #2, 4S#2, or 6S#2. Any one of modification patterns 1S-6S may include a GalNAc ligand attached to the 3' end. Any one of modification patterns 1S-6S may include a GalNAc ligand attached to the 5' end. Any one of modification patterns 1S-6S#2 may include a GalNAc ligand attached to the 3' end. Any one of modification patterns 1S-6S#2 may include a GalNAc ligand attached to the 5' end.

In some embodiments, the composition comprises an oligonucleotide that binds to a target oligonucleotide, wherein the oligonucleotide comprises an siRNA comprising a sense strand and an antisense strand, wherein the antisense strand comprises a modification pattern. In some embodiments, the antisense strand comprises modification pattern 1AS: 5'-nsNfsnNfhNtiiNfiiNftniliNfriNfnNfnsnsii-3', wherein "Nf" is a 2' fluoro-modified nucleoside, "n" is a 2' O-methyl modified nucleoside, and "s" is a phosphorothioate linkage. In some embodiments, the antisense strand comprises modification pattern 2AS: 5'-nsNfsnrinNfnNfNf-mumNfriNfilrinsrisri-3', wherein "Nf" is a 2' fluoro-modified nucleoside, "n" is a 2' O-methyl modified nucleoside, and "s" is a phosphorothioate linkage. In some embodiments, the antisense strand comprises modification pattern 3AS: 5'-nsNfsmiliNfnnrinntiliNfnNfnnrisnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 4l AS: 5'-nsNfstiNftiNfiumnrintiNfuN-frinnsnsn-3', wherein ' is a 2' fluoro-modified nucleoside. "n" is a 2' O-methyl modified nucleoside, and "s" is a phosphorothioate linkage. In some embodiments, the antisense strand comprises modification pattern 5AS: 5'-nsNfsn-ruiNfuNfimnnnNfliNflumsnsn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 6AS: 5'-nsNfsnNfnNthNfhNtiiNfiiNfiiNfiiNflistisn-3', wherein "Nf" is a 2' fluoro-modified nucleoside, "n" is a 2' O-methyl modified nucleoside, and "s" is a phosphorothioate linkage. In some embodiments, the antisense strand comprises modification pattern 7AS: 5'-nsNfsriN-friNfnNfNfmumNfriNfiirinsrisn.-3', wherein "Nf" is a 2' fluoro-modified nucleoside, "n" is a 2' O-methyl modified nucleoside, and "s" is a phosphorothioate linkage. In some embodiments, the antisense strand comprises modification pattern 8AS: 5'-nsNfsminnnnimminNfnniumsnsn-3', wherein "Ni" is a 2' fluoro-modified nucleoside, "n" is a 2' O-methyl modified nucleoside, and "s" is a phosphorothioate linkage. In some embodiments, the antisense strand comprises modification pattern 9AS: 5'-nsNfsnrinNfrinrum-rinNfnNfriNfrisnsn-3', wherein "Nf" is a 2' fluoro-modified nucleoside, "n" is a 2' O-methyl modified nucleoside, and "s" is a phosphorothioate linkage. Any one of modification patterns 1AS-9AS may include a GalNAc ligand attached to the 3' end. Any one of modification patterns 1AS-9AS may include a GalNAc ligand attached to the 5' end.

The modifications in any of the modification patterns may be optional. For example, 1, 2, 3 or more phosphorothioate linkages in any of modification patterns 1S-6S, 1 S#2-6S#2, or 1AS-9AS may be replaced with an unmodified linkage, or with a different modified linkage. In some cases, 1, 2, 3, or more modified nucleosides in any of modification patterns 1S-6S or 1AS-9AS may be replaced with an unmodified nucleoside, or with a different modified nucleoside.

In some embodiments, the composition comprises an oligonucleotide that inhibits the expression of a target mRNA wherein the oligonucleotide comprises an siRNA comprising a sense strand and an antisense strand, wherein the sense strand comprises modification pattern 1S and the antisense strand comprises modification pattern 1AS, 2AS, 3AS, 4AS, 5AS, 6AS, 7AS, 8AS, or 9AS. In some embodiments, the sense strand comprises modification pattern 2S and the antisense strand comprises modification pattern 1AS, 2AS, 3AS, 4AS, 5AS, 6AS, 7AS, 8AS, or 9AS. In some embodiments, the sense strand comprises modification pattern 3S and the antisense strand comprises modification pattern 1AS, 2AS, 3AS, 4AS, 5AS, 6AS, 7AS, 8AS, or 9AS. In some embodiments, the sense strand comprises modification pattern 4S and the antisense strand comprises modification pattern 1AS, 2AS, 3AS, 4AS, 5AS, 6AS, 7AS, 8AS, or 9AS. In some embodiments, the sense strand comprises modification pattern 5S and the antisense strand comprises modification pattern 1AS, 2AS, 3AS, 4AS, 5AS, 6AS, 7AS, 8AS, or 9AS. In some embodiments, the sense strand comprises modification pattern 6S and the antisense strand comprises modification pattern 1AS, 2AS, 3AS, 4AS, 5AS, 6AS, 7AS. 8AS, or 9AS. In some embodiments, the sense strand comprises modification pattern 1AS, 2AS, 3AS, 4AS, 5AS, 6AS, 7AS, 8AS, or 9AS, In some embodiments, the sense strand comprises modification pattern 1S #2 and the antisense strand comprises modification pattern 1AS, 2AS, 3AS, 4AS, 5AS. 6AS, 7AS. 8AS or 9AS. In some embodiments, the sense strand comprises modification pattern 2S#2 and the antisense strand comprises modification pattern 1AS, 2AS, 3AS, 4AS, 5AS, 6AS, 7AS, 8AS, or 9AS. In some embodiments, the sense strand comprises modification pattern 3S#2 and the antisense strand comprises modification pattern 1AS, 2AS, 3AS, 4AS, 5AS, 6AS, 7AS, 8AS, or 9AS. In some embodiments, the sense strand comprises modification pattern 4S #2 and the antisense strand comprises modification pattern 1AS, 2AS, 3AS, 4AS, 5AS, 6AS, 7AS, 8AS, or 9AS. In some embodiments, the sense strand comprises modification pattern 5S #2 and the antisense strand comprises modification pattern 1AS, 2AS, 3AS, 4AS, 5AS, 6AS, 7AS, 8AS or 9AS. In some embodiments, the sense strand comprises modification pattern 6S#2 and the antisense strand comprises modification pattern 1AS, 2AS, 5AS, 4AS, 5AS, 6AS, 7AS, 8AS, or 9AS. In some embodiments, the antisense strand comprises modification pattern 1AS, 2AS, 3AS, 4AS, 5AS. 6AS, 7AS, 8AS, or 9AS, In some embodiments, the sense strand or the antisense strand comprises modification pattern ASO1.

Any combination of sense and antisense modification patterns may be used. In some embodiments, the sense strand comprises modification pattern 1S, and the antisense strand comprises modification pattern 1AS. In some embodiments, the sense strand comprises modification pattern 2S, and the antisense strand comprises modification pattern 2AS. In some embodiments, the sense strand comprises modification pattern 2S, and the antisense strand comprises modification pattern 3AS. In some embodiments, the sense strand comprises modification pattern 3S, and the antisense strand comprises modification pattern 1AS. In some embodiments, the sense strand comprises modification pattern 3S, and the antisense strand comprises modification pattern 4AS. In some embodiments, the sense strand comprises modification pattern 3S, and the antisense strand comprises modification pattern 5AS. In some embodiments, the sense strand comprises modification pattern 3S, and the antisense strand comprises modification pattern 6AS. In some embodiments, the sense strand comprises modification pattern 3S, and the antisense strand comprises modification pattern 7AS, In some embodiments, the sense strand comprises modification pattern 3S, and the antisense strand comprises modification pattern 8AS. In some embodiments, the sense strand comprises modification pattern 6S, and the antisense strand comprises modification pattern 1AS. In some embodiments, the sense strand comprises modification pattern 6S, and the antisense strand comprises modification pattern 4AS. In some embodiments, the sense strand comprises modification pattern 6S, and the antisense strand comprises modification pattern 5AS. In some embodiments, the sense strand comprises modification pattern 6S, and the antisense strand comprises modification pattern 6AS. In some embodiments, the sense strand comprises modification pattern 6S, and the antisense strand comprises modification pattern 7AS. In some embodiments, the sense strand comprises modification pattern 6S, and the antisense strand comprises modification pattern 8AS. In some embodiments, the sense strand comprises modification pattern 1S#2, and the antisense strand comprises modification pattern 1AS. In some embodiments, the sense strand comprises modification pattern 2S#2, and the antisense strand comprises modification pattern 2AS. In some embodiments, the sense strand comprises modification pattern 2S#2, and the antisense strand comprises modification pattern 3AS. In some embodiments, the sense strand comprises modification pattern 3S #2, and the antisense strand comprises modification pattern 1AS. In some embodiments, the sense strand comprises modification pattern 3S#2, and the antisense strand comprises modification pattern 4AS. In some embodiments, the sense strand comprises modification pattern 3S#2, and the antisense strand comprises modification pattern 5AS. In some embodiments, the sense strand comprises modification pattern 3S#2, and the antisense strand comprises modification pattern 6AS. In some embodiments, the sense strand comprises modification pattern 3S#2, and the antisense strand comprises modification pattern 7AS. In some embodiments, the sense strand comprises modification pattern 3S #2, and the antisense strand comprises modification pattern 8AS. In some embodiments, the sense strand comprises modification pattern 6S#2, and the antisense strand comprises modification pattern 1AS. In some embodiments, the sense strand comprises modification pattern 6S#2, and the antisense strand comprises modification pattern 4AS. In some embodiments, the sense strand comprises modification pattern 6S #2, and the antisense strand comprises modification pattern 8AS. In some embodiments, the sense strand comprises modification pattern 6S#2, and the antisense strand comprises modification pattern 6AS. In some embodiments, the sense strand comprises modification pattern 6S #2, and the antisense strand comprises modification pattern 7AS, In some embodiments, the sense strand comprises modification pattern 6S#2, and the antisense strand comprises modification pattern 8AS.

In some embodiments, purines of the sense strand comprise 2' fluoro modified purines. In some embodiments, purines of the sense strand comprise 2'O-methyl modified purines. In some embodiments, purines of the sense strand comprise a mixture of 2' fluoro and 2'-O-methyl modified purines. In some embodiments, all purines of the sense strand comprise 2' fluoro modified purines. In some embodiments, all purines of the sense strand comprise 2'O-methyl modified purities. In some embodiments, all purines of the sense strand comprise a mixture of 2' fluoro and 2'O-methyl modified purines.

In some embodiments, pyrimidines of the sense strand comprise 2' fluoro modified pyrimidines. In some embodiments, pyrimidines of the sense strand comprise 2'O-methyl modified pyrimidines. In some embodiments, pyrimidines of the sense strand comprise a mixture of 2' fluoro and 2'-O-methyl modified pyrimidines. In some embodiments, all pyrimidines of the sense strand comprise 2' fluoro modified pyrimidines. In some embodiments, all pyrimidines of the sense strand comprise 2'O-methyl modified pyrimidines. In some embodiments, all pyrimidines of the sense strand comprise a mixture of 2' fluoro and 2'-O-methyl modified pyrimidines. In some embodiments, purities of the sense strand comprise 2' fluoro modified purines, and pyrimidines of the sense strand comprise a mixture of 2' fluoro and 2'O-methyl modified pyrimidines. In some embodiments, purines of the sense strand comprise 2'O-methyl modified purines, and pyrimidines of the sense strand comprise a mixture of 2' fluoro and 2'-O-methyl modified pyrimidines. In some embodiments, purities of the sense strand comprise 2' fluoro modified purines, and pyrimidines of the sense strand comprise 2'-O-methyl modified pyrimidines. In some embodiments, purines of the sense strand comprise 2'O-methyl modified purines, and pyrimidines of the sense strand comprise 2' fluoro modified pyrimidines. In some embodiments, pyrimidines of the sense strand comprise 2' fluoro modified pyrimidines, and purines of the sense strand comprise a mixture of 2' fluoro and 2'-O-methyl modified purines. In some embodiments, pyrimidines of the sense strand comprise 2'O-methyl modified pyrimidines, and purines ofthe sense strand comprise a mixture of 2' fluoro and 2'O-methyl modified purines. In some embodiments, pyrimidines of the sense strand comprise 2' fluoro modified pyrimidines, and purines of the sense strand comprise 2'-O-methyl modified purines. In some embodiments, pyrimidines of the sense strand comprise 2'-O-methyl modified pyrimidines, and purines of the sense strand comprise 2' fluoro modified purines.

In some embodiments, all purines of the sense strand comprise 2: fluoro modified purines, and all pyrimidines of the sense strand comprise a mixture of 2' fluoro and 2'-O-methyl modified pyrimidines. In some embodiments, all purines of the sense strand comprise 2'-O-methyl modified purines, and all pyrimidines of the sense strand comprise a mixture of 2' fluoro and 2'-O-methyl modified pyrimidines, Iii some embodiments, all purines of the sense strand comprise 2' fluoro modified purities, and all pyrimidines of the sense strand comprise 2'43-methyl modified pyrimidines. In some embodiments, all purities of the sense strand comprise 2'O-methyl modified purines, and all pyrimidines of the sense strand comprise 2' fluoro modified pyrimidines. In some embodiments, all pyrimidines of the sense strand comprise 2' fluoro modified pyrimidines, and all purines of the sense strand comprise a mixture of 2' fluoro and 2'-O-methyl modified purines. In some embodiments, all pyrimidines of the sense strand comprise 2'-O-methyl modified pyrimidines, and all purines of the sense strand comprise a mixture of 2' fluoro and 2'O-methyl modified purines. In some embodiments, all pyrimidines of the sense strand comprise 2' fluoro modified pyrimidines, and all purities of the sense strand comprise 2'-O-methyl modified purines. In sonnei embodiments, all pyrimidines of the sense strand comprise 2'43-methyl modified pyrimidines, and all purines of the sense strand comprise 2' fluoro modified purines.

In some embodiments, purines of the antisense strand comprise 2' fluoro modified purines. In some embodiments, purines of the antisense strand comprise 2'O-methyl modified purines. In some embodiments, purines of the antisense strand comprise a mixture of 2' fluoro and 2'O-methyl modified purines. In some embodiments, all purines of the antisense strand comprise 2' fluoro modified purines. In some embodiments, all purines of the antisense strand comprise 2s-O-methyl modified purines. In some embodiments, all purines of the antisense strand comprise a mixture of 2' fluoro and 2s-O-methyl modified purines.

In some embodiments, pyrimidines of the antisense strand comprise 2' fluoro modified pyrimidines. In some embodiments, pyrimidines of the antisense strand comprise 2s-O-methyl modified pyrimidines. In some embodiments, pyrimidines of the antisense strand comprise a mixture of 2' fluoro and 2s-O-methyl modified pyrimidines. In some embodiments, all pyrimidines of the antisense strand comprise 2' fluoro modified pyrimidines. In some embodiments, all pyrimidines of the antisense strand comprise 2s-O-methyl modified pyrimidines. In some embodiments, all pyrimidines of the antisense strand comprise a mixture of 2' fluoro and 2'-O-methyl modified pyrimidines.

In some embodiments, purines of the antisense strand comprise 2' fluoro modified purines, and pyrimidines of the antisense strand comprise a mixture of 2' fluoro and 2'-O-methyl modified pyrimidines. In some embodiments, purines of the antisense strand comprise 2'O-methyl modified purines, and pyrimidines of the antisense strand comprise a mixture of 2' fluoro and 2'-O-methyl modified pyrimidines. In some embodiments, purines of the antisense strand comprise 2' fluoro modified purines, and pyrimidines of the antisense strand comprise 2'-O-methyl modified pyrimidines. In some embodiments, purines of the antisense strand comprise 2'-O-methyl modified purines, and pyrimidines of the antisense strand comprise 2' fluoro modified pyrimidines. In some embodiments, pyrimidines of the antisense strand comprise 2' fluoro modified pyrimidines, and purines of the antisense strand comprise a mixture of 2' fluoro and 2'-O-methyl modified purines. In some embodiments, pyrimidines of the antisense strand comprise 2'-O-methyl modified pyrimidines, and purities of the antisense strand comprise a mixture of 2' fluoro and 2'-O-methyl modified purines. In some embodiments, pyrimidines of the antisense strand comprise 2' fluoro modified pyrimidines, and purines of the antisense strand comprise 2'-O-methyl modified purines. In some embodiments, pyrimidines of the antisense strand comprise 2'-O-methyl modified pyrimidines, and purines of the antisense strand comprise 2' fluoro modified purines.

In some embodiments, all purines of the antisense strand comprise 2' fluoro modified purines, and all pyrimidines of the antisense strand comprise a mixture of 2' fluoro and 2'-O-methyl modified pyrimidines. In some embodiments, all purines of the antisense strand comprise 2'-O-methyl modified purines, and all pyrimidines of the antisense strand comprise a mixture of 2' fluoro and 2'-O-methyl modified pyrimidines. In some embodiments, all purities of the antisense strand comprise 2' fluoro modified purines, and all pyrimidines of the antisense strand comprise 2'-O-methyl modified pyrimidines. In some embodiments, all purines of the antisense strand comprise 2'-O-methyl modified purines, and all pyrimidines of the antisense strand comprise 2' fluoro modified pyrimidines. In some embodiments, all pyrimidines of the antisense strand comprise 2' fluoro modified pyrimidines, and all purines of the antisense strand comprise a mixture of 2' fluoro and 2'-O-methyl modified purines. In some embodiments, all pyrimidines of the antisense strand comprise 2'-O-methyl modified pyrimidines, and all purities of the antisense strand comprise a mixture of 2' fluoro and 2'-O-methyl modified purines. In some embodiments, all pyrimidines of the antisense strand comprise 2' fluoro modified pyrimidines, and all purines of the antisense strand comprise 2'-O-methyl modified purines. In some embodiments, all pyrimidines of the antisense strand comprise 2'-O-methyl modified pyrimidines, and all purities of the antisense strand comprise 2' fluoro modified purities.

In some cases, the oligonucleotide comprises a particular modification pattern. In some embodiments, position 9 counting from the 5' end of the of a strand of the oligonucleotide may have a 2'F modification. In some embodiments, when position 9 of a strand of time oligonucleotide is a pyrimidine, then all purines in a strand of the oligonucleotide have a 2'OMe modification. In some embodiments, when position 9 is the only pyrimidine between positions 5 and 11 of the sense stand, then position 9 is the only position with a 2'F modification in a strand of the oligonucleotide. In some embodiments, when position 9 and only one other base between positions 5 and 11 of a strand of the oligonucleotide are pyrimidines, then both of these pyrimidines are the only two positions with a 2'F modification in a strand of the oligonucleotide. In some embodiments, when position 9 and only two other bases between positions 5 and 11 of a strand of the oligonucleotide are pyrimidines, and those two other pyrimidines are in adjacent positions so that there would be not three 2'F modifications in a row, then any combination of 2'F modifications can be made that give three 2'F' modifications in total. In some, embodiments, when there are more than 2 pyrimidines between positions 5 and 11 of a strand of the oligonucleotide, then all combinations of pyrimidines having the 2'F modification are allowed that have three to five 2'F modifications in total, provided that a strand of the oligonucleotide does not have three 2'F modifications in a row. In some cases, a strand of the oligonucleotide of any of the siRNAs comprises a modification pattern which conforms to any or all of these a strand of the oligonucleotide rules.

In some embodiments, when position 9 of a strand of the oligonucleotide is a purine, then all purines in a strand of the oligonucleotide have a 2'OMe modification. In some embodiments, when position 9 is the only purine between positions 5 and 11 of the sense stand, then position 9 is the only position with a modification in a strand of the oligonucleotide. In some, embodiments, when position 9 and only one other base between positions 5 and 11 of a strand of the oligonucleotide are purines, then both of these purines are the only two positions with a 2'F modification in a strand of the oligonucleotide. In some embodiments, when position 9 and only two other bases between positions 5 and 11 of a strand of the oligonucleotide are purines, and those two other parities are in adjacent positions so that there would be not three 2'F modifications in a row, then any combination of 2'F modifications can be made that give three 2'F modifications in total. In some embodiments, when there are more than 2 purines between positions 5 and 11 of a strand of the oligonucleotide, then all combinations of purines having the 2'F modification are allowed that have three to five 2'F modifications in total, provided that a strand of the oligonucleotide does not have three 2'F modifications in a row. In some cases, a strand of the oligonucleotide of any of the siRNAs comprises a modification pattern which conforms to any or all of these a strand of the oligonucleotide rules.

In some cases, position 9 of a strand of the oligonucleotide can be a 2' doxy. In these cases, 2'F and 2' Me modifications may occur at the other positions of a strand of the oligonucleotide. In some cases, a strand of the oligonucleotide of any of the siRNAs comprises a modification pattern which conforms to these a strand of the oligonucleotide rules.

In some embodiments, position nine of the sense strand comprises a 2' fluoro-modified pyrimidine. In some embodiments, all purines of the sense strand comprise 2'-O-methyl modified purines. In some embodiments, 1, 2, 3, 4, or 5 pyrimidines between positions 5 and 11 comprise a 2' flouro-modified pyrimidine, provided there are not three 2' fluoro-modified pyrimidines in a row. In some embodiments, the odd-numbered positions of the antisense strand comprise 2'-O-methyl modified nucleotides. In some embodiments, the even-numbered positions of the antisense strand comprise 2' flouro-modified nucleotides and unmodified deoxyribonucleotide. In some embodiments, the even-numbered positions of the antisense strand comprise 2' flouro-modified nucleotides, 2'O-methyl modified nucleotides and unmodified deoxyribonucleotide. In some embodiments, position nine of the sense strand comprises a 2' fluoro-modified pyrimidine; all purines of the sense strand comprises 2'-O-methyl modified purines; 1, 2, 3, 4, or 5 pyrimidines between positions 5 and 11 comprise a 2' flouro-modified pyrimidine, provided there are not three 2' fluoro-modified pyrimidines in a row, the odd-numbered positions of the antisense strand comprise 2T-O-methyl modified nucleotides; and the even-numbered positions of the antisense strand comprise 2' flouro-modified nucleotides and unmodified deoxyribonucleotides.

In some embodiments, position nine of the sense strand comprises a 2' fluoro-modified purine. In some embodiments, all pyrimidines of the sense strand comprise 2'-O-methyl modified purines. In some embodiments, 1, 2, 3, 4, or 5 purines between positions 5 and 11 comprise a 2' flouro-modified purine, provided there are not three 2' fluoro-modified purine in a row. In some embodiments, the odd-numbered positions of the antisense strand comprise 2'-O-methyl modified nucleotides. In some embodiments, the even-numbered positions of the antisense strand comprise 2' flouro-modified nucleotides and unmodified deoxyribonucleotide. In some embodiments, the even-numbered positions of the antisense strand comprise 2' flouro-modified nucleotides, 2'-O-methyl modified nucleotides and unmodified deoxyribonucleotide. In some embodiments, position nine of the sense strand comprises a 2' fluoro-modified purine; all pyrimidine of the sense strand comprises 2'-O-methyl modified pyrimidines; 1, 2, 3, 4, or 5 purines between positions 5 and 11 comprise a 2' flouro-modified purines, provided there are not three 2' fluoro-modified purines in a row; the odd-numbered positions of the antisense strand comprise 2'-O-methyl modified nucleotides; and the even-numbered positions of the antisense strand comprise 2' flouro-modified nucleotides and unmodified deoxyribonucleotides. In some embodiments, there are not three 2' fluoro-modified purines in a row. In some embodiments, there are not three 2' fluoro-modified pyrimidines in a row.

In some embodiments, position nine of the sense strand comprises an unmodified deoxyribonucleotide. In some embodiments, positions 5, 7, and 8 of the sense strand comprise 2' fluoro-modified nucleotides. In some embodiments, all pyrimidines in positions 10 to 21 of the sense strand comprise 2'O-methyl modified pyrimidines and all purines in positions 10 to 21 of the comprise 2'-O-methyl modified purines or 2' fluoro-modified purines. In some embodiments, the odd-numbered positions of the antisense strand comprise 2'-O-methyl modified nucleotides. In some embodiments, the even-numbered positions of the antisense strand comprise 2' flouro-modified nucleotides and unmodified deoxyribonucleotides. In some embodiments, the even-numbered positions of the antisense strand comprise 2' flouro-modified nucleotides, 2'-O-methyl modified nucleotides and unmodified deoxyribonucleotides. In some embodiments, position nine of the sense strand comprises an unmodified deoxyribonucleotide; positions 5, 7, and 8 of the sense strand comprise 2fluoro-modified nucleotides; all pyrimidines in positions 10 to 21 of the sense strand comprise 2-O-methyl modified pyrimidines and all purines in positions 10 to 21 of the comprise 2'-O-methyl modified purines or 2' fluoro-modified purines; the odd-numbered positions of the antisense strand comprise 2-O-methyl modified nucleotides; and the even-numbered positions of the antisense strand comprise 2' flouro-modified nucleotides and unmodified deoxyribonucleotides.

In some embodiments, position nine of the sense strand comprises an unmodified deoxyribonucleotide. In some embodiments, positions 5, 7, and 8 of the sense strand comprise 2fluoro-modified nucleotides. In some embodiments, all purines in positions 10 to 21 of the sense strand comprise 2-O-methyl modified purines and all pyrimidines in positions 10 to 21 of the comprise 2'-O-methyl modified pyrimidines or 2' fluoro-modified pyrimidines. In some embodiments, the odd-numbered positions of the antisense strand comprise 2'-O-methyl modified nucleotides. In some embodiments, the even-numbered positions of the antisense strand comprise 2' flouro-modified nucleotides and unmodified deoxyribonucleotides. In some embodiments, the even-numbered positions of the antisense strand comprise 2flouro-modified-d nucleotides, 2'-O-methyl modified nucleotides and unmodified deoxyribonucleotides. In some embodiments, position nine of the sense strand comprises an unmodified deoxyribonucleotide; positions 5, 7, and 8 of the sense strand comprise 2fluoro-modified nucleotides; all purifies in positions 10 to 21 of the sense strand comprise 2'-O-methyl modified purines and all pyrimidines in positions 10 to 21 of the comprise 2'-O-methyl modified pyrimidines or 2' fluoro-modified pyrimidines; the odd-numbered positions of the antisense strand comprise 2'-O-methyl modified nucleotides; and the even-numbered positions of the antisense strand comprise 2flouro-modified nucleotides and unmodified deoxyribonucleotide.

3. ASO modification patterns

In some embodiments, the composition comprises an oligonucleotide that binds to a target oligonucleotide, wherein the oligonucleotide comprises an antisense oligonucleotide (ASO). In some embodiments, the ASO comprises modification pattern ASO 1: 5'-nsnsrisnsnsdNsdNsdNsdNsdNsdNsdNsdNsdNsnsnsnsnsri-3', wherein "dN" is any deoxynucleotide, "n" is a 2'O-methyl or 2'-methoxyethyl-modified nucleoside, and "s" is a phosphorothioate linkage. In some embodiments, the ASO comprises modification pattern 1S, 2S, 3S, 4S, 5S, 6S, 1AS, 2AS, 3AS, 4AS, 5AS, 6AS, 7AS, 8AS or 9AS.

In some embodiments, the ASO is conjugated to a GalNAc moiety. The GalNAc moiety may be conjugated to the ASO at a 5' terminus or the 3' terminus. In some embodiments, the GalNAc moiety is conjugated to the 5' terminus of the ASO. In some embodiments, the GalNAc moiety is conjugated to the 3' terminus of the ASO.

C. Formulations

In some embodiments, the composition is a pharmaceutical composition. In some embodiments, the composition is sterile. In some embodiments, the composition farther comprises a pharmaceutically acceptable carrier. The formulation may include a compound such as a GalNAc moiety, and an oligonucleotide conjugated to a GalNAc moiety described herein.

In some embodiments, the pharmaceutically acceptable carrier comprises water. In some embodiments, the pharmaceutically acceptable carrier comprises a buffer. In some embodiments, the pharmaceutically acceptable carrier comprises a saline solution. In some embodiments, the pharmaceutically acceptable carrier comprises water, a buffer, or a saline solution. In some embodiments, the composition comprises a liposome. In some embodiments, the pharmaceutically acceptable carrier comprises liposomes, lipids, nanoparticles, proteins, protein-antibody complexes, peptides, cellulose: nanogel, or a combination thereof.

Il Methods and Uses

Disclosed herein, in some embodiments, are methods of administering a composition described herein to a subject. Some embodiments relate to use a composition described herein, such as administering the composition to a subject.

Some embodiments relate to a method of treating a disorder in a subject in need thereof. Some embodiments relate to use of a composition described herein in the method of treatment. Some embodiments include administering a composition described herein to a subject with the disorder. In some embodiments, the administration treats the disorder in the subject. In some embodiments, the composition treats the disorder in the subject.

In some embodiments, the treatment comprises prevention, inhibition, or reversion of the disorder in the subject. Some embodiments relate to use of a composition described herein in the method of preventing, inhibiting, or reversing the disorder. Some embodiments relate to a method of preventing, inhibiting, or reversing a disorder a disorder in a subject in need thereof. Some embodiments include administering a composition described herein to a subject with the disorder. In some embodiments, the administration prevents, inhibits, or reverses the disorder in the subject. In some embodiments, the composition prevents, inhibits, or reverses the disorder in the subject.

Some embodiments relate to a method of preventing a disorder a disorder in a subject in need thereof. Some embodiments relate to use of a composition described herein in the method of preventing the disorder. Some embodiments include administering a composition described herein to a subject with the disorder. In some embodiments, the administration prevents the disorder in the subject. In some embodiments, the composition prevents the disorder in the subject.

Some embodiments relate to a method of inhibiting a disorder a disorder in a subject in need thereof. Some embodiments relate to use of a composition described herein in the method of inhibiting the disorder. Some embodiments include administering a composition described herein to a subject with the disorder. In some embodiments, the administration inhibits the disorder in the subject. In some embodiments, the composition inhibits the disorder in the subject.

Some embodiments relate to a method of reversing a disorder a disorder in a subject in need thereof. Some embodiments relate to use of a composition described herein in the method of reversing the disorder. Some embodiments include administering a composition described herein to a subject with the disorder. In some embodiments, the administration reverses the disorder in the subject. In some embodiments, the composition reverses the disorder in the subject.

A. Disorders

Some embodiments of the methods described herein include treating a disorder in a subject in need thereof. In some embodiments, the disorder is a liver disorder. Non-limiting examples of liver disorders include liver inflammation, liver cancer, liver fibrosis, cholestasis, a gall bladder disease, a biliary tree disease, alcoholic liver disease, non-alcoholic steatohepatitis, a liver infection, or an inherited liver disorder. In some embodiments, the liver disorder comprises liver inflammation. In some embodiments, the liver disorder comprises liver cancer. In some embodiments, the liver disorder comprises liver fibrosis. In some embodiments, the liver disorder comprises cholestasis. In some embodiments, the liver disorder comprises a gall bladder disease. In some embodiments, the liver disorder comprises a biliary tree disease. In some embodiments, the liver disorder comprises alcoholic liver disease. In some embodiments, the liver disorder comprises non-alcoholic steatohepatitis.

In some embodiments, the liver disorder comprises a liver infection. In some embodiments, the liver infection comprises hepatitis A. In some embodiments, the liver infection comprises hepatitis B. In some embodiments, the liver infection comprises hepatitis C.

In some embodiments, the liver disorder comprises an inherited liver disorder. In some embodiments, the inherited liver disorder comprises hemochromatosis. In some embodiments, the inherited liver disorder comprises Wilson disease.

B, Subjects

Some embodiments of the methods described herein include treatment of a subject. Non-limiting examples of subjects include vertebrates, animals, mammals, dogs, cats, cattle, rodents, mice, rats, primates, monkeys, and humans. In some embodiments, the subject is a vertebrate. In some embodiments, the subject is an animal. In some embodiments, the subject is a mammal. In some embodiments, the subject is a dog. In some embodiments, the subject is a cat. In some embodiments, the subject is a cattle. In some embodiments, the subject is a mouse. In some embodiments, the subject is a rat. In some embodiments, the subject is a primate. In some embodiments, the subject is a monkey. In some embodiments, the subject is an animal, a mammal, a dog, a cat, cattle, a rodent, a mouse, a rat, a primate, or a monkey. In some embodiments, the subject is a human.

In some embodiments, the subject is male. In some embodiments, the subject is female.

In some embodiments, the subject has a body mass index (BMI) of 25, 26, 27, 28, 29, 30, 31, 32, 33, 34, 35, 36, 37, 38, 39, 40, 41, 42, 43, 44, 45, 46, 47, 48, 49, 50, or more, or a range defined by any two of the aforementioned integers. In some embodiments, the subject is overweight. In some embodiments, the subject has a BMI of 25 or more. In some embodiments, the subject has a BMI of 25-29. In some embodiments, the subject is obese. In some embodiments, the subject has a BMI of 30 or more. In some embodiments, the subject has a BMI of 30-39. In some embodiments, the subject has a BMI of 40-50. In some embodiments, the subject has a BMI of 25-50.

In some embodiments, the subject is ≥90 years of age. In some embodiments, the subject is ≥85 years of age. In some embodiments, the subject is ≥80 years of age. In some embodiments, the subject is ≥70 years of age. In some embodiments, the subject is ≥60 years of age. In some embodiments, the subject is ≥50 years of age. In some embodiments, the subject is ≥40 years of age. In some embodiments, the subject is ≥30 years of age. In some embodiments, the subject is ≥20 years of age. In some embodiments, the subject is ≥10 years of age. In some embodiments, the subject is ≥1 years of age. In some embodiments, the subject is ≥0 years of age.

In some embodiments, the subject is ≤100 years of age. In some embodiments, the subject is ≤90 years of age. In some embodiments, the subject is ≤85 years of age. In some embodiments, the subject is ≤80 years of age. In some embodiments, the subject is ≤70 years of age. In some embodiments, the subject is ≤60 years of age. In some embodiments, the subject is ≤50 years of age. In some embodiments, the subject is ≤40 years of age. In some embodiments, the subject is ≤30 years of age. In some embodiments, the subject is ≤20 years of age. In some embodiments, the subject is ≤10 years of age. In some embodiments, the subject is ≤1 years of age.

In some embodiments, the subject is between 0 and 100 years of age. In some embodiments, the subject is between 20 and 90 years of age. In some embodiments, the subject is between 30 and 80 years of age. In some embodiments, the subject is between 40 and 75 years of age. In some embodiments, the subject is between 50 and 70 years of age. In some embodiments, the subject is between 40 and 85 years of age.

C. Baseline measurements

Some embodiments of the methods described herein include obtaining a baseline measurement from a subject. For example, in some embodiments, a baseline measurement is obtained from the subject prior to treating the subject. Non-limiting examples of baseline measurements include a baseline symptom (e.g. a liver disorder symptom) measurement, a baseline protective phenotype measurement, a baseline target oligonucleotide (e.g. mRNA) measurement or a baseline target protein measurement.

In some embodiments, the baseline measurement is obtained directly from the subject. In some embodiments, the baseline measurement is obtained by observation, for example by observation of the subject or of the subject's tissue. In some embodiments, the baseline measurement is obtained noninvasively using an imaging device. In some embodiments, the baseline measurement is obtained in a sample from the subject. In some embodiments, the baseline measurement is obtained in one or more histological tissue sections. In some embodiments, the baseline measurement is obtained by performing an assay such as an immunoassay, a colorimetric assay, or a fluorescence assay, on the sample obtained from the subject. In some embodiments, the baseline measurement is obtained by an immunoassay, a colorimetric assay, or a fluorescence assay. In some embodiments, the baseline measurement is obtained by PCR.

In some embodiments, the baseline measurement is a baseline symptom measurement. The symptom may be a symptom of a disorder associated with a target oligonucleotide. The disorder may be a liver disorder.

In some embodiments, the baseline measurement is a baseline protective phenotype measurement. The protective phenotype may protect a subject from having a disorder associated with a target oligonucleotide. The protective phenotype may be inversely correlated with an incidence of the disorder.

In some embodiments, the baseline measurement is a baseline target protein measurement. In some embodiments, the baseline target protein measurement comprises a baseline target protein level. In some embodiments, the baseline target protein level is indicated as a mass or percentage of target protein per sample weight. In some embodiments, the baseline target protein level is indicated as a mass or percentage of target protein per sample volume. In some embodiments, the baseline target protein level is indicated as a mass or percentage of target protein per total protein within the sample. In some embodiments, the baseline target protein measurement is a baseline liver or hepatocyte target protein measurement. In some embodiments, the baseline target protein measurement is a baseline circulating target protein measurement. In some embodiments, the baseline target protein measurement is obtained by an assay such as an immunoassay, a colorimetric assay, or a fluorescence assay.

In some embodiments, the baseline measurement is a baseline target mRNA measurement. In some embodiments, the baseline target mRNA measurement comprises a baseline target mRNA level. In some embodiments, the baseline target mRNA level is indicated as a mass or percentage of target mRNA per sample weight. In some embodiments, the baseline target mRNA level is indicated as a mass or percentage of target mRNA per sample volume. In some embodiments, the baseline target mRNA level is indicated as a mass or percentage of target mRNA per total mRNA within the sample. In some embodiments, the baseline target mRNA level is indicated as a mass or percentage of target mRNA per total nucleic acids within the sample. In some embodiments, the baseline target mRNA level is indicated relative to another mRNA level, such as an mRNA level of a housekeeping gene, within the sample. In some embodiments, the baseline target mRNA measurement is a baseline liver or hepatocyte target mRNA measurement. In some embodiments, the baseline target mRNA measurement is obtained by an assay such as a polymerase chain reaction (PCR) assay. In some embodiments, the PCR comprises quantitative PCR (qPCR), In some embodiments, the PCR comprises reverse transcription of the target mRNA.

Some embodiments of the methods described herein include obtaining a sample from a subject. In some embodiments, the baseline measurement is obtained in a sample obtained from the subject. In some embodiments, the sample is obtained from the subject prior to administration or treatment of the subject with a composition described herein. In some embodiments, a baseline measurement is obtained in a sample obtained from the subject prior to administering the composition to the subject. In some embodiments, the sample is obtained from the subject in a fasted state. In some embodiments, the sample is obtained from the subject after an overnight fasting period. In some embodiments, the sample is obtained from the subject in a fed state.

In some embodiments, the sample comprises a fluid. In some embodiments, the sample is a fluid sample. In some embodiments, the sample is a blood, plasma, or serum sample. In some embodiments, the sample comprises blood. In some embodiments, the sample is a blood sample. In some embodiments, the sample is a whole-blood sample. In some embodiments, the blood is fractionated or centrifuged. In some embodiments, the sample comprises plasma. In some embodiments, the sample is a plasma sample. In some embodiments, the sample comprises serum. In some embodiments, the sample is a serum sample.

In some embodiments, the sample comprises a tissue. In some embodiments, the sample is a tissue sample. In some embodiments, the sample comprises liver tissue. In some embodiments, the sample is a liver sample. In some embodiments, the sample comprises hepatocytes. In some embodiments, the sample consists of hepatocytes. For example, the baseline target mRNA measurement, or the baseline target protein measurement, may be obtained in a liver or hepatocyte sample from the patient. In some embodiments, the sample comprises adipose tissue. In some embodiments, the sample is an adipose sample. The adipose sample may comprise or consist of white adipose tissue. The adipose sample may comprise or consist of brown adipose tissue. In some embodiments, the sample comprises kidney tissue. In some embodiments, the sample is an kidney sample. In some embodiments, the sample comprises cardiac tissue such as ventricular or atrial tissue. In some embodiments, the sample is a cardiac sample. In some embodiments, the sample comprises intestinal tissue such as small intestinal tissue. In some embodiments, the sample is a small intestine sample. In some embodiments, the sample comprises lymph node tissue such as mesenteric lymph node tissue. In some embodiments, the sample is a mesenteric lymph node sample. In some embodiments, the sample comprises muscle tissue. In some embodiments, the sample is an muscle sample. In some embodiments, the tissue sample comprises liver, adipose, kidney, or cardiac tissue. In some embodiments, the tissue sample comprises brown adipose tissue, white adipose tissue, kidney tissue, intestinal tissue, mesenteric lymph node, or muscle tissue.

D. Effects

In some embodiments, the composition or administration of the composition affects a measurement such as symptom (e.g. a liver disorder symptom) measurement, a protective phenotype measurement, a target oligonucleotide (e.g. mRNA) measurement or a target protein measurement (e.g. liver tissue target protein levels), relative to the baseline measurement.

Some embodiments of the methods described herein include obtaining the measurement from a subject. For example, the measurement may be obtained from the subject after treating the subject. In some embodiments, the measurement is obtained in a second sample (such as a fluid or tissue sample described herein) obtained from the subject after the composition is administered to the subject. In some embodiments, the measurement is an indication that the disorder has been treated.

In some embodiments, the measurement is obtained directly from the subject. In some embodiments, the measurement is obtained noninvasively using an imaging device. In some embodiments, the measurement is obtained in a second sample from the subject. In some embodiments, the measurement is obtained in one or more histological tissue sections. In some embodiments, the measurement is obtained by performing an assay on the second sample obtained from the subject. In some embodiments, the measurement is obtained by an assay, such as an assay described herein. In some embodiments, the assay is an immunoassay, a colorimetric assay, a fluorescence assay, or a PCR assay. In some embodiments, the measurement is obtained by an assay such as an immunoassay, a colorimetric assay, or a fluorescence assay. In some embodiments, the measurement is obtained by PCR. In some embodiments, the measurement is obtained by histology. In some embodiments, the measurement is obtained by observation. In some embodiments, additional measurements are made, such as in a 3rd sample, a 4th sample, or a fifth sample.

In some embodiments, the measurement is obtained within 1 hour, within 2 hours, within 3 hours, within 4 hours, within 5 hours, within 6 hours, within 12 hours, within 18 hours, or within 24 hours after the administration of the composition. In some embodiments, the measurement is obtained within 1 day, within 2 days, within 3 days, within 4 days, within 5 days, within 6 days, or within 7 days after the administration of the composition. In some embodiments, the measurement is obtained within 1 week, within 2 weeks, within 3 weeks, within 1 month, within 2 months, within 3 months, within 6 months, within 1 year, within 2 years, within 3 years, within 4 years, or within 5 years after the administration of the composition. In some embodiments, the measurement is obtained after 1 hour, after 2 hours, after 3 hours, after 4 hours, after 5 hours, after 6 hours, after 12 hours, after 18 hours, or after 24 hours after the administration of the composition. In some embodiments, the measurement is obtained after 1 day, after 2 days, after 3 days, after 4 days, after 5 days, after 6 days, or after 7 days after the administration of the composition. In some embodiments, the measurement is obtained after 1 week, after 2 weeks, after 3 weeks, after 1 month, after 2 months, after 3 months, after 6 months, after 1 year, after 2 years, after 3 years, after 4 years, or after 5 years, following the administration of the composition.

In some embodiments, the measurement of the symptom or the parameter related to the disorder in the subject is decreased or affected for an extended period of time, relative to the baseline measurement. In some embodiments, the measurement is decreased or affected for at least about 1 day about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, about 30 days, about 35 days, about 40 days, about 45 days, about 50 days, about 55 days, about 60 days, about 65 days, about 70 days, about 75 days, about 80 days, about 85 days, about 90 days, about 95 days, about 100 days, about 105 days about 110 days, about 115 days, or about 120 days, following administration, or a range of time following administration comprising a range defined by any two of the aforementioned numbers of days. In some embodiments, the measurement is decreased or affected for at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days, at least 22 days, at least 23 days, at least 24 days, at least 25 days, at least 26 days, at least 27 days, at least 28 days, at least 29 days, at least 30 days, at least 35 days, at least 40 days, at least 45 days, at least 50 days, at least 55 days, at least 60 days, at least 65 days, at least 70 days, at least 75 days, at least 80 days, at least 85 days, at least 90 days, at least 95 days, at least 100 days, at least 105 days, at least 110 days, at least 115 days, or at least 120 days, following administration. In some embodiments, the measurement is decreased or affected for no more than 1 day, no more than 2 days, no more than 3 days, no more than 4 days, no more than 5 days, no more than 6 days, no more than 7 days, no more than 8 days, no more than 9 days, no more than 10 days, no more than 11 days, no more than 12 days, no more than 13 days, no more than 14 days, no more than 15 days, no more than 16 days, no more than 17 days, no more than 18 days, no more than 19 days, no more than 20 days, no more than 21 days, no more than 22 days, no more than 23 days, no more than 24 days, no more than 25 days, no more than 26 days, no more than 27 days, no more than 28 days, no more than 29 days, no more than 30 days, no more than 35 days, no more than 40 days, no more than 45 days, no more than 50 days, no more than 55 days, no more than 60 days, no more than 65 days, no more than 70 days, no more than 75 days, no more than 80 days, no more than 85 days, no more than 90 days, no more than 95 days, no more than 100 days, no more than 105 days, no more than 110 days, no more than 115 days, or no more than 120 days, following administration. In some embodiments, the measurement is decreased or affected for at least about 5 days. In some embodiments, the measurement is decreased or affected for at least about 10 days. In some embodiments, the measurement is decreased or affected for at least about 15 days. In some embodiments, the measurement is decreased or affected for at least about 20 days. In some embodiments, the measurement is decreased or affected for at least about 25 days. In some embodiments, the measurement is decreased or affected for at least about 30 days. In some embodiments, the measurement is decreased or affected for at least about 40 days. In some embodiments, the measurement is decreased or affected for at least about 50 days. In some embodiments, the measurement is decreased or affected for at least about 60 days. In some embodiments, the measurement is decreased or affected for at least about 70 days. In some embodiments, the measurement is decreased or affected for at least about 80 days. In some embodiments, the measurement is decreased or affected for at least about 90 days. In some embodiments, the measurement is decreased or affected for at least about 100 days. In some embodiments, the measurement is decreased or affected for at least about 110 days. In some embodiments, the measurement is decreased or affected for at least about 120 days. An example of a measurement of a symptom or parameter related to a disorder may include a target mRNA measurement, a target protein measurement, a biomarker measurement, or a physiological measurement. The measurement may be in a tissue (e.g. liver) or in a biofluid (e.g. blood, serum, or plasma).

In some embodiments, the composition reduces the symptom measurement relative to the baseline symptom measurement. In some embodiments, the reduction is measured in a second tissue sample obtained from the subject after administering the composition to the subject. In some embodiments, the reduction is measured directly in the subject after administering the composition to the subject. In some embodiments, the symptom measurement is decreased by about 2.5% or more, about 5% or more, or about 7.5% or more, relative to the baseline symptom measurement. In some embodiments, the symptom measurement is decreased by about 10% or more, relative to the baseline symptom measurement. In some embodiments, the symptom measurement is decreased by about 20% or more, about 30% or more, about 40% or more, about 50% or more, about 60% or more, about 70% or more, about 80% or more, about 90% or more, relative to the baseline symptom measurement. In some embodiments, the symptom measurement is decreased by no more than about 2.5%, no more than about 5%, or no more than about 7.5%, relative to the baseline symptom measurement. In some embodiments, the symptom measurement is decreased by no more than about 10%, relative to the baseline symptom measurement. In some embodiments, the symptom measurement is decreased by no more than about 20%, no more than about 30%, no more than about 40%, no more than about 50%, no more than about 60%, no more than about 70%, no more than about 80%, no more than about 90%, or no more than about 100% relative to the baseline symptom measurement. In some embodiments, the symptom measurement is decreased by 2.5%, 5%, 7.5%, 10%, 20%, 30%, 40%, 50%, 60%, 70%, 80%, 90%, or 100%, or by a range defined by any of the two aforementioned percentages.

In some embodiments, the composition increases the protective phenotype measurement relative to the baseline protective phenotype measurement. In some embodiments, the increase is measured in a second tissue sample obtained from the subject after administering the composition to the subject. In some embodiments, the increase is measured directly in the subject after administering the composition to the subject. In some embodiments, the protective phenotype measurement is increased by about 2.5% or more, about 5% or more, or about 7.5% or more, relative to the baseline protective phenotype measurement. In some embodiments, the protective phenotype measurement is increased by about 10% or more, relative to the baseline protective phenotype measurement. In some embodiments, the protective phenotype measurement is increased by about 20% or more, about 30% or more, about 40% or more, about 50% or more, about 60% or more, about 70% or more, about 80% or more, about 90% or more, relative to the baseline protective phenotype measurement. In some embodiments, the protective phenotype measurement is increased by about 100% or more, increased by about 250% or more, increased by about 500% or more, increased by about 750% or more, or increased by about 1000% or more, relative to the baseline protective phenotype measurement. In some embodiments, the protective phenotype measurement is increased by no more than about 2.5%, no more than about 5%, or no more than about 7.5%, relative to the baseline protective phenotype measurement. In some embodiments, the protective phenotype measurement is increased by no more than about 10%, relative to the baseline protective phenotype measurement. In some embodiments, the protective phenotype measurement is increased by no more than about 20%, no more than about 30%, no more than about 40%, no more than about 50%, no more than about 60%, no more than about 70%, no more than about 80%, no more than about 90%, or no more than about 100% relative to the baseline protective phenotype measurement. In some embodiments, the protective phenotype measurement is increased by no more than about 100%, increased by no more than about 250%, increased by no more than about 500%, increased by no more than about 750%, or increased by no more than about 1000%, relative to the baseline protective phenotype measurement. In some embodiments, the protective phenotype measurement is increased by 2.5%, 5%, 7.5%, 10%, 20%, 30%, 40%, 50%, 60%, 70%, 80%, 90%, 100%, 250%, 500%, 750%, or 1000%, or by a range defined by any of the two aforementioned percentages.

In some embodiments, the measurement is a target protein measurement. In some embodiments, the target protein measurement comprises a target protein level. In some embodiments, the target protein level is indicated as a mass or percentage of target protein per sample weight. In some embodiments, the target protein level is indicated as a mass or percentage of target protein per sample volume. In some embodiments, the target protein level is indicated as a mass or percentage of target protein per total protein within the sample. In some embodiments, the target protein measurement is a cell (e.g. hepatocyte) target protein measurement. In some embodiments, the target protein measurement is a tissue (e.g, liver tissue) target protein measurement. In some embodiments, the target protein measurement is a circulating target protein measurement. In some embodiments, the baseline target protein measurement is obtained by an assay such as an immunoassay, a colorimetric assay, or a fluorescence assay.

In some embodiments, the composition reduces the target protein measurement relative to the baseline target protein measurement. In some embodiments, the composition reduces tissue target protein levels (such as, but not limited to, liver tissue target protein levels) relative to the baseline target protein measurement. In some embodiments, the composition reduces cell target protein levels (such as, but not limited to, hepatocyte target protein levels) relative to the baseline target protein measurement. In some embodiments, the composition reduces circulating target protein levels relative to the baseline target protein measurement. In some embodiments, the reduced target protein levels are measured in a second sample obtained from the subject after administering the composition to the subject.

In some embodiments, the target protein measurement is decreased by about 2.5% or more, about 5% or more, or about 7.5% or more, relative to the baseline target protein measurement. In some embodiments, the target protein measurement is decreased by about 10% or more, relative to the baseline target protein measurement. In some embodiments, the target protein measurement is decreased by about 20% or more, about 30% or more, about 40% or more, about 50% or more, about 60% or more, about 70% or more, about 80% or more, about 90% or more, or about 100% relative to the baseline target protein measurement. In some embodiments, the target protein measurement is decreased by no more than about 2.5%, no more than about 5%, or no more than about 7.5%, relative to the baseline target protein measurement. In some embodiments, the target protein measurement is decreased by no more than about 10%, relative to the baseline target protein measurement. In some embodiments, the target protein measurement is decreased by no more than about 20%, no more than about 30%, no more than about 40%, no more than about 50%, no more than about 60%, no more than about 70% no more than about 80%, no more than about 90%, or about 100% relative to the baseline target protein measurement. In some embodiments, the target protein measurement is decreased by 2.5%, 5%, 7.5%, 19%, 20%, 30%, 40%, 50%, 60%, 70%, 80%, 90%, or 100%, or by a range defined by any of the two aforementioned percentages. The target protein measurement may be decreased for an extended period of time. In some embodiments, the target protein measurement is decreased for 7 days, 14 days, 28 days, 42 days, 56 days, 70 days, 77 days, 84 days, 91 days, 98 days, 105 days, or a range therebetween. In some embodiments, the target protein measurement is decreased for about 7 days, about 14 days about 28 days, about 42 days, about 56 days about 70 days, about 77 days, about 84 days, about 91 days, about 98 days, about 105 days, or a range therebetween.

In some embodiments, the measurement is a target mRNA measurement. In some embodiments, the target snRNA measurement comprises a target snRNA level. In some embodiments, the target mRNA level is indicated as a mass or percentage of target mRNA per sample weight. In some embodiments, the target mRNA level is indicated as a mass or percentage of target mRNA per sample volume. In some embodiments, the target mRNA level is indicated as a mass or percentage of target mRNA per total mRNA within the sample. In some embodiments, the target mRNA level is indicated as a mass or percentage of target snRNA per total nucleic acids within the sample. In some embodiments, the target mRNA level is indicated relative to another mRNA level, such as an mRNA level of a housekeeping gene, within the sample. In some embodiments, the target mRNA measurement is obtained by an assay such as a PCR assay. In some embodiments, the PCR comprises qPCR. In some embodiments, the PCR comprises reverse transcription of the target mRNA.

In some embodiments, the composition reduces the target mRNA measurement relative to the baseline target mRNA measurement. In some embodiments, the target mRNA measurement is obtained in a second sample obtained from the subject after administering the composition to the subject. In some embodiments, the composition reduces target mRNA levels relative to the baseline target mRNA levels. In some embodiments, the reduced target mRNA levels are measured in a second sample obtained from the subject after administering the composition to the subject. In some embodiments, the second sample is a second liver sample. In some embodiments, the second sample is second hepatocyte sample.

In some embodiments, the target mRNA measurement is reduced by about 2.5% or more, about 5% or more, or about 7.5% or more, relative to the baseline target mRNA measurement. In some embodiments, the target mRNA measurement is decreased by about 10% or more, relative to the baseline target mRNA measurement. In some embodiments, the target mRNA measurement is decreased by about 20% or more, about 30% or more, about 40% or more, about 50% or more, about 60% or more, about 70% or more, about 80% or more, about 90% or more, or about 100% relative to the baseline target mRNA measurement. In some embodiments, the target mRNA measurement is decreased by no more than about 2.5%, no more than about 5%, or no more than about 7.5%, relative to the baseline target mRNA measurement. In some embodiments, the target mRNA measurement is decreased by no more than about 10%, relative to the baseline target mRNA measurement. In some embodiments, the target mRNA measurement is decreased by no more than about 20%, no more than about 30%, no more than about 40%, no more than about 50%, no more than about 60%, no more than about 70%, no more than about 80%, no more than about 90%, or about 100% relative to the baseline target mRNA measurement. In some embodiments, the target mRNA measurement is decreased by 2.5%, 5%, 7.5%, 10%, 20%, 30%, 40%, 50%, 60%, 70% 80%, 90%, 100%, or by a range defined by any of the two aforementioned percentages. The target mRNA measurement may be decreased for an extended period of time. In some embodiments, the target mRNA measurement is decreased for 7 days. 14 days. 28 days, 42 days, 56 days, 70 days, 77 days, 84 days, 91 days, 98 days, 105 days, or a range therebetween. In some embodiments, the target protein measurement is decreased for about 7 days, about 14 days, about 28 days, about 42 days, about 56 days, about 70 days, about 77 days, about 84 days, about 91 days, about 98 days, about 105 days, or a range therebetween. Some embodiments include decreasing an RNA measurement other than an mRNA measurement.

III Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

Throughout this application, various embodiments may be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example 1, 2, 3, 4, 5, and 6. This applies regardless of the breadth of the range.

As used in the specification and claims, the singular forms "a", "an" and "the" include plural references unless the context clearly dictates otherwise. For example, the term "a sample" includes a plurality of samples, including mixtures thereof.

Some examples relate to a sequence. To any extent that the sequence listing contradicts the disclosure in the specification, the specification takes precedent.

The terms "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present absent depending on the context.

The terms "subject," and "patient" may be used interchangeably herein. A "subject" can be a biological entity containing expressed genetic materials. The biological entity can be a plant, animal, or microorganism, including, for example, bacteria, viruses, fungi, and protozoa. The subject can be a mammal. The mammal can be a human. The subject may be diagnosed or suspected of being at high risk for a disease. In some cases, the subject is not necessarily diagnosed or suspected of being at high risk fbr the disease.

As used herein, the term "about" a number refers to that number plus or minus 10% of that number. The term "about" a range refers to that range minus 10% of its lowest value and plus 10% of its greatest value.

As used herein, the terms "treatment" or "treating" are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

"Treatment" or "treating" may include an approach for obtaining beneficial or desired results with respect to a disease, disorder, or medical condition including but not limited to a therapeutic benefit and/or a prophylactic benefit. A therapeutic benefit can include, for example, the eradication or amelioration of the underlying disorder being treated.

Also, a therapeutic benefit can include, for example, the eradication or amelioration of one or more of the physiological symptoms associated with the underlying disorder such that an improvement is observed in the subject, notwithstanding that the subject may still be afflicted with the underlying disorder. In certain embodiments, for prophylactic benefit, the compositions are administered to a subject at risk of developing a particular disease, or to a subject reporting one or more of the physiological symptoms of a disease, even though a diagnosis of this disease may not have been made. Treatment via administration of a compound described herein does not necessarily require the involvement of a medical professional.

The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkyl is meant to include groups that contain from x to y carbons in the chain. For example, the term "$C_{1-6}$ alkyl" refers to substituted or unsubstituted saturated hydrocarbon groups, including straight-chain alkyl and branched-chain alkyl groups that contain from 1 to 6 carbons. The term "$C_{x-y}$" or "$C_x$-$C_y$" is not meant to limit the number of carbon atoms which may be attached to the chemical moiety when the chemical moiety is substituted with a second chemical moiety. For example, the term "$C_{1-6}$ alkyl" or "$C_1$ to $C_6$ alkyl" refers to saturated, substituted or unsubstituted, hydrocarbon groups, including straight-chain alkyl groups (e.g., linear alkyl groups) and branched alkyl groups that contain 1, 2, 3, 4, 5, or 6 carbon atoms, plus however many carbon atoms may be present in any substituents of the $C_{1-6}$ alkyl. For example, if a $C_{1-6}$ alkyl is optionally substituted with a second chemical moiety comprising two carbon atoms, then it will be understood that the ($C_{1-6}$ alkyl can include between 1 and 8 carbon atoms.

The terms "$C_{x-y}$ alkenyl" and "$C_{x-y}$ alkynyl" refer to substituted or unsubstituted unsaturated aliphatic groups analogous in length and possible substitution to the alkyls described above, but that contain at least one double or triple bond, respectively.

"Amino" refers to the —$NH_2$ moiety.

"Cyano" refers to the —CN moiety.

"Nitro" refers to the —$NO_2$ moiety,

"Oxa" refers to the —O— moiety.

"Oxo" refers to the =O moiety.

"Thioxo" refers to the =S moiety.

"Imino" refers to the =N—H moiety.

"Oximo" refers to the =N—OH moiety,

"Hydrazino" refers to the =N—$NH_2$ moiety,

"Alkyl" refers to a straight or branched hydrocarbon moiety consisting solely of carbon and hydrogen atoms, fully saturated. In certain embodiments, "alkyl" comprises one to fifteen carbon atoms $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In certain embodiments, an alkyl comprises one to six carbon atoms (e.g., $C_1$-$C_6$ alkyl). In other embodiments, an alkyl comprises one to five carbon atoms (e.g., $C_1$-$C_5$ alkyl). In other embodiments, an alkyl comprises one to four carbon atoms e. $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl, e.g., methyl). In other embodiments, an alkyl comprises five to fifteen carbon atoms (e.g., $C_5$-$C_{15}$ alkyl). In other embodiments, an alkyl comprises fire to eight carbon atoms (e.g., $C_5$-$C_5$ alkyl). In other embodiments, an alkyl comprises two to five carbon atoms (e.g., $C_2$-$C_5$ alkyl), In other embodiments, an alkyl comprises three to five carbon atoms (e.g., $C_3$-$C_5$ alkyl). In other embodiments, the alkyl group is selected from methyl, ethyl, 1-propyl (n-propyl), -methylethyl(2-propyl, iso-propyl), 1-butyl (n-butyl), 1-methylpropyl (sec-butyl), 2-methylpropyl (iso-butyl), 1,1-dimethylethyl (tert-butyl), and 1-pentyl (n-pentyl). The alkyl is attached to the rest of the molecule by a single bond.

"Aminoalkyl" refers to a moiety boded through a nitrogen atom of the form —N(H)(alkyl) or N(alkyl)(alkyl), wherein when the moiety is N(alkyl)(alkyl), the two alkyl groups bonded to nitrogen can be the same alkyl groups or different alkyl groups.

"Alkoxy" refers to a moiety bonded through an oxygen atom of the formula —O-alkyl, where alkyl is an alkyl chain as defined above.

"Alkenyl" refers to a straight or branched hydrocarbon moiety consisting solely of carbon and hydrogen atoms, containing at least one carbon-carbon double bond. In certain embodiments, an alkenyl comprises two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl allyl), but-1-enyl, pent-1-enyl, Penta-1,4-dienyl, and the like.

"Alkynyl" refers to a straight or branched hydrocarbon moiety consisting solely of carbon and hydrogen atoms, containing at least one carbon-carbon triple bond, having from two to twelve carbon atoms, and optionally further comprising at least one carbon-carbon double bond. In certain embodiments, an alkynyl comprises two to eight carbon atoms. In other embodiments, an alkynyl comprises two to six carbon atoms. In other embodiments, an alkynyl comprises two to four carbon atoms. The alkynyl is attached to the rest of the molecule by a single bond, for example, ethynyl, propynyl, butynyl, pentynyl, hexynyl, and the like.

"Alkylene" or "alkylene chain" refers to a linear (e.g., straight), or branched, divalent, hydrocarbon moiety. An "alkylene" or "alkylene chain" can link a portion of the molecule to a second moiety, An "alkylene" or "alkylene chain" consists solely of carbon and hydrogen atoms (substitution of an alkylene with one or more substituents comprising atoms other than hydrogen, such as N, O, and S, may be specified). An "alkylene" or "alkylene chain" can contain no unsaturation (notwithstanding the points of attachment of an alkylene to the rest of the molecule). In certain embodiments, the "alkylene" or "alkylene chain" and comprises one to twelve carbon atoms, for example, methylene, ethylene, propylene, n-butylene, and the like. The alkylene chain can be attached to the portion of the molecule through a single bond and to the second moiety through a single bond. The points of attachment of an alkylene chain to the rest of the molecule and to the second moiety can be through one carbon in the alkylene chain or through any two carbons within the alkylene. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene).

"Alkenylene" or "alkenylene chain" refers to a linear (e.g., straight), or branched, divalent, hydrocarbon moiety. An "alkenylene" or "alkenylene chain" can link a portion of the molecule to a second moiety. An "alkenylene" or "alkenylene chain" consists solely of carbon and hydrogen atoms (substitution of an alkenylene with one or more substituents comprising atoms other than hydrogen, such as N, O, and S, may be specified). An "alkenylene." or "alkenylene chain" comprises at least one carbon-carbon double bond. In certain embodiments, an "alkenylene" or "alkenylene chain" comprises from two to twelve carbon atoms. The alkenylene chain can be attached to the portion of the molecule through a single bond and to the second moiety through a single bond. The points of attachment of an alkenylene chain to the rest of the molecule and to the second moiety can be through one carbon in the alkenylene chain or through any two carbons within the alkenylene chain. In certain embodiments, an alkenylene comprises two to eight carbon atoms (e.g.; $C_2$-$C_8$ alkenylene). In other embodiments, an alkenylene comprises two to five carbon atoms (e.g., $C_2$-$C_5$ alkenylene). In other embodiments, an alkenylene comprises two to four carbon atoms (e.g., $C_2$-$C_4$ alkenylene). In other embodiments, an alkenylene comprises two to three carbon atoms (e. g, $C_2$-$C_3$ alkenylene). In other embodiments, an alkenylene comprises five to eight carbon atoms (e.g., $C_5$-$C_8$ alkenylene). In other embodiments, an alkenylene comprises two to five carbon atoms (e.g., $C_2$-$C_5$ alkenylene). In other embodiments, an alkenylene comprises three to five carbon atoms (e.g, $C_3$-$C_5$ alkenylene).

"Alkynylene" or "alkynylene chain" refers to a linear (e.g., straight), or branched, divalent, hydrocarbon moiety. An "alkynylene" or "alkynylene chain" can link a portion of the molecule to a second moiety. An "alkynylene" or "alkynylene chain" consists solely of carbon and hydrogen (substitution of an alkynylene with one or more substituents comprising atoms other than hydrogen, such as N, O, and S, may be specified). An "alkynylene" or "alkynylene chain" comprises at least one carbon-carbon triple bond. In certain embodiments, an "alkynylene" or "alkynylene chain" comprises from two to twelve carbon atoms. An alkynylene chain can be attached to the portion of the molecule through a single bond and to the second moiety through a single bond. The points of attachment of an alkynylene chain to the rest of the molecule and to the second moiety can be through one carbon in the alkynylene chain or through any two carbons within the alkynylene chain. In certain embodiments, an alkynylene comprises two to eight carbon atoms (e.g., $C_2$-$C_6$ alkynylene). In other embodiments, an alkynylene comprises two to five carbon atoms (e.g., $C_2$-$C_5$ alkynylene). In other embodiments, an alkynylene comprises two to four carbon atoms (e.g., $C_2$-$C_4$ alkynylene). In other embodiments, an alkynylene comprises two to three carbon atoms e.g., $C_2$-$C_3$ alkynylene). Iii other embodiments, an alkynylene comprises two carbon atom (e.g., $C_2$ alkylene). In other embodiments, an alkynylene comprises five to eight carbon atoms (e.g., $C_5$-$C_8$ alkynylene). In other embodiments, an alkynylene comprises three to five carbon atoms (e.g., $C_3$-$C_5$ alkynylene).

The term "carbocycle" as used herein refers to a saturated, unsaturated or aromatic ring in which each atom of the ring is carbon. Carbocycle includes 3- to 10-membered monocyclic rings, 5-to 12-membered bicyclic rings, 5-to 12-membered. Spiro bicycles, and 5-to 12-membered bridged rings. Each ring of a bicyclic carbocycle may be selected from saturated, unsaturated, and aromatic rings. In an exemplary embodiment, an aromatic ring, e.g., phenyl, may be fused to a saturated or unsaturated ring, e.g., cyclohexane, cyclopentane, or cyclohexane. A bicyclic carbocycle includes any combination of saturated, unsaturated and aromatic bicyclic rings, as valence permits. A bicyclic carbocycle further includes spiro bicyclic rings such as spiropentane. A bicyclic carbocycle includes any combination of ring sizes such as 3-3 spiro ring systems, 4-4 Spiro ring systems, 4-5 fused ring systems. 5-5 fused ring systems, 5-6 fused ring systems, 6-6 fused ring systems, 5-7 fused ring systems, 6-7 fused ring systems, 5-8 fused ring systems, and 6-8 fused ring systems. Exemplary carbocycles include cyclopentyl, cyclohexyl, cyclohexenyl, adamantyl, phenyl, indanyl, naphthyl, and bicyclo[1.1.1]pentanyl. "Carbocycle" may include "aryl" and "cycloalkyl."

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized (4n+2) π-electron system in accordance with the Hückel theory. The ring system from which aryl groups are derived include, but are not limited to, groups such as benzene, fluorene, indane, indene, tetralin and naphthalene. In some embodiments, the aryl substituent is positively or negatively charged. In some embodiments, the aryl substituent is neutral. In some embodiments, the aryl substituent is zwitterionic; alternatively, or in addition, in some embodiments, the aryl substituent is not charged. In some embodiments, the aryl substituent bears no charges. In some embodiments, the aryl substituent bears no net charge. In some embodiments, the aryl substituent bears no net charge and is not zwitterionic.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, 5- to 12-membered spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and Cyclooctyl. Polycyclic cycloalkyl radicals include, for example, adamantyl, spiropentane, norbornyl (i.e., bicyclo[2.2.1]heptanyl), decalinyl, 7,7 dimethyl bicyclo[2.2.1]heptanyl, bicyclo[1.1.1]pentanyl, and the like.

The term "cycloalkenyl" refers to a saturated ring in which each atom of the ring is carbon and there is at least one double bond between two ring carbons. Cycloalkenyl may include monocyclic and polycyclic rings such as 3- to 10-membered monocyclic rings, 6-to 12-membered bicyclic rings, and 5-to 12-membered bridged rings. In other embodiments, a cycloalkenyl comprises five to seven carbon atoms. The cycloalkenyl may be attached to the rest of the molecule by a single bond. Examples of monocyclic cycloalkenyls include, e.g., cyclopentenyl, cyclohexenyl, cycloheptenyl, and cyclooctenyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trichloromethyl, dichloromethyl, bromomethyl, 2,2,2-trifluormethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro bicycles, and 5-to 12-membered bridged rings bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems. 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicyclic rings, e.g., 5 to 12-membered Spiro bicycles, such as 2-oxa-azaspiro[3.3] heptane. "Heterocycle" may include "heteroaryl" and "heterocycloalkyl".

The term "heteroaryl" refers to a radical derived from a 5 to 18 membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is aromatic, i.e., it contains a cyclic, delocalized (4n+2) electron system in accordance with the Hückel theory, Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazol. 4, benzo[d]thiazolyl, benzothiadiazolyl, benzo[b][,4]dioxepanyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d-]pyrimidinyl, benzotriazolyl, benzo[4,6]imidazo[1,2-a]pyridinyl, carbazolyl, cinnolinyl cyclopenta[d]pyrimidinyl, 6,7-dihydro-5H-cyclopenta[4,5]thieno[2,3-d]pyrimidinyl, 5,6-dihydrobenzo[h] quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d] pyrimidinyl, pyrido[3,4-d]pyrimidinyl, pyrazinyl, pyrimidinyl pyridazinyl, pyrrolyl, quinazolinyl quinoxalinyl, quinolinyl, isoquinolinyl, tetrahydroquinolinyl, 5,6,7,8-tetrahydroquinazolinyl, 5,6,7,8-tetrahydrobenzo[4,5]thieno [2,3-d]pyrimidinyl, 6,7,8,9-tetrahydro-5H-cyclohepta[4,5] thieno[2,3-d]pyrimidinyl, 5,6,7,8-tetrahydropyrido[4,5-c] pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenol (i.e. thienyl).

One or more nitrogen atoms, if present, may be optionally quaternized. In some embodiments, the heterocycle substituent is positively or negatively charged. In some embodiments, the heterocycle substituent is neutral. In some embodiments, the heterocycle substituent is zwitterionic; alternatively, or in addition, in some embodiments, the heterocycle substituent is not charged. In some embodiments, the heterocycle substituent bears no charges. In some embodiments, the heterocycle substituent bears no net charge. In some embodiments, the heterocycle substituent bears no net charge and is not zwitterionic.

The term "heterocycloalkyl" refers to a saturated ring with carbon atoms and at least one heteroatom. Exemplary heteroatoms include N, O, Si, P, B, and S atoms, Heterocycloalkyl may include monocyclic and polycyclic rings such as 3- to 10-membered monocyclic rings, 6-to 12-membered bicyclic rings. 5-to 12-membered Spiro bicycles, and 5- to 12-membered bridged rings. The heteroatoms in the heterocycloalkyl radical are optionally oxidized. One or more nitrogen atoms, if present, are optionally quaternized. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl pyrazolidinyl, thiazolidinyl, tetrahydrofuryl, trithianyl, tetrahydropyranyl, thiomorpholinyl, thiamorpholinyl, 1-oxo-thiomorpholinyl, 2-oxa,-6-azaspiro[3.3]heptane, and 1,1-dioxo-thiomorpholinyl. In some embodiments, a heterocycloalkyl comprises one heteroatom. In some embodiments, a heterocycloalkyl comprises one heteroatom selected from N, O, and S. In some embodiments, a heterocycloalkyl comprises multiple heteroatoms. In some embodiments, a heterocycloalkyl comprises multiple heteroatoms selected from N, O, and S.

The term "heterocycloalkenyl" refers to an unsaturated ring with carbon atoms and at least one heteroatom and there is at least one double bond between two ring carbons. Heterocycloalkenyl does not include heteroaryl rings. Exemplary heteroatoms include N. O. Si, P. B, and S atoms. Heterocycloalkenyl may include monocyclic and polycyclic rings such as 3- to 10-membered monocyclic rings, 6-to 12-membered bicyclic rings, and 5-to 12-membered bridged rings. In other embodiments, a heterocycloalkenyl comprises five to seven ring atoms. The heterocycloalkenyl may be attached to the rest of the molecule by a single bond. Examples of monocyclic cycloalkenyls include, e.g., pyrroline (dihydropyrrole), pyrazoline (dihydropyrazole), imidazoline (dihydroimidazole), triazoline (dihydrotriazolo), dihydrofuran, dihydrothiophene, oxazoline (dihydrooxazole), isoxazoline (dihydroisoxazole), thiazoline (dihydrothiazole), isothiazoline (dihydroisothiazole), oxadiazoline (dihydroxadiazole), thiadiazoline (dihydrothiadiazole), dihydropyridine, tetrahydropyridine, dihydropyridazine, tetrahydropyridazine, dihydropyrimidine, tetrahydropyrimidine, dihydropyrazine, tetrahydropyrazine, pyran, dihydropyran, thiopyran, dihydrothiopyran, dioxine, dihydrodioxine, oxazine, dihydrooxazine, thiazide, and dihydrothiazine.

The term "substituted" refers to moieties having substituents replacing a hydrogen on one or more carbons or substitutable heteroatoms, e.g., an NH or NH$_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. in certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—NO$_2$), imino (=N—H)), oximo (=N—OH), hydrazino (=N—NH$_2$), —R$^b$—OR$^a$, —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)R$^a$ (where t is 1 or 2), —R$^b$—S(O)R$^a$ (where t is 1 or 2), —R$^b$—S(O)OR$^a$ (where t is 1 or 2), and —R$^b$—S(O)$_t$N(R$^a$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally-substituted by alkyl, alkenyl, alkynyl, halogen, haloalkyl, haloalkenyl, haloalkynyl, oxo (=O), thioxo (=S), cyano (—CN), nitro (—NO$_2$), imino (=N—H), oximo (=N—OH), hydrazine (=N—NH$_2$), —R$^b$—OC(O)—R$^a$, —R$^b$—OC(O)—OR$^7$, —R$^b$—OC(O)—N(R$^a$)$_2$, —R$^b$—C(O)R$^a$, —R$^b$—C(O)OR$^a$, —R$^b$—C(O)N(R$^a$)$_2$, R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)R$^a$ (where t is 1 or 2), —R$^b$—S(O)R$^a$ (where t is 1 or 2), —R$^b$—S(O)PR' (where t is 1 or 2) and —R$^b$—S(O)$_t$N(R$^a$)$_2$ (where t is 1 or 2); wherein each W is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each W, valence permitting, may be optionally substituted with alkyl, alkenyl, alkynyl, halogen, haloalkyl, haloalkenyl, haloalkynyl, oxo (=O), thioxo (=S), cyano (—CN), nitro (—NO$_2$) imino (=N—H), oximo (=N—OH), hydrazine (=N—NH$_2$), —R$^b$—OC(O)—R$^a$, —R$^b$—OC(O)—OR$^a$, —R$^b$—OC(O)—N(R$^a$)$_2$, —R$^b$—N(R$^a$)$_2$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^a$, —R$^b$—N(R$^a$)C(O)R$^a$, —R$^b$—N(R$^a$)S(O)R$^a$ (where t is 1 or 2), —R$^b$—S(O)R$^a$ (where t is 1 or 2), —R$^b$—S(O)OR$^a$ (where t is 1 or 2) and —R$^b$—S(O)$_t$N(R$^a$)$_2$ (where t is 1 or 2); and wherein each R$^b$ is independently selected from a direct bond or a straight or branched alkylene, alkenylene, or alkynylene chain, and each R$^5$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrases "parenteral administration" and "administered parenterally" as used herein means modes of administration other than enteral and topical administration, usually by injection, and includes, without limitation, intravenous, intramuscular, intra-arterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil; cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesufonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like.

Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

VI. EXAMPLES

Example 1: Identification of Variants in a Target Oligonucleotide Associated with Increased or Decreased Risk of a Disorder Approximately 30,000,000 imputed variants are to be analyzed in 4375,000 individuals from a Biohank cohort for associations with liver disorders such as non-alcoholic steatohepatitis.

Protective or maladaptive associations are observed between specific allelic variants of various target genes and liver diseases. The associations will suggest that in some cases therapeutic inhibition or modulation of a target protein encoded by any of the target genes may be an effective genetically-informed method of treatment for any of the liver disorders.

Example 2: Bioinformatic Selection of Sequences in Order to Identify Therapeutic siRNAs to Downmodulate Expression of a Target mRNA Screening sets are to be defined based on bioinformatic analysis. Therapeutic siRNAs are designed to bind human target mRNAs, and the target snRNA sequence of at least one toxicology-relevant species such as a non-human primate (NHP) species (e.g. a rhesus or cynomolgus monkey). Drivers for the design of the screening set are predicted specificity of the siRNAs against the transcriptome of the relevant species as well as cross-reactivity between species. Predicted specificity in human, rhesus monkey, cynomolgus monkey, mouse and rat are determined for sense (S) and antisense (AS) strands. These are assigned a "specificity score" which considers the likelihood of unintended downregulation of any other transcript by full or partial complementarity of an siRNA strand (up to 4 mismatches within positions 2-18) as well as the number and positions of mismatches. Thus, off-target(s) for antisense and sense strands of each siRNA are identified. In addition, the number of potential off-targets are used as an additional specificity factor in the specificity score. As identified, siRNAs with high specificity and a low number of predicted off-targets provide a benefit of increased targeting specificity.

In addition to selecting siRNA sequences with high sequence specificity to the target mRNA, siRNA sequences within a seed region are analyzed for similarity to seed regions of known miRNAs siRNAs can function in a miRNA like manner via base-pairing with complementary sequences within the 3'-UTR of mRNA molecules. The complementarity typically encompasses the 5'-bases at positions 2-7 of the miRNA (seed region). To circumvent siRNAs to act via functional miRNA binding sites, siRNA strands containing natural miRNA seed regions are avoided. Seed regions identified in miRNAs from human, mouse, rat, rhesus monkey, dog, rabbit and pig are referred to as "conserved". Combining the "specificity score" with miRNA seed analysis yields a "specificity category". This is divided into categories 1-4, with 1 having the highest specificity and 4 having the lowest specificity. Each strand of the siRNA is assigned to a specificity category.

Species cross-reactivity are assessed for human, cynomolgus monkey, rhesus monkey, mouse and rat. The analysis is based on a canonical siRNA design using 19 bases and 17 bases (without considering positions 1 and 19) for cross-reactivity. Full match as well as single mismatch analyses are included.

Analysis of the human Single Nucleotide Polymorphism (SNP) database (NCBI-DB-SNP) to identify siRNAs targeting regions with known SNPs are also carried out to identify siRNAs that may be non-functional in individuals containing the SNP. Information regarding the positions of SNPs within the target sequence as well as minor allele frequency (MAF) in case data are obtained in this analysis.

The above methods can be used to identify therapeutic siRNAs to downmodulate expression of a target mRNA. Bioinformatic methods may, also be used to identify ASOs that bind and downmodulate expression of a target mRNA.

Example 3: Chemically Modified siRNAs siRNAs that bind a target mRNA can be synthesized with chemical modifications with the sense strand having a modification such as modification pattern 1 S, and the antisense strand having a modification such as modification pattern 1AS. In addition, adenosine can be placed at position 19 in the sense strand and uridine at position 1 in the antisense strand.

The siRNAs that bind a target snRNA can also be synthesized with chemical modifications with the sense strand having modification pattern 2S and the antisense strand having modification pattern 3AS, In addition, adenosine can be placed at position 19 in the sense strand and uridine at position 1 in the antisense strand.

The siRNAs that bind a target mRNA can also be synthesized with chemical modifications with the sense strand having modification pattern 2S and the antisense strand having modification pattern 9AS. In addition, adenosine can be placed at position 19 in the sense strand and uridine at position 1 in the antisense strand.

The siRNAs targeting that bind a target mRNA can also be synthesized with chemical modifications with the sense strand having modification pattern 3S and the antisense strand having modification pattern 3AS, In addition, adenosine can be placed at position 19 in the sense strand and uridine at position 1 in the antisense strand.

The siRNAs targeting that bind a target mRNA can also be synthesized with chemical modifications with the sense strand having any of the following: all purines comprising 2' fluor© modified purines, and all pyrimidines comprising a mixture of 2' fluoro and 2'-O-methyl modified pyrimidines; all purines comprising 2'43-methyl modified purines, and all pyrimidines comprising a mixture of 2' fluoro and 2'-O-methyl modified pyrimidines; all purines comprising 2' fluoro modified purines, and all pyrimidines comprising 2'-O-methyl modified pyrimidines; all pyrimidines comprising 2' fluoro modified pyrimidines, and all purines comprising a mixture of 2' fluoro and 2'-O-methyl modified purines: pyrimidines comprising 2'-O-methyl modified pyrimidines, and all purines comprising a mixture of 2' fluoro and 2'-O-methyl modified purities; or till pyrimidines comprising 2' fluoro modified pyrimidines, and all purines comprising 2'43-methyl modified purines; and further with the antisense strand having any of the following: all purines comprising 2' fluoro modified purines, and all pyrimidines comprising a mixture of 2' fluoro and 2'43-methyl modified pyrimidines; all purines comprising 2'43-methyl modified purines, and all pyrimidines comprising a mixture of 2' fluoro and 2'-O-methyl modified pyrimidines; all purines comprising 2'43-methyl modified purines, and all pyrimidines comprising 2' fluoro modified pyrimidines; all pyrimidines comprising 2' fluoro modified pyrimidines, and all purities comprising a mixture of 2' fluoro and 2'-O-methyl modified purines; all pyrimidines comprising 2'-O-methyl modified pyrimidines, and all purines comprising a mixture of 2' fluoro and 2'-O-methyl modified purines; or all pyrimidines comprising 2'-O-methyl modified pyrimidines, and all purines comprising 2' fluoro modified purines.

Example 4: Screening siRNAs for Activity in Cells in Culture

The chemically modified siRNAs derived from sequences in the previous Examples will be assayed for target snRNA knockdown activity in cells in culture. A cell line that expresses the target mRNA is to be seeded in 96-well tissue culture plates at a cell density of 10,000 cells per well in DMEM supplemented with 10% fetal bovine serum and incubated overnight in a water-jacketed, humidified incubator at 37° C. in an atmosphere composed of air plus 5% carbon dioxide. The siRNAs are individually transfected into cells in duplicate wells at 10 nM final concentration using 0.3 µL: Lipofectamine RNAiMax (Fisher) per well. Silencer Select Negative Control #1 (ThermoFisher, Catalog#4390843) and a positive control siRNA are transfected at 10 nM final concentration as controls. After incubation for 48 hours at 37° C., total RNA is harvested from each well and cDNA prepared using TaqMan® Fast Advanced Cells-to-Crum Kit (Thermaisher, Catalog#A35374) according to the manufacturer's instructions. The level of target m-RNA in each well will be measured in triplicate by real-time qPCR on an Applied Biosystems 7500 Fast Real-Time PCR machine using TaqMan Gene Expression Assay for the human target snRNA. The level of PPIA mRNA will be measured using TaqMan Gene Expression Assay (ThermoFisher) and used to determine relative target mRNA levels in each well using the delta-delta Ct method. Data will be normalized to relative target mRNA levels in untreated cells.

The siRNAs showing the greatest degree of knockdown of target mRNA at 10 nM will be tested in a second screen for activity at 1 nM concentration using the transfection procedures as described above. Similar experiments may be performed using ASOs. Thus, siRNAs and ASOs may be identified that most effectively downmodulate expression of the target mRNA.

Example 5: GalNAc Ligands for Hepatocyte Targeting of Oligonucleotides

Without limiting the disclosure to these individual methods, there are at least two general methods for attachment of multivalent N-acetylgalactosamine (GalNAc) ligands to oligonucleotides: solid or solution-phase conjugations. GalNAc ligands may be attached to solid phase resin for 3' conjugation or at the 5' terminus using GalNAc phosphoramidite reagents. GalNAc phosphoramidites may be coupled on solid phase as for other nucleosides in the oligonucleotide sequence at any position in the sequence. A non-limiting example of a phosphoramidite reagent for GalNAc conjugation to a 5' end oligonucleotide is shown in Table 1.

TABLE 1

GalNAc Conjugation Reagent

| Type of conjugation | Structure |
|---|---|
| Solid phase 5' attachment phosphoramidite | 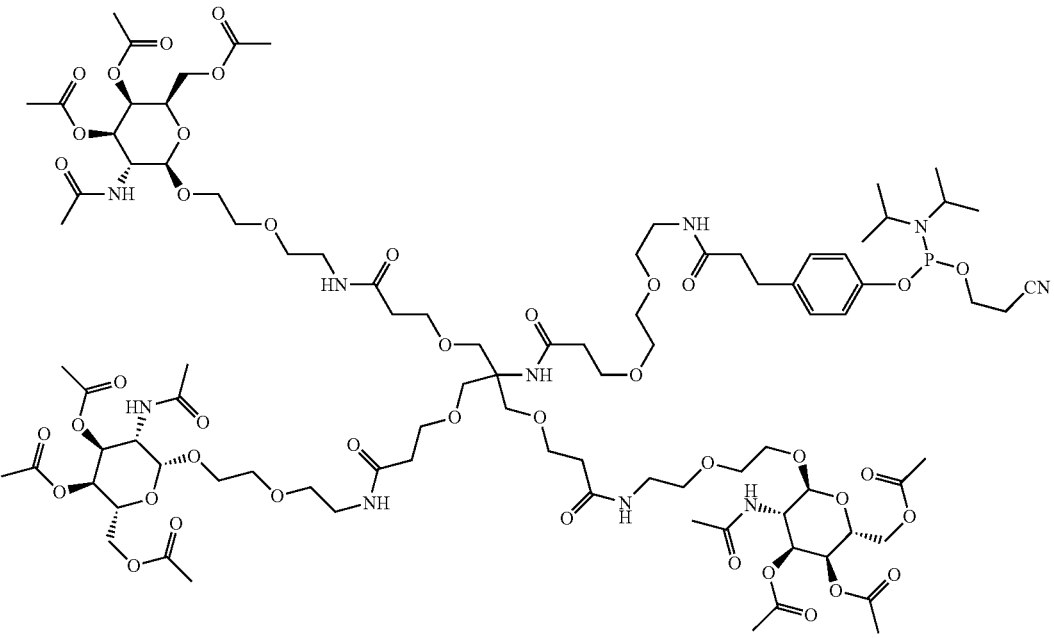 [SMILES: CC(=O)N[C@@H]1[C@H](OCCOCCNC(=O)CCOCC(COCCC(=O)NCCOCCO[C@H]2O[C@H](COC(C)=O)[C@@H](OC(C)=O)[C@@H](OC(C)=O)[C@@H]2NC(C)=O)(COCCC(=O)NCCOCCO[C@@H]2O[C@H](COC(C)=O)[C@H](OC(C)=O)[C@H](OC(C)=O)[C@H]2NC(C)=O)NC(=O)CCOCCOCCNC(=O)CCc2ccc(OP(OCCC#N)N(C(C)C)C(C)C)cc2)O[C@H](COC(C)=O)[C@@H](OC(C)=O)[C@H]1OC(C)=O] |

Example 6: Synthesis of GalNAc Ligands

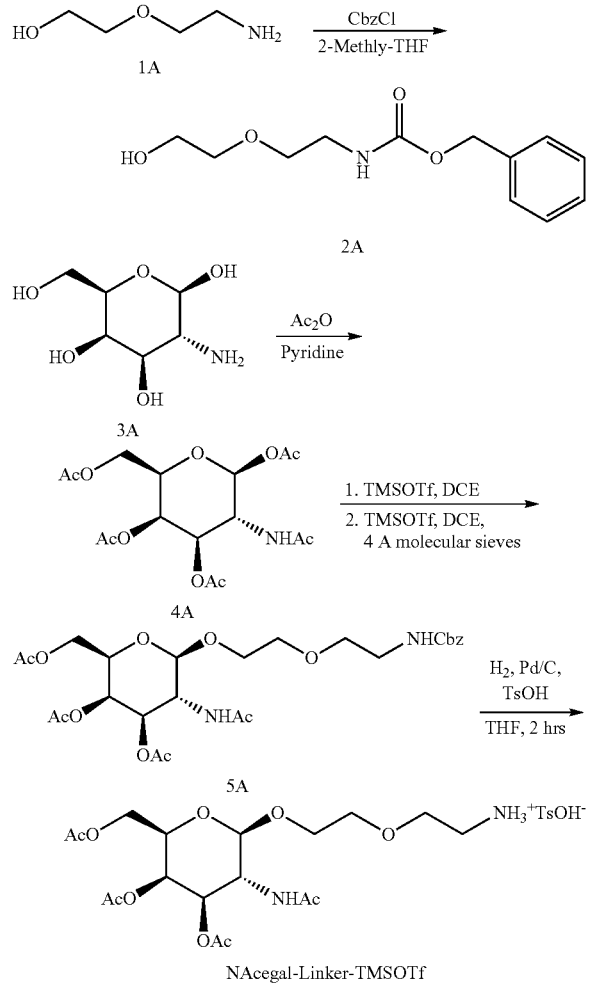

General procedure for preparation of Compound 2A

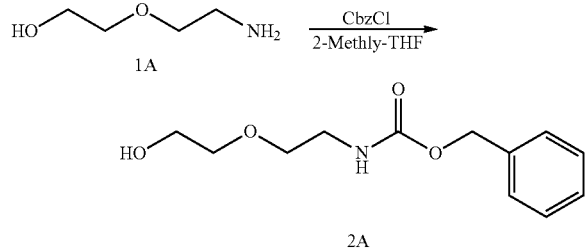

To a solution of Compound 1A (500 g, 4.76 mol, 476 mL) in 2-Methly-THF (2.00 L) was added CbzCl (406 g, 2.38 mot, 338 mL) in 2-Methyl-THF (750 mL) dropwise at 0° C. The mixture was stirred at 25° C. for 2 hrs under N$_2$ atmosphere. TLC (DCM: MeOH=20:1, PMA) indicated CbzCl was consumed completely and one new spot (R$_f$=0.43) formed. The reaction mixture was added HCl/ EtOAc (I N, 180 mL) and stirred for 30 mins, white solid was removed by filtration through celite, the filtrate was concentrated under vacuum to give Compound 2A (540 g, 2.26 mol, 47.5% yield) as a pale yellow oil and used into the next step without further purification. $^1$H NMR: δ 7.28-7.41 (m, 5H), 5.55 (br s, 1H), 5.01-5.22 (m, 2 to, 3.63-3.80 (m, 2H), 3.46-3.59 (m, 4H). 3.29-3.44 (m, 2H), 2.83-3.02 (in, 1H).

General procedure for preparation of Compound 4A

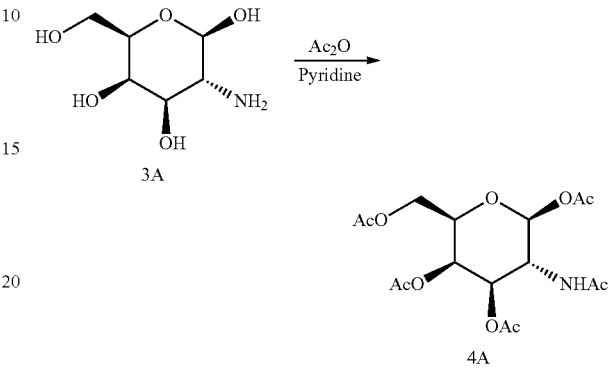

To a solution of Compound 3A (1.00 kg, 4.64 mol, HCl) in pyridine (5.00 L) was added acetyl acetate (4.73 kg, 46.4 mol. 4.34 L) dropwise at 0° C. under N$_2$ atmosphere. The mixture was stirred at 25° C. for 16 hrs wider N$_2$ atmosphere. TLC (DCM: MeOH=20:1, PMA) indicated Compound 3A was consumed completely and two new spots (R$_f$=0.35) formed. The reaction mixture was added to cold water (30.0 L) and stirred at 0° C. for 0.5 hr, white solid formed, filtered and dried to give Compound 4A (1.55 kg, 3.98 mol, 85.8% yield) as a white solid and used in the next step without further purification, $^1$H NMR: δ 7.90 (d, J 9.29 Hz, 1H), 5.64 (d, J=8.78 Hz, 1H), 5.26 (d, 3.01 Hz, 1H), 5.06 (dd, J=11.29, 3.261-1z, 1. H), 4.22 (t, J 6.15 Hz, 1H), 3.95-4.16 (m, 3H), 2.12 (s, 3H), 2.03 (s, 3H), 1.99 (s, 3H), 1.90 (s, 3H), 1.78 (s, 3 H).

General procedure for preparation of Compound 5A

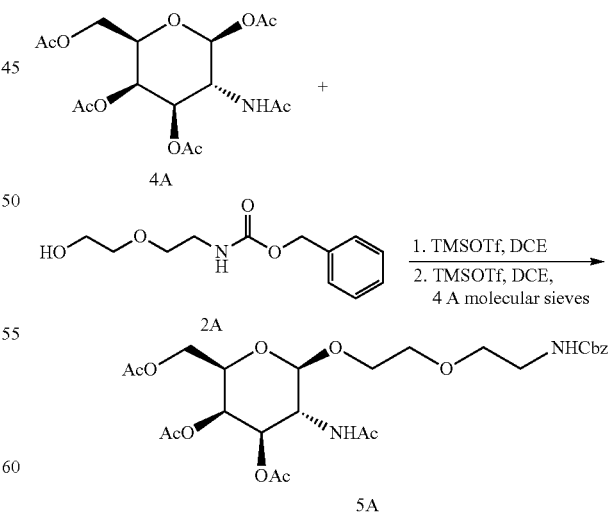

To a solution of Compound 4A (300 g, 771 mmol) in DCE (1.50 L) was added TMSOTF (257 g, 1.16 mol. 209 mL) and stirred for 2 hrs at 60° C., and then stirred for 1 hr at 25° C. Compound 2A (203 g, 848 mmol) was dissolved in DCE (1.50 L) and added 4 A powder molecular sieves (150 g) stirring for 30 mins under $N_2$ atmosphere. Then the solution of Compound 4A in DCE was added dropwise to the mixture at 0° C. The mixture was stirred at 25 for 16 hrs under $N_2$ atmosphere, TLC (DCM:MeOH=25:1, PMA) indicated Compound 4A was consumed completely and new spot ($R_1$=0.24) formed. The reaction mixture was filtered and washed with sat. $NaHCO_3$(2.00 L), water (2.00 L) and sat. brine (2.00 L). The organic layer was dried over anhydrous Na2SO4, filtered and concentrated under reduced pressure to give a residue. The residue was triturated with 2-Me-THF/heptane (5/3, v/v, 1.80 L) for 2 hrs, filtered and dried to give Compound 5A (225 g, 389 mmol, 50.3% yield, 98.4% purity) as a white solid. $^1$H NMR: δ 7.81 (d, 9.29 Hz, 1H), 7.20-7.42 (m, 6H), 5.21 (d, 3.26 Hz, 1H), 4.92-5.05 (m, 3H), 4.55 (d, J 8.28 Hz, 1H), 3.98-4.07 (m, 3H), 3.82-3.93 (m, 1H), 3.71-3.81 (m, 1 H), 3.55-3.62 (m, 1H), 3.43-3.53 (m, 2H), 3.37-3.43 (m, 2H), 3.14 (q, J–5.77 Hz, 2H), 2.10 (s, 3H), 1.99 (s, 3H), 1.89 (s, 3 H). 1.77 (s, 3H).

General procedure for preparation of NAcegal-Linker-Tosylate salt

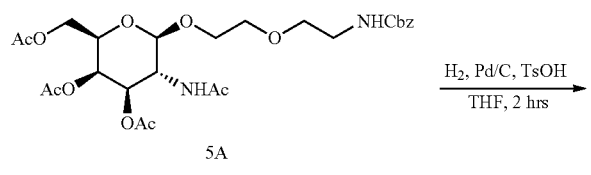

NAcegal-Linker-TMSOTf

To a solution of Compound 5A (200 n, 352 mmol) in THE (1.01) was added Pd/C (15.0 g, 10% purity) and TsOH (60.6 g. 352 mmol) under $N_2$ atmosphere. The suspension was degassed under vacuum and purged with $H_2$ several times. The mixture was stirred at 25° C. for 3 hrs under 1-12 (45 psi) atmosphere. TLC (DCM: MeOH=10:1, PMA) indicated Compound 5A was consumed completely and one new spot ($R_1$=0.04) was formed. The reaction mixture was filtered and concentrated (≤40° C.) under reduced pressure to give a residue. Diluted with anhydrous DCM (500 mL, dried overnight with 4 A molecular sieves (dried at 300° C. for 12 hrs)) and concentrate to give a residue and run Karl Fisher (KF) to check for water content. This was repeated 3 times with anhydrous DCM (500 mL) dilutions and concentration to give NAcegal-Linker-TMSOIT (205 g, 95.8% yield, TsOH salt) as a foamy white solid. $^1$H NMR: δ 7.91 (d, J 9.03 Hz. 1 H), 7.53-7,86 (m, 2H). 7.49 (d, 8.03 Hz, 2H), 7.13 (d, 8.03 Hz, 2H), 5.22 (dJ 3.26 Hz, 1H), 4.98 (dd, –11.29, 3.26 Hz, 1 H), 4.57 (d. –8.53 Hz, 1H), 3.99-4.05 (m, 3H), 3.87-3.94 (m, 1 H), 3.79-3.85 (m, 1H), 3.51-3.62 (m, 5H), 2.96 (br 5.14 Hz, 2H), 2.29 (s, 3H), 2.10 (s, 3 H), 2.00 (s, 3H), 1.89 (s, 3H). 1.78 (s. 3 H).

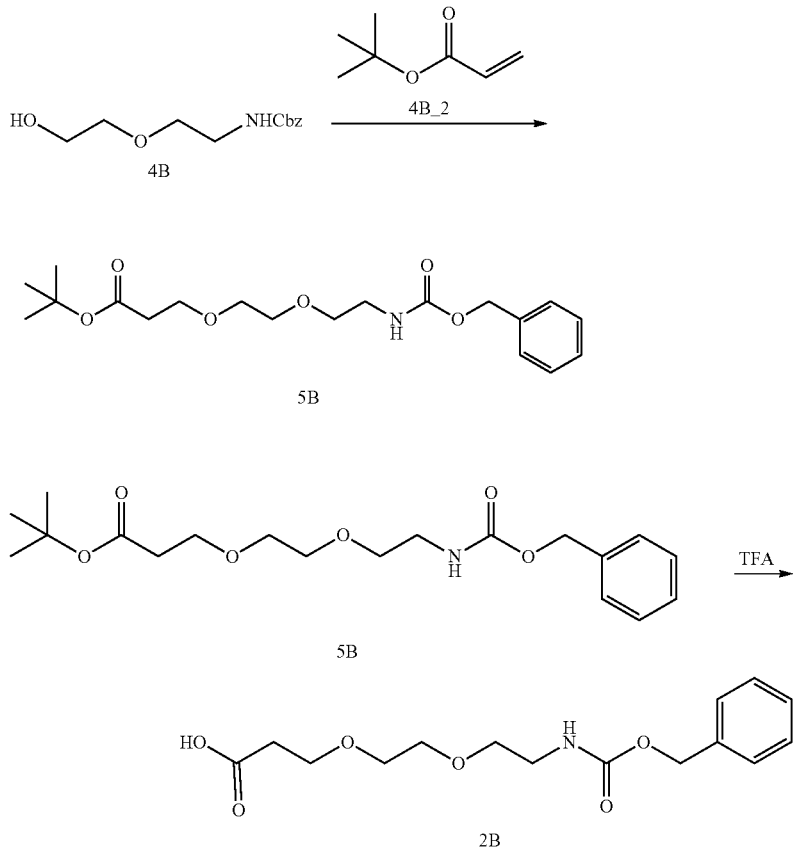

-continued
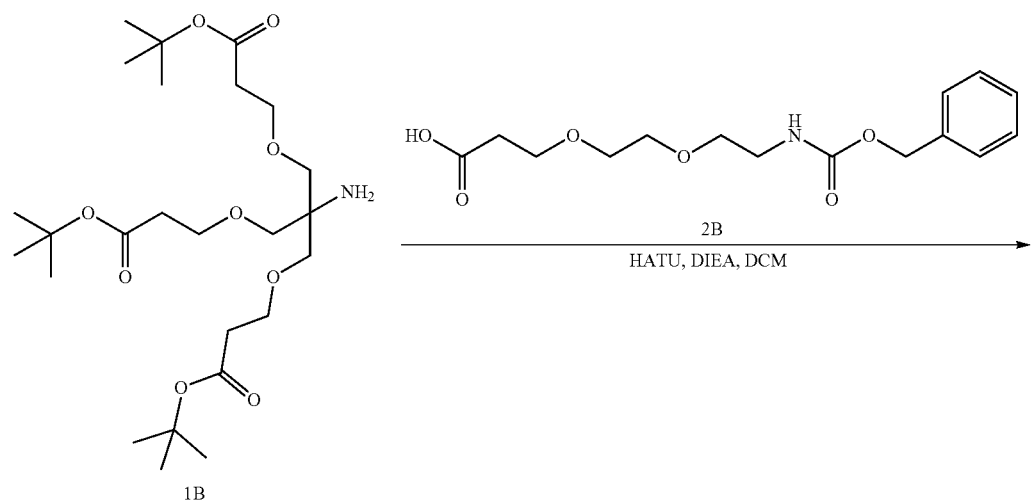
1B
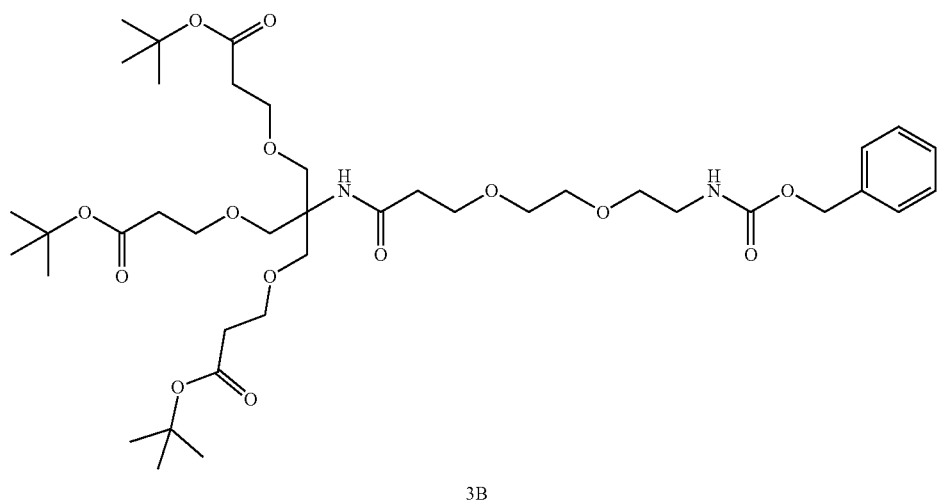
3B
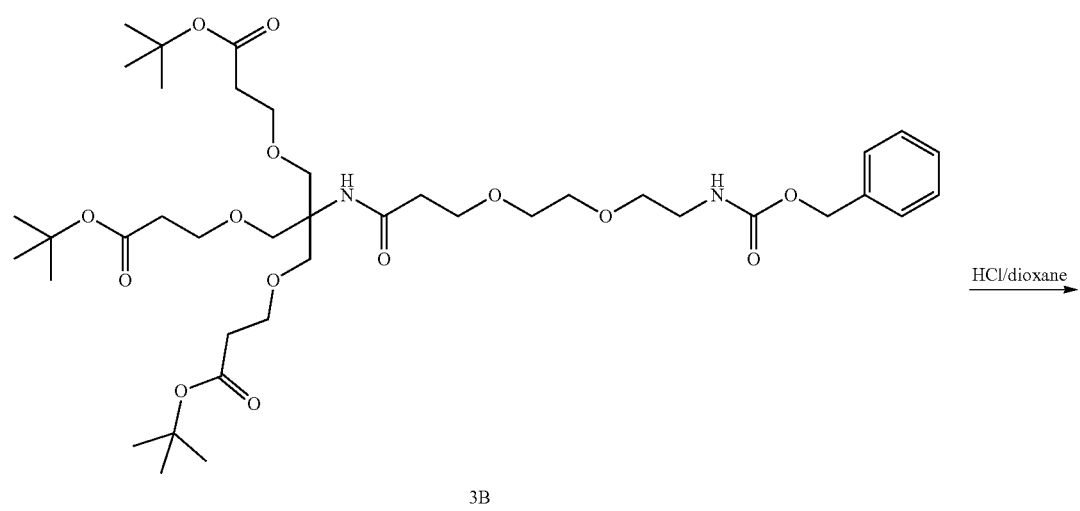
3B

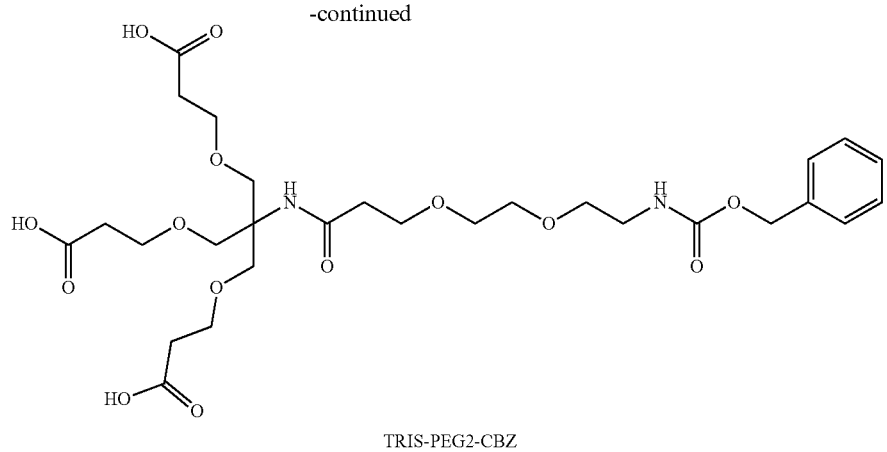

TRIS-PEG2-CBZ

General procedure for preparation of Compound 513

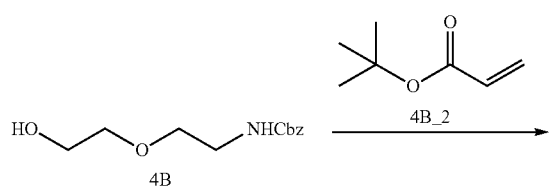

water (6.00 L), extracted with ethyl acetate (3.00 L*3), the combined organic layer was washed with brine (3.00 L), dried over $Na_2SO_4$, filtered and concentrated under vacuum. The crude was purified by column chromatography ($SiO_2$, petroleum ether: ethyl acetate=100:1-10:1, $R_1$=0.5) to give Compound 5B (2.36 kg, 6.43 mol, 76.9% yield) as light yellow oil. HNMR: δ7.31-7.36 (m, 5H). 5.38 (s, 1 H), 5.11-5.16 (m, 2H), 3.75 (t, J=6.4 Hz), 3.54-3.62 (m, 6H), 3.39 (dJ=5.2 Hz), 2.61 (t1=6.0 Hz).

General procedure fin preparation of 3-oxo-1-phenyl-2,7,10-trioxa-4-azatridecan-13-oic acid (Compound 2B below)

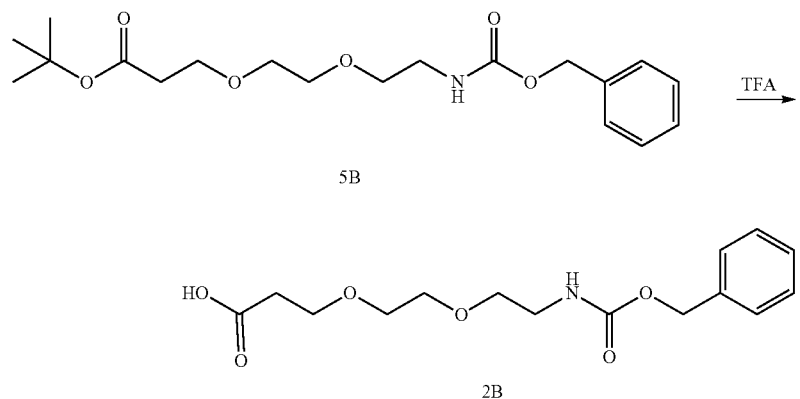

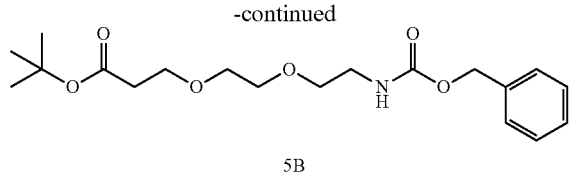

To a solution of Compound 4B (400 g, 1.67 mol, 1.00 eq) and NaOH (10 M, 16.7 mL 0.10 eq) in THF (2.00 L) was added Compound 4B_2 (1.07 kg, 8.36 mol, 1.20 L, 5.00 eq), the mixture was stirred at 30° C. for 2 hrs. LCMS showed the desired MS was given. Five batches of solution were combined to one batch, then the mixture was diluted with To a solution of Compound 5B (741 g, 2.02 mol, 1.00 eq) in DCM (2.80 L) was added TFA (1.43 kg, 12.5 mol, 928 mL, 6.22 eq), the mixture was stirred at 25° C. for 3 hrs. LCMS showed the desired MS was given. The mixture was diluted with DCM (5.00 L), washed with water (3.00 L*3), brine (2.00 L), the combined organic layer was dried over $Na_2SO_4$, filtered and concentrated under vacuum to give Compound 2B (1800 g, crude) as light yellow oil. HNMR: δ9.46 (s, 5 H), 7.27-7.34 (m, 5H), 6.50-6.65 (m, 1 H), 5.71 (s, 1H), 5.10-5.15 (m, 2H), 3.68-3.70 (m, 14 H), 3.58-3.61 (m, 6H), 3.39 (s, 2H), 2.55 (s, 6H), 2.44 (s, 2 H).

General procedure for preparation of Compound 3B

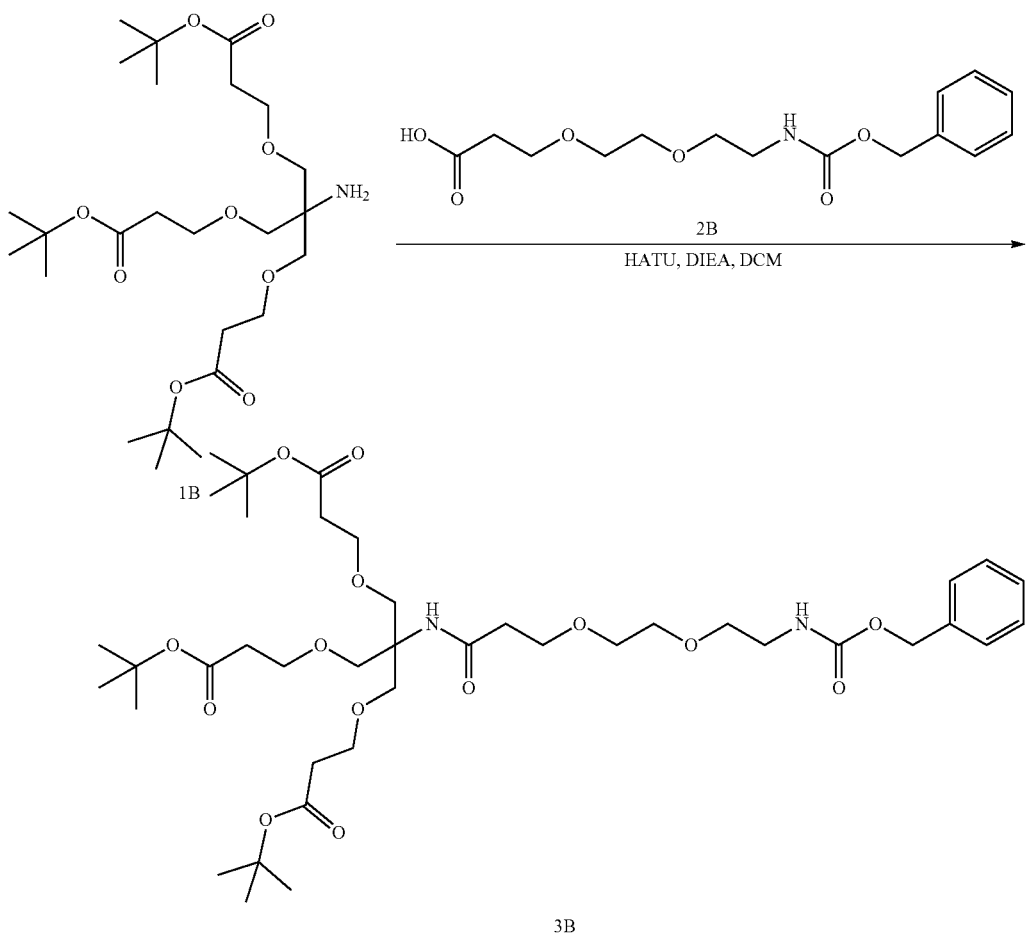

To a solution of Compound 2B (375 g, 999 mmol, 83.0% purity, 1.00 eq) in DCM (1.80 L) was added HATU (570 g, 1.50 mol, 1.50 eq) and DIEA (258 g, 2.00 mol, 348 mL, 2.00 eq) at 0° C., the mixture was stirred at 0° C. for 30 min, then Compound 1B (606 g, 120 mol, 1.20 eq) was added, the mixture was stirred at 25° C. for 1 hr. LCMS showed desired MS was given. The mixture was combined to one batch, then the mixture was diluted with DCM (5.00 L), washed with 1 N HO aqueous solution (2.00 L*2), then the organic layer was washed with saturated Na$_2$CO$_2$ aqueous solution (2.00 L*2) and brine (2.00 L), the organic layer was dried over Na$_2$SO$_4$, filtered and concentrated under vacuum to give Compound 3B (3.88 kg, crude) as yellow oil.

General procedure for preparation of

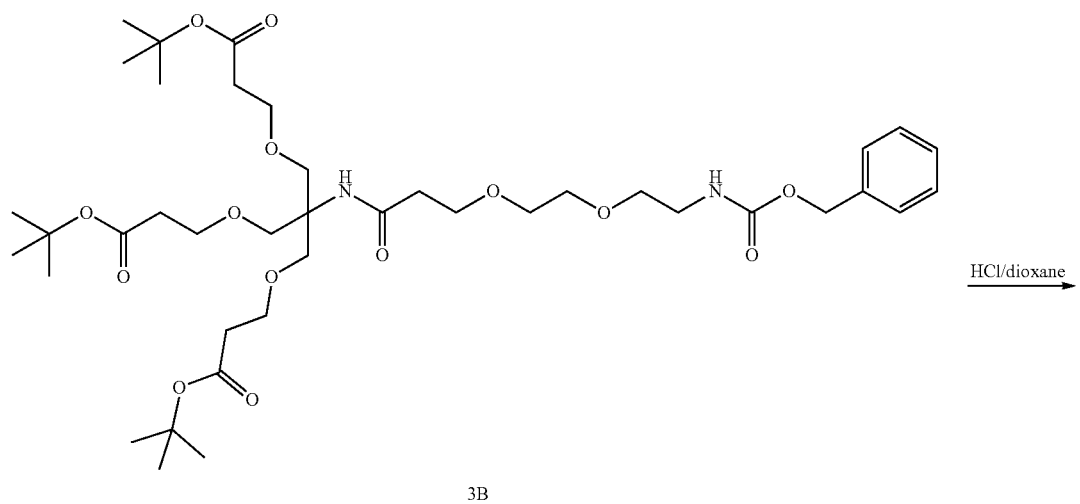

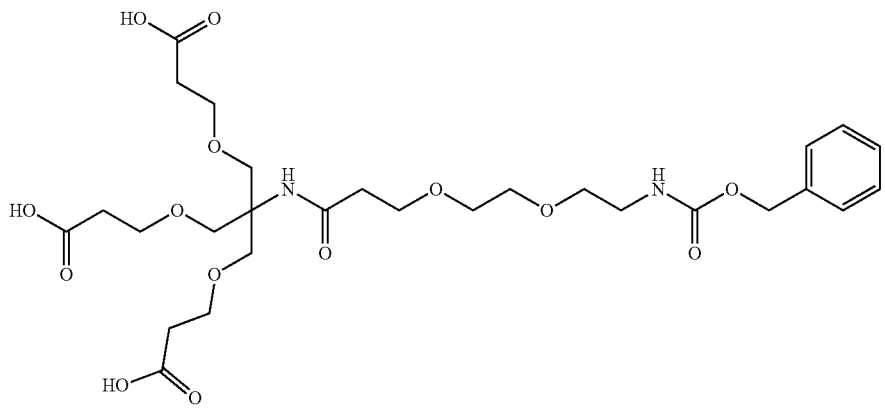

TRIS-PEG2-CBZ

A solution of Compound 3B (775 g, 487 mmol. 50.3% purity, 1.00 eq) in HCl/dioxane (4 M, 2.91 L, 23.8 eq) was stirred at 25° C. for 2 hrs. LCMS showed the desired MS was given. 'The mixture was concentrated under vacuum to give a residue. Then the combined residue was diluted with DCM (5.00 L), adjusted to pH=8 with 2.5 M NaOH' aqueous solution, and separated. The aqueous phase was extracted with DCM (3.00 L) again, then the aqueous solution was adjusted to pH=3 with 1 N HCl aqueous solution, then extracted with DCM (5.00 L*2), the combined organic layer was washed with brine (3.00 L), dried over $Na_2SO_4$, filtered and concentrated under vacuum. The crude was purified by column chromatography ($SiO_2$, DCM: MeOH=0:1-12:1, 0.1% HOAc, $R_1$=0.4). The residue was diluted with DCM (5.00 L), adjusted to pH=8 with 2.5 M NaOH aqueous solution, separated, the aqueous solution was extracted with DCM (3.00 L) again, then the aqueous solution was adjusted to pH=3 with 6 N HCl aqueous solution, extracted with DCM:MeOH=10:1 (5.00 L*2), the combined organic layer was washed with brine (100 L), dried over $Na_2SO_4$, filtered and concentrated under vacuum to give a residue. Then the residue was diluted with MeCN (5.00 L), concentrated under vacuum, repeat this procedure twice to remove water to give TRIS-PEG2-CBZ (1.25 kg, 1.91 mol, 78.1% yield, 95.8% purity) as light yellow oil. $^1$HNMR: 400 MHz, MeOD, δ7.30-7.35 (5 H), 5.07 (s, 2H), 3.65-3.70 (m, 16H), 3.59 (c, 1 H), 3.45 (tJ=5.6 Hz), 2.51 (t, J=6.0 Hz), 2.43 (t, 6.4 Hz).

Scheme for the preparation of Tri-NGal-TRIS-Peg2-Phosph 8c

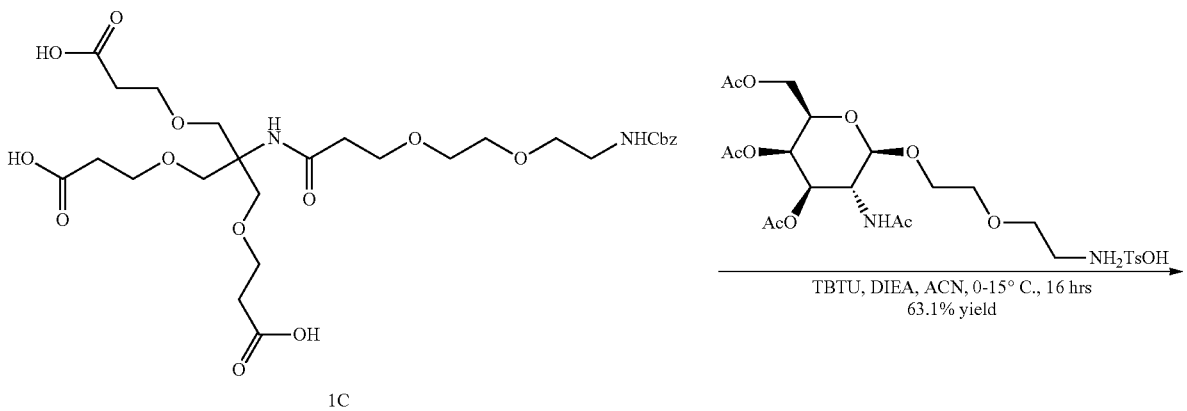

-continued
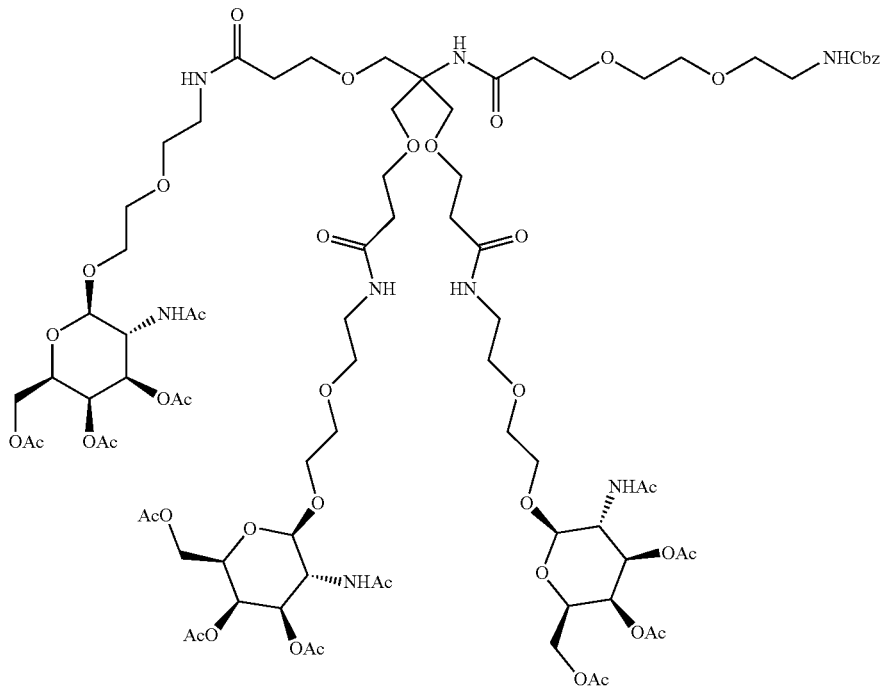
3C
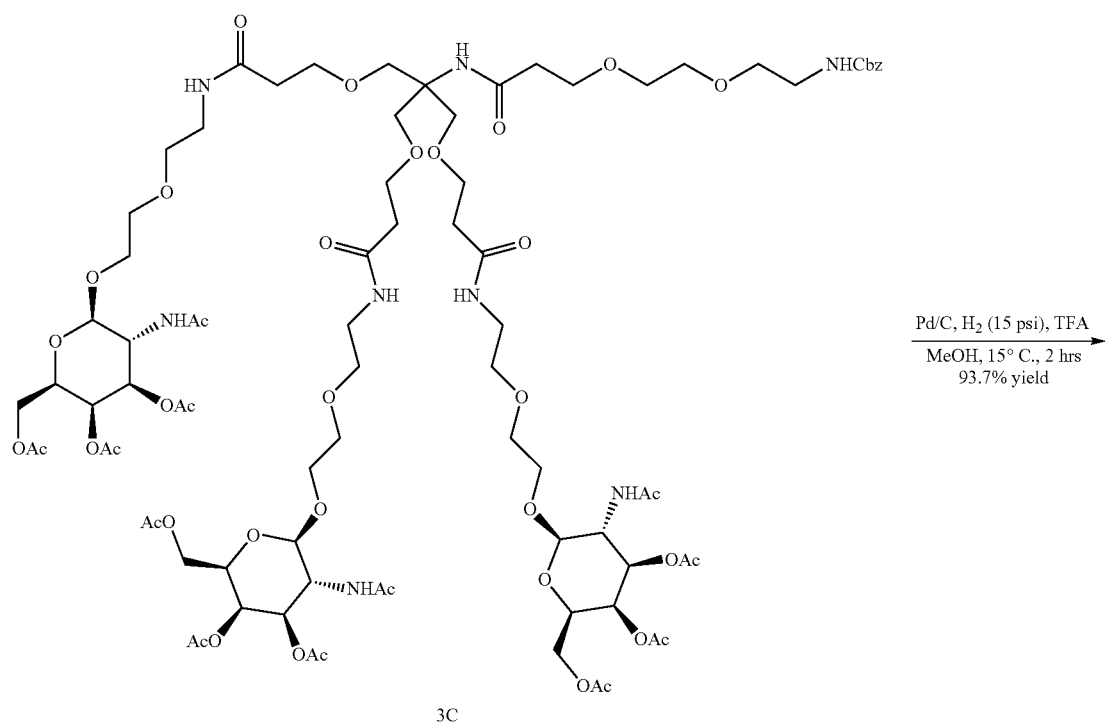
3C
Pd/C, H₂ (15 psi), TFA
MeOH, 15° C., 2 hrs
93.7% yield

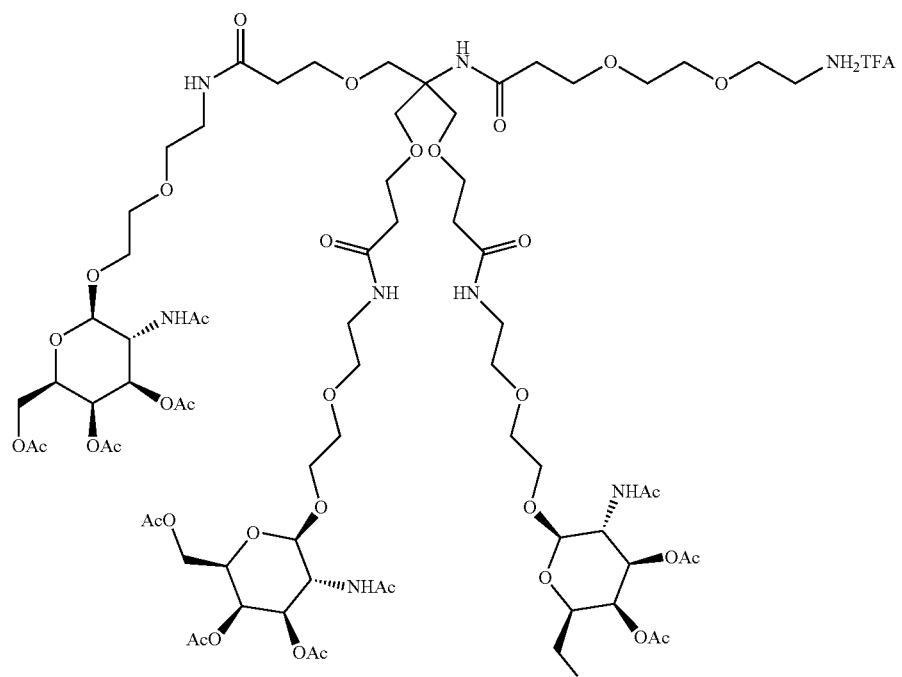
4C
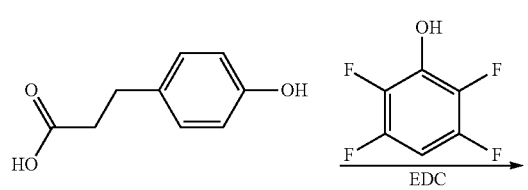
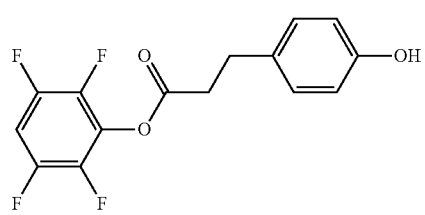
5c

-continued
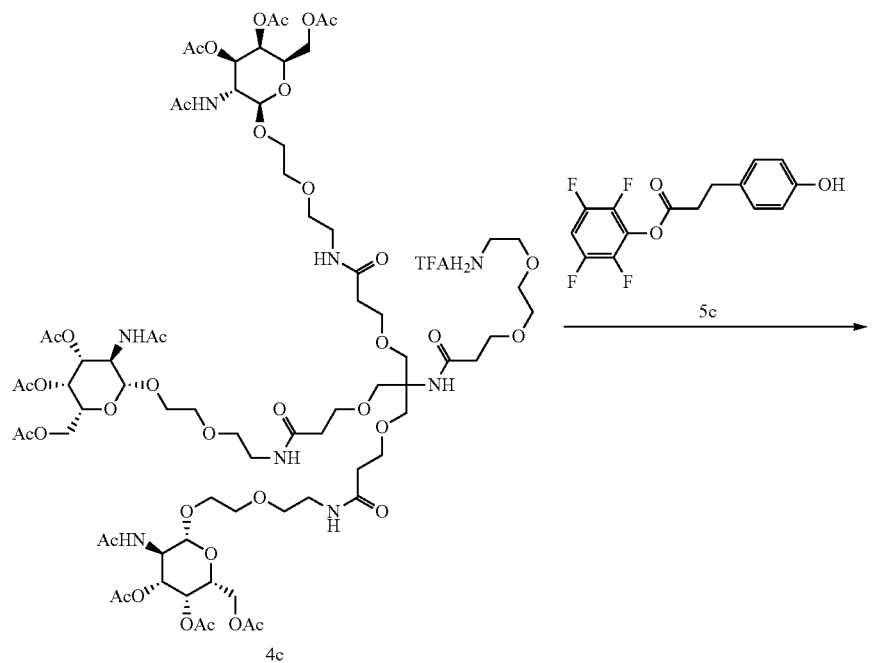
4c
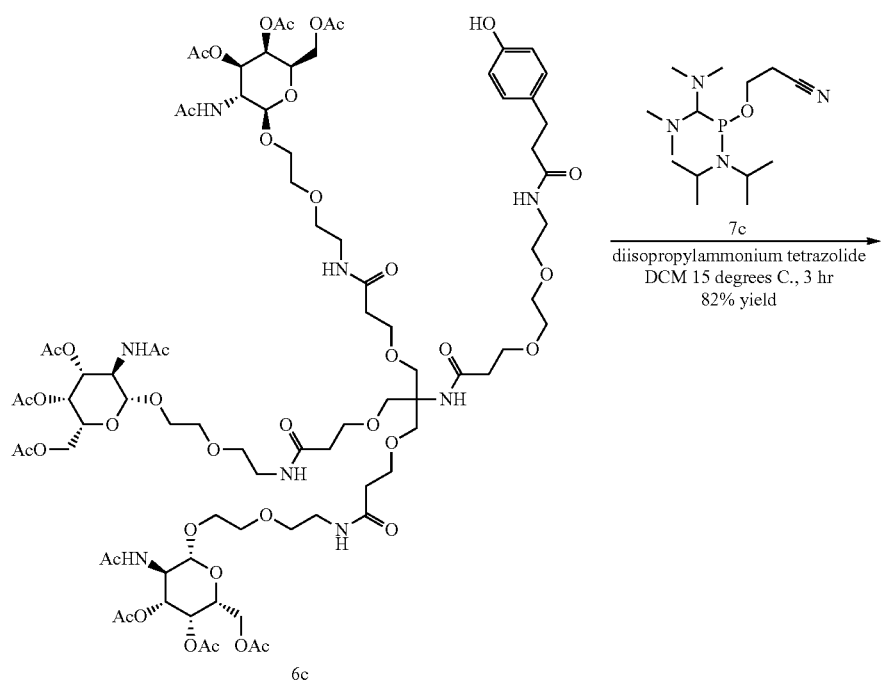
6c

-continued
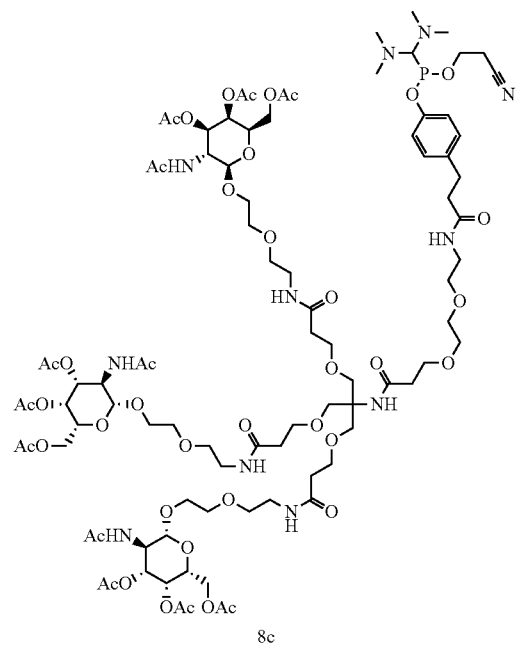
General procedure for preparation of Compound 3C
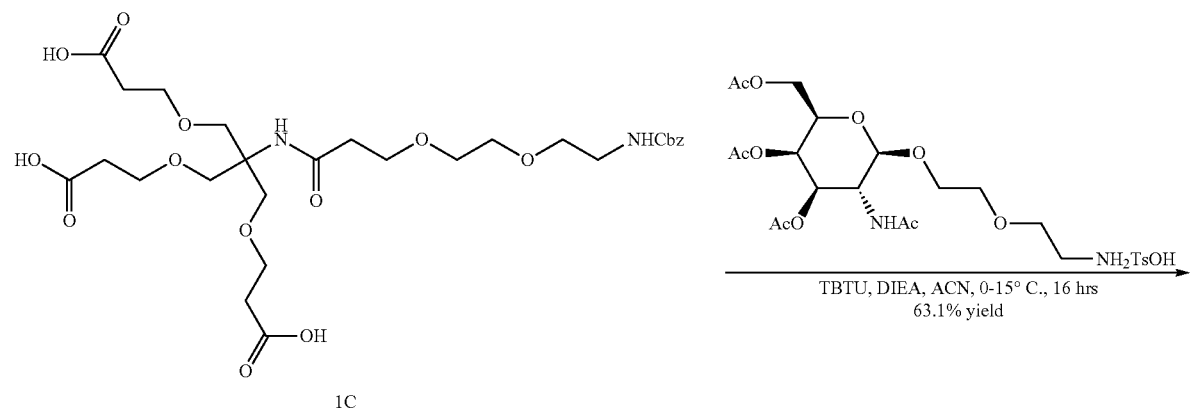

-continued

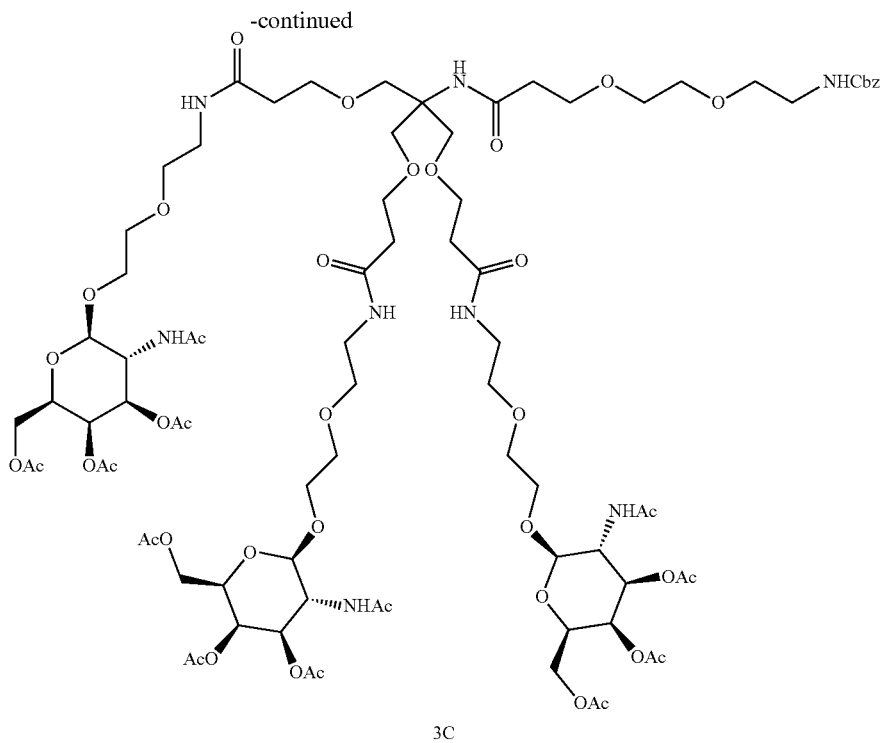

3C

To a solution of Compound 1C (155 g, 245 mmol, 1.00 eq) ill ACN (1500 mL) was added TBTU (260 g, 811 mmol, 3.30 eq), DIEA (209 g, 1.62 mol, 282 ml, 6.60 eq) and Compound 2C (492 g, 811 mmol, 3.30 eq, TsOH) at 0° C., the mixture was stirred at 15° C. for 16 hrs. LCMS showed the desired MS was given. The mixture was concentrated under vacuum to give a residue, then the mixture was diluted with DCM (2000 mL), washed with 1 N HCl aqueous solution (700 mL*2), then saturated NaHCO₃ aqueous solution (700 mL*2) and concentrated under vacuum. The crude was purified by column chromatography to give Compound 3C (304 g, 155 mmol, 63.1% yield, 96.0% purity) as a yellow solid.

General procedure for preparation of Compound 4C

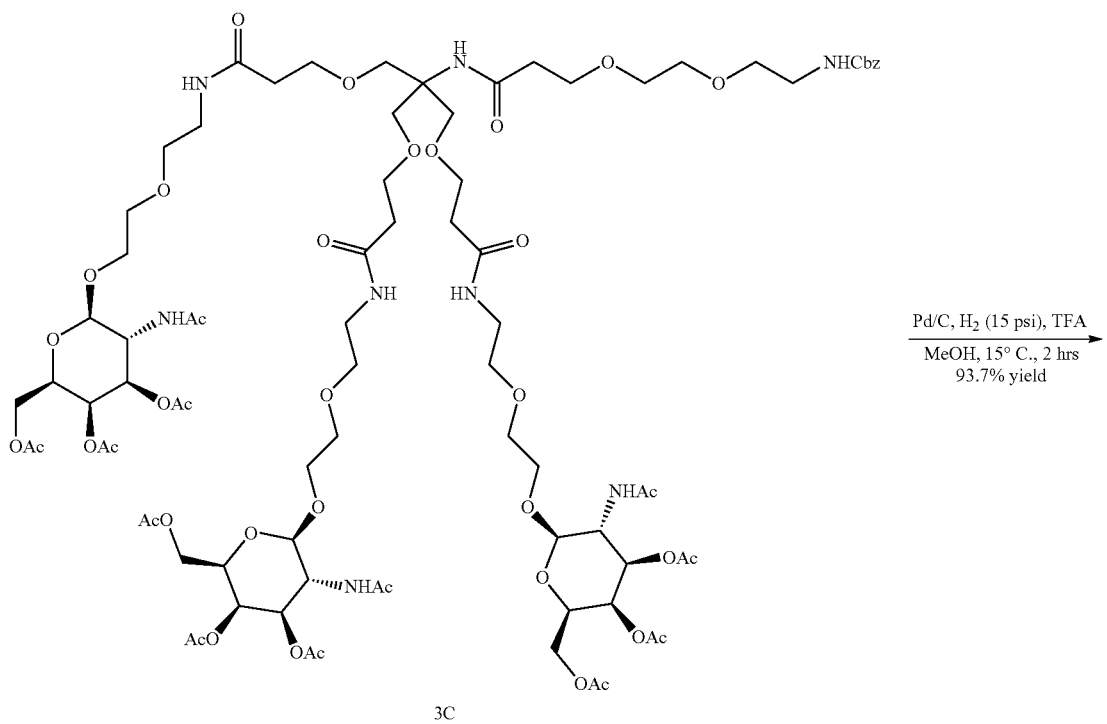

3C

Pd/C, H₂ (15 psi), TFA
—————————————→
MeOH, 15° C., 2 hrs
93.7% yield

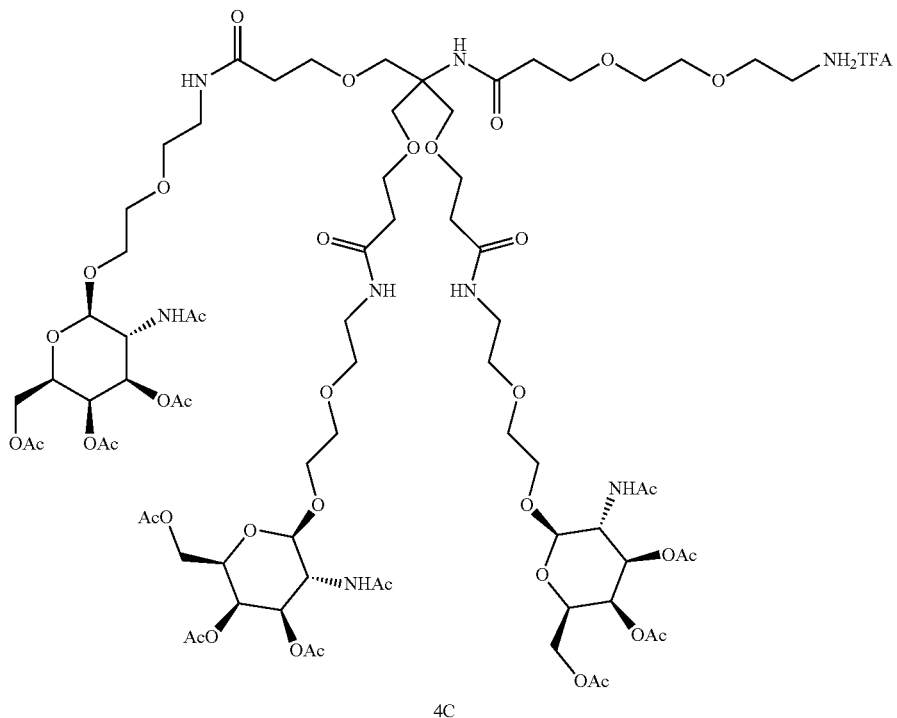

4C

Two batches solution of Compound 3C (55.0 g, 29.2 mmol, 1.00 eq) in MeOH (1600 mL) was added Pd/C (6.60 g, 19.1 mmol, 10.0% purity) and TEA (3.34 a, 29.2 mmol, 2.17 mL, 1.00 eq), the mixture was degassed under vacuum and purged with $H_2$. The mixture was stirred under $H_2$ (15 psi) at 15° C. for 2 hours. LCMS showed the desired MS was given. The mixture was filtered and the filtrate was concentrated under vacuum to give Compound 4C (106 g, 54.8 mmol, 93.7% yield, 96.2% purity, TEA) as a white solid.

General procedure for preparation of compound 5C

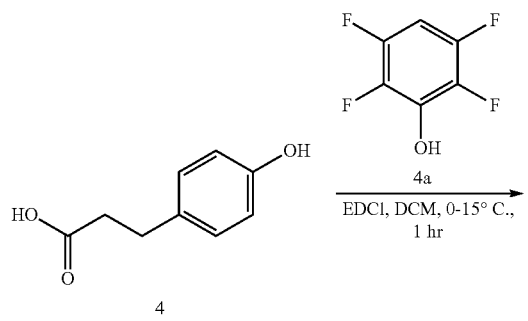

4

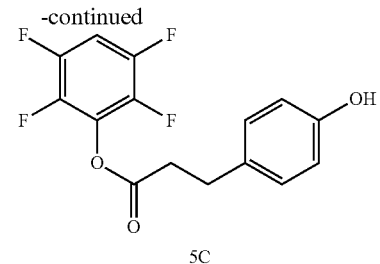

5C

Two batches in parallel. To a solution of EDCI (28.8 g, 150 mmol, 1.00 eq) in DCM (125 mL) was added compound 4a (25.0 g, 150 mmol, 1.00 eq) dropwise at 0° C., then the mixture was added to compound 4 (25.0 g, 150 mmol, 1.00 eq) in DCM (125 mL) at 0° C., then the mixture was stirred at 25° C. for 1 hr. TLC (Petroleum ether: Ethyl acetate 3: 1, $R_f$=0.45) showed the reactant was consumed and one new spot was formed. The reaction mixture was diluted with DCM (100 mL) then washed with aq.NaHCO$_3$(250 mL*1) and brine (250 mL), dried over Na$_2$SO$_4$, filtered and concentrated under reduced pressure to give a residue. The residue was purified by column chromatography (SiO$_2$, Petroleum ether: Ethyl acetate=100: 1 to 3: 1), TLC (SiO$_2$, Petroleum ether: Ethyl acetate=3:1), $R_f$=0.45, then concentrated under reduced pressure to give a residue. Compound 5C (57.0 g, 176 mmol, 58.4% yield, 96.9% purity) was obtained as colorless oil and confirmed $^1$HNMR: EW33072-2-P1A, 400 MHz, DMSO δ9.21 (s, 1H), 07-7.09 (m, 2H), 6.67-6.70 (m, 2H), 3.02-3.04 (m, 2H), 2.86-2.90 (n r, 2H).

General procedure for preparation of compound 6

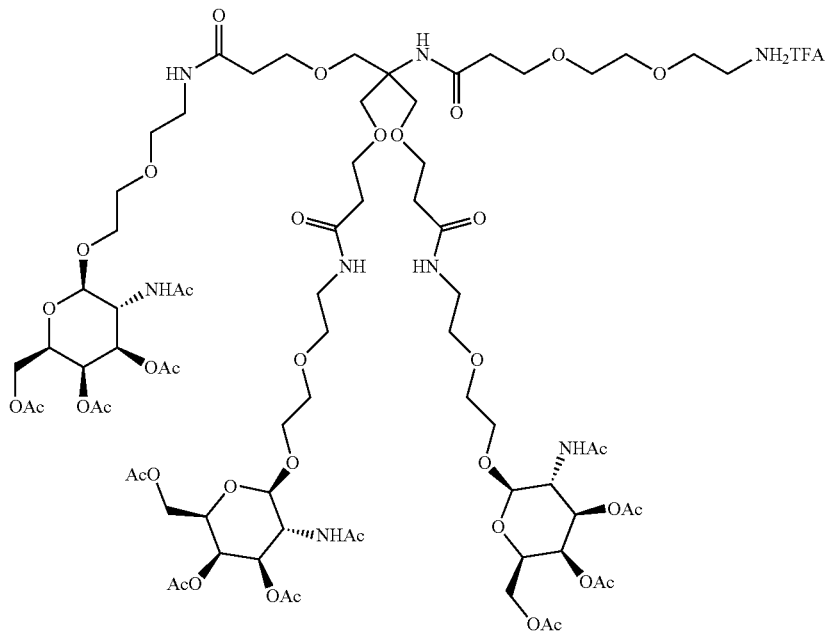
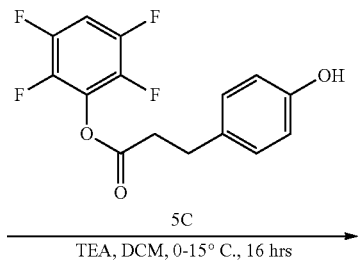
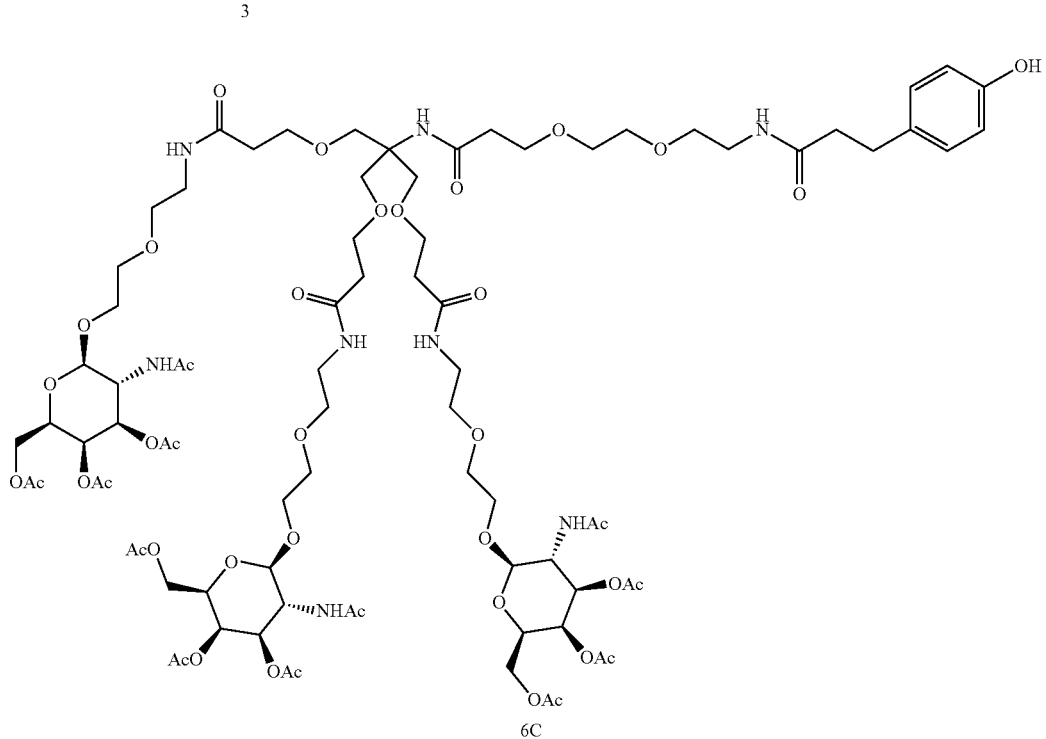

To a mixture of compound 3 (79.0 g, 41.0 mmol, 96.4% purity, 1.00 eq, TFA) and compound 6C (14.2 g, 43.8 mmol, 96.9% purity, 1.07 eq) in DCM (800 mL) was added TEA (16.6 g, 164 mmol, 22.8 mL, 4.00 eq) dropwise at 0° C., the mixture was stirred at 15° C. for 16 hrs. LCMS (EW33072-12-P1B, Rt=0.844 mm) showed the desired mass was detected. The reaction mixture was diluted with DCM (400 mL) and washed with aq.NaHCO$_3$(400 nit*1) and brine(400 mL*1), then the mixture was diluted with DCM (2.00 L) and washed with 0.7 M Na$_2$CO$_3$ (1000 mL*3) and brine(800 mL*3), dried over Na$_2$SO$_4$, filtered and concentrated under reduced pressure to give a residue. The residue was used to next step directly without purification. Compound 6 (80.0 g, crude) was obtained as white solid and confirmed via 1HNMR: EW33072-12-P1A, 400 MHz, MeOD δ7.02-7.04 (m, 2H), 6.68-6.70 (m, 2H), 5.34-5.35 (s, 3H), 5.07-5.08 (d, J=4.00 Hz, 3H), 4.62-4.64 (d, J 8.00 Hz, 3H), 3.71-4.16 (m, 16H), 3.31-3.70 (m, 44H), 2.80-2.83 (m, 2H), 2.68 (m, 2H), 2.46-2.47 (m, 10H), 2.14 (s, 9H), 2.03 (s, 9H), 1.94-1.95 (di=4.00 Hz, 18H).

General procedure for preparation of TriGNal-TRIS-Peg2-Phosph 8c

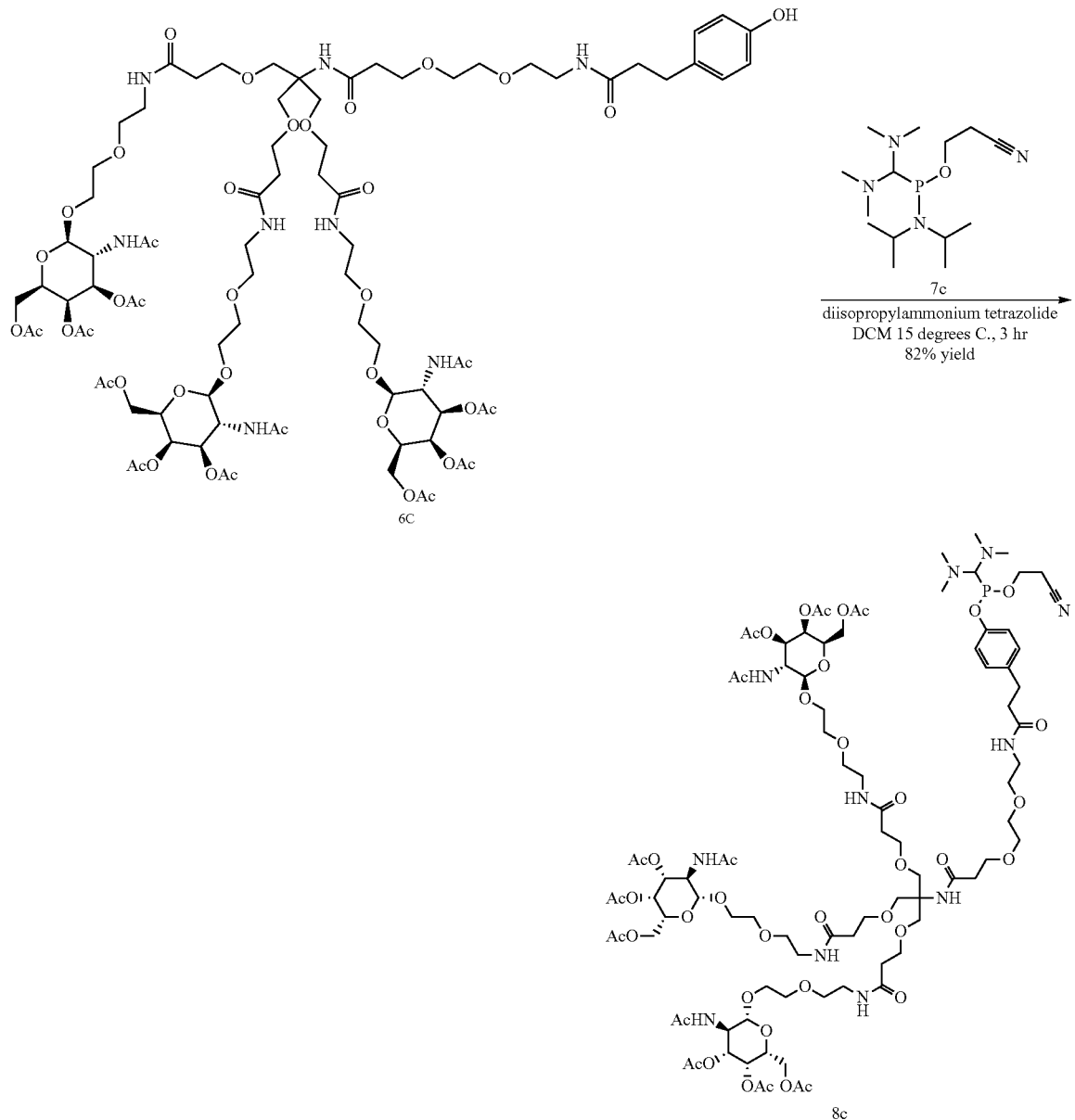

Two batches were synthesized in parallel. To a solution of compound 6C (40.0 g, 21.1 mmol, 1.00 eq in DCM (600 mL) was added diisopropylammonium tetrazolide (3.62 g, 21.1 mmol, 1.00 eq) and compound 7c (6.37 g, 21.1 mmol, 6.71 mL, 1.00 eq) in DCM (8.00 mL) drop-wise, the mixture was stirred at 30° C. for 1 hr, then added compound 7c (3.18 g, 10.6 mmol, 3.35 mL, 0.50 eq) in DCM (8.00 mL) drop-wise, the mixture was stirred at 30° C. for 30 mins, then added compound 7c (3.18 a, 10.6 mmol, 3.35 mL, 0.50 eq) in DCM (8.00 mL) drop-wise, the mixture was stirred at 30° C. for 1.5 hrs. LCMS (EW33072-17-P1C$_1$, Rt=0.921 min) showed the desired MS+1 was detected. LCMS (EW33072-17-P1C2, Rt=0.919 min) showed the desired MS+1 was detected. Two batches were combined for work-up. The mixture was diluted with DCM (1.20 L), washed with saturated NaHCO$_3$ aqueous solution (1.60 L 2), 3% DMF in H$_2$O (1.60 L*2), H$_2$O (1.60 L 3), brine (1.60 L), dried over Na$_2$SO$_4$, filtered and concentrated under reduced pressure to give a residue. The residue was purified by column chromatography (SiO$_2$, DCM: MeOH: TEA=100: 3: 2) TLC (SiO$_2$, DCM: MeOH=10:1, R$_1$=0.45), then concentrated under reduced pressure to give a residue. Compound 8C (76.0 g, 34.8 mmol, 82.5% yield, 96.0% purity) Was obtained as white solid and confirmed via $^1$HNMR: EW33072-19-P1C. 400 MHz, MeOD
δ7.13-7.15 (d, J=8.50 Hz, 2H), 6.95-6.97 (d.d, =8.38, 1.13 Hz, 2H). 5.34 (d, J=2.88 Hz, 3H), 0.09 (dd, =11.26, 3.381-1z, 3H), 4.64 (d, J=8.50 Hz, 3H), 3.99-4.20 (in. 121-1), 3.88-3.98 (m, 5H), 3.66-3.83 (m, 20H), 3.51-3.65 (m, 17H). 3.33-3.50 (m, 9H), 2.87 (t, J=7.63 Hz, 2H), 2.76 (t, J-5.94 Hz, 2H), 2.42-2.50 (m, 10H). 2.14 (s, 9H), 2.03 (s. 9 H), 1.94-1.95 (d, 0.1=6.13 Hz, 18H), 1.24-1.26 (d, J=6.75 Hz, 6H). 1.18-1.20 (d, J=6.75 Hz, 6H)

Example 7: In Vitro Hepatocyte Targeting Using GalNAc-Conjugated siRNAs and ASOs In this experiment, a hepatocyte cell line expressing asialoglycoprotein receptors and GFP will be treated with anti-GFP siRNAs or ASOs conjugated to a GalNAc moiety compared to a control experiment where the hepatocyte cell line is treated with anti-GFP siRNAs or ASOs that are not conjugated to the GalNAc moiety. GFP mRNA and protein expression are measured, and the amount of GFP mRNA or protein expression in cells treated with the GalNAc-conjugated siRNAs or ASOs is normalized and compared to the amount of GFP mRNA or protein expression in cells treated with the siRNAs or ASOs that are not GalNAc-conjugated. This may allow for a determination of the hepatocyte targeting ability of the GalNAc moiety. Multiple GalNAc moieties may be conjugated to the siRNAs or ASOs and compared to see which GalNAc moiety results in optimal hepatocyte targeting. The GalNAc moieties to be tested in these experiments may a GalNAc moiety described herein.

Similar experiments may be performed in primary hepatocytes treated with the siRNAs or ASOs conjugated or not to a GalNAc moiety, and a target mRNA or target protein other than GFP may be assessed in the primary hepatocytes.

Example 8: In Vivo Hepatocyte Targeting Using GalNAc-Conjugated siRNAs and ASOs In this experiment, siRNAs or ASOs targeting a target mRNA will be conjugated to a GalNAc moiety and administered to mice (n=5/group), and compared to a control experiment where the mice are administered siRNAs or ASOs without GalNAc conjugation. Mice are sacrificed 2 days later, and livers are frozen, later homogenized, and tested for target mRNA and protein expression. The amount of target mRNA or protein expression in the livers of mice treated with the GalNAc-conjugated siRNAs or ASOs is normalized and compared to the amount of GFP mRNA or protein expression in the livers of mice treated with the siRNAs or ASOs that are not GalNAc-conjugated. This may allow for a determination of the liver targeting ability of the GalNAc moiety. Multiple GalNAc moieties may be conjugated to the siRNAs or ASOs and compared to see which GalNAc moiety results in optimal liver targeting. The GalNAc moieties included in this experiment may be those that exhibit the greatest degree of hepatocyte targeting. The GalNAc moieties to be tested in these experiments may a GalNAc moiety described herein.

Example 9: Inhibition of a Target mRNA in a Mouse Model of a Liver Disease Using GAN/V.-Conjugated siRNAs and ASOs In this experiment, a marine model of a liver disease (in this case, fatty liver disease) will be used to evaluate the effect of siRNA or ASO inhibition of a target mRNA. The target mRNA may encode any target protein where overexpression or overactivation plays a pathological role in the liver disease in the murine model, fatty liver disease is induced by feeding mice a Western Diet (WD) containing 21.1% fat, 41% Sucrose, and 1.25% Cholesterol by weight (Teklad diets. TD. 120528) and a high sugar solution (23.1 g/L d-fructose (Sigma-Aldrich, G8270) and 18.9 g/L d-glucose (Sigma-Aldrich. F0127)) for 12 weeks. At 4-week-old $C_{57}BL/6.1$ mice are fed a Western Diet instead of regular chow for 12 weeks. The GalNAc moieties to be used in this experiments may a GalNAc moiety described herein.

Briefly, mice are divided into five groups: Group 1: a fatty liver disease group treated with non-targeting control siRNA. Group 2: a fatty, liver disease group treated with non-targeting control ASO, Group 3: a fatty liver disease group treated with an siRNA targeting a target mRNA, Group 4: a fatty liver disease group treated with an ASO targeting a target mRNA. Group 5: control mice on a normal chow diet. Each group contains eight mice (4 males, 4 females). The siRNAs and ASOs of Groups 1~4 each include a GalNAc moiety attached to the siRNA or ASO.

At weeks 12 weeks of Western Diet, blood samples are to be collected from each group prior first treatment.

Administration of siRNA or ASO is achieved with a 200 µL, subcutaneous injection of naked siRNA or ASO resuspended in PBS at concentration of 10 µM. On Study Day 0, Group 1 mice will be injected subcutaneously with non-targeting control siRNA, Group 2 mice will be injected subcutaneously with non-targeting control ASO, Group 3 mice will be injected subcutaneously with siRNA1 targeting the target mRNA in a mouse, Group 4 mice will be injected subcutaneously with ASO1 targeting the target mRNA in a mouse, and Group 5 mice will be injected subcutaneously with vehicle. Every other week thereafter starting on Day 14 the animals from each group will be dosed as on Day 0 for a total of 5 injections.

Weekly blood draws will be taken and serum and plasma isolated. Serum ALT, AST, total cholesterol and triglyceride levels are measured using VITROS 5,1 FS (Ortho Clinical Diagnostics). Non-fasting plasma insulin is measured with the Ultrasensitive Mouse Insulin ELISA kit (Crystal Chem, 90080) according to the manufacturer's instructions. Non-fasting blood glucose is assayed with the One Touch Ultra (Life Scan). HOMA 1R and QUICKI will be calculated.

At the end of 12 weeks of Western Diet and siRNA/ASO treatment, mice are to be sacrificed by cervical dislocation following an intraperitoneal injection of 0.3 ml Nembutal (5 mg/ml). Terminal serum draw is collected via cardiac puncture and final serum ALT, AST, total cholesterol and triglyceride levels are measure along with non-fasting plasma insulin and glucose. Livers are removed and divided into three sections; one section placed in RNAlater for mRNA isolation, one section flash-frozen for protein isolation, one section fixed in formalin and then paraffin-embedded.

mRNA is isolated from tissue placed in RNAlater solution using the PureLink kit according to the manufacturer's protocol (ThermoFisher Cat. No. 12183020). The reverse transcriptase reaction is performed according to the manufacturer's protocol. Samples are stored at −80° C. until real-time qPCR is performed in triplicate using TaqMan Gene Expression Assays (Applied Biosystems FAM-probes using a BioRad iCycler). A decrease in target mRNA expression in the liver tissue from mice is dosed with the siRNAs and ASOs compared to target mRNA levels in the liver tissue from mice is dosed with the non-specific control siRNA and ASO. There is an expected decrease in the amount of SDF-1 in the liver tissue from mice that receive the siRNAs and ASOs compared to the amount of SDF-1 in the liver tissue from mice that receive the non-specific control siRNA or ASO. These results show that the siRNAs and ASOs elicit knockdown of the target mRNA and target protein in liver tissue, and that the decrease in target mRNA and target protein expression is correlated with a decrease in SDF-1 production.

Formalin-fixed, paraffin-embedded liver sections are stained with hematoxylin and eosin (H&E) for assessment of liver histology, with Sirius Red (Sigma. 365548-5G)/Fast Green (Sigma, F258) for assessment of fibrosis, and with periodic acid-Schiff (PAS) for assessment of glycogen accumulation. NAFLD Activity Score (NAS) and fibrosis stage are evaluated by an expert pathologist according to the NASH CRN scoring system13. The histological scoring is performed blinded, with no knowledge by the pathologist of the treatments) received. These results show that the siRNAs and ASOs elicit knockdown of the target mRNA and target protein in liver tissue, and that the decrease in expression of the target mRNA and target protein is correlated with a decrease in NAS and NASH CRN.

Example 10: Inhibition of a Mouse Model of a Liver Disease

In this experiment, a murine model of a liver disease (in this case, hypertriglyceridemia) will be used to evaluate the effect of siRNA or ASO inhibition of a target protein expressed in the liver compared to an anti-mouse target protein antibody. The mouse strain C57131/6 Apoetml Unc mice will be maintained on a high fat Western diet (Research Diets, D-12492; 60% fat by calories). The target protein may be any target protein where overexpression or overactivation plays a pathological role in the liver disease. The GalNAc moieties to be used in this experiments may a GalNAc moiety described herein.

Four groups of mice (n=16/group) will be utilized in this study. Animals will be maintained on a high fat diet during the study. On Day −4 before the first injection, chow will be removed for an overnight fast. On Day −3 before the first injection, all animals will be anesthetized and 300 μL of blood collected in serum separator tubes via the submandibular vein to assess baseline triglyceride, serum glucose, insulin sensitivity, total cholesterol levels, HDL Cholesterol levels, liver function and serum levels of target protein. On Study Day 0, Group 1 mice will be injected intraperitoneally with 600 μL normal saline, Group 2 mice will be injected intraperitoneally with 600 μg of anti-mouse target protein antibody in 600 μL, Group 3 mice will be injected subcutaneously with 150 μg of GalNAc-siRNA targeting an mRNA encoding the target protein in a mouse in 200 μL of normal saline, and Group 4 mice will be injected subcutaneously with 15014; of GalNAc-ASO targeting the mRNA encoding the target protein in 200 PL of normal saline. On the afternoon of Day 3, the chow will be removed from all Groups for an overnight fast. On Day 4, the animals from all Groups will be anesthetized and 150 fit of blood collected in serum separator tubes via the submandibular vein to assess serum triglycerides, glucose, total cholesterol, HDL cholesterol and levels of the target protein. Animals from all groups will then undergo an oral glucose tolerance test and insulin tolerance test to evaluate insulin sensitivity. Chow will be supplied again as normal after blood has been collected and insulin sensitivity tests conducted. Weekly thereafter starting on Day 7 the animals from Group 2 will be dosed as on Day 0 for a total of 15 injections. Every other week thereafter starting on Day 14 the animals from Group 3 and Group 4 will be dosed as on Day 0 for a total of 8 injections. Every other week starting on Day 10, the mice from all Groups will be fasted (overnight) and bled (150 μL into serum separator tubes) to assess serum triglyceride, glucose, total cholesterol, HDL cholesterol and levels of target protein, and undergo insulin sensitivity tests. On the third day after the final injection, the chow will be removed from all Groups for an overnight fast. On the fourth day after the final injection, the animals from all Groups will be anesthetized, euthanized and bled via cardiac puncture to collect 500 μL of blood into serum separator tubes to assess triglyceride, serum glucose, insulin sensitivity, total cholesterol levels, HDL cholesterol levels, liver function and serum levels of target protein. Tissue from the liver, small intestine and mesenteric lymph nodes will be collected from all animals and immersed in 10% neutral buffered formalin for histopathological analysis. A liver sample will also be collected from all animals and placed in RNAlater. The levels of target mRNA will be assessed by RT-qPCR, using TaqMan assays for the mouse target protein and the mouse housekeeping gene PPIA.

Animals treated with the antibody (Group 2), mice treated with the GalNAc-siRNA (Group 3), and mice treated with the GalNAc-ASO (Group 4) are expected to have decreased triglycerides, total serum cholesterol, serum glucose as well as decreased serum target protein levels, and increased. HDL, cholesterol and insulin sensitivity, compared with mice from Group 1 (saline). Animals in Group 2 and Group 3 are also expected to have decreased target mRNA in liver samples.

Example 11: Inhibition of a Target mRNA in Non-Human Primates Using GalNAc-siRNA and GalNAs-ASO In this experiment, a NHP model of hypertriglyceridemia is used to evaluate the effect of siRNA or ASO inhibition of the target mRNA expressed in the liver. The target protein may be any target protein where overexpression or overactivation plays a pathological role in the liver disease. Three groups of cynomolgus monkeys will be used (n=5/group) that are placed on a high-fat diet (Western Primate Diet, 552T) before the initiation of the study. Alternatively, three groups of rhesus monkeys will be used (n=5/group) that are placed on a high fructose diet before the initiation of the study. Animals are to be given 7 biweekly subcutaneous injections of saline (Group 1), GalNAc-siRNA (Group 2), or GalNAc-ASO (Group 3). The modified GalNAc-siRNA sequences may include any modification pattern described herein. The GalNAc moieties to be used in this experiments may a GalNAc moiety described herein. Blood samples for lipid and glycemic measurements will be collected at baseline and at 4, 8, and 14 weeks of the study and analyzed for lipid content, serum glucose, insulin sensitivity and target protein. All animals from each group are necropsied 2 weeks after the last blood collection. Tissue from the liver, small intestine and mesenteric lymph nodes will be collected from all animals and immersed in 10% neutral buffered formalin for histopathological analysis. A liver sample will also be collected from all animals and placed in RNAlater. The levels of target mRNA will be assessed by RT-qPCR using TaqMan assays for cynomolgus or rhesus target protein and the cynomolgus or rhesus housekeeping gene PPIA.

It is expected that animals treated with the GalNAc-siRNA (Group 2) and animals treated with the GalNAc-ASO (Group 3) will show decreased triglycerides, total serum cholesterol and serum glucose as well as decreased serum target protein levels, and increased HDL cholesterol and insulin sensitivity, compared with animals from Group 1 (saline). It is also expected that animals in Group 1 and Group 3 will show decreased target mRNA in liver samples.

Example 12: Inhibition of a Target mRNA in a Clinical Trial Using GalNAc-siRNA and GalNAc-ASO In this study, human subjects with hypertriglyceridemia are used to evaluate the effect of siRNA or ASO inhibition of a target mRNA expressed in the liver. The target protein may be any target protein where overexpression or overactivation plays a pathological role in the liver disease. Selection criteria for inclusion in the study are ages 40-90, BMI≥30 and serum triglycerides ≥250 mg/dL. Three groups of subjects will be included (n=15/group) in the study. Subjects are to be given 5 weekly subcutaneous injections of saline (Group 1), GalNAc-siRNA (Group 2), or GalNAc-ASO (Group 3). The GalNAc moieties to be used in these experiments may include a GalNAc moiety described herein.

The siRNA or ASO sequences are to be from a selection set that shows high activity in cells in culture or in experiments describe in the other examples. Blood samples for lipid and glycemic measurements will be collected at baseline and at 3, 6, and 12 weeks of the study and analyzed for lipid content, serum glucose, insulin sensitivity, target protein, and liver and kidney function.

It is expected that subjects treated with the GalNAc-siRNA (Group 2) and subjects treated with GalNAc-ASO (Group 3) will show decreased triglycerides, total serum cholesterol and serum glucose as well as decreased serum target protein levels, and increased HDL cholesterol and insulin sensitivity, compared with subjects from Group 1 (saline)

Example 13: Oligonucleotide Synthesis

RNAi agents (e.g. siRNAs) were synthesized according to phosphoramidite technology on a solid phase used in oligonucleotide synthesis. A K&A oligonucleotide synthesizer was used. Syntheses were performed on a solid support made of controlled pore glass (CPG, 500 A or 600 A, obtained from AM Chemicals, Oceanside, CA, USA). All 2'-OMe and 2'-F phosphoramidites were purchased from Hongene Biotech (Union City, CA, USA). All phosphoramidites were dissolved in anhydrous acetonitrile (100 mM) and molecular sieves (3 A) were added. 5-Benzylthio-1H-tetrazole (BTT, 250 mM in acetonitrile) or 5-Ethylthio-1H-tetrazole (ETT, 250 mM in acetonitrile) was used as activator solution. Coupling times were 9-18 min (EmpGalNAc), 6 min (2'OMe and 2'F). In order to introduce phosphorothioate linkages, a 100 mM solution of 3-phenyl 1,2,4-dithiazocine-5- one (POS, obtained from PolyOrg, Inc., Leominster, Mass., USA) in anhydrous acetonitrile was employed.

After solid phase synthesis, the dried solid support was treated with a 1:1 volume solution of 40 wt. % methylamine in water and 28% ammonium hydroxide solution (Aldrich) for two hours at 30° C. The solution was evaporated and the solid residue was reconstituted in water and purified by anionic exchange HPLC using a TKSgel SuperQ-5PW 13u column. Buffer A was 20 mM Tris, 5 mM EDTA, pH 9.0 and contained 20% Acetonitrile and buffer B was the same as buffer A with the addition of 1 M sodium chloride. UV traces at 260 nm were recorded. Appropriate fractions were pooled then desalted using Sephadex G-25 medium.

Equimolar amounts of sense and antisense strand were combined to prepare a duplex. The duplex solution was prepared in 0.1×PBS (Phosphate-Buffered Saline, lx, Gibco). The duplex solution was annealed at 95° C. for 5 min, and cooled to room temperature slowly. Duplex concentration was determined by measuring the solution absorbance on a UV-Vis spectrometer at 260 nm in 0,1×PBS. For some experiments, a conversion factor was calculated from an experimentally determined extinction coefficient.

Example 14: In Vivo Hepatocyte Targeting Using GalNAc-Conjugated siRNAs and ASOs In this experiment, siRNAs or ASOs targeting a target mRNA will be conjugated to a GalNAc moiety and administered to mice (n=5/group), and compared to a control experiment where the mice are administered siRNAs or ASOs without GalNAc conjugation. Mice are sacrificed. 2 days later, and livers are frozen, later homogenized, and tested for target mRNA and protein expression. The amount of target mRNA or protein expression in the livers of mice treated with the GalNAc-conjugated siRNAs or ASOs is normalized and compared to the amount of GFP mRNA or protein expression in the livers of mice treated with the siRNAs or ASOs that are not GalNAc-conjugated. This may allow for a determination of the liver targeting ability of the GalNAc moiety. Multiple GalNAc moieties may be conjugated to the siRNAs or ASOs and compared to see which GalNAc moiety results in optimal liver targeting. The GalNAc moieties may be those that exhibit the greatest degree of hepatocyte targeting in Example 6. The GalNAc moieties to be tested in these experiments may a GalNAc moiety described herein such as Compound 1 or Compound 2.

Example 15: Knockdown of PLIN1 in Mice by GalNAc-Conjugated siRNAs

An example GalNAc Moiety, ETL17, was conjugated to siRNAs targeting an example target mRNA. Sequences are shown in Table 2. In the table, Nf (e.g. Af, Cf, Gf, Tf, or Lt) is a 2' fluoro-modified nucleoside, n (e.g. a, c, g, t, or u) is a 2' O-methyl modified nucleoside, and "s" is a phosphorothioate linkage. The siRNAs were tested for activity in mice.

Six to eight week old female mice (C5713116) were injected with 10 uL, of a recombinant adeno-associated virus 8 (AAV8) vector (1.7×10E$^{13}$ genome copies/mL) by the retroorbital route on Day −14. The recombinant AAV8 contained the sequence of human PLIN1. (NM_002666.5) under the control of the human thyroxine binding globulin promoter in an AAV2 backbone packaged in AAV8 capsid (AAV8-TBG-h-PLIN1). On Day 0, infected mice (n=4) were given a subcutaneous injection of a single 100 ug dose of a. GalNAc-conjugated siRNA or PBS as vehicle control.

Mice were euthanized on Day 10 after subcutaneous injection and a liver sample from each was collected and placed in RNAlater (ThermoFisher Catalog #AM7020) until processing. Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. Preparation of cDNA was performed using Quanta qScript cDNA SuperMix (VWR, Catalog 95048-500) according to the manufacturer's instructions. The relative levels of liver PLIN1 mRNA were assessed by RT-q-PCR in triplicate on a QuantStudio™ 6 Pro Real-Time PCR System using TaqMan assays for human PLIN1 (ThermoFisher, assay #Hs01106925_ml) and the mouse housekeeping gene PPIA (ThermoFisher, assay #Mm02342430_g1) and PerfeCTat qPCR FastMix®, Low ROX™ (VWR, Catalog#101419-

222). Data were normalized to the mean PLIN1 mRNA level in animals receiving PBS. Results are shown in Table 3. All of the siRNAs tested caused a reduction in mean liver PLIN1 mRNA on Day 10 relative to mice receiving PBS. These data indicate that siRNAs conjugated to a GaINAc moiety such as ETL17 are useful for knocking down a target mRNA in the liver.

TABLE 2

Example siRNA Sequences

| siRNA Name | SEQ ID NO | Sense Strand Sequence (5'-3') with GalNAc moiety | SEQ ID NO | Antisense Strand Sequence (5'-3') |
|---|---|---|---|---|
| ETD01899 | 1 | [ETL17]scaguuuuuAfaGfggacaccasusu | 8 | usGfsgUfgUfcCfcUfuAfaAfaAfcUfgsusu |
| ETD01900 | 2 | [ETL17]suuuuuAfAfGfGfgAfcaccagaasusu | 9 | usUfscUfgGfuGfuCfcCfuUfaAfaAfasusu |
| ETD01901 | 3 | [ETL17]suuuugaCfaCfaUfucuuagcasusu | 10 | usGfscUfaAfgAfaUfgUfgUfcAfaAfasusu |
| ETD01902 | 4 | [ETL17]suugaCfaCfaUfuCfuuagcacasusu | 11 | usGfsuGfcUfaAfgAfaUfgUfgUfcAfasusu |
| ETD01903 | 5 | [ETL17]sacauucuuAfGfcacugaacasusu | 12 | usGfsuUfcAfgUfgCfuAfaGfaAfuGfsusu |
| ETD01904 | 6 | [ETL17]sugcaUfagUfCfaCfucuuuugasusu | 13 | usCfsaAfaAfgAfgUfgAfcUfaUfgCfasusu |
| ETD01905 | 7 | [ETL17]saacuaCfUfgCfaUfaauauggasusu | 14 | usCfscAfuAfuUfaUfgCfaGfuAfgUfususu |

TABLE 3

Relative human PLIN1 mRNA Levels in Livers of Mice

| Group | n | Treatment | Dose (ug) | Mean PLIN1 mRNA (Normalized to Group 1, Day 10) |
|---|---|---|---|---|
| 1 | 4 | PBS | 0 | 1.00 |
| 2 | 4 | ETD01899 | 100 | 0.79 |
| 3 | 4 | ETD01900 | 100 | 0.30 |
| 4 | 4 | ETD01901 | 100 | 0.37 |
| 5 | 4 | ETD01902 | 100 | 0.24 |
| 6 | 4 | ETD01903 | 100 | 0.83 |
| 7 | 4 | ETD01904 | 100 | 0.58 |

Example 16: Knockdown of MST1 in Mice by GaINAc-Configured siRNAs

ETL17 was conjugated to siRNAs targeting another example target mRNA. The siRNAs were attached to the GaINAc ligand ETL17 followed by a phosphorothioate linkage at the 5' end of the sense strand. The siRNAs are described in Table 6. In the table, Nf (e.g. Ai', Cf, Tf, or Uf) is a 2' fluoro-modified nucleoside, dN (e.g. dA, dC, dG, dT, or dU) is a 2' deoxy-modified nucleoside, n (e.g. a, c, g, t, or u) is a 2' O-methyl modified nucleoside, and "s" is a phosphorothioate linkage.

Six to eight week old female mice (C57B1/6) were injected with 5 uL of a recombinant adeno-associated virus 8 (AAV8) vector (2.7×10E13 genome copies/mL) by the retroorbital route. The recombinant AAV8 contained the open reading frame and the majority of the 3'UTR of the human MST1 sequence (NM_920998.4) under the control of the human thyroxine binding globulin promoter in an AAV2 backbone packaged in AAV8 capsid (AAV8-TBG-h-MST1), On Day 13 after infection, serum was collected and the level of human MSP in each mouse was measured using the Human MSP/MST1 DuoSet ELISA from R&D (Catalog#DY352). The manufacturer's instructions regarding all reagent preparations for buffers and solutions was followed. A serum sample dilution of 1:50 was utilized for all test samples. Recombinant MSP included in the kit was used to create a standard curve of 10,000 pg/mL to 0 pg/mL. The optical density of the plate was read at 450 nm using a PerkinElmer Envision multimode plate reader. The concentration of MSP in each mouse serum sample was calculated from the standard curve by interpolation using least squares fit (Prism version 9, Software MacKiev).

Mice were allocated into groups (n=3) such that the groups had similar serum levels of MSP and then given a subcutaneous injection of a single 60 ug dose of a GaINAc-conjugated siRNA or PBS as vehicle control. On Days 0.4 and 12 after injection, serum was collected to assess serum MSP concentrations by ELISA using the methods described above. The MSP serum concentration at each timepoint was made relative to the level of MSP in the Day 0 sample for each individual mouse. The results are shown in Table 4. These data indicate that siRNAs conjugated to a GaINAc moiety such as ETL17 are useful for knocking down proteins secreted by an additional target mRNA in the liver.

Mice were sacrificed on Day 12 and a liver sample from each was collected and placed in RNAlater (ThermoFisher Cat#AM7020) until processing. Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. Preparation of cDNA was performed using Quanta qScript cDNA SuperMix (VWR, Catalog 95048-500) according to the manufacturer's instructions. The relative levels of liver MST1 mRNA were assessed by RT-OCR in triplicate on a QuantStudio™ 6 Pro Real-Time PCR System using TaqMan assays for human MST1 (ThermoFisher, assay #Hs00360684_ml) and the mouse housekeeping gene PPIA (ThermoFisher, assay #Mm02342430 g1) and PerfeCTa® qPCR FastMix®. Low ROX™ (VWR, Catalog#101419-222). Data were normalized to the level in animals receiving PBS. Results are shown in Table 5. These data indicated that siRNAs conjugated to a GaINAc moiety such as ETL17 are useful for knocking down the additional target mRNA in the liver

TABLE 4

Relative Mean Serum Human MSP Levels in AAV8-TBG-h-MST1 Mice

| Group | n | Treatment | Dose (ug) | Mean serum human MSP (Relative to Day 0) | | |
|---|---|---|---|---|---|---|
| | | | | Day 0 | Day 4 | Day 12 |
| 1 | 3 | PBS | | 1.00 | 1.12 | 1.54 |
| 2 | 3 | ETD01867 | 60 | 1.00 | 0.35 | 0.24 |
| 3 | 3 | ETD01963 | 60 | 1.00 | 0.46 | 0.42 |
| 4 | 3 | ETD01964 | 60 | 1.00 | 0.35 | 0.15 |
| 5 | 3 | ETD01965 | 60 | 1.00 | 0.32 | 0.26 |

TABLE 4-continued

Relative Mean Serum Human MSP Levels in AAV8-TBG-h-MST1 Mice

| Group | n | Treatment | Dose (ug) | Mean serum human MSP (Relative to Day 0) | | |
|---|---|---|---|---|---|---|
| | | | | Day 0 | Day 4 | Day 12 |
| 6 | 3 | ETD01966 | 60 | 1.00 | 0.30 | 0.16 |
| 7 | 3 | ETD01868 | 60 | 1.00 | 0.67 | ND |
| 8 | 3 | ETD01967 | 60 | 1.00 | 0.41 | 0.27 |
| 9 | 3 | ETD01968 | 60 | 1.00 | 0.53 | 0.30 |
| 10 | 3 | ETD01969 | 60 | 1.00 | 0.68 | 0.45 |
| 11 | 3 | ETD01970 | 60 | 1.00 | 0.51 | 0.59 |
| 12 | 3 | ETD01971 | 60 | 1.00 | 0.60 | 0.42 |
| 13 | 3 | ETD01972 | 60 | 1.00 | 0.24 | 0.17 |

ND, not determined

TABLE 5

Relative Human MST1 mRNA Levels in Livers of AAV8-TBG-h-MST1 Mice

| Group | n | Treatment | Dose (ug) | Mean human MST1 mRNA (Relative to Group 1, Day 12) |
|---|---|---|---|---|
| 1 | 3 | PBS | | 1.00 |
| 2 | 3 | ETD01867 | 60 | 0.40 |
| 3 | 3 | ETD01963 | 60 | 0.76 |
| 4 | 3 | ETD01964 | 60 | 0.60 |
| 5 | 3 | ETD01965 | 60 | 0.25 |
| 6 | 3 | ETD01966 | 60 | 0.33 |
| 7 | 3 | ETD01868 | 60 | 0.28 |
| 8 | 3 | ETD01967 | 60 | 0.07 |
| 9 | 3 | ETD01968 | 60 | 0.32 |
| 10 | 3 | ETD01969 | 60 | 0.15 |
| 11 | 3 | ETD01970 | 60 | 0.24 |
| 12 | 3 | ETD01971 | 60 | 0.31 |
| 13 | 3 | ETD01972 | 60 | 0.08 |

TABLE 6 siRNAs Screened for Activity in AAV8-TBG-h-MST1 Mice

| SIRNA Name | SEQ ID NO | Sense Strand Sequence (5'-3') with GalNAc Moiety | SEQ ID NO. | Antisense Strand Sequence (5'-3') |
|---|---|---|---|---|
| ETD01867 | 43 | [ETL17]sucuuGfucAfGfacauaaagcasusu | 54 | usGfscUfuUfaUfgUfcUfgAfcAfaGfasusu |
| ETD01963 | 44 | [ETL17]sucuuGfucAfGfacauaaagcasusu | 55 | usGfscuuUfaUfgUfcUfgAfcAfaGfasusu |
| ETD01964 | 45 | [ETL17]sucuuGfucAfGfacauaaagcasusu | 56 | usGfscuuUfaugUfcUfgAfcAfaGfaSUSU |
| ETD01965 | 46 | [ETL17]sucuuGfucAfGfacauaaagcasusu | 57 | usGfscUfuUfaUfgucUfgAfcAfaGfasusu |
| ETD01966 | 47 | [ETL17]sucuuGfucAfGfacauaaagcasusu | 58 | usGfscUfuuAfugUfcUfgAfcAfaGfasusu |
| ETD01967 | 48 | [ETL17]suuguCfadGaCfaUfaaagccaasusu | 59 | usUfsgGfcUfuUfaUfgUfcUfgAfcAfasusu |
| ETD01968 | 49 | [ETL17]suugucagaCfdAUfaaagccaasusu | 60 | usUfsgGfcUfuUfaUfgUfcUfgAfcAfasusu |
| ETD01969 | 50 | [ETL17]suuguCfagaCfaUfaaagccaasusu | 61 | usUfsggcUfuUfaUfgUfcUfgAfcAfasusu |
| ETD01970 | 51 | [ETL17]suuguCfagaCfaUfaaagccaasusu | 62 | usUfsgGfcUfuUfaugUfcUfgAfcAfasusu |
| ETD01971 | 52 | [ETL17]suuguCfagaCfaUfaaagccaasusu | 63 | usUfsggcUfuUfaugUfcUfgAfcAfaSUSU |
| ETD01972 | 53 | [ETL17]suuguCfagaCfaUfaaagccaasusu | 64 | usUfsggCfuuuaUfgUfcUfgAfcAfasusu |

Example 17: Knockdown of an Additional Target mRNA in Mice by GalNAc-Configured siRNAs Three groups (n=4/group) of 8-week-old male ICR mice (invigo) were utilized in a study. On Study Day 0, Group 1 mice were injected subcutaneously with 100 uL of sterile PBS, Group 2 mice were subcutaneously injected with 60 ug of siRNA 1811 in 100 uL of sterile PBS, and Group 3 mice were subcutaneously injected with 200 ug siRNA 1818 in 100 uL of sterile PBS. On Study Day 14, the animals from all Groups were anesthetized and then euthanized. A liver sample was collected from all animals and placed in RNAlater™ Stabilization Solution (Thermo Fisher, Catalog #AM7020). The liver samples were processed in homogenization buffer (Maxwell RSC simplyRNA Tissue Kit) using Soft Tissue Homogenizing Kit CK14 (Bertin Instruments, catalog#P000933-LYSK0-A) in a Percellys 24 tissue homogenizer (Bertin Instruments) set at 5000 rpm for two 10 second cycles. Total RNA from the liver lysate was purified on a. Maxwell RSC 48 platform (Promega Corporation) according to the manufacturer's recommendations. The relative level of Gene A mRNA in each liver sample was assessed by RT-qPCR on a QuantStudio 6 Pro instrument (Applied Biosystems) using TaqMan assays for mouse Gene A and the mouse housekeeping gene PPIA, and then normalized to the mean value of the control mice (Group 1) using the delta.-delta. Ct method.

In this example, an additional GalNAc moiety (ETL1) was compared to ETL17. The results of the liver mRNA analyses are shown in Table 7. Animals treated with ETL1-targeted siRNA (ETD01811, Group 2) had 78% relative knockdown while ETL17-targeted siRNA (siRNA 181$. Group 3) had 83% knockdown of liver Gene A mRNA levels, compared with mice injected with PBS (Group 1). Thus, a compound having a. GalNAc moiety described herein may be superior or at least as effective relative to another GalNAc moiety in knocking down a target such as a target mRNA.

TABLE 7

Day 14 Gene A mRNA liver levels in mice treated with siRNAs targeting Gene A

| Group # | Treatment | Mean |
|---|---|---|
| 1 | PBS | 1.00 |
| 2 | siRNA 1811 (with control GalNAc ETL1) | 0.22 |
| 3 | SiRNA 1818 (with ETL17) | 0.17 |

ETU is shown below, in which J indicates an attachment to an oligonucleotide:

Example 18. Testing the Activity of MST1 siRNAs ETD01821, ETD01822, ETD01823 and ETD01826 in Non-Human Primates Four groups (n=3/group) of 3-6 kg male cynomolgus monkeys (Zhaoqing Chuangyao Biotechnology Co., Ltd and Guangzhou Xiaringsuan Biotechnology Co., Ltd) were utilized for this study.

On Study Day 0, Group 1 cynomolgus monkeys were injected subcutaneously with a single 5 mg/kg dose (0.2 mL dose volume/kg body weight) of ETD01821 at an siRNA concentration of 25 mg/mL formulated in PBS, Group 2 cynomolgus monkeys were injected with a single 5 mg/kg dose (0.2 ml, dose volume/kg body weight) of ETD01822 at an siRNA concentration of 25 mg/mL formulated in PBS, Group 3 cynomolgus monkeys were injected with a single 5 mg/kg dose (0.2 mL dose volume/kg body weight) of ETD01823 at an siRNA concentration of 25 mg/mL formulated in PBS, Group 4 cynomolgus monkeys were injected with a single 5 mg/kg dose (0.2 mL dose volume/kg body weight) of ETD01826 at an siRNA concentration of 25 mg/mL formulated in PBS, The siRNA sequences are shown in Table 8, where is a 2' fluoro-modified nucleoside, "n" is a 2' O-methyl modified nucleoside, and "s" is a phosphorothioate linkage. The injection was generally well-tolerated as measured by clinical symptoms.

All cynomolgus monkeys had no abnormal clinical symptoms during the duration of the study except animal No. 101 which was found dead on Day 65 post-dose. Necropsy revealed severe gastric perforation that may have been the cause of death. This can spontaneously occur in cynomolgus monkeys.

On Study Days −8, −1, 7, 14, 21 and Day 28 body weights were recorded. Results are shown in Table 9. Data indicates that the animals in group 1 to 4 did not have a meaningful change in their body weight.

On Study Days −8, −2, 7, 14, and Day 28 blood was collected into tubes with no anti-coagulant and serum col-

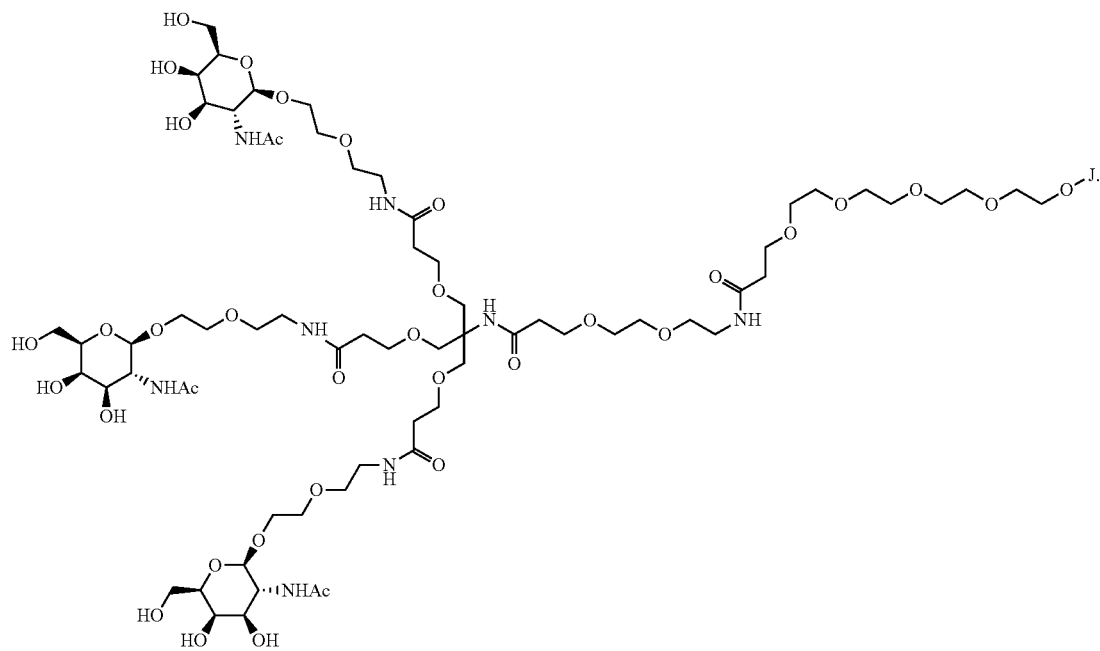

lected. Clinical chemistry parameters containing ALT, AST, ALP, TBIL, DBIL, GLU, GGT, TP, TG, CHOL, HDL, LDL, BUN and CREA were analyzed. Animals treated with ETD01821, ETD01822, ETD01823, or ETD01926 showed no meaningful change in ALT, AST. ALP, TBIL, DBIL, GLU, GGT, TP, TG, CHOL, HDL, LDL, BUN and CREA starting on Study Day 7 though Study Day 28 when compared to Study Day −8 and Study Day −2, prior to treatment. The results from the clinical chemistry indicated that all the siRNAs were generally well tolerated. Results are shown in Tables 10-14.

On Study Days −8 , −2, 7, 14, and Day 28 about 1 mL of whole blood was collected into tubes with EDTA-K2 as the anti-coagulant. Hematology parameters including WBC, NEUT, LYMP, MONO, EOS, BASO, RBC, HGB, HCT, MCV, MCH, MCHC, RDW, PLT, MPV, PCT and PDW were analyzed. Animals treated with ETD01821, ETD01822, ETD01823, or ETD01926 showed no meaningful change in these hematological parameters starting on Study Day 7 though Study Day 28 when compared to Study Day −8 and Study Day −2, prior to treatment. The results from the hematological analyses indicated that all the siRNAs were generally well tolerated. Results are shown in Tables 15-19.

On Study Days −8 , −2, 7, 14, 28, 42, 56, 70, 77, 84, 91, 98 and Day 105, blood was collected into tubes with no anti-coagulant and serum collected for determination of serum macrophage stimulating protein (MSP) levels, Additional serum samples were taken at later timepoints, namely on Days 42, 56, 70, 77, 84, 91, 98 and Day 105. A custom AlphaLISA assay (PerkinElmer) was used to evaluate individual macrophage stimulating protein (MSP) concentrations in the monkey serum samples. Briefly, 5 uL of serum sample diluted 1:50 in ix AlphaLISA HiBlock was placed into a well of a 96 well plate followed by addition of 5 uL of 4x anti-MSP acceptor bead solution. After incubation at room temperature for 30 minutes, 5 of 4x biotinylated anti-MSP antibody solution was added and the plate incubated at room temperature for 60 minutes. Next, 5 μL of 4x streptavidin donor bead solution was added and the plate incubated for a further 30 minutes at room temperature. The plate was analyzed on an Envision 2105 Multimode Plate Reader (PerkinElmer). A standard curve was generated using recombinant human MSP (R&D Systems). The MSP serum concentration for each individual at each timepoint was made relative to the mean of the MSP serum concentration for that individual on Days −2 and Day −8. Results for Group means are shown in Table 20 and individual values are shown in Table 21. Serum levels of MSP were decreased in all animals after treatment with test articles starting at Day 7 and remained decreased at least through Day 28. Monkeys treated with ETD01821 had the greatest decrease in serum MSP levels relative to pre-dose levels, showing decreased mean serum MSP level compared to pre-dose levels through Day 105.

On Study Day −8 and Day 28, the animals were anesthetized with Zoletil (1.5-5.0 mg/kg, i.m.) and xylazine (0.5-2.0 mg/kg, i.m.) and 3-4 mg liver biopsy was collected. The biopsy was then placed in 10 v/v RNAlater in 20 seconds and stored for 24 hrs at 4° C. the RNAlater™ Stabilization Solution (Thermo Fisher. Catalog #AM7020) was then removed and the liver tissue was stored in freezer until they were shipped to Empiric®. There were no abnormal clinical observations for all animals after liver biopsy collection on Day −2 or Day 28. The liver samples were processed in homogenization buffer (Maxwell RSC simplyRNA Tissue Kit) using Soft Tissue Homogenizing Kit CK14 (Bertin Instruments, catalog #P000933-LYSK0-A) in a. Percellys 24 tissue homogenizer (Bertin Instruments) set at 5000 rpm for two 10 second cycles. Total RNA from the liver lysate was purified on a Maxwell RSC 48 platform (Promega. Corporation) according to the manufacturer's recommendations. Preparation of cDNA was performed using Quanta qScript cDNA SuperMix (VWR, Catalog#95048-500) according to the manufacturer's instructions. The relative levels of liver MST1 mRNA were assessed in biplexed reactions by RT-qPCR in triplicate using TaqMan assays for Macaca fascicularis MST1 (ThermoFisher, assay#Mf1117426_gl) and the Macaca fascicularis housekeeping gene GAPDH (ThermoFisher, assay#Mf04392546 g) in Per-feCTa qPCR Fast-Mix Reaction Mix (VWR). The samples were assessed on a QuantStudio™ 6 Pro Real-Time PCR System. The delta-delta Ct method was used to calculate relative amounts of MST1 snRNA. Group mean relative MST1 mRNA levels relative to Day −8 are shown in Table 22, Consistent with the decrease in serum MSP levels as measured by AlphaLISA, treatment with 5 mg/kg of the test articles ETD01821, ETD01822, ETD01823 or ETD01826 resulted in a decrease in the liver levels of MST1 mRNA on Day 28 compared to the pre-dose Da.,-8 levels.

TABLE 8

Example siRNA Sequences

| SIRNA Name | Sense Strand SEQ ID NO: | Sense Strand Sequence (5'-3') with GalNAc moiety | Antisense Strand SEQ ID NO: | Antisense Strand Sequence (5'-3') |
| --- | --- | --- | --- | --- |
| ETD01821 | 15 | [ETL17]sgguccuGfGfAfAfGfg aauuauasusu | 19 | usAfsuAfaUfuCfcUfuCfcAfg GfaCfcsusu |
| ETD01822 | 16 | [ETL17]sAfaCfuUfcUfudGuCf agaCfaUfaasusu | 20 | usUfsaUfgUfcUfgAfcAfaGfa AfgUfususu |
| ETD01823 | 17 | [ETL17]scuucUfUfgUfCfagaca uaaaasusu | 21 | usUfsuUfaUfgUfcUfgAfcAfa GfaAfgsusu |
| ETD01826 | 18 | [ETL17]scaaccAfGfGfAfAfGfug Cacauasusu | 22 | usAfsuGfuUfaCfaCfuCfcUfg GfuUfgsusu |

TABLE 9

| Treatment group | Animal No. | Gender | ~8 | 1 | 0 | 7 | 14 | 21 | 28 |
|---|---|---|---|---|---|---|---|---|---|
| G1: ETD01821 | 101 | Male | 5.6 | 5.5 | 5.6 | 5.7 | 5.7 | 5.8 | 5.6 |
|  | 102 | Male | 6.0 | 6.0 | 6.0 | 5.9 | 6.1 | 6.2 | 6.1 |
|  | 103 | Male | 4.5 | 4.6 | 4.5 | 4.6 | 4.6 | 4.7 | 4.5 |
| G2: ETD01822 | 201 | Male | 6.5 | 6.5 | 6.5 | 6.6 | 6.5 | 6.5 | 6.5 |
|  | 202 | Male | 4.3 | 4.3 | 4.4 | 4.4 | 4.5 | 4.6 | 4.4 |
|  | 203 | Male | 5.5 | 5.5 | 5.6 | 5.6 | 5.6 | 5.4 | 5.6 |
| G3: ETD01823 | 301 | Male | 4.7 | 4.5 | 4.6 | 4.7 | 4.8 | 4.7 | 4.9 |
|  | 302 | Male | 4.6 | 4.6 | 4.6 | 4.6 | 4.6 | 4.7 | 4.5 |
|  | 303 | Male | 3.8 | 3.8 | 3.7 | 3.8 | 3.7 | 3.6 | 3.7 |
| G4: ETD01826 | 401 | Male | 3.7 | 3.6 | 3.7 | 3.8 | 3.7 | 3.8 | 3.7 |
|  | 402 | Male | 5.9 | 5.9 | 6.0 | 5.9 | 6.0 | 6.1 | 6.0 |
|  | 403 | Male | 4.5 | 4.6 | 4.6 | 4.6 | 4.5 | 4.5 | 4.6 |

Body Weight (kg); Days prior to dose and post-dose

TABLE 10

Individual and Mean Clinical Chemistry Parameters Results on Pre-dose (Day-8)

| Treatment group | | G1: ETD01821 | | | | |
|---|---|---|---|---|---|---|
| Animal No. | | 101 | 102 | 103 | | |
| Gender | | Male | Male | Male | | |
| Animal ID | | SC1702037 | SC1509029 | 175151C | Mean | SD |
| Parameters (unit) | ALT (U/L) | 27.5 | 15.2 | 27.0 | 23.2 | 6.96 |
| | AST (U/L) | 29.9 | 22.8 | 29.6 | 27.4 | 4.02 |
| | ALP (U/L) | 530 | 228↓ | 667 | 475 | 224 |
| | TBIL (μmol/L) | 1.54 | 1.37 | 1.28 | 1.40 | 0.13 |
| | DBIL (μmol/L) | 0.11 | 0.53 | 0.46 | 0.37 | 0.23 |
| | GLU (mmol/L) | 3.92 | 3.38 | 3.03 | 3.44 | 0.45 |
| | GGT (U/L) | 102 | 76.2 | 91.4 | 89.8 | 12.8 |
| | TP (g/L) | 73.4 | 68.2 | 70.2 | 70.6 | 2.60 |
| | TG (mmol/L) | 0.96 | 0.37 | 0.78 | 0.70 | 0.30 |
| | BUN (mmol/L) | 14.3 | 10.9 | 13.6 | 13.0 | 1.78 |
| | CREA (μmol/L) | 75.2 | 64.9 | 71.5 | 70.5 | 5.22 |

| Treatment group | | G2: ETD01822 | | | | |
|---|---|---|---|---|---|---|
| Animal No. | | 201 | 202 | 203 | | |
| Gender | | Male | Male | Male | | |
| Animal ID | | SC1508015 | SC1704115 | SC1703011 | Mean | SD |
| Parameters (unit) | ALT (U/L) | 15.0 | 29.0 | 31.4 | 25.1 | 8.86 |
| | AST (U/L) | 20.6 | 42.3 | 29.2 | 30.7 | 10.9 |
| | ALP (U/L) | 209↓ | 473 | 675 | 453 | 234 |
| | TBIL (μmol/L) | 1.04 | 1.68 | 2.06 | 1.59 | 0.52 |
| | DBIL (μmol/L) | 0.17 | 0.38 | 0.36 | 0.30 | 0.12 |
| | GLU (mmol/L) | 2.88 | 2.92 | 3.54 | 3.11 | 0.37 |
| | GGT (U/L) | 71.0 | 69.4 | 64.2 | 68.2 | 3.57 |
| | TP (g/L) | 64.4 | 69.1 | 67.8 | 67.1 | 2.40 |
| | TG (mmol/L) | 0.31 | 0.22 | 0.55 | 0.36 | 0.17 |
| | BUN (mmol/L) | 17.4 | 10.7 | 15.3 | 14.5 | 3.44 |
| | CREA (μmol/L) | 76.9 | 67.2 | 76.7 | 73.6 | 5.54 |

| Treatment group | | G3: ETD01823 | | | | |
|---|---|---|---|---|---|---|
| Animal No. | | 301 | 302 | 303 | | |
| Gender | | Male | Male | Male | | |
| Animal ID | | 177695C | SC1704077 | 176313C | Mean | SD |
| Parameters (unit) | ALT (U/L) | 41.2 | 35.4 | 26.5 | 34.4 | 7.40 |
| | AST (U/L) | 33.4 | 32.5 | 29.2 | 31.7 | 2.21 |
| | ALP (U/L) | 735 | 837 | 585 | 719 | 127 |
| | TBIL (μmol/L) | 2.03 | 2.71 | 1.47 | 2.07 | 0.62 |
| | DBIL (μmol/L) | 0.49 | 1.00 | 0.29 | 0.59 | 0.37 |
| | GLU (mmol/L) | 4.13 | 3.17 | 3.82 | 3.71 | 0.49 |
| | GGT (U/L) | 119 | 100 | 91.1 | 104 | 14.2 |
| | TP (g/L) | 64.5 | 60.5 | 67.3 | 64.1 | 3.41 |
| | TG (mmol/L) | 0.31 | 0.19 | 0.70 | 0.40 | 1.27 |
| | BUN (mmol/L) | 13.4 | 11.5 | 17.2 | 14.0 | 2.93 |
| | CREA (μmol/L) | 61.0 | 59.3 | 79.4 | 66.6 | 11.1 |

TABLE 10-continued

Individual and Mean Clinical Chemistry Parameters Results on Pre-dose (Day-8)

| Treatment group | | G4: ETD01826 | | | | |
|---|---|---|---|---|---|---|
| Animal No. | | 401 | 402 | 403 | | |
| Gender | | Male | Male | Male | | |
| Animal ID | | SC1708089 | SC1604087 | SC1703023 | Mean | SD |
| Parameters (unit) | ALT (U/L) | 19.6 | 32.4 | 12.0 | 21.3 | 10.31 |
| | AST (U/L) | 28.2 | 28.0 | 28.7 | 28.3 | 0.36 |
| | ALP (U/L) | 775 | 346 | 492 | 538 | 218 |
| | TBIL (μmol/L) | 1.80 | 3.67 | 1.49 | 2.32 | 1.18 |
| | DBIL (μmol/L) | 0.89 | 2.40 | 0.70 | 1.33 | 0.93 |
| | GLU (mmol/L) | 2.93 | 4.14 | 3.49 | 3.52 | 0.61 |
| | GGT (U/L) | 84.1 | 69.5 | 47.2 | 66.9 | 18.6 |
| | TP (g/L) | 62.5 | 61.2 | 50.3 | 58.0 | 6.68 |
| | TG (mmol/L) | 0.45 | 0.22 | 0.53 | 0.40 | 0.16 |
| | BUN (mmol/L) | 11.5 | 11.9 | 17.9 | 13.7 | 3.59 |
| | CREA (μmol/L) | 64.3 | 90.2 | 85.5 | 80.0 | 13.8 |

Note:
The ↓ next to the value means the result was slightly lower than that of other animals.

TABLE 11

Individual and Mean Clinical Chemistry Parameters Results on Pre-dose (Day-2)

| Treatment group | | G1: ETD01821 | | | | | G2: ETD01822 | | | | |
|---|---|---|---|---|---|---|---|---|---|---|---|
| Animal No. | | 101 | 102 | 103 | | | 201 | 202 | 203 | | |
| Gender | | Male | Male | Male | | | Male | Male | Male | | |
| Animal ID | | SC1702037 | SC1509029 | 175151C | Mean | SD | SC1508015 | SC1704115 | SC1703011 | Mean | SD |
| Parameters (unit) | ALT (U/L) | 34.4 | 23.3 | 45.4 | 34.4 | 11.1 | 21.0 | 31.5 | 33.4 | 28.6 | 6.68 |
| | AST (U/L) | 20.9 | 20.3 | 44.7 | 28.6 | 13.9 | 20.1 | 30.0 | 34.0 | 28.0 | 7.16 |
| | ALP (U/L) | 477 | 251↓ | 634 | 454 | 192 | 279↓ | 489 | 630 | 466 | 177 |
| | TBIL (μmol/L) | 1.83 | 1.48 | 1.07 | 1.46 | 0.38 | 1.52 | 2.07 | 2.69 | 2.09 | 0.59 |
| | DBIL (μmol/L) | 0.26 | 0.05 | 0.02 | 0.11 | 0.13 | 0.01 | 0.38 | 0.58 | 0.32 | 0.29 |
| | GLU (mmol/L) | 3.31 | 3.56 | 3.41 | 3.43 | 0.13 | 4.40 | 3.15 | 3.45 | 3.67 | 0.65 |
| | GGT (U/L) | 104 | 79.4 | 97.2 | 93.6 | 12.7 | 98.2 | 70.2 | 68.7 | 79.0 | 16.6 |
| | TP (g/L) | 79.9 | 74.9 | 77.0 | 77.3 | 2.53 | 79.3 | 76.6 | 77.2 | 77.7 | 1.43 |
| | TG (mmol/L) | 0.73 | 0.47 | 1.48 | 0.89 | 0.52 | 0.47 | 0.24 | 0.47 | 0.39 | 0.13 |
| | BUN (mmol/L) | 13.8 | 11.9 | 13.9 | 13.2 | 1.12 | 14.1 | 11.1 | 15.4 | 13.5 | 2.22 |
| | CREA (μmol/L) | 85.4 | 70.8 | 66.1 | 74.1 | 10.1 | 86.5 | 63.3 | 81.4 | 77.1 | 12.2 |

| Treatment group | | G3: ETD01823 | | | | | G4: ETD01826 | | | | |
|---|---|---|---|---|---|---|---|---|---|---|---|
| Animal No. | | 301 | 302 | 303 | | | 401 | 402 | 403 | | |
| Animal ID | | 177695C | SC1704077 | 176313C | Mean | SD | SC1708089 | SC1604087 | SC1703023 | Mean | SD |
| Parameters (unit) | ALT (U/L) | 32.6 | 12.6 | 38.3 | 37.8 | 5.02 | 24.5 | 42.5 | 11.9 | 26.3 | 15.4 |
| | AST (U/L) | 28.7 | 30.9 | 33.0 | 30.9 | 2.15 | 25.7 | 31.7 | 24.1 | 27.2 | 4.01 |
| | ALP (U/L) | 679 | 821 | 580 | 693 | 121 | 762 | 478 | 427 | 556 | 180 |
| | TBIL (μmol/L) | 2.89 | 2.74 | 2.33 | 2.65 | 0.29 | 2.15 | 1.89 | 0.74 | 1.59 | 0.75 |
| | DBIL (μmol/L) | 0.72 | 0.39 | 0.69 | 0.60 | 0.18 | 0.51 | 0.21 | — | 0.36 | 0.21 |
| | GLU (mmol/L) | 3.50 | 3.76 | 3.85 | 3.70 | 0.18 | 3.98 | 6.44 | 4.04 | 4.82 | 1.40 |
| | GGT (U/L) | 116 | 100 | 96.9 | 104 | 10.0 | 86.4 | 86.3 | 50.6 | 74.4 | 20.6 |
| | TP (g/L) | 70.8 | 65.4 | 71.5 | 69.2 | 3.31 | 67.9 | 75.8 | 52.7 | 65.5 | 11.7 |
| | TG (mmol/L) | 0.32 | 0.24 | 0.39 | 0.32 | 0.08 | 0.48 | 0.32 | 1.08 | 0.63 | 0.40 |
| | BUN (mmol/L) | 12.7 | 10.3 | 17.5 | 13.5 | 3.66 | 12.6 | 11.9 | 16.0 | 13.5 | 2.16 |
| | CREA (μmol/L) | 60.1 | 57.7 | 74.6 | 64.1 | 9.14 | 63.0 | 106 | 69.8 | 79.5 | 22.9 |

Note:
The ↓ next to the value means the result was slightly lower than that of other animals. '—' means that DBIL of some samples cannot be detected due to the low concentration.

Individual and Mean Clinical Chemistry Parameters Results on Day 7 post-dose

| Treatment group | | G1: ETD01821 | | | | | G2: ETD01822 | | | | |
|---|---|---|---|---|---|---|---|---|---|---|---|
| Animal No. | | 101 | 102 | 103 | | | 201 | 202 | 203 | | |
| Gender | | Male | Male | Male | | | Male | Male | Male | | |
| Animal ID | | SC1702037 | SC1509029 | 175151C | Mean | SD | SC1508015 | SC1704115 | SC1703011 | Mean | SD |
| Parameters (unit) | ALT (U/L) | 32.5 | 22.7 | 38.2 | 31.1 | 7.84 | 19.9 | 36.2 | 28.7 | 28.3 | 8.16 |
| | AST (U/L) | 22.7 | 20.0 | 32.1 | 24.8 | 6.43 | 16.4 | 34.2 | 25.4 | 25.3 | 8.90 |
| | ALP (U/L) | 453 | 276↓ | 749 | 493 | 239 | 272↓ | 535 | 628 | 479 | 185 |

| | Individual and Mean Clinical Chemistry Parameters Results on Day 7 post-dose | | | | | | | | | |
|---|---|---|---|---|---|---|---|---|---|---|
| | TBIL (μmol/L) | 1.56 | 1.50 | 1.92 | 1.66 | 0.23 | 1.66 | 2.22 | 2.11 | 2.00 | 0.30 |
| | DBIL (μmol/L) | 0.09 | — | 0.30 | 0.20 | 0.15 | 0.58 | — | 0.97 | 0.78 | 0.28 |
| | GLU (mmol/L) | 3.69 | 3.91 | 3.83 | 3.81 | 0.11 | 4.49 | 4.53 | 4.32 | 4.45 | 0.11 |
| | GGT (U/L) | 104 | 78.4 | 103 | 95.1 | 14.4 | 90.8 | 71.2 | 64.5 | 75.5 | 13.7 |
| | TP (g/L) | 82.8 | 78.8 | 82.8 | 81.4 | 2.30 | 76.1 | 80.8 | 76.5 | 77.8 | 2.58 |
| | TG (mmol/L) | 0.64 | 0.59 | 0.81 | 0.68 | 0.12 | 0.30 | 0.34 | 0.65 | 0.43 | 0.19 |
| | BUN (mmol/L) | 14.1 | 10.5 | 13.9 | 12.5 | 2.02 | 11.8 | 11.2 | 14.2 | 12.4 | 1.58 |
| | CREA (μmol/L) | 82.1 | 68.0 | 62.8 | 71.0 | 9.99 | 85.0 | 67.7 | 76.9 | 76.5 | 8.66 |

| Treatment group | | G3: ETD01823 | | | | | G4: ETD01826 | | | | |
|---|---|---|---|---|---|---|---|---|---|---|---|
| | Animal No. | 301 | 302 | 303 | | | 401 | 402 | 403 | | |
| | Gender | Male | Male | Male | | | Male | Male | Male | | |
| | Animal ID | 177695C | SC1704077 | 176313C | Mean | SD | SC1708089 | SC1604807 | SC1703023 | Mean | SD |
| Parameters (unit) | ALT (U/L) | 29.9 | 41.6 | 30.7 | 34.1 | 6.51 | 23.0 | 19.4 | 15.1 | 29.2 | 18.0 |
| | AST (U/L) | 28.0 | 29.6 | 26.2 | 27.9 | 1.70 | 24.5 | 28.2 | 21.4 | 24.7 | 3.40 |
| | ALP (U/L) | 806 | 776 | 570 | 718 | 129 | 659 | 510 | 433 | 534 | 115 |
| | TBIL (μmol/L) | 2.70 | 1.91 | 1.79 | 2.13 | 0.49 | 2.15 | 2.29 | 1.61 | 2.02 | 0.36 |
| | DBIL (μmol/L) | 0.39 | 0.81 | 0.61 | 0.61 | 0.21 | 0.30 | 0.31 | 0.30 | 0.40 | 0.17 |
| | GLU (mmol/L) | 3.93 | 4.27 | 3.86 | 4.02 | 0.22 | 3.64 | 4.60 | 4.41 | 4.22 | 0.51 |
| | GGT (U/L) | 129 | 96.2 | 87.0 | 103.9 | 21.8 | 82.0 | 94.0 | 55.9 | 77.3 | 19.5 |
| | TP (g/L) | 75.2 | 66.4 | 73.4 | 71.7 | 4.67 | 71.4 | 83.0 | 58.6 | 71.0 | 12.2 |
| | TG (mmol/L) | 0.36 | 0.37 | 0.47 | 0.40 | 0.06 | 0.47 | 0.27 | 0.46 | 0.40 | 0.11 |
| | BUN (mmol/L) | 11.7 | 10.2 | 18.7 | 13.6 | 4.52 | 13.7 | 13.6 | 14.0 | 13.8 | 0.19 |
| | CREA (μmol/L) | 65.8 | 55.4 | 70.7 | 64.0 | 7.81 | 60.9 | 101 | 75.6 | 79.0 | 20.0 |

Note:
The ↓ next to the value means the result was slightly lower than that of other animals. '—' means that DBIL of some samples cannot be detected due to the low concentration.

TABLE 13

| Individual and Mean Clinical Chemistry Parameters Results on Day 14 post-dose | | | | | | | | | | | |
|---|---|---|---|---|---|---|---|---|---|---|---|
| Treatment group | | G1: ETD01821 | | | | | G2: ETD01822 | | | | |
| | Animal No | 101 | 102 | 103 | | | 201 | 202 | 203 | | |
| | Gender | Male | Male | Male | | | Male | Male | Male | | |
| | Animal ID | SC1702037 | SC1509029 | 175151C | Mean | SD | SC1508015 | SC1704115 | SC1703011 | Mean | SD |
| Parameters (unit) | ALT (U/L) | 37.0 | 25.4 | 66.9 | 43.1 | 21.4 | 20.0 | 30.4 | 29.1 | 26.5 | 5.67 |
| | AST (U/L) | 26.0 | 20.5 | 178 | 74.9 | 89.6 | 18.2 | 26.1 | 25.5 | 23.3 | 4.40 |
| | ALP (U/L) | 557 | 275↓ | 781 | 538 | 254 | 298↓ | 509 | 630 | 479 | 168 |
| | TBIL (μmol/L) | 1.60 | 1.74 | 1.82 | 1.72 | 0.11 | 1.73 | 1.88 | 2.18 | 1.93 | 0.23 |
| | DBIL (μmol/L) | — | 0.28 | — | 0.28 | 0.00 | — | 0.40 | 0.73 | 0.57 | 0.23 |
| | GLU (mmol/L) | 3.32 | 3.50 | 5.43 | 4.08 | 1.17 | 1.57 | 3.52 | 4.01 | 4.03 | 0.53 |
| | GGT (U/L) | 118 | 76.7 | 101 | 98.6 | 20.8 | 102 | 66.3 | 63.3 | 77.1 | 21.4 |
| | TP (g/L) | 88.7 | 76.8 | 83.9 | 83.1 | 5.97 | 80.2 | 79.4 | 75.2 | 78.3 | 2.69 |
| | TG (mmol/L) | 1.09 | 0.53 | 0.60 | 0.74 | 0.31 | 0.32 | 0.24 | 0.65 | 0.40 | 0.22 |
| | BUN (mmol/L) | 14.0 | 10.1 | 16.5 | 13.5 | 3.25 | 15.9 | 11.7 | 13.3 | 13.6 | 2.13 |
| | CREA (μmol/L) | 98.9 | 67.8 | 69.1 | 78.6 | 17.6 | 95.2 | 69.8 | 78.7 | 81.2 | 12.9 |
| Treatment group | | G3: ETD01823 | | | | | G4: ETD01826 | | | | |
| | Animal No. | 301 | 302 | 303 | | | 401 | 402 | 403 | | |
| | Gender | Male | Male | Male | | | Male | Male | Male | | |
| | Animal ID | 177695C | SC1704077 | 176313C | Mean | SD | SC1708089 | SC1604087 | SC1703023 | Mean | SD |
| Parameters (unit) | ALT (U/L) | 34.6 | 47.0 | 23.1 | 34.9 | 12.0 | 22.1 | 16.0 | 46.3 | 28. | 16.0 |
| | AST (U/L) | 26.3 | 30.7 | 25.0 | 27.3 | 2.99 | 29.1 | 29.6 | 27.9 | 28.9 | 0.87 |
| | ALP (U/L) | 782 | 864 | 569 | 738 | 153 | 679 | 467 | 469 | 538 | 122 |
| | TBIL (μmol/L) | 1.92 | 2.66 | 1.63 | 2.07 | 0.53 | 1.43 | 0.88 | 1.78 | 1.36 | 0.45 |
| | DBIL (μmol/L) | 0.37 | 0.65 | 0.46 | 0.49 | 0.14 | 0.27 | — | 0.22 | 0.25 | 0.04 |
| | GLU (mmol/L) | 3.59 | 3.70 | 4.04 | 3.78 | 0.23 | 3.29 | 4.64 | 4.18 | 4.04 | 0.69 |
| | GGT (U/L) | 128 | 101 | 96.4 | 108 | 17.1 | 75.1 | 54.3 | 83.7 | 71.0 | 15.1 |
| | TP (g/L) | 71.2 | 67.8 | 71.7 | 70.2 | 2.13 | 65.1 | 53.6 | 73.5 | 64.1 | 9.99 |
| | TG (mmol/L) | 0.38 | 0.30 | 0.59 | 0.42 | 0.15 | 0.56 | 0.78 | 0.26↓ | 0.53 | 0.26 |
| | BUN (mmol/L) | 12.3 | 10.3 | 15.9 | 12.8 | 2.82 | 13.1 | 18.1 | 13.7 | 15.0 | 2.78 |
| | CREA (μmol/L) | 66.1 | 61.7 | 74.8 | 67.5 | 6.67 | 65.1 | 92.2 | 100 | 85.8 | 18.3 |

Note:
The ↓ next to the value means the result was slightly lower than that of other animals. '—' means that DBIL of some samples cannot be detected due to the low concentration.

TABLE 14

Individual and Mean Clinical Chemistry Parameters Results on Day 28 post-dose

| Treatment group | | G1: ETD01821 | | | | | G2: ETD01822 | | | | |
|---|---|---|---|---|---|---|---|---|---|---|---|
| Animal No. | | 101 | 102 | 103 | | | 201 | 202 | 203 | | |
| Gender | | Male | Male | Male | | | Male | Male | Male | | |
| Animal ID | | SC1702037 | SC1509029 | 175151C | Mean | SD | SC1508015 | SC1704115 | SC1703011 | Mean | SD |
| Parameters (unit) | ALT (U/L) | 34.8 | 22.1 | 45.3 | 34.1 | 11.6 | 33.5 | 45.4 | 48.8 | 42.6 | 8.03 |
| | AST (U/L) | 30.1 | 30.4 | 35.0 | 31.8 | 2.75 | 25.8 | 42.4 | 51.9 | 40.0 | 13.2 |
| | ALP (U/L) | 364 | 216↓ | 503 | 361 | 144 | 226↓ | 467 | 634 | 442 | 205 |
| | TBIL (μmol/L) | 1.17 | 1.33 | 1.15 | 1.22 | 0.10 | 1.72 | 1.08 | 1.09 | 1.30 | 0.37 |
| | DBIL (μmol/L) | 0.10 | 0.33 | 0.28 | 0.24 | 0.12 | 0.29 | — | — | 0.29 | 0.00 |
| | GLU (mmol/L) | 3.06 | 2.97 | 3.04 | 3.02 | 0.05 | 4.56 | 3.79 | 4.61 | 4.32 | 0.46 |
| | GGT (U/L) | 87.8 | 66.5 | 79.8 | 78.0 | 10.7 | 86.6 | 63.9 | 62.3 | 70.9 | 13.6 |
| | TP (g/L) | 72.3 | 72.4 | 71.7 | 72.1 | 0.36 | 82.4 | 74.7 | 72.4 | 76.5 | 5.23 |
| | TG (mmol/L) | 0.79 | 0.43 | 0.62 | 0.61 | 0.18 | 0.41 | 0.13 | 0.40 | 0.31 | 0.16 |
| | BUN (mmol/L) | 18.2 | 14.1 | 15.9 | 16.1 | 2.05 | 16.1 | 11.4 | 15.5 | 14.3 | 2.54 |
| | CREA (μmol/L) | 75.0 | 63.0 | 65.9 | 68.0 | 6.26 | 89.3 | 60.3 | 76.9 | 5.5 | 14.6 |
| Treatment group | | G3: ETD01823 | | | | | G4: ETD01826 | | | | |
| Animal No. | | 301 | 302 | 30 | | | 401 | 402 | 403 | | |
| Gender | | Male | Male | Male | | | Male | Male | Male | | |
| Animal ID | | 177695C | SC1704077 | 176313C | Mean | SD | SC1708089 | SC1604087 | SC1703023 | Mean | SD |
| Parameters (unit) | ALT (U/L) | 23.9 | 34.3 | 28.4 | 28.9 | 22 | 22.8 | 40.5 | 24.4 | 29.2 | 9.79 |
| | AST (U/L) | 24.5 | 43.1 | 27.1 | 31.6 | 10.1 | 31.5 | 30.3 | 34.6 | 32.1 | 2.22 |
| | ALP (U/L) | 193 | 447 | 563 | 401 | 189 | 570 | 344 | 382 | 432 | 121 |
| | TBIL (μmol/L) | 1.53 | 1.69 | 1.30 | 1.51 | 0.20 | 1.37 | 0.96 | 0.58 | 1.97 | 0.40 |
| | DBIL (μmol/L) | 0.45 | 0.37 | 0.56 | 0.46 | 0.10 | — | 0.05 | — | 0.05 | 0.00 |
| | GLU (mmol/L) | 3.83 | 3.21 | 3.30 | 3.45 | 0.34 | 2.97 | 5.57 | 4.58 | 4.37 | 1.31 |
| | GGT (U/L) | 77.2 | 65.3 | 59.2 | 67.2 | 9.13 | 73.5 | 75.9 | 53.8 | 67.7 | 12.1 |
| | TP (g/L) | 73.5 | 73.7 | 68.1 | 71.7 | 3.17 | 65.0 | 62.4 | 58.1 | 61.8 | 3.48 |
| | TG (mmol/L) | 0.28 | 0.17 | 0.42 | 0.29 | 0.13 | 0.54 | 0.15 | 0.36 | 0.35 | 0.20 |
| | BUN (mmol/L) | 16.0 | 11.2 | 14.9 | 14.0 | 2.53 | 14.8 | 16.9 | 16.2 | 16.0 | 1.05 |
| | CREA (μmol/L) | 86.3 | 55.1 | 14.3 | 71.9 | 15.7 | 62.4 | 96.8 | 62.2 | 73.8 | 19.9 |

Note:
The ↓ next to the value means the result was slightly lower than that of other animals. '—' means that DBIL of some samples cannot be detected due to the low concentration.

TABLE 15

Individual and Mean Hematology Results on Pre-dose (Day-8)

| Treatment group | | G1: ETD01821 | | | | | G2: ETD01822 | | | | |
|---|---|---|---|---|---|---|---|---|---|---|---|
| Animal No. | | 101 | 102 | 103 | | | 201 | 202 | 203 | | |
| Gender | | Male | Male | Male | | | Male | Male | Male | | |
| Animal ID | | SC1702037 | SC1509029 | 175151C | Mean | SD | SC1508015 | SC1704115 | SC1703011 | Mean | SD |
| Parameters (unit) | WBC ($\times 10^9$/L) | 10.4 | 7.99 | 3.57 | 8.99 | 1.26 | 6.69 | 10.4 | 17.4 | 11.5 | 5.43 |
| | abs_nouts ($\times 10^9$/L) | 3.14 | 2.59 | 1.33 | 2.35 | 0.93 | 2.52 | 2.97 | 3.13 | 2.87 | 0.32 |
| | abs_lymphs ($\times 10^9$/L) | 6.55 | 4.82 | 6.61 | 5.99 | 1.02 | 3.76 | 6.77 | 13.48 | 8.00 | 4.98 |
| | abs_monos ($\times 10^9$/L) | 0.65 | 0.48 | 0.46 | 0.53 | 0.10 | 0.31 | 0.59 | 0.66 | 0.52 | 0.19 |
| | abs_cos ($\times 10^9$/L) | 0.07 | 0.10 | 0.17 | 0.11 | 0.05 | 0.10 | 1.04 | 0.10 | 0.08 | 0.03 |
| | abs_basos ($\times 10^9$/L) | 0.00 | 0.00 | 0.00 | 0.00 | 0.00 | 0.00 | 0.00 | 0.00 | 0.00 | 0.00 |
| | %NEUT (%) | 30.1 | 32.4 | 15.6 | 26.0 | 9.11 | 37.6 | 28.6 | 18.0 | 28.1 | 9.81 |
| | %LYM (%) | 63.0 | 60.4 | 77.0 | 66.8 | 8.93 | 56.2 | 65.3 | 77.6 | 66.4 | 10.7 |
| | %MONO (%) | 6.20 | 6.00 | 5.40 | 5.87 | 0.42 | 4.70 | 5.70 | 3.80 | 4.73 | 0.95 |
| | %EOS (%) | 0.70 | 1.20 | 2.00 | 1.30 | 0.66 | 1.50 | 0.40 | 0.60 | 0.83 | 0.59 |
| | %BASO (%) | 0.00 | 0.00 | 0.00 | 0.00 | 0.00 | 0.00 | 0.00 | 0.00 | 0.00 | 0.00 |
| | RBC ($\times 10^{12}$/L) | 5.43 | 5.48 | 5.35 | 5.42 | 0.07 | 5.01 | 5.33 | 5.29 | 5.21 | 0.17 |
| | HGB (g/L) | 135 | 134 | 124 | 131 | 6.08 | 126 | 128 | 131 | 128 | 2.52 |
| | HCT (%) | 15.2 | 43.5 | 40.4 | 43.0 | 2.43 | 41.0 | 42.1 | 42.5 | 41.9 | 0.78 |
| | MCV (fL) | 83.3 | 79.5 | 75.6 | 79.5 | 3.85 | 82.0 | 79.1 | 80.4 | 80.5 | .45 |
| | MCH (pg) | 24.8 | 24.4 | 23.2 | 24.1 | 0.83 | 25.2 | 24.1 | 24.9 | 24.7 | 0.57 |
| | MCHC (g/L) | 298 | 307 | 307 | 304 | 5.20 | 308 | 304 | 309 | 307 | 2.65 |
| | RDW-SD (fL) | 37.1 | 43.6 | 38.8 | 39.8 | 3.37 | 41.2 | 36.7 | 36.9 | 38.3 | 2.54 |
| | RDW-CV (%) | 12.2 | 15.1 | 14.1 | 13.8 | 1.47 | 13.7 | 12.7 | 12.6 | 13.0 | 0.61 |
| | PLT ($\times 10^9$/L) | 380 | 371 | 247↓ | 333 | 74.3 | 361 | 301 | 285 | 316 | 40.1 |
| | MPV (fL) | 13.1 | 12. | 9.60 | 11.7 | 1.87 | 11.6 | 14.2 | 12.4 | 12.7 | 1.33 |
| | PCT (%) | 0.50 | 0.46 | 0.24↓ | 0.40 | 0.14 | 0.42 | 0.43 | 0.36 | 0.40 | 0.04 |
| | PDW (fL) | 15.5 | 15.0 | 15.4 | 15.3 | 0.26 | 14.9 | 15.6 | 15.3 | 15.3 | 0.35 |

TABLE 15-continued

Individual and Mean Hematology Results on Pre-dose (Day-8)

| | Treatment group | G3: ETD01823 | | | | | G4: ETD01826 | | | | |
|---|---|---|---|---|---|---|---|---|---|---|---|
| | Animal No. | 301 | 302 | 303 | | | 401 | 102 | 403 | | |
| | Gender | Male | Male | Male | | | Male | Male | Male | | |
| | Animal ID | 177695C | SC1704077 | 176313C | Mean | SD | SC1708089 | SC1604087 | SC1703023 | Mean | SD |
| Parameters (unit) | WBC ($\times 10^9$/L) | 13.9 | 9.37 | 8.40 | 10.6 | 2.93 | 9.50 | 5.65↓ | 15.8 | 10.3 | 5.13 |
| | abs_nouts ($\times 10^9$/L) | 1.19 | 2.31 | 1.82 | 1.77 | 0.56 | 3.72 | 1.04↓ | 6.22 | 3.66 | 2.59 |
| | abs_lymphs ($\times 10^9$/L) | 11.3 | 6.45 | 6.09 | 7.96 | 2.93 | 5.09 | 4.13 | 8.76 | 5.99 | 2.44 |
| | abs_monos ($\times 10^9$/L) | 1.28 | 0.53 | 0.29 | 0.70 | 0.52 | 0.55 | 0.38 | 0.57 | 0.50 | 0.10 |
| | abs_cos ($\times 10^9$/L) | 0.09 | 0.08 | 0.20 | 0.12 | 0.07 | 0.14 | 0.10 | 0.26 | 0.17 | 0.08 |
| | abs_basos ($\times 10^9$/L) | 0.00 | 0.00 | 0.00 | 0.00 | 0.00 | 0.00 | 0.00 | 0.01 | 0.00 | 0.01 |
| | %NEUT (%) | 8.6 | 24.7 | 21.6 | 18.3 | 8.54 | 39.2 | 18.5 | 39.3 | 32.3 | 12.0 |
| | %LYM (%) | 81.5 | 68.9 | 72.6 | 74.3 | 64.8 | 53.5 | 72.9 | 55.4 | 60.6 | 10.7 |
| | %MONO (%) | 9.20 | 5.60 | 3.40 | 6.07 | 2.93 | 5.80 | 6.80 | 3.60 | 5.40 | 1.64 |
| | %EOS (%) | 0.70 | 0.80 | 2.40 | 1.30 | 0.95 | 1.50 | 1.80 | 1.70 | 1.67 | 0.15 |
| | %BASO (%) | 0.00 | 0.00 | 0.00 | 0.00 | 0.00 | 0.00 | 0.00 | 0.00 | 0.00 | 0.00 |
| | RBC ($\times 10^{12}$/L) | 5.36 | 5.61 | 5.07 | 5.35 | 0.27 | 5.29 | 5.09 | 5.39 | 5.26 | 0.15 |
| | HGB (g/L) | 130 | 137 | 114 | 127 | 11.8 | 129 | 122 | 133 | 128 | 5.57 |
| | HCT (%) | 43.6 | 43.3 | 37.3 | 41.4 | 3.55 | 42.2 | 40.3 | 43.3 | 41.9 | 1.52 |
| | MCV (fL) | 81.3 | 77.3 | 73.6 | 77.4 | 3.85 | 79.6 | 79.2 | 80.3 | 79.7 | 0.56 |
| | MCH (pg) | 24.2 | 24.5 | 22.6 | 23.8 | 1.02 | 24.3 | 24.1 | 24.6 | 24.3 | 0.25 |
| | MCHC (g/L) | 298 | 316 | 307 | 307 | 9.00 | 305 | 304 | 306 | 305 | 1.00 |
| | RDW-SD (fL) | 41.1 | 38.9 | 36.5 | 38.8 | 2.30 | 36.9 | 40.2 | 40.3 | 39.1 | 1.93 |
| | RDW-CV (%) | 13.8 | 13.8 | 13.6 | 13.7 | 0.12 | 12.7 | 14.0 | 13.8 | 13.5 | 0.70 |
| | PLT ($\times 10^9$/L) | 372 | 307 | 229↓ | 303 | 71.6 | 339 | 201↓ | 398 | 313 | 101 |
| | MPV (fL) | 11.1 | 11.9 | 14.4 | 12.5 | 1.72 | 13.1 | 14.2 | 10.3 | 12.5 | 2.01 |
| | PCT (%) | 0.41 | 0.37 | 0.33 | 0.37 | 0.04 | 1.44 | 0.29↓ | 0.41 | 0.38 | 0.08 |
| | PDW (fL) | 15.5 | 15.3 | 15.8 | 15.5 | 0.25 | 15.5 | 15.6 | 15.3 | 15.5 | 0.15 |

Note:
The ↓ next to the value means the result was slightly lower than that of other animals.

TABLE 16

Individual and Mean Hematology Results on Pre-dose (Day-2)

| | Treatment group | G1: ETD01821 | | | | | G2: ETD01822 | | | | |
|---|---|---|---|---|---|---|---|---|---|---|---|
| | Animal No. | 101 | 102 | 103 | | | 201 | 202 | 203 | | |
| | Gender | Male | Male | Male | | | Male | Male | Male | | |
| | Animal ID | SC1702037 | SC1509029 | 175151C | Mean | SD | SC1508015 | SC1704115 | SC1703011 | Mean | SD |
| Parameters (unit) | WBC ($\times 10^9$/L) | 8.98 | 14.8 | 15.4 | 13.1 | 3.55 | 7.48 | 13.5 | 19.3 | 13.4 | 5.90 |
| | abs_nouts ($\times 10^9$/L) | 3.44 | 6.07 | 5.05 | 4.85 | 1.33 | 3.20 | 4.94 | 4.64 | 4.26 | 0.93 |
| | abs_lymphs ($\times 10^9$/L) | 4.69 | 7.74 | 9.41 | 7.28 | 2.39 | 3.80 | .46 | 13.62 | 8.29 | 4.96 |
| | abs_monos ($\times 10^9$/L) | 0.76 | 0.76 | 0.75 | 0.76 | 0.01 | 0.41 | 0.99 | 0.96 | 0.79 | 0.33 |
| | abs_cos ($\times 10^9$/L) | 0.09 | 0.20 | 0.22 | 0.17 | 0.07 | 0.07 | 0.08 | 0.05 | 0.07 | 0.02 |
| | abs_basos ($\times 10^9$/L) | 0.00 | 0.00 | 0.00 | 0.00 | 0.00 | 0.00 | 0.00 | 0.00 | 0.00 | 0.00 |
| | %NEUT (%) | 38.3 | 41.1 | 32.7 | 37.4 | 4.28 | 42.8 | 36.7 | 24.1 | 34.5 | 9.54 |
| | %LYM (%) | 52.3 | 52.4 | 61.1 | 55.3 | 5.05 | 50.9 | 55.3 | 70.6 | 58.9 | 10.3 |
| | %MONO (%) | 8.40 | 5.20 | 4.80 | 6.13 | 1.97 | 5.40 | 7.40 | 5.00 | 5.93 | 1.29 |
| | %EOS (%) | 1.00 | 1.30 | 1.40 | 1.23 | 0.21 | 0.90 | 0.60 | 0.30 | 0.60 | 0.30 |
| | %BASO (%) | 0.00 | 0.00 | 0.00 | 0.00 | 0.00 | 0.00 | 0.00 | 0.00 | 0.00 | 0.00 |
| | RBC ($\times 10^{12}$/L) | 5.63 | 5.70 | 5.95 | 5.76 | 0.17 | 5.68 | 5.75 | 5.54 | 5.66 | 0.11 |
| | HGB (g/L) | 142 | 144 | 140 | 142 | 2.00 | 145 | 143 | 141 | 143 | 2.00 |
| | HCT (%) | 47.1 | 46.1 | 45.4 | 46.2 | 0.85 | 47.2 | 45.9 | 44.9 | 46.0 | 1.15 |
| | MCV (fL) | 83.7 | 80.8 | 76.3 | 80.3 | 3.73 | 83.1 | 79.8 | 81.1 | 81.3 | 1.66 |
| | MCH (pg) | 25.2 | 25.2 | 23.5 | 24.6 | 0.98 | 25.5 | 24.8 | 25.4 | 25.2 | 0.38 |
| | MCHC (g/L) | 301 | 312 | 308 | 307 | 5.57 | 307 | 311 | 313 | 310 | 3.06 |
| | RDW-SD (fL) | 36.7 | 43.3 | 38.8 | 39.6 | 3.37 | 41.1 | 37.1 | 36.9 | 38.4 | 2.37 |
| | RDW-CV (%) | 12.1 | 14.7 | 13.9 | 13.6 | 1.33 | 13.6 | 12.7 | 12.6 | 13.0 | 0.55 |
| | PLT ($\times 10^9$/L) | 468 | 258 | 292 | 339 | 113 | 346 | 354 | 343 | 348 | 5.7 |
| | MPV (fL) | 11.0 | 13.5 | 11.0 | 11.8 | 1.44 | 12.0 | 13.1 | 11.5 | 12.2 | 0.82 |
| | PCT (%) | 0.51 | 0.35 | 0.32 | 0.39 | 0.10 | 0.42 | 0.47 | 0.40 | 0.43 | 0.04 |
| | PDW (fL) | 15.1 | 15.6 | 15.4 | 15.4 | 0.25 | 15.6 | 15.7 | 15.4 | 15.6 | 0.15 |

| | Treatment group | G3: ETD01823 | | | | | G4: ETD01826 | | | | |
|---|---|---|---|---|---|---|---|---|---|---|---|
| | Animal No. | 301 | 302 | 303 | | | 401 | 402 | 403 | | |
| | Gender | Male | Male | Male | | | Male | Male | Male | | |
| | Animal ID | 177695C | SC1704077 | 176313C | Mean | SD | SC1708089 | SC1604087 | SC1703023 | Mean | SD |
| Parameters (unit) | WBC ($\times 10^9$/L) | 10.9 | 12.0 | 12.1 | 11.7 | 0.70 | 11.4 | 9.31 | 19.0 | 13.2 | 5.13 |
| | abs_nouts ($\times 10^9$/L) | 1.34 | 2.94 | 3.64 | 2.64 | 1.18 | 3.68 | 1.59 | 7.33 | 4.20 | 2.91 |
| | abs_lymphs ($\times 10^9$/L) | 8.59 | 8.05 | 7.86 | 8.17 | 0.38 | 6.76 | 6.87 | 10.76 | 8.13 | 2.28 |

TABLE 16-continued

Individual and Mean Hematology Results on Pre-dose (Day-2)

| | | | | | | | | | | | |
|---|---|---|---|---|---|---|---|---|---|---|---|
| abs_monos (×10⁹/L) | 0.86 | 0.87 | 0.38 | 0.70 | 0.28 | 0.66 | 0.70 | 0.51 | 0.62 | 0.10 |
| abs_cos (×10⁹/L) | 0.06 | 0.12 | 0.25 | 0.14 | 0.10 | 0.27 | 0.14 | 0.44 | 0.28 | 0.15 |
| abs_basos (×10⁹/L) | 0.00 | 0.00 | 0.00 | 0.00 | 0.00 | 0.00 | 0.01 | 0.00 | 0.00 | 0.01 |
| %NEUT (%) | 12.3 | 24.6 | 30.0 | 22.3 | 9.07 | 32.4 | 17.1 | 38.5 | 29.3 | 11.0 |
| %LYM (%) | 79.2 | 67.2 | 64.8 | 70.4 | 7.71 | 59.4 | 73.8 | 56.5 | 63.2 | 9.27 |
| %MONO (%) | 7.90 | 7.20 | 3.20 | 6.10 | 2.54 | 5.80 | 7.50 | 2.70 | 5.33 | 2.43 |
| %EOS (%) | 0.60 | 1.00 | 2.00 | 1.20 | 0.72 | 2.40 | 1.50 | 2.30 | 2.07 | 0.49 |
| %BASO (%) | 0.00 | 0.00 | 0.00 | 0.00 | 0.00 | 0.00 | 0.10 | 0.00 | 0.03 | 0.06 |
| RBC (×10¹²/L) | 5.41 | 5.86 | 5.34 | 5.54 | 0.28 | 5.69 | 5.76 | 5.19 | 5.55 | 0.31 |
| HGB (g/L) | 132 | 144 | 122 | 133 | 11.0 | 140 | 141 | 126 | 136 | 8.39 |
| HCT (%) | 44.1 | 45.4 | 39.6 | 43.0 | 3.04 | 45.5 | 46.0 | 41.6 | 44.4 | 2.41 |
| MCV (fL) | 81.5 | 77.5 | 74.2 | 77.7 | 3.66 | 80.0 | 79.9 | 80.1 | 80.0 | 0.10 |
| MCH (pg) | 24.5 | 24.5 | 22.9 | 24.0 | 0.92 | 24.6 | 24.5 | 24.2 | 24.4 | 0.21 |
| MCHC (g/L) | 300 | 317 | 309 | 309 | 8.50 | 308 | 306 | 302 | 305 | 3.06 |
| RDW-SD (fL) | 41.5 | 39.1 | 37.7 | 39.4 | 1.92 | 36.7 | 40.2 | 38.9 | 38.6 | 1.77 |
| RDW-CV (%) | 14.0 | 13.9 | 13.9 | 13.5 | 0.06 | 12.6 | 13.9 | 13.4 | 13.3 | 0.66 |
| PLT (×10⁹/L) | 379 | 349 | 237↓ | 322 | 74.8 | 445 | 302 | 393 | 380 | 72.4 |
| MPV (fL) | 11.4 | 11.6 | 15.4 | 12.8 | 2.25 | 11.9 | 15.5 | 11.0 | 12.8 | 2.38 |
| PCT (%) | 0.43 | 0.41 | 0.37 | 0.40 | 0.03 | 0.53 | 0.47 | 0.43 | 0.48 | 0.05 |
| PDW (fL) | 16.0 | 15.1 | 15.9 | 15.7 | 0.49 | 15.7 | 15.5 | 15.9 | 15.7 | 0.20 |

Note:
The ↓ next to the value means the result was slightly lower than that of other animals.

TABLE 17

Individual and Mean Hematology Results on Day 7 post-dose

| Treatment group | | G1: ETD01821 | | | | | G2: ETD01822 | | | | |
|---|---|---|---|---|---|---|---|---|---|---|---|
| | Animal No. | 101 | 102 | 103 | | | 201 | 202 | 203 | | |
| | Gender | Male | Male | Male | | | Male | Male | Male | | |
| | Animal ID | SC1702037 | SC1509029 | 175151C | Mean | SD | SC1508015 | SC1704115 | SC1703011 | Mean | SD |
| Para-meters (unit) | WBC (×10⁹/L) | 8.52 | 13.8 | 11.5 | 11.3 | 2.67 | 8.62 | 12.3 | 17.4 | 12.8 | 4.43 |
| | abs_nouts (×10⁹/L) | 2.00 | 4.12 | 2.54 | 2.89 | 1.10 | 4.27 | 3.44 | 3.85 | 3.85 | 0.42 |
| | abs_lymphs (×10⁹/L) | 5.75 | 8.63 | 8.17 | 7.52 | 1.55 | 3.88 | 8.07 | 12.64 | 8.20 | 4.38 |
| | abs_monos (×10⁹/L) | 0.64 | 0.70 | 0.61 | 0.65 | 0.05 | 0.43 | 0.68 | 0.87 | 0.66 | 0.22 |
| | abs_cos (×10⁹/L) | 0.13 | 0.39 | 0.21 | 0.24 | 0.13 | 0.04 | 0.06 | 0.08 | 0.06 | 0.02 |
| | abs_basos (×10⁹/L) | 0.00 | 0.00 | 0.00 | 0.00 | 0.00 | 0.00 | 0.01 | 0.00 | 0.00 | 0.01 |
| | %NEUT (%) | 23.4 | 29.7 | 22.1 | 25.1 | 4.06 | 49.5 | 28.1 | 22.1 | 33.2 | 14.4 |
| | %LYM (%) | 67.6 | 62.4 | 70.8 | 66.9 | 4.24 | 45.1 | 65.8 | 72.4 | 61.1 | 14.2 |
| | %MONO (%) | 7.50 | 5.10 | 5.30 | 5.97 | 1.33 | 5.00 | 5.50 | 5.00 | 5.17 | 0.29 |
| | %EOS (%) | 1.50 | 2.80 | 1.80 | 2.03 | 0.68 | 0.40 | 0.50 | 0.50 | 0.47 | 0.06 |
| | %BASO (%) | 0.00 | 0.00 | 0.00 | 0.00 | 0.00 | 0.00 | 0.10 | 0.00 | 0.03 | 0.06 |
| | RBC (×10¹²/L) | 5.49 | 5.70 | 6.24 | 5.81 | 0.39 | 5.75 | 6.04 | 5.54 | 5.78 | 0.25 |
| | HGB (g/L) | 141 | 146 | 146 | 144 | 2.89 | 146 | 149 | 140 | 145 | 4.58 |
| | HCT (%) | 46.2 | 46.5 | 47.7 | 46.8 | 0.79 | 47.2 | 49.0 | 45.0 | 47.1 | 2.00 |
| | MCV (fL) | 84.0 | 81.5 | 76.4 | 80.6 | 3.87 | 82.2 | 81.1 | 81.3 | 81.5 | 0.59 |
| | MCH (pg) | 25.6 | 25.7 | 23.5 | 24.9 | 1.24 | 25.4 | 24.6 | 25.3 | 25.1 | 0.44 |
| | MCHC (g/L) | 305 | 315 | 307 | 309 | 5.29 | 309 | 303 | 311 | 308 | 4.16 |
| | RDW-SD (fL) | 37.8 | 44.4 | 39.3 | 40.5 | 3.46 | 40.4 | 38.4 | 38.3 | 39.0 | 1.18 |
| | RDW-CV (%) | 12.3 | 15.0 | 14.1 | 13.8 | 1.37 | 13.5 | 13.1 | 13.0 | 13.2 | 0.26 |
| | PLT (×10⁹/L) | 527 | 390 | 253↓ | 390 | 137 | 371 | 283 | 341 | 332 | 44.7 |
| | MPV (fL) | 12.6 | 13.7 | 11.8 | 12.7 | 0.95 | 12.1 | 15.3 | 11.7 | 13.0 | 1.97 |
| | PCT (%) | 0.67 | 0.54 | 0.30 | 0.50 | 0.19 | 0.45 | 0.43 | 0.40 | 0.43 | 0.02 |
| | PDW (fL) | 15.4 | 15.3 | 15.8 | 15.5 | 0.26 | 15.3 | 15.4 | 15.4 | 15.4 | 0.06 |
| Treatment group | | G3: ETD01823 | | | | | G4: ETD01826 | | | | |
| | Animal No. | 301 | 302 | 303 | | | 401 | 402 | 403 | | |
| | Gender | Male | Male | Male | | | Male | Male | Male | | |
| | Animal ID | 177695C | SC1704077 | 176313C | Mean | SD | SC1708089 | SC1604087 | SC1703023 | Mean | SD |
| Para-meters (unit) | WBC (×10⁹/L) | 9.86 | 14.2 | 9.42 | 11.2 | 2.63 | 10.8 | 8.50 | 16.7 | 12.0 | 4.22 |
| | abs_nouts (×10⁹/L) | 1.06 | 3.85 | 2.05 | 2.32 | 1.41 | 4.77 | 1.67 | 5.55 | 4.00 | 2.05 |
| | abs_lymphs (×10⁹/L) | 7.99 | 9.18 | 6.90 | 8.02 | 1.14 | 5.25 | 6.17 | 10.3 | 7.23 | 2.68 |
| | abs_monos (×10⁹/L) | 0.73 | 1.04 | 0.29 | 0.69 | 0.38 | 0.61 | 0.52 | 0.51 | 0.55 | 0.06 |
| | abs_cos (×10⁹/L) | 0.08 | 0.11 | 0.18 | 0.12 | 0.05 | 0.21 | 0.14 | 0.35 | 0.23 | 0.11 |
| | abs_basos (×10⁹/L) | 0.00 | 0.00 | 0.00 | 0.00 | 0.00 | 0.00 | 0.00 | 0.00 | 0.00 | 0.00 |
| | %NEUT (%) | 10.8 | 27.1 | 21.7 | 19.9 | 8.30 | 44.0 | 19.6 | 33.3 | 32.3 | 12.2 |
| | %LYM (%) | 81.0 | 64.8 | 73.3 | 73.0 | 8.10 | 48.4 | 72.7 | 61.6 | 60.9 | 12.2 |
| | %MONO (%) | 7.40 | 7.30 | 3.10 | 5.93 | 2.45 | 5.60 | 6.10 | 3.00 | 4.90 | 1.66 |
| | %EOS (%) | 0.80 | 0.80 | 1.90 | 1.17 | 0.64 | 2.00 | 1.60 | 2.10 | 1.90 | 0.26 |
| | %BASO (%) | 0.00 | 0.00 | 0.00 | 0.00 | 0.00 | 0.00 | 0.00 | 0.00 | 0.00 | 0.00 |
| | RBC (×10¹²/L) | 5.74 | 5.42 | 5.58 | 5.58 | 0.16 | 5.59 | 6.15 | 5.62 | 5.79 | 0.32 |

TABLE 17-continued

Individual and Mean Hematology Results on Day 7 post-dose

| | | | | | | | | | | |
|---|---|---|---|---|---|---|---|---|---|---|
| HGB (g/L) | 143 | 133 | 130 | 135 | 6.81 | 141 | 151 | 136 | 143 | 7.64 |
| HCT (%) | 16.9 | 42.1 | 41.0 | 43.3 | 3.14 | 45.0 | 49.2 | 45.0 | 46.4 | 2.42 |
| MCV (fL) | 81.8 | 77.7 | 73.5 | 77.7 | 4.15 | 80.6 | 80.1 | 80.0 | 80.2 | 0.32 |
| MCH (pg) | 24.9 | 24.5 | 23.3 | 24.2 | 0.83 | 25.3 | 24.6 | 24.2 | 24.7 | 0.56 |
| MCHC (g/L) | 304 | 315 | 317 | 312 | 7.00 | 314 | 307 | 303 | 308 | 5.57 |
| RDW-SD (fL) | 42.9 | 39.3 | 36.4 | 39.5 | 3.26 | 37.9 | 41.3 | 39.3 | 39.5 | 1.71 |
| RDW-CV (%) | 14.4 | 13.9 | 13.6 | 14.0 | 0.40 | 12.5 | 14.2 | 13.5 | 13.5 | 0.65 |
| PLT ($\times 10^9$/L) | 441 | 317 | 256↓ | 338 | 94.3 | 478 | 258↓ | 369 | 368 | 110 |
| MPV (fL) | 10.7 | 12.5 | 15.0 | 12.7 | 2.16 | 12.2 | 15.6 | 11.5 | 13.1 | 2.19 |
| PCT (%) | 0.47 | 0.40 | 0.39 | 0.42 | 0.05 | 0.59 | 0.40 | 0.42 | 0.47 | 0.10 |
| PDW (fL) | 15.6 | 15.3 | 15.9 | 15.6 | 0.30 | 15.3 | 15.3 | 15.8 | 15.5 | 0.29 |

Note:
The ↓ next to the value means the result was slightly lower than that of other animals.

Individual and Mean Hematology Results on Day 14 post-dose

| | | Treatment group | G1: ETD01821 | | | | | G2: ETD01822 | | | | |
|---|---|---|---|---|---|---|---|---|---|---|---|---|
| | | Animal No. | 101 | 102 | 103 | | | 201 | 202 | 203 | | |
| | | Gender | Male | Male | Male | | | Male | Male | Male | | |
| | | Animal ID | SC1702037 | SC1509029 | 175151C | Mean | SD | SC1508015 | SC1704115 | SC1703011 | Mean | SD |
| Parameters | WBC ($\times 10^9$/L) | | 9.93 | 10.4 | 20.7 | 13.7 | 6.08 | 12.0 | 12.1 | 17.9 | 14.0 | 3.39 |
| (unit) | abs_nouts ($\times 10^9$/L) | | 1.82 | 3.09 | 13.5↑ | 6.13 | 6.40 | 7.15 | 2.75 | 3.78 | 4.56 | 2.30 |
| | abs_lymphs ($\times 10^9$/L) | | 7.15 | 6.21 | 5.59 | 6.32 | 0.79 | 4.26 | 8.44 | 12.97 | 8.56 | 4.36 |
| | abs_monos ($\times 10^9$/L) | | 0.81 | 0.73 | 1.53 | 1.02 | 0.44 | 0.55 | 0.86 | 1.06 | 0.82 | 0.26 |
| | abs_cos ($\times 10^9$/L) | | 0.14 | 0.35 | 0.07 | 0.19 | 0.15 | 0.04 | 0.05 | 0.11 | 0.07 | 0.04 |
| | abs_basos ($\times 10^9$/L) | | 0.01 | 0.00 | 0.00 | 0.00 | 0.01 | 0.01 | 0.00 | 0.00 | 0.00 | 0.01 |
| | %NEUT (%) | | 18.3 | 29.8 | 65.2↑ | 37.8 | 24.4 | 59.6 | 22.7 | 21.1 | 34.5 | 21.8 |
| | %LYM (%) | | 72.1 | 59.7 | 27.1 | 53.0 | 23.2 | 35.5 | 69.8 | 72.4 | 59.2 | 20.6 |
| | %MONO (%) | | 8.10 | 7.10 | 7.40 | 7.53 | 0.51 | 4.60 | 7.10 | 5.90 | 5.87 | 1.25 |
| | %EOS (%) | | 1.40 | 3.40 | 0.30 | 1.70 | 1.57 | 0.30 | 0.40 | 0.60 | 0.43 | 0.15 |
| | %BASO (%) | | 0.10 | 0.00 | 0.00 | 0.03 | 0.06 | 0.00 | 0.00 | 0.00 | 0.00 | 0.00 |
| | RBC ($\times 10^{12}$/L) | | 5.99 | 5.33 | 6.52 | 5.95 | 0.60 | 5.84 | 6.02 | 5.39 | 5.75 | 0.32 |
| | HGB (g/L) | | 152 | 140 | 157 | 150 | 8.74 | 151 | 151 | 138 | 147 | 7.51 |
| | HCT (%) | | 50.1 | 44.1 | 49.3 | 47.8 | 3.26 | 49.3 | 48.5 | 44.3 | 47.4 | 2.69 |
| | MCV (fL) | | 83.7 | 82.7 | 75.7 | 80.7 | 4.36 | 84.5 | 80.6 | 82.2 | 82.4 | 1.96 |
| | MCH (pg) | | 25.4 | 26.3 | 24.1 | 25.3 | 1.11 | 25.9 | 25.0 | 25.7 | 25.5 | 0.47 |
| | MCHC (g/L) | | 304 | 318 | 318 | 313 | 8.08 | 307 | 311 | 312 | 310 | 2.65 |
| | RDW-SD (fL) | | 37.0 | 44.1 | 38.1 | 39.7 | 3.82 | 41.5 | 37.8 | 39.1 | 39.5 | 1.88 |
| | RDW-CV (%) | | 12.2 | 14.6 | 13.9 | 13.6 | 1.23 | 13.5 | 12.9 | 13.2 | 13.2 | 0.30 |
| | PLT ($\times 10^9$/L) | | 570 | 311 | 192↓ | 358 | 193 | 279 | 240 | 322 | 280 | 41.0 |
| | MPV (fL) | | 12.3 | 13.8 | 11.80 | 12.6 | 1.04 | 12.8 | 15.0 | 11.80 | 13.2 | 1.64 |
| | PCT (%) | | 0.70 | 0.43 | 0.23↓ | 0.45 | 0.24 | 0.36 | 0.36 | 0.38 | 0.37 | 0.01 |
| | PDW (fL) | | 14.9 | 15.5 | 15.9 | 15.4 | 0.50 | 15.8 | 15.7 | 15.6 | 15.7 | 0.10 |
| | | Treatment group | G3: ETD01823 | | | | | G4: ETD01826 | | | | |
| | | Animal No. | 301 | 302 | 303 | | | 401 | 402 | 403 | | |
| | | Gender | Male | Male | Male | | | Male | Male | Male | | |
| | | Animal ID | 177695C | SC1704077 | 176313C | Mean | SD | SC1708089 | SC1604087 | SC1703023 | Mean | SD |
| Parameters | WBC ($\times 10^9$/L) | | 9.24 | 12.1 | 10.0 | 10.4 | 1.45 | 10.3 | 7.73 | 16.9 | 11.7 | 4.74 |
| (unit) | abs_nouts ($\times 10^9$/L) | | 0.54↓ | 2.62 | 3.13 | 2.10 | 1.37 | 4.47 | 1.34 | 5.81 | 3.87 | 2.29 |
| | abs_lymphs ($\times 10^9$/L) | | 7.95 | 8.52 | 6.34 | 7.60 | 1.13 | 5.08 | 5.65 | 10.25 | 6.99 | 2.83 |
| | abs_monos ($\times 10^9$/L) | | 0.67 | 0.85 | 0.30 | 0.61 | 0.28 | 0.59 | 0.57 | 0.46 | 0.54 | 0.07 |
| | abs_cos ($\times 10^9$/L) | | 0.08 | 0.07 | 0.26 | 0.14 | 0.11 | 0.19 | 0.17 | 0.39 | 0.25 | 0.12 |
| | abs_basos ($\times 10^9$/L) | | 0.00 | 0.00 | 0.00 | 0.00 | 0.00 | 0.00 | 0.00 | 0.01 | 0.00 | 0.01 |
| | %NEUT (%) | | 5.90↓ | 21.7 | 31.3 | 19.6 | 12.8 | 43.3 | 17.4 | 34.4 | 31.7 | 13.2 |
| | %LYM (%) | | 86.0 | 70.6 | 63.1 | 73.2 | 11.7 | 49.2 | 73.0 | 60.6 | 60.9 | 11.9 |
| | %MONO (%) | | 7.30 | 7.10 | 3.00 | 5.80 | 2.43 | 5.70 | 7.40 | 2.70 | 5.27 | 2.38 |
| | %EOS (%) | | 0.80 | 0.60 | 2.60 | 1.33 | 1.10 | 1.80 | 2.20 | 2.30 | 2.10 | 0.26 |
| | %BASO (%) | | 0.00 | 0.00 | 0.00 | 0.00 | 0.00 | 0.00 | 0.00 | 0.00 | 0.00 | 0.00 |
| | RBC ($\times 10^{12}$/L) | | 5.59 | 5.58 | 5.52 | 5.56 | 0.04 | 5.25 | 5.59 | 5.68 | 5.51 | 0.23 |
| | HGB (g/L) | | 141 | 138 | 128 | 136 | 5.81 | 131 | 139 | 141 | 137 | 5.29 |
| | HCT (%) | | 45.7 | 43.9 | 40.7 | 43.4 | 2.53 | 42.4 | 45.1 | 45.5 | 44.3 | 1.69 |
| | MCV (fL) | | 81.7 | 78.8 | 73.8 | 78.1 | 4.00 | 80.8 | 80.7 | 80.1 | 80.5 | 0.38 |
| | MCH (pg) | | 25.2 | 24.8 | 23.1 | 24.4 | 1.12 | 24.9 | 25.0 | 24.8 | 24.9 | 0.10 |
| | MCHC (g/L) | | 308 | 314 | 313 | 312 | 3.21 | 309 | 309 | 310 | 309 | 0.58 |
| | RDW-SD (fL) | | 42.6 | 40.6 | 36.6 | 39.9 | 3.06 | 37. | 41.6 | 38.4 | 39.0 | 2.32 |
| | RDW-CV (%) | | 14.2 | 14.3 | 13.6 | 14.0 | 0.38 | 12.6 | 14.2 | 13.2 | 13.3 | 0.81 |
| | PLT ($\times 10^9$/L) | | 376 | 278 | 218↓ | 291 | 79.8 | 380 | 250↓ | 460 | 363 | 106 |

-continued

| | Individual and Mean Hematology Results on Day 14 post-dose | | | | | | | | | |
|---|---|---|---|---|---|---|---|---|---|---|
| MPV (fL) | 10.2 | 12.6 | 16.1 | 13.0 | 2.97 | 11.9 | 15.1 | 10.2 | 12.4 | 2.49 |
| PCT (%) | 0.38 | 0.35 | 0.35 | 0.36 | 0.02 | 0.45 | 0.38 | 0.47 | 0.43 | 0.05 |
| PDW (fL) | 15.5 | 15.5 | 15.7 | 15.6 | 0.12 | 15.7 | 15.5 | 15.5 | 15.6 | 0.12 |

Note:
The ↓ next to the value means the result was slightly lower than that of other animals.

TABLE 19

Individual and Mean Hematology Results on Day 28 post-dose

| | Treatment group | G1: ETD01821 | | | | | G2: ETD01822 | | | | |
|---|---|---|---|---|---|---|---|---|---|---|---|
| | Animal No. | 101 | 102 | 103 | | | 201 | 202 | 203 | | |
| | Gender | Male | Male | Male | | | Male | Male | Male | | |
| | Animal ID | SC1702037 | SC1509029 | 175151C | Mean | SD | SC1508015 | SC1704115 | SC1703011 | Mean | SD |
| Para-<br>meters<br>(unit) | WBC (×10⁹/L) | 5.30↓ | 8.44 | 9.93 | 7.89 | 2.36 | 12.4 | 12.6 | 11.7 | 12.2 | 0.47 |
| | abs_nouts (×10⁹/L) | 1.75 | 3.52 | 4.22 | 3.16 | 1.27 | 8.91 | 7.55 | 4.53 | 7.00 | 2.24 |
| | abs_lymphs (×10⁹/L) | 3.20 | 4.41 | 5.27 | 4.29 | 1.04 | 2.78 | 4.40 | 6.49 | 4.56 | 1.86 |
| | abs_monos (×10⁹/L) | 0.32 | 0.39 | 0.28 | 0.33 | 0.06 | 0.67 | 0.62 | 0.66 | 0.65 | 0.03 |
| | abs_cos (×10⁹/L) | 0.03 | 0.12 | 0.16 | 0.10 | 0.07 | 0.02 | 0.02 | 0.01 | 0.02 | 0.01 |
| | abs_basos (×10⁹/L) | 0.00 | 0.00 | 0.00 | 0.00 | 0.00 | 0.00 | 0.00 | 0.00 | 0.00 | 0.00 |
| | %NEUT (%) | 33.1 | 41.7 | 42.5 | 39.1 | 5.21 | 72.0 | 59.9 | 38.8 | 56.9 | 16.8 |
| | %LYM (%) | 60.3 | 52.3 | 53.1 | 55.2 | 1.41 | 22.5 | 34.9 | 55.4 | 37.6 | 16.6 |
| | %MONO (%) | 6.00 | 4.60 | 2.80 | 4.47 | 1.60 | 5.40 | 5.00 | 5.70 | 5.37 | 0.35 |
| | %EOS (%) | 0.60 | 1.40 | 1.60 | 1.20 | 0.53 | 0.10 | 0.20 | 0.10 | 0.13 | 0.06 |
| | %BASO (%) | 0.00 | 0.00 | 0.00 | 0.00 | 0.00 | 0.00 | 0.00 | 0.00 | 0.00 | 0.00 |
| | RBC (×10¹²/L) | 5.15 | 5.19 | 5.09 | 5.14 | 0.05 | 5.90 | 5.61 | 5.46 | 5.66 | 0.22 |
| | HGB (g/L) | 131 | 136 | 121 | 129 | 7.64 | 154 | 140 | 142 | 145 | 7.57 |
| | HCT (%) | 42.6 | 43.6 | 38.5 | 41.6 | 2.70 | 49.6 | 44.8 | 44.7 | 46.4 | 2.80 |
| | MCV (fL) | 82.8 | 84.0 | 75.7 | 80.8 | 4.49 | 84.1 | 79.8 | 82.0 | 82.0 | 2.15 |
| | MCH (pg) | 25.4 | 26.2 | 23.7 | 25.1 | 1.28 | 26.1 | 25.0 | 26.1 | 25.7 | 0.64 |
| | MCHC (g/L) | 307 | 312 | 313 | 311 | 3.21 | 311 | 313 | 318 | 314 | 3.61 |
| | RDW-SD (fL) | 36.4 | 41.3 | 37.2 | 38.3 | 2.63 | 41.0 | 37.4 | 39.7 | 39.4 | 1.82 |
| | RDW-CV (%) | 12.1 | 13.5 | 13.5 | 13.0 | 0.81 | 13.4 | 12.9 | 13.3 | 13.2 | 0.26 |
| | PLT (×10⁹/L) | 480 | 368 | 329 | 392 | 78.4 | 399 | 355 | 346 | 367 | 28.4 |
| | MPV (fL) | 11.2 | 14.2 | 10.4 | 11.9 | 2.00 | 11.6 | 14.0 | 11.5 | 12.4 | 1.42 |
| | PCT (%) | 0.54 | 0.53 | 0.34 | 0.47 | 0.11 | 0.46 | 0.50 | 0.40 | 0.45 | 0.05 |
| | PDW (fL) | 14.9 | 15.3 | 15.2 | 15.1 | 0.21 | 15.5 | 15.6 | 15.4 | 15.5 | 0.10 |
| | Treatment group | G3: ETD01823 | | | | | G4: ETD01826 | | | | |
| | Animal No. | 301 | 302 | 303 | | | 401 | 402 | 403 | | |
| | Gender | Male | Male | Male | | | Male | Male | Male | | |
| | Animal ID | 177695C | SC1704077 | 176313C | Mean | SD | SC1708089 | SC1604087 | SC1703023 | Mean | SD |
| Para-<br>meters<br>(unit) | WBC (×10⁹/L) | 6.49↓ | 12.5 | 14.2 | 11.1 | 4.05 | 6.51↓ | 7.22 | 12.7 | 8.79 | 3.36 |
| | abs_nouts (×10⁹/L) | 3.84 | 4.42 | 4.13 | 4.13 | 0.29 | 3.62 | 4.15 | 6.51 | 4.76 | 1.54 |
| | abs_lymphs (×10⁹/L) | 2.27↓ | 7.35 | 9.37 | 6.33 | 3.66 | 2.53↓ | 2.62↓ | 5.64 | 3.60 | 1.77 |
| | abs_monos (×10⁹/L) | 0.36 | 0.65 | 0.69 | 0.57 | 0.18 | 0.30 | 0.37 | 0.34 | 0.34 | 0.04 |
| | abs_cos (×10⁹/L) | 0.02 | 1.05 | 0.03 | 0.03 | 0.02 | 0.06 | 0.08 | 0.15 | 0.10 | 0.05 |
| | abs_basos (×10⁹/L) | 0.00 | 0.00 | 0.00 | 0.00 | 0.00 | 0.00 | 0.00 | 2.01 | 0.00 | 0.01 |
| | %NEUT (%) | 59.2 | 35.5 | 29.0 | 41.2 | 15.9 | 55.6 | 57.5 | 51.5 | 54.9 | 3.07 |
| | %LYM (%) | 35.0 | 58.9 | 65.9 | 53.3 | 16.2 | 38.9 | 36.2 | 44.5 | 39.9 | 4.23 |
| | %MONO (%) | 5.50 | 5.20 | 4.90 | 5.20 | 0.30 | 4.60 | 5.10 | 2.70 | 4.13 | 1.27 |
| | %EOS (%) | 0.30 | 0.40 | 0.20 | 0.30 | 0.10 | 0.90 | 1.20 | 1.20 | 1.10 | 0.17 |
| | %BASO (%) | 0.00 | 0.00 | 0.00 | 0.00 | 0.00 | 0.00 | 0.00 | 0.10 | 0.03 | 0.06 |
| | RBC (×10¹²/L) | 5.02 | 5.78 | 4.91 | 5.24 | 0.47 | 5.12 | 5.05 | 5.07 | 5.08 | 0.04 |
| | HGB (g/L) | 132 | 143 | 126 | 134 | 8.62 | 128 | 126 | 124 | 126 | 2.00 |
| | HCT (%) | 42.1 | 45.2 | 40.4 | 42.6 | 2.43 | 41.1 | 40.5 | 40.6 | 40.7 | 0.32 |
| | MCV (fL) | 83.8 | 78.2 | 82.4 | 81.5 | 2.91 | 80.3 | 80.2 | 80.0 | 80.2 | 0.15 |
| | MCH (pg) | 26.3 | 24.8 | 25.6 | 25.6 | 0.75 | 25.1 | 25.0 | 24.5 | 24.9 | 0.32 |
| | MCHC (g/L) | 314 | 316 | 311 | 314 | 2.52 | 312 | 312 | 306 | 310 | 3.46 |
| | RDW-SD (fL) | 40.5 | 39.1 | 39.9 | 39.8 | 0.70 | 36.0 | 41.3 | 39.5 | 38.9 | 2.70 |
| | RDW-CV (%) | 13.3 | 13.8 | 13.4 | 13.5 | 0.26 | 12.2 | 14.1 | 13.6 | 13.3 | 0.98 |
| | PLT (×10⁹/L) | 355 | 384 | 307 | 349 | 38.9 | 402 | 162↓ | 399 | 321 | 137.7 |
| | MPV (fL) | 12.4 | 11.8 | 11.9 | 12.0 | 0.32 | 11.8 | 15.3 | 9.40 | 12.2 | 2.97 |
| | PCT (%) | 0.44 | 0.45 | 0.37 | 0.42 | 0.05 | 0.48 | 0.25 | 0.38 | 0.37 | 0.11 |
| | PDW (fL) | 15.4 | 15.1 | 15.2 | 15.2 | 0.15 | 15.5 | 15.8 | 15.5 | 15.6 | 0.17 |

Note:
The ↓ next to the value means the result was slightly lower than that of other animals.

TABLE 20

Relative Mean Serum MSP Level in Cynomolgus Monkeys

| | | | Dose | \-8 | \-2 | 7 | 14 | 28 | 42 | 56 | 70 | 77 | 84 | 91 | 98 | 105 |
|---|---|---|---|---|---|---|---|---|---|---|---|---|---|---|---|---|
| Group | n | Treatment | (mg/kg) | \multicolumn{13}{c}{Mean Serum MSP Level (Relative to mean of pre-dose level (Day −2 and Day −8))} | | | | | | | | | | | | |
| 1 | 3 | ETD01821 | 5 | 1.09 | 0.91 | 0.22 | 0.06 | 0.04 | 0.07 | 0.15 | 0.18 | 0.18 | 0.31 | 0.42 | 0.45 | 0.46 |
| 2 | 3 | ETD01822 | 5 | 0.99 | 1.01 | 0.71 | 0.32 | 0.42 | 0.37 | 0.76 | 1.24 | 1.16 | 1.48 | 1.34 | 1.34 | 1.57 |
| 3 | 3 | ETD01823 | 5 | 1.01 | 0.99 | 0.44 | 0.08 | 0.34 | 0.10 | 0.20 | 0.45 | 0.39 | 0.52 | 0.59 | 0.91 | 1.03 |
| 4 | 3 | ETD01826 | 5 | 0.78 | 1.22 | 0.37 | 0.20 | 0.30 | 0.58 | 0.88 | 1.01 | 1.63 | 1.32 | 1.86 | 1.98 | 1.95 |

TABLE 21

Relative Individual Serum MSP Level in Cynomolgus Monkeys

| Group | n | Treatment | Dose (mg/kg) | Animal # | \-8 | \-2 | 7 | 14 | 28 | 42 | 56 | 70 | 1 77 | 84 | 91 | 98 | 105 |
|---|---|---|---|---|---|---|---|---|---|---|---|---|---|---|---|---|---|
| 1 | 3 | ETD01821 | 5 | 101M | 0.99 | 1.01 | 0.28 | 0.08 | 0.07 | 0.11 | 0.23 | | | | | | |
| | | | | 102M | 1.12 | 0.88 | 0.18 | 0.07 | 0.04 | 0.01 | 0.16 | 0.26 | 0.21 | 0.31 | 0.47 | 0.51 | 0.39 |
| | | | | 103M | 1.16 | 0.84 | 0.19 | 0.02 | 0.01 | 0.08 | 0.07 | 0.09 | 0.15 | 0.31 | 0.37 | 0.38 | 0.52 |
| 2 | 3 | ETD01822 | 5 | 201M | 0.99 | 1.01 | 0.64 | 0.43 | 0.75 | 0.59 | 0.90 | 1.26 | 0.95 | 1.56 | 1.69 | 1.75 | 1.49 |
| | | | | 202M | 0.99 | 1.01 | 0.75 | 0.30 | 0.23 | 0.29 | 0.86 | 1.39 | 1.58 | 0.96 | 1.23 | 1.14 | 1.82 |
| | | | | 203M | 1.00 | 1.00 | 0.74 | 0.24 | 0.28 | 0.23 | 0.53 | 1.07 | 0.96 | 1.92 | 1.10 | 1.13 | 1.39 |
| 3 | 3 | ETD01823 | 5 | 301M | 0.76 | 1.24 | 0.24 | 0.05 | 0.50 | 0.06 | 0.15 | 0.19 | 0.18 | 0.36 | 0.30 | 0.41 | 0.56 |
| | | | | 302M | 1.18 | 0.82 | 0.46 | 0.09 | 0.31 | 0.15 | 0.26 | 0.71 | 0.57 | 0.84 | 0.83 | 1.44 | 1.40 |
| | | | | 303M | 1.09 | 0.91 | 0.61 | 0.11 | 0.22 | 0.10 | 0.20 | 0.43 | 0.42 | 0.37 | 0.65 | 0.89 | 1.14 |
| 4 | 3 | ETD01826 | 5 | 401M | 0.95 | 1.05 | 0.26 | 0.16 | 0.25 | 0.43 | 0.91 | 0.91 | 1.32 | 1.51 | 1.51 | 2.25 | 2.16 |
| | | | | 402M | 0.91 | 1.09 | 0.35 | 0.07 | 0.15 | 0.15 | 0.41 | 0.77 | 1.55 | 0.89 | 1.23 | 1.81 | 1.54 |
| | | | | 403M | 0.49 | 1.51 | 0.51 | 0.36 | 0.49 | 1.16 | 1.31 | 1.35 | 2.02 | 1.56 | 2.84 | 1.87 | 2.15 |

TABLE 22

Relative MST1 mRNA Level in Liver of Cynomolgus Monkeys

| Group | n | Treatment | Dose (mg/kg) | Mean MST1 mRNA (Relative to Day −8) | |
|---|---|---|---|---|---|
| | | | | Day −8 | Day 28 |
| 1 | 3 | ETD01821 | 5 | 1.00 | 0.33 |
| 2 | 3 | ETD01822 | 5 | 1.00 | 0.33 |
| 3 | 3 | ETD01823 | 5 | 1.00 | 0.27 |
| 4 | 3 | ETD01826 | 5 | 1.00 | 0.57 |

Example 19: Screening siRNAs Targeting Human and Mouse MTRES1 in Mice

The following example demonstrates the usefulness of GalNAc moieties described herein in vho when combined oligonucleotides targeting an additional target (MTRES1). Several siRNAs designed to be cross-reactive with human, mouse and cynomolgus monkey MTRES1 mRNA were tested for activity in mice. The siRNAs were attached to the GalNAc ligand ETL1 or ETL17. The siRNA sequences are shown in Table 23, where Nf is a 2' fluoro-modified nucleoside, n is a 2' O-methyl modified nucleoside, "d" is a deoxynucleoside, and "s" is a phosphorothioate linkage.

Six to eight week old female mice (strain ICR, n-3) were given a subcutaneous injection on Day 0 of a single 200 ug dose of a GalNAc-conjugated siRNA or PBS as vehicle control.

Mice were euthanized on Day 10 after injection and a liver sample from each was collected and placed in RNAlater (ThermoFisher Catalog AM7020) until processing. Total liver RNA was prepared by homogenizing the liver tissue in homogenization buffer (Maxwell RSC simplyRNA Tissue Kit) using a Percellys 24 tissue homogenizer (Bertin Instruments) set at 5000 rpm for two 10 second cycles. Total RNA from the lysate was purified on a Maxwell RSC 48 platform (Promega Corporation) according to the manufacturer's recommendations. Preparation of cDNA was performed using Quanta qScript cDNA SuperMix (VWR, Catalog #95048-500) according to the manufacturer's instructions. The relative levels of liver MIRES/mRNA were assessed by RT-qPCR in triplicate on a QuantStudio™ 6 Pro Real-Time PCR System using TaqMan assays for mouse MTRES1 (ThermoFisher, assay #Mm01229834 Jul) and the mouse housekeeping gene PPIA (ThermoFisher, assay#Mm02342430_g1) and PerfeCTa® qPCR FastMix®, Low ROX™ (VWR, Catalog #101419-222). Data were normalized to the mean MIRE: SI mRNA level in animals receiving PBS. Results are shown in Table 24. Mice injected with ETD01597, ETD01955, ETD01958, and had substantially lower levels in mean liver MTRES1 mRNA on Day 10 relative to mice receiving PBS.

TABLE 23

Example siRNA Sequences

| SIRNA Name | SEQ ID NO: | Sense Strand Sequence (5'-3') with GalNAc moiety | SEQ ID NO: | Antisense Strand Sequence (5'-3') |
|---|---|---|---|---|
| ETD01597 | 23 | [ETL1]sguaucuccAfgAfauguuauasusu | 33 | usAfsuAfaCfaUfuCfuGfgAfgAfuAfcsusu |
| ETD01954 | 24 | [ETL17]sacuuccuGfGfAfAfucgauacasusu | 34 | usGfsuAfsuCfgAfuUfcCfaGfgAfaGfususu |
| ETD01955 | 25 | [ETL17]scuuccuGfGfAfAfucgauacuasusu | 35 | usAfsgUfaUfcGfaUfuCfcAfgGfaAfgsusu |
| ETD01956 | 26 | [ETL17]scuggAfAfucGfAfuacuuguaasusu | 36 | usUfsaCfaAfgUfaUfcGfaUfuCfcAfgsusu |
| ETD01957 | 27 | [ETL17]sggaaUfCfgaUfaCfuuguauuasusu | 37 | usAfsaUfaCfaAfgUfaUfcGfaUfuCfcsusu |
| ETD01958 | 28 | [ETL17]sgaugCfUfuUfCfuacaaagguasusu | 38 | usAfscCfuUfuGfuAfgAfaAfgCfaUfcsusu |
| ETD01959 | 29 | [ETL17]sagaaAfAfgcAfGfaacggugaasusu | 39 | usUfscAfcCfgUfuCfuGfcUfuUfuCfususu |
| ETD01960 | 30 | [ETL17]saagcagAfAfdCGfgugaaaguasusu | 40 | usAfscUfuUfcAfcCfgUfuCfuGfcUfususu |
| ETD01961 | 31 | [ETL17]sagugGfGfaGfAfuAfcauuggaasusu | 41 | usUfscCfaAfuGfuAfuCfuCfcCfaCfususu |
| ETD01962 | 32 | [ETL17]sugggAfGfauAfcAfu | 42 | usGfsaUfcCfaAfuGfuAfuCfuCfcCfasusu |

TABLE 24

Relative MTRES1 mRNA Levels in Livers of Mice

| Group | n | Treatment | Dose (ug) | Mean MTRES1 mRNA (Normalized to Group 1, Day 10) |
|---|---|---|---|---|
| 1 | 3 | PBS | | 1.00 |
| 2 | 3 | ETD01597 | 200 | 0.13 |
| 3 | 3 | ETD01954 | 200 | 1.03 |
| 4 | 3 | ETD01955 | 200 | 0.16 |
| 5 | 3 | ETD01956 | 200 | 0.62 |
| 6 | 3 | ETD01957 | 200 | 0.31 |
| 7 | 3 | ETD01958 | 200 | 0.18 |
| 8 | 3 | ETD01959 | 200 | 0.53 |
| 9 | 3 | ETD01960 | 200 | 0.69 |
| 10 | 3 | ETD01961 | 200 | 0.33 |
| 11 | 3 | ETD01962 | 200 | 0.79 |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound represented by Formula (I) or (II):

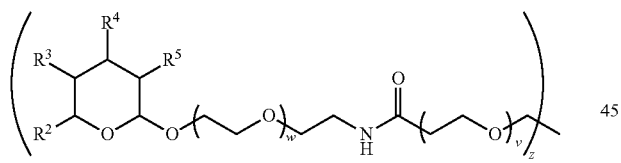

(I)

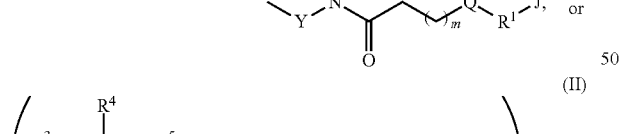

(II)

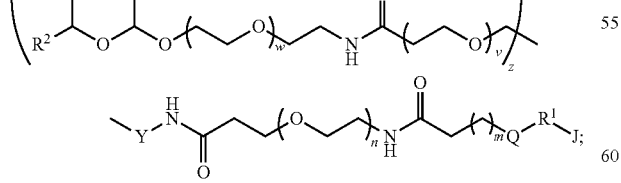

or a salt thereof, wherein

J is an oligonucleotide;

each w is independently selected from any value from 1 to 20;

each v is independently selected from any value from 1 to 20;

n is selected from any value from 1 to 20;

m is selected from any value from 1 to 20;

z is selected from any value from 1 to 3, wherein
   if z is 3, Y is C
   if z is 2, Y is $CR^6$, or
   if z is 1, Y is $C(R^6)_2$;

Q is selected from:
   $C_{3-10}$ carbocycle optionally substituted with one or more substituents independently selected from halogen, —CN, —$NO_2$, —$OR^7$, —$N(R^7)_2$, —$C(O)R^7$, —$C(O)N(R^7)_2$, —$N(R^7)C(O)R^7$, —$N(R^7)C(O)N(R^7)_2$, —$OC(O)N(R^7)_2$, —$N(R^7)C(O)OR^7$, —$C(O)OR^7$, —$OC(O)R^7$, —$S(O)R^7$, and $C_{1-6}$ alkyl, wherein the $C_{1-6}$ alkyl, is optionally substituted with one or more substituents independently selected from halogen, —CN, —OH, —SH, —$NO_2$, and —$NH_2$;

$R^1$ is a linker selected from:
   —O—, —S—, —$N(R^7)$—, —C(O)—, —C(O)N($R^7$)—, —$N(R^7)C(O)$—, —$N(R^7)C(O)N(R^7)$—, —$OC(O)N(R^7)$—, —$N(R^7)C(O)O$—, —C(O)O—, —OC(O)—, —S(O)—, —$S(O)_2$—, —$OS(O)_2$—, —OP(O)($OR^7$)O—, —SP(O)($OR^7$)O—, —OP(S)($OR^7$)O—, —OP(O)($SR^7$)O—, —OP(O)($OR^7$)S—, —OP(O)(O)O—, —SP(O)(O—)O—, —OP(S)(O—)O—, —OP(O)(S—)O—, —OP(O)(O—)S—, —OP(O)($OR^7$)$NR^7$—, —OP(O)$(N(R^7)_2)NR^7$—, —OP(OR⁷)O—, —OP(N(R⁷)₂)O—, —OP(OR⁷)N(R⁷)—, and —OPN(R⁷)₂NR⁷—;

each R² is independently selected from:
  C₁₋₆ alkyl optionally substituted with one or more substituents independently selected from halogen, —OR⁷, —N(R⁷)₂, —C(O)R⁷, —C(O)N(R⁷)₂, —N(R⁷)C(O)R⁷, —N(R⁷)C(O)N(R⁷)₂, —OC(O)N(R⁷)₂, —N(R⁷)C(O)OR⁷, —C(O)OR⁷, —OC(O)R⁷, and —S(O)R⁷;

R³ and R⁴ are each independently selected from:
  —OR⁷, —SR⁷, —N(R⁷)₂, —C(O)R⁷, —C(O)N(R⁷)₂, —N(R⁷)C(O)R⁷, —N(R⁷)C(O)N(R⁷)₂, —OC(O)N(R⁷)₂, —N(R⁷)C(O)OR⁷, —C(O)OR⁷, —OC(O)R⁷, and —S(O)R⁷;

each R⁵ is independently selected from:
  —OC(O)R⁷, —OC(O)N(R⁷)₂, —N(R⁷)C(O)R⁷, —N(R⁷)C(O)N(R⁷)₂, —N(R⁷)C(O)OR⁷, —C(O)R⁷, —C(O)OR⁷, and —C(O)N(R⁷)₂;

each R⁶ is independently selected from:
  hydrogen;
  halogen, —CN, —NO₂, —OR⁷, —SR⁷, —N(R⁷)₂, —C(O)R⁷, —C(O)N(R⁷)₂, —N(R⁷)C(O)R⁷, —N(R⁷)C(O)N(R⁷)₂, —OC(O)N(R⁷)₂, —N(R⁷)C(O)OR⁷, —C(O)OR⁷, —OC(O)R⁷, and —S(O)R⁷; and
  C₁₋₆ alkyl optionally substituted with one or more substituents independently selected from halogen, —CN, —NO₂, —OR⁷, —SR⁷, —N(R⁷)₂, —C(O)R⁷, —C(O)N(R⁷)₂, —N(R⁷)C(O)R⁷, —N(R⁷)C(O)N(R⁷)₂, —OC(O)N(R⁷)₂, —N(R⁷)C(O)OR⁷, —C(O)OR⁷, —OC(O)R⁷, and —S(O)R⁷;

each R⁷ is independently selected from:
  hydrogen;
  C₁₋₆ alkyl, C₂₋₆ alkenyl, and C₂₋₆ alkynyl, each of which is optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₃₋₁₀ carbocycle, and 3- to 10-membered heterocycle; and
  C₃₋₁₀ carbocycle, and 3- to 10-membered heterocycle, each of which is optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₁₋₆ alkyl, C₂₋₆ alkenyl, C₂₋₆ alkynyl, C₃₋₁₀ carbocycle, 3- to 10-membered heterocycle, and C₁₋₆ haloalkyl.

2. The compound or salt of claim 1, wherein each w, v, n and m is independently selected from any value from 1 to 5.

3. The compound or salt of claim 1, wherein each w is 1, v is 1, n is 1 or 2, and m is 1 or 2.

4. The compound or salt claim 1, wherein Q is selected from C₅₋₆ carbocycle optionally substituted with one or more substituents independently selected from halogen, —CN, —OH, —SH, —NO₂, and —NH₂.

5. The compound or salt of claim 1, wherein R¹ is selected from —OP(O)(OR⁷)O—, —OP(S)(OR⁷)O—, —OP(O)(O—)O—, —OP(S)(O—)O—, —OP(O)(S—)O—, and —OP(OR⁷)O—.

6. The compound or salt of claim 1, wherein R² is selected from C₁₋₃ alkyl substituted with one or more substituents independently selected from —OR⁷, —OC(O)R⁷, —SR⁷, and —N(R⁷)₂.

7. The compound or salt of claim 1, wherein R³ is selected from —OR⁷—SR⁷, —OC(O)R⁷, and —N(R⁷)₂.

8. The compound or salt of claim 1, wherein R⁴ is selected from —OR⁷—SR⁷, —OC(O)R⁷, and —N(R⁷)₂.

9. The compound or salt of claim 1, wherein R⁵ is selected from —OC(O)R⁷ and —N(R⁷)C(O)R⁷.

10. The compound or salt of claim 1, wherein each R⁷ is independently selected from:
  hydrogen; and
  C₁₋₆ alkyl optionally substituted with one or more substituents independently selected from halogen, —CN, —OH, —SH, —NO₂, —NH₂, =O, =S, —O—C₁₋₆ alkyl, —S—C₁₋₆ alkyl, —N(C₁₋₆ alkyl)₂, —NH(C₁₋₆ alkyl), C₃₋₁₀ carbocycle, or 3- to 10-membered heterocycle.

11. The compound of claim 1, wherein the compound comprises:

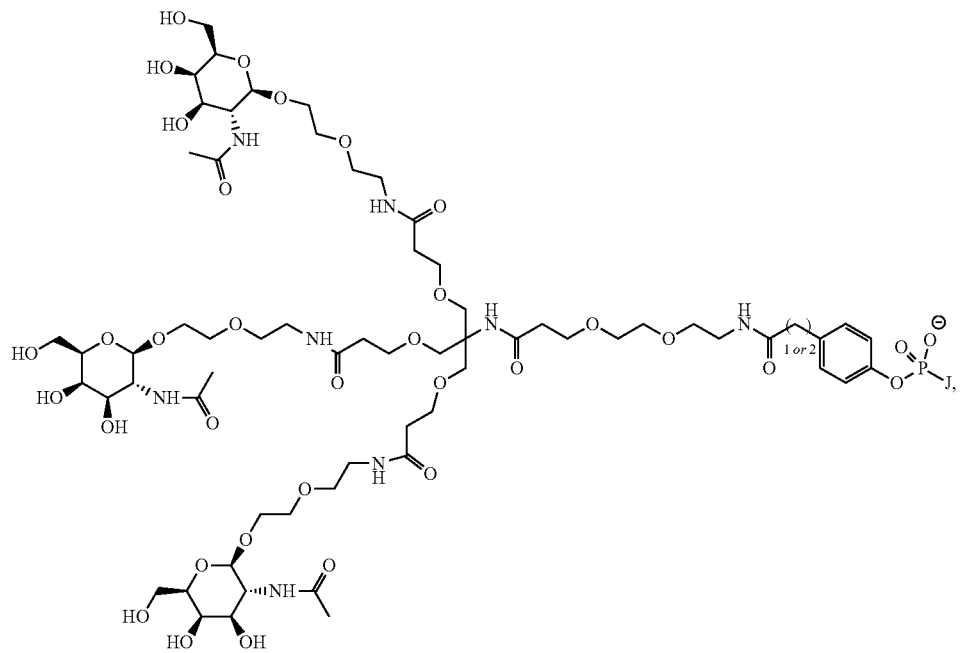
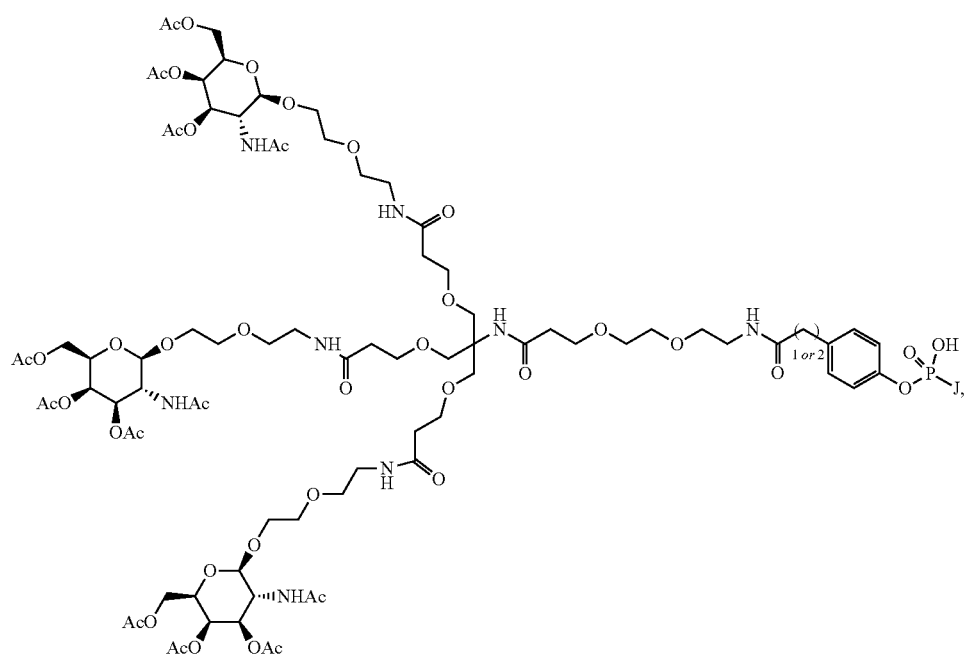

-continued
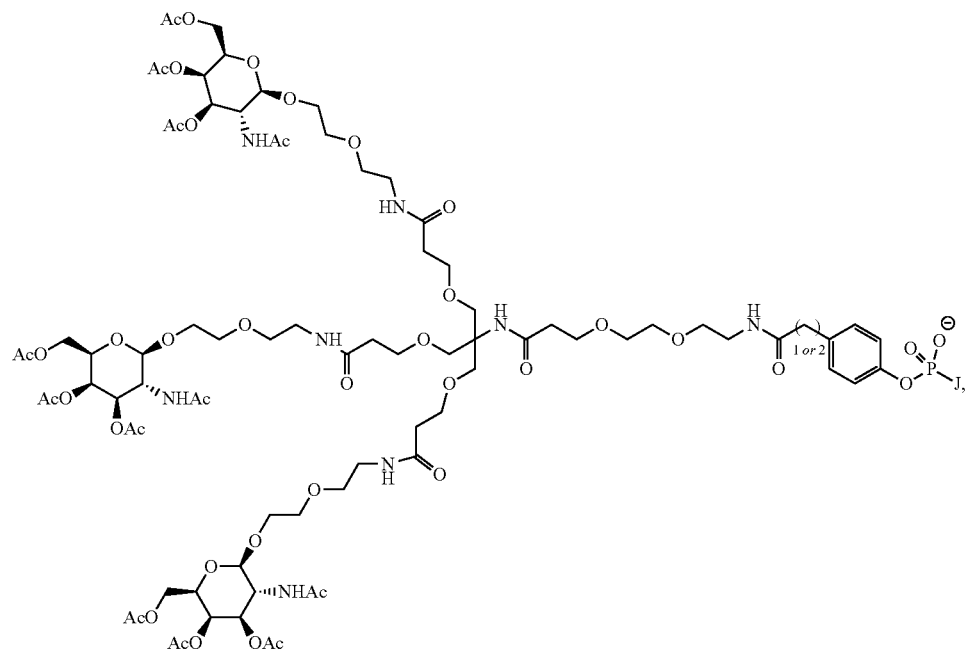
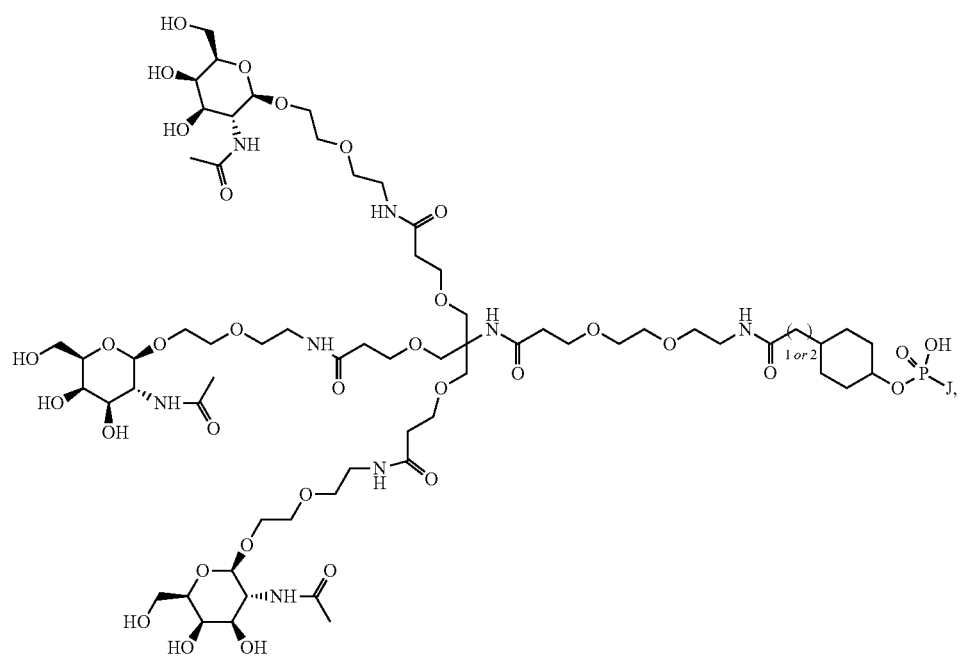

-continued
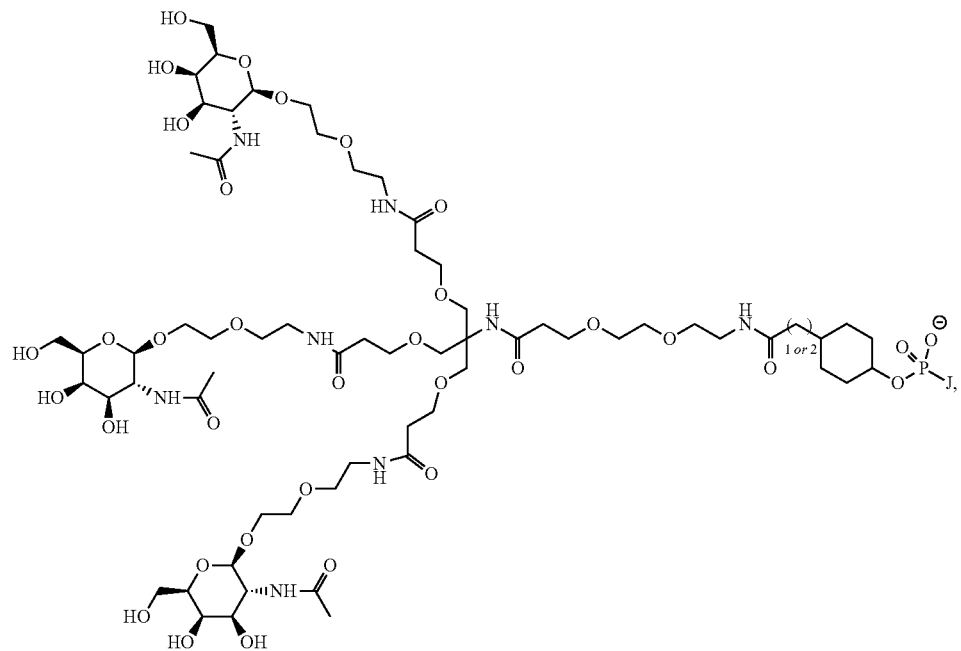
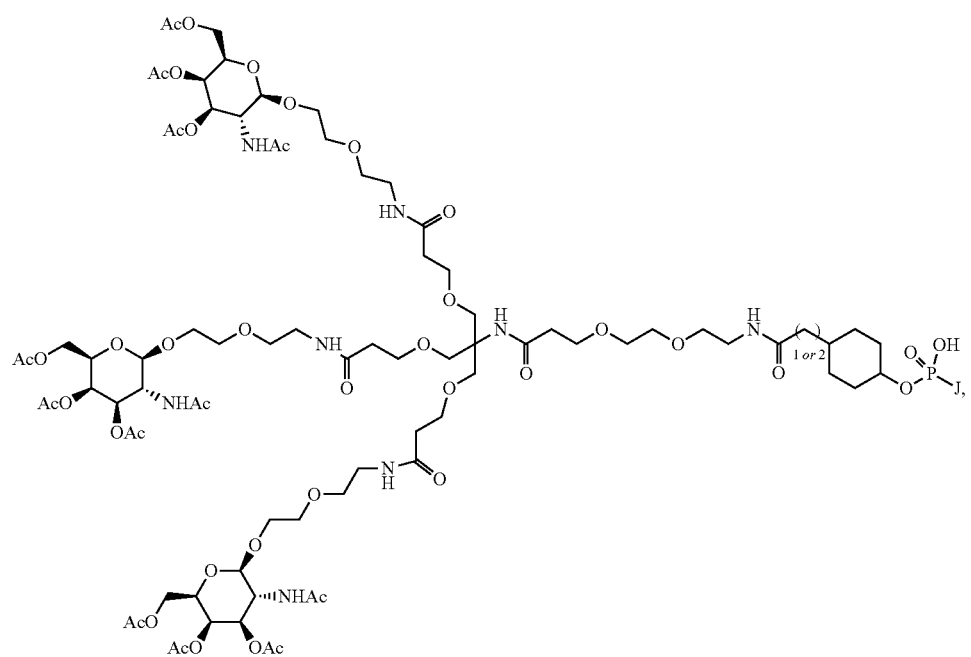

-continued
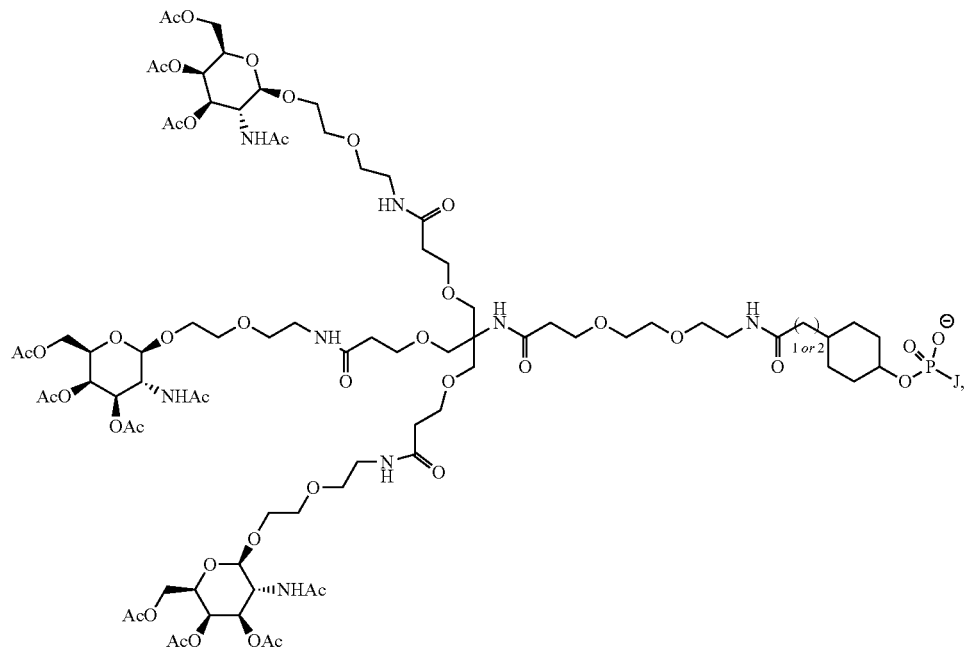
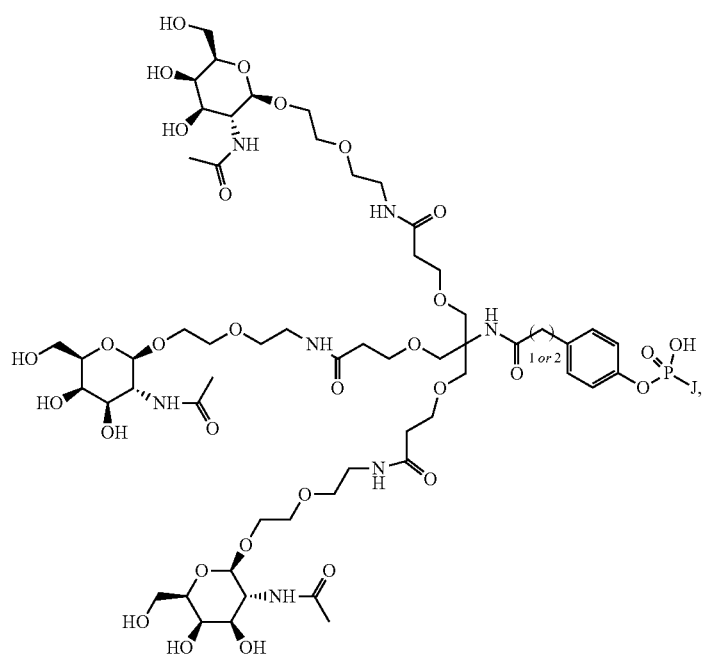

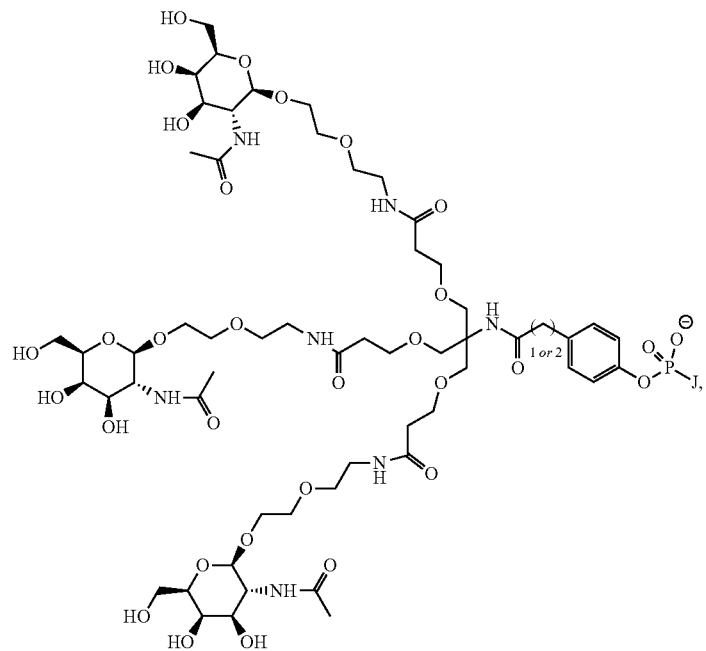
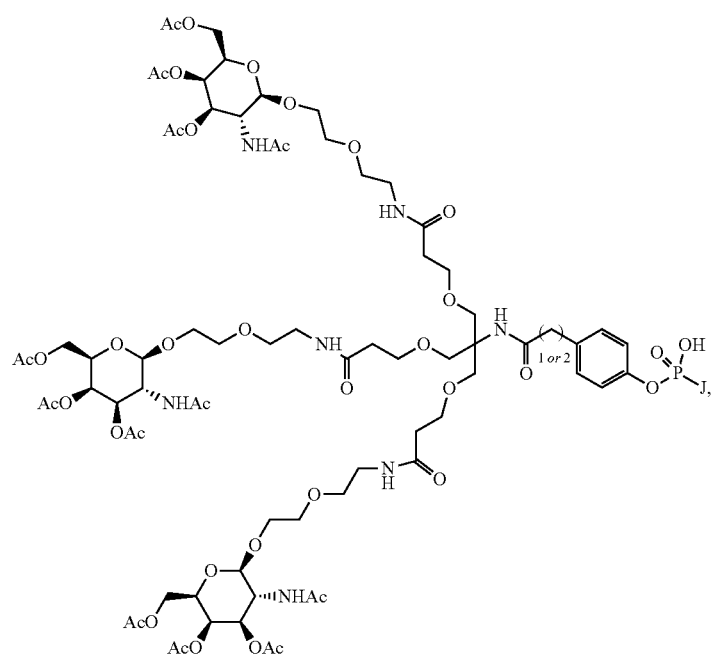

-continued
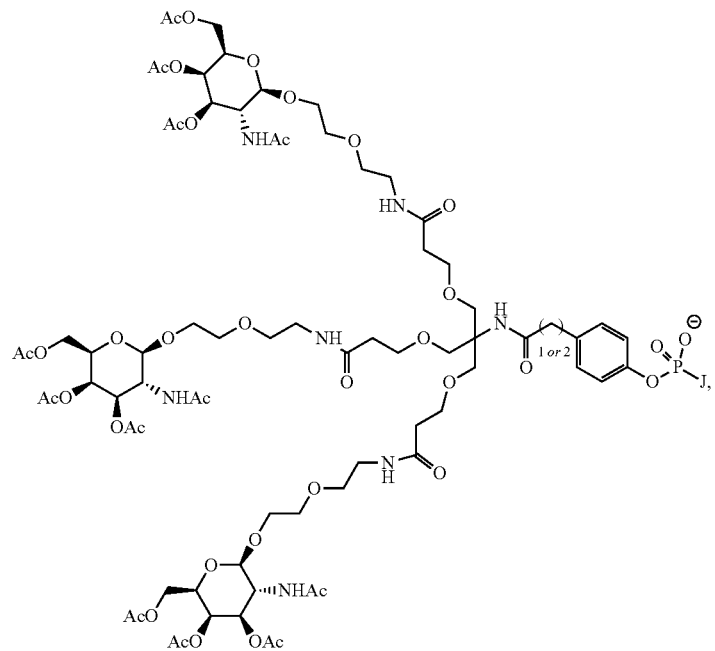
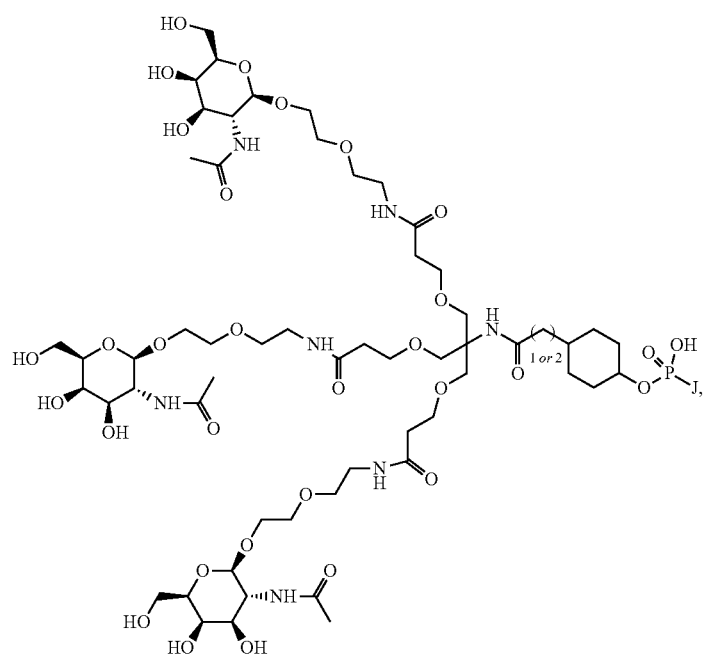

-continued
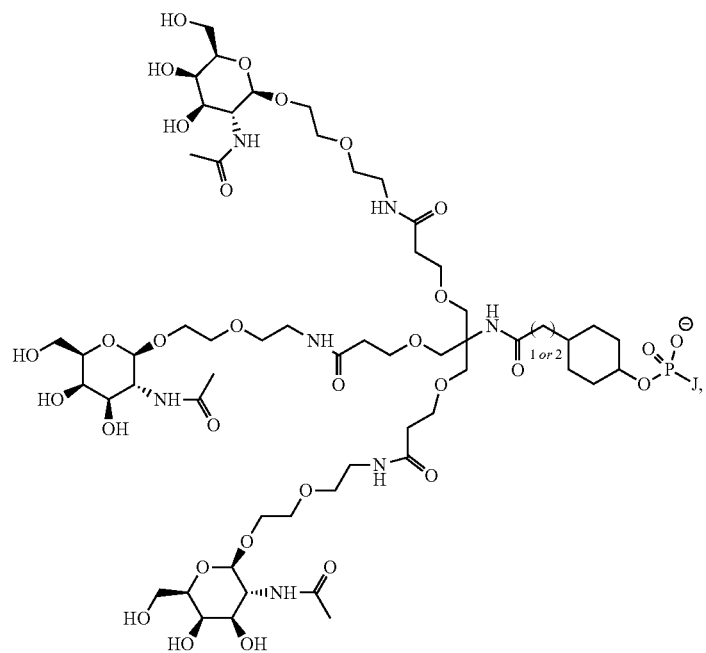
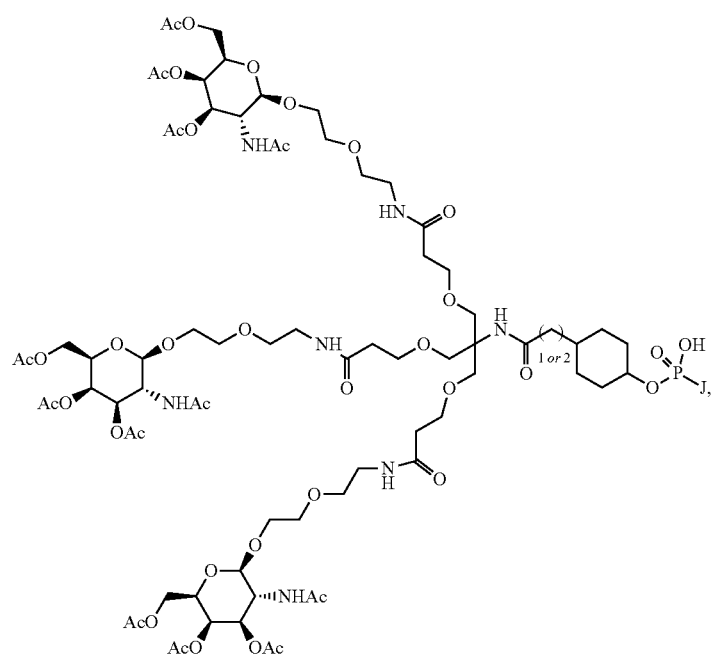

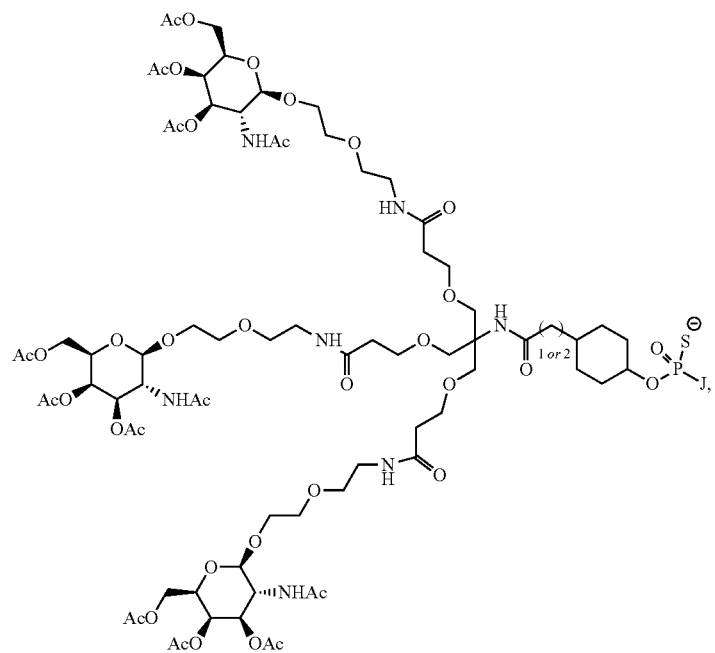
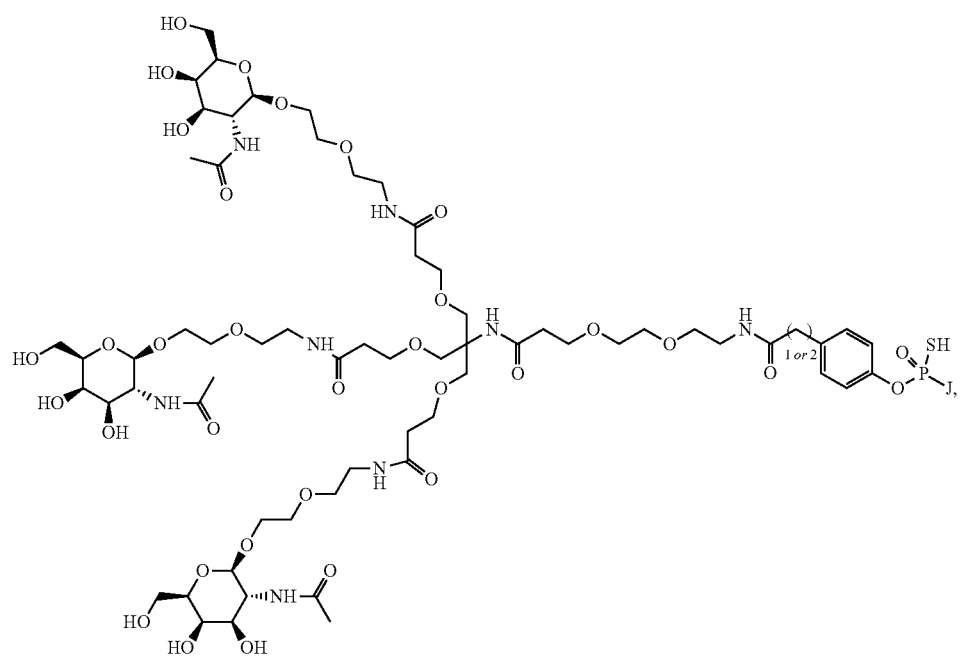

-continued
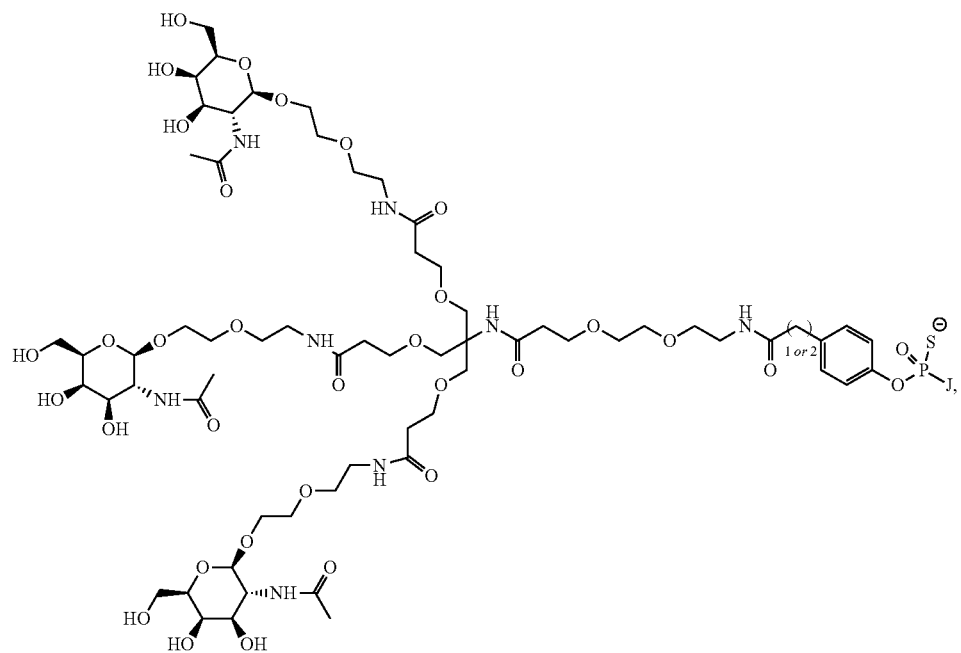
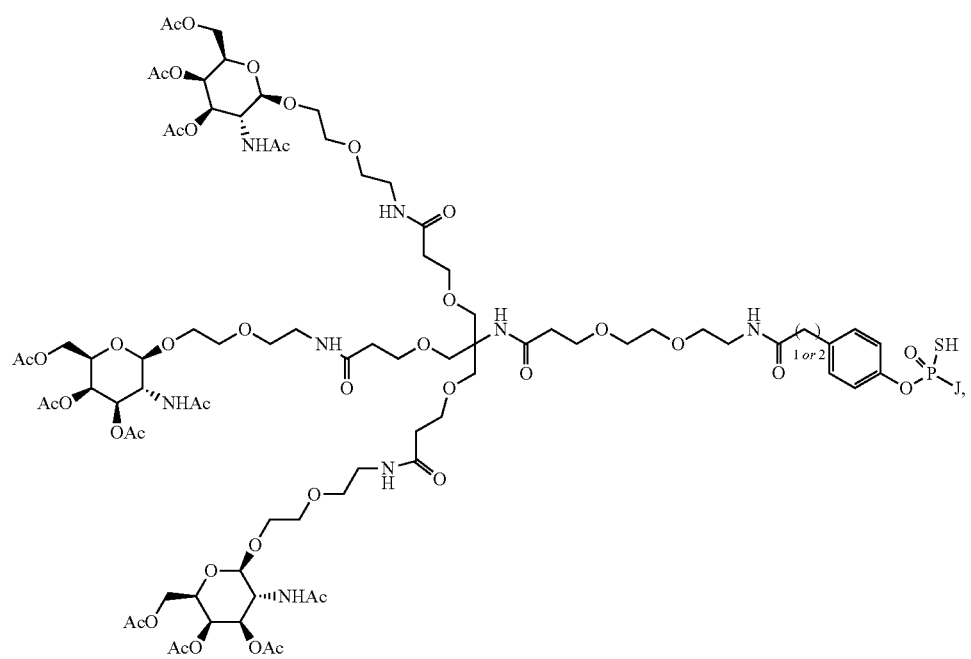

-continued
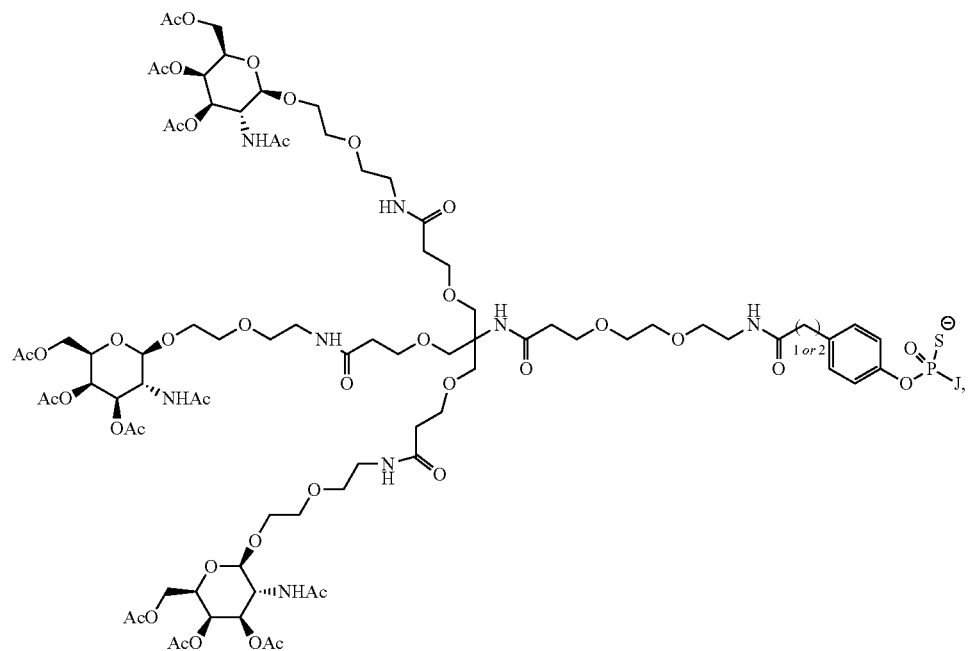
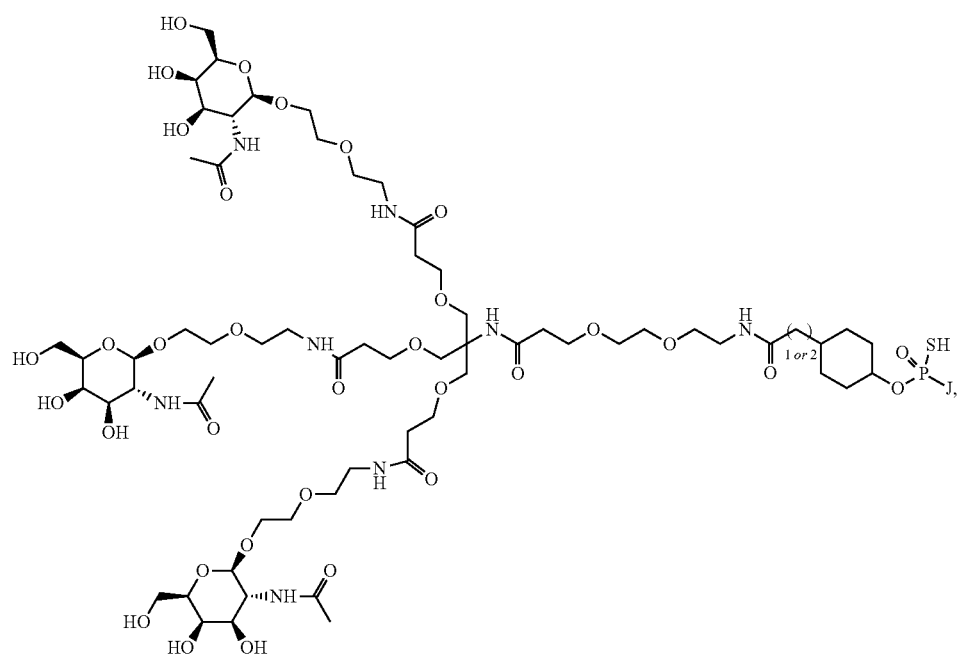

-continued
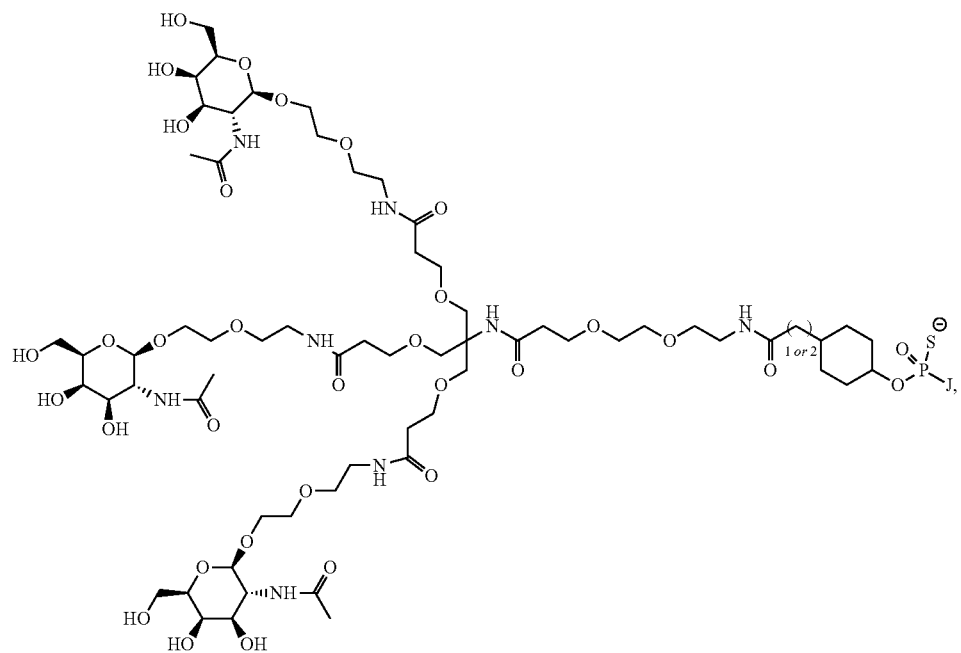
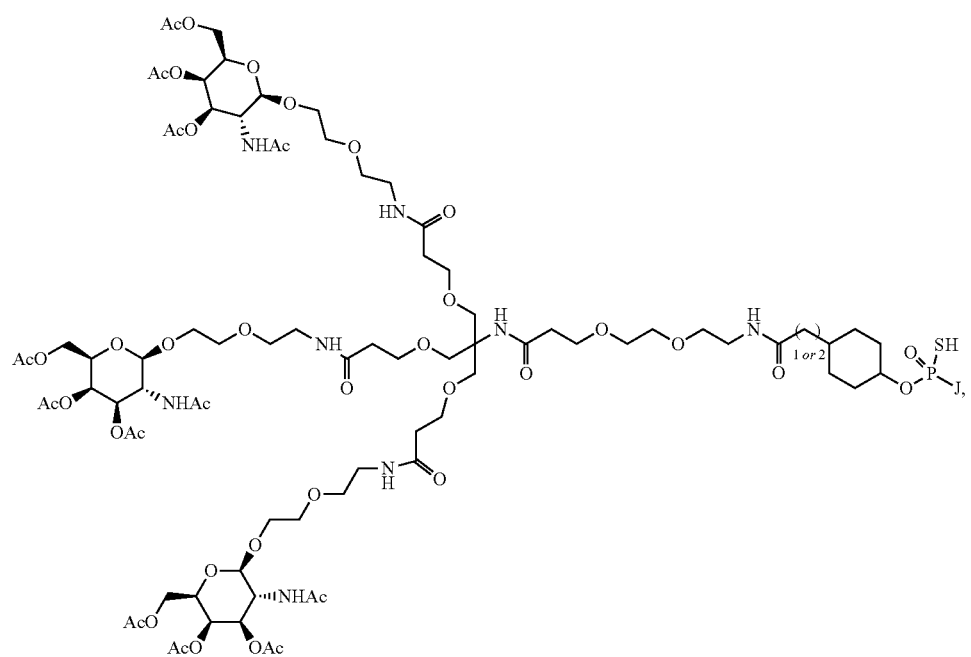

-continued
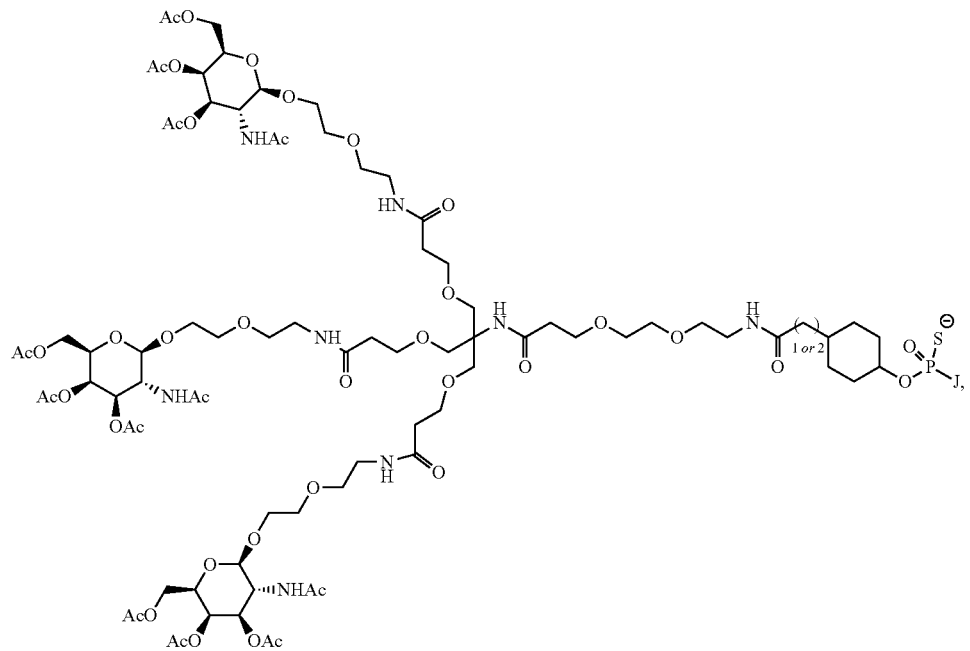
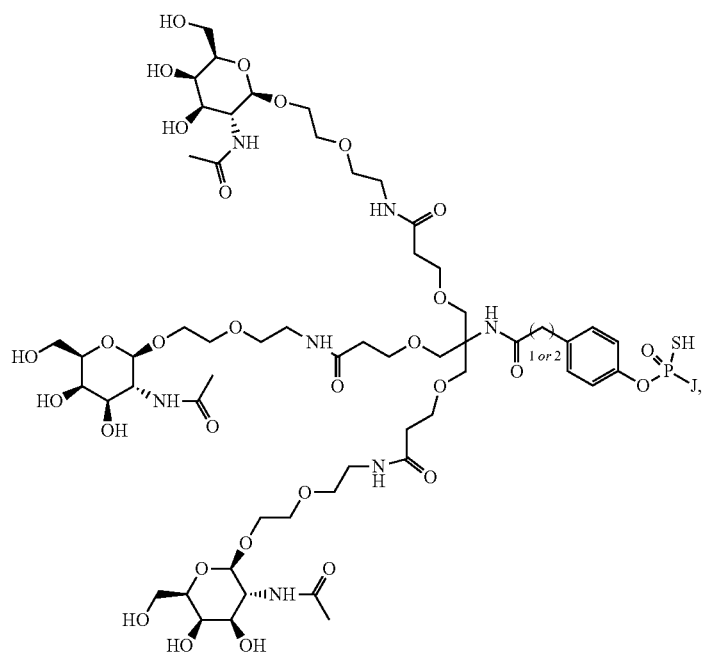

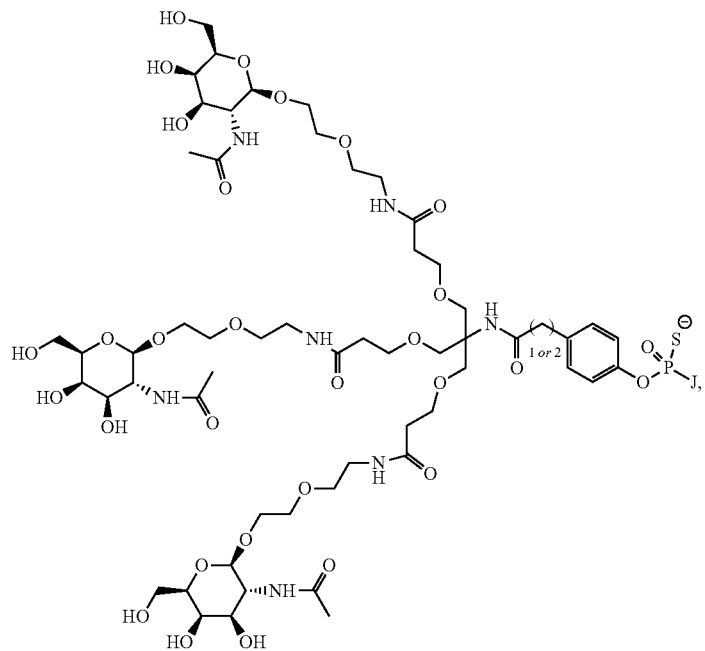
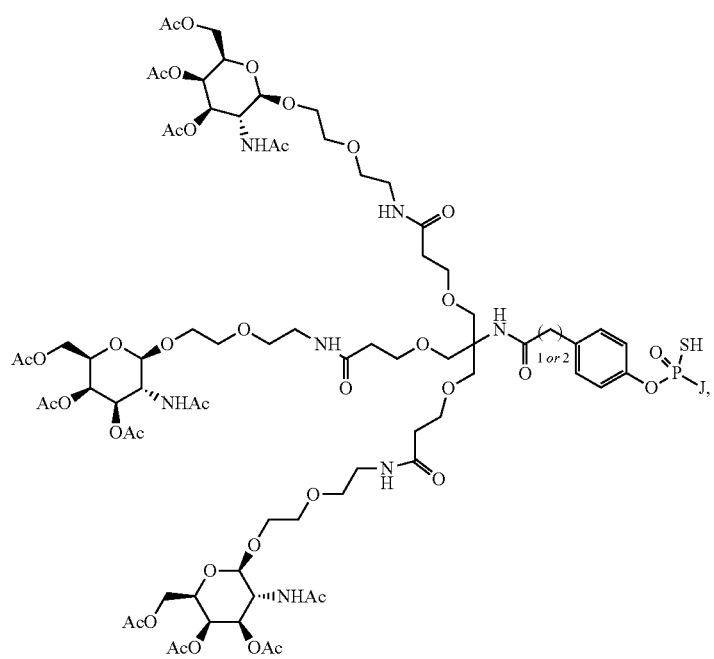

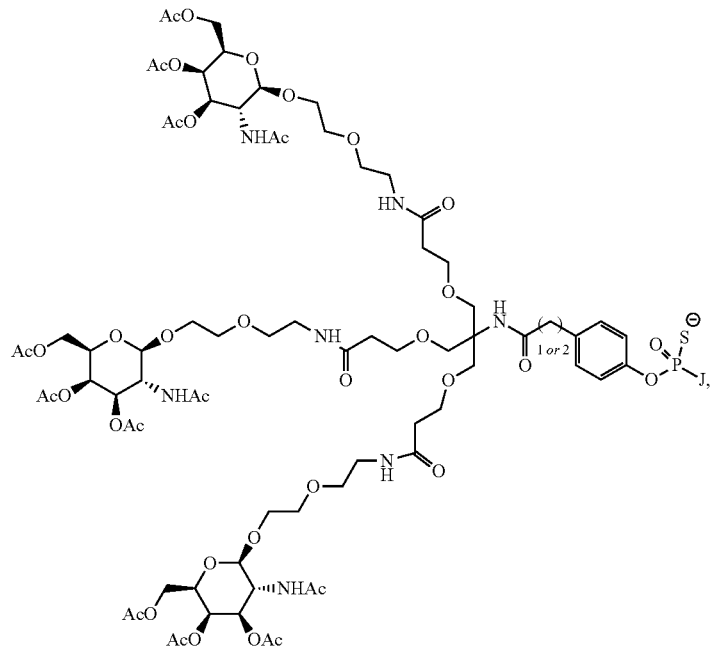
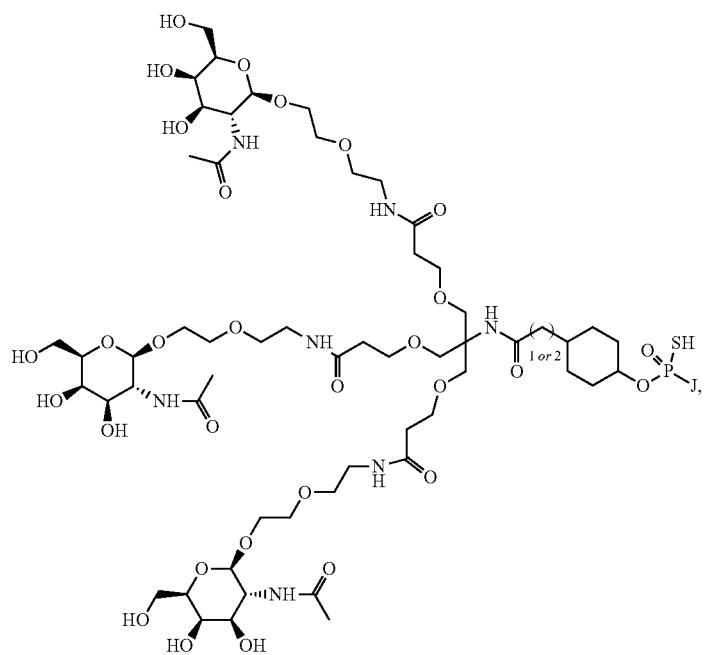

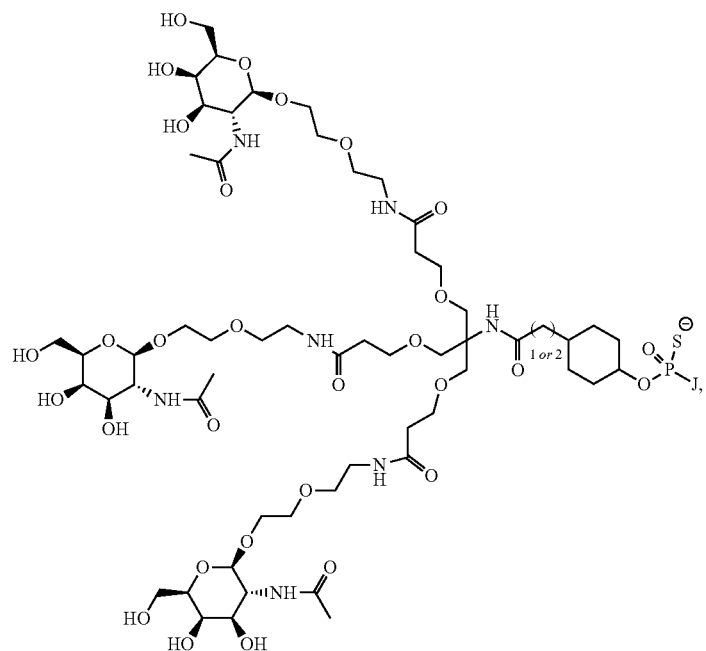
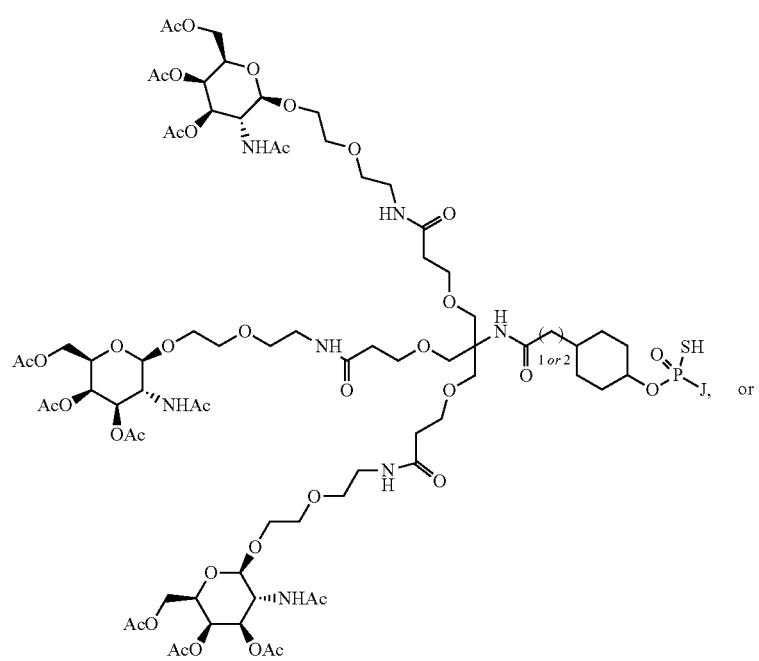

-continued

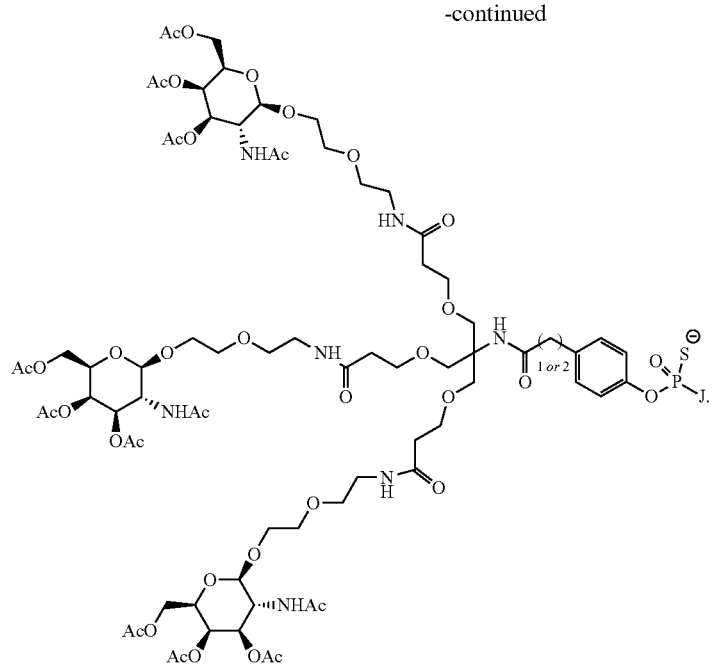

12. The compound of claim 1, wherein the oligonucleotide (J) is attached to $R^1$ at a 5' end of the oligonucleotide.

13. The compound of claim 12, wherein the 5' end of the oligonucleotide comprises a phosphate.

14. The compound of claim 12, wherein the 5' end of the oligonucleotide comprises a phosphorothioate.

15. The compound of claim 1, wherein the oligonucleotide comprises a phosphorothioate linkage.

16. The compound of claim 1, wherein the oligonucleotide comprises a 2' O-methyl or 2' fluoro modified nucleoside.

17. The compound of claim 1, wherein the oligonucleotide comprises a small interfering RNA (siRNA).

18. A pharmaceutical composition comprising the compound of claim 1, and a pharmaceutically acceptable carrier, excipient, or diluent.

19. A compound comprising:

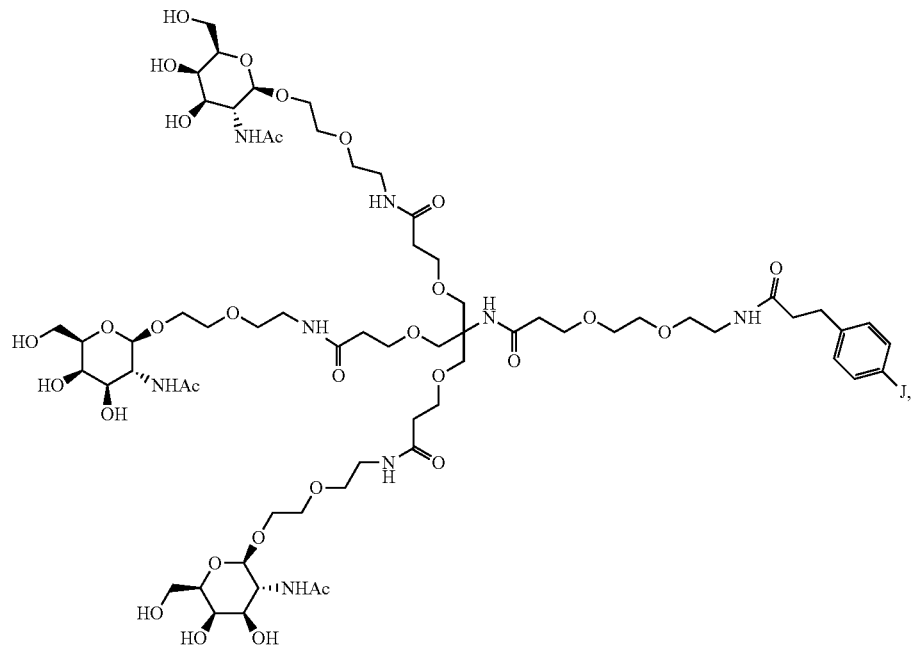

wherein J comprises an oligonucleotide.

20. The compound of claim 19, wherein the oligonucleotide comprises a siRNA.

\* \* \* \* \*

SEQUENCE LISTING

```
Sequence total quantity: 64
SEQ ID NO: 1            moltype = RNA   length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = phosphorothioate linkage
                        note = 2-O-methyl modified nucleoside
```

```
modified_base      19^20
                   mod_base = OTHER
                   note = phosphorothioate linkage
modified_base      20^21
                   mod_base = OTHER
                   note = phosphorothioate linkage
modified_base      11
                   mod_base = OTHER
                   note = 2-fluoro-modified nucleoside
modified_base      6
                   mod_base = OTHER
                   note = 2-O-methyl modified nucleoside
modified_base      12
                   mod_base = OTHER
                   note = 2-O-methyl modified nucleoside
modified_base      13
                   mod_base = OTHER
                   note = 2-O-methyl modified nucleoside
modified_base      2
                   mod_base = OTHER
                   note = 2-O-methyl modified nucleoside
modified_base      3
                   mod_base = OTHER
                   note = 2-O-methyl modified nucleoside
modified_base      4
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      8
                   mod_base = OTHER
                   note = 2-O-methyl modified nucleoside
modified_base      9
                   mod_base = OTHER
                   note = 2-fluoro-modified nucleoside
modified_base      10
                   mod_base = OTHER
                   note = 2-O-methyl modified nucleoside
modified_base      14
                   mod_base = OTHER
                   note = 2-O-methyl modified nucleoside
modified_base      15
                   mod_base = OTHER
                   note = 2-O-methyl modified nucleoside
modified_base      16
                   mod_base = OTHER
                   note = 2-O-methyl modified nucleoside
modified_base      17
                   mod_base = OTHER
                   note = 2-O-methyl modified nucleoside
modified_base      18
                   mod_base = OTHER
                   note = 2-O-methyl modified nucleoside
modified_base      19
                   mod_base = OTHER
                   note = 2-O-methyl modified nucleoside
modified_base      21
                   mod_base = OTHER
                   note = 2-O-methyl modified nucleoside
modified_base      20
                   mod_base = OTHER
                   note = 2-O-methyl modified nucleoside
SEQUENCE: 1
cagttttaa gggacaccat t                                             21

SEQ ID NO: 2        moltype = RNA  length = 21
FEATURE             Location/Qualifiers
source              1..21
                    mol_type = other RNA
                    note = GalNAc moiety-ETL17
                    organism = synthetic construct
modified_base       1
                    mod_base = OTHER
                    note = phosphorothioate linkage
                    note = 2-O-methyl modified nucleoside
```

```
modified_base        19^20
                     mod_base = OTHER
                     note = phosphorothioate linkage
modified_base        20^21
                     mod_base = OTHER
                     note = phosphorothioate linkage
modified_base        8
                     mod_base = OTHER
                     note = 2-fluoro-modified nucleoside
modified_base        9
                     mod_base = OTHER
                     note = 2-fluoro-modified nucleoside
modified_base        10
                     mod_base = OTHER
                     note = 2-O-methyl modified nucleoside
modified_base        17
                     mod_base = OTHER
                     note = 2-O-methyl modified nucleoside
modified_base        2
                     mod_base = OTHER
                     note = 2-O-methyl modified nucleoside
modified_base        3
                     mod_base = OTHER
                     note = 2-O-methyl modified nucleoside
modified_base        4
                     mod_base = OTHER
                     note = 2-O-methyl modified nucleoside
modified_base        5
                     mod_base = OTHER
                     note = 2-O-methyl modified nucleoside
modified_base        6
                     mod_base = OTHER
                     note = 2-fluoro-modified nucleoside
modified_base        7
                     mod_base = OTHER
                     note = 2-fluoro-modified nucleoside
modified_base        12
                     mod_base = OTHER
                     note = 2-O-methyl modified nucleoside
modified_base        11
                     mod_base = OTHER
                     note = 2-fluoro-modified nucleoside
modified_base        13
                     mod_base = OTHER
                     note = 2-O-methyl modified nucleoside
modified_base        14
                     mod_base = OTHER
                     note = 2-O-methyl modified nucleoside
modified_base        15
                     mod_base = OTHER
                     note = 2-O-methyl modified nucleoside
modified_base        16
                     mod_base = OTHER
                     note = 2-O-methyl modified nucleoside
modified_base        18
                     mod_base = OTHER
                     note = 2-O-methyl modified nucleoside
modified_base        19
                     mod_base = OTHER
                     note = 2-O-methyl modified nucleoside
modified_base        20
                     mod_base = OTHER
                     note = 2-O-methyl modified nucleoside
modified_base        21
                     mod_base = OTHER
                     note = 2-O-methyl modified nucleoside
SEQUENCE: 2
tttttaaggg acaccagaat t                                              21

SEQ ID NO: 3         moltype = RNA  length = 21
FEATURE              Location/Qualifiers
source               1..21
                     mol_type = other RNA
                     note = GalNAc moiety-ETL17
                     organism = synthetic construct
modified_base        1
                     mod_base = OTHER
                     note = phosphorothioate linkage
                     note = 2-O-methyl modified nucleoside
```

```
modified_base         2
                      mod_base = OTHER
                      note = 2-O-methyl modified nucleoside
modified_base         3
                      mod_base = OTHER
                      note = 2-O-methyl modified nucleoside
modified_base         4
                      mod_base = OTHER
                      note = 2-O-methyl modified nucleoside
modified_base         5
                      mod_base = OTHER
                      note = 2-O-methyl modified nucleoside
modified_base         6
                      mod_base = OTHER
                      note = 2-O-methyl modified nucleoside
modified_base         7
                      mod_base = OTHER
                      note = 2-fluoro-modified nucleoside
modified_base         8
                      mod_base = OTHER
                      note = 2-O-methyl modified nucleoside
modified_base         9
                      mod_base = OTHER
                      note = 2-fluoro-modified nucleoside
modified_base         10
                      mod_base = OTHER
                      note = 2-O-methyl modified nucleoside
modified_base         11
                      mod_base = OTHER
                      note = 2-fluoro-modified nucleoside
modified_base         12
                      mod_base = OTHER
                      note = 2-O-methyl modified nucleoside
modified_base         13
                      mod_base = OTHER
                      note = 2-O-methyl modified nucleoside
modified_base         14
                      mod_base = OTHER
                      note = 2-O-methyl modified nucleoside
modified_base         15
                      mod_base = OTHER
                      note = 2-O-methyl modified nucleoside
modified_base         16
                      mod_base = OTHER
                      note = 2-O-methyl modified nucleoside
modified_base         17
                      mod_base = OTHER
                      note = 2-O-methyl modified nucleoside
modified_base         18
                      mod_base = OTHER
                      note = 2-O-methyl modified nucleoside
modified_base         19
                      mod_base = OTHER
                      note = 2-O-methyl modified nucleoside
modified_base         20
                      mod_base = OTHER
                      note = 2-O-methyl modified nucleoside
modified_base         21
                      mod_base = OTHER
                      note = 2-O-methyl modified nucleoside
modified_base         19^20
                      mod_base = OTHER
                      note = phosphorothioate linkage
modified_base         20^21
                      mod_base = OTHER
                      note = phosphorothioate linkage
SEQUENCE: 3
ttttgacaca ttcttagcat t                                              21

SEQ ID NO: 4          moltype = RNA  length = 21
FEATURE               Location/Qualifiers
source                1..21
                      mol_type = other RNA
                      note = GalNAc moiety-ETL17
                      organism = synthetic construct
modified_base         1
                      mod_base = OTHER
                      note = 2-O-methyl modified nucleoside
                      note = phosphorothioate linkage
```

```
modified_base      2
                   mod_base = OTHER
                   note = 2-O-methyl modified nucleoside
modified_base      3
                   mod_base = OTHER
                   note = 2-O-methyl modified nucleoside
modified_base      4
                   mod_base = OTHER
                   note = 2-O-methyl modified nucleoside
modified_base      5
                   mod_base = OTHER
                   note = 2-fluoro-modified nucleoside
modified_base      6
                   mod_base = OTHER
                   note = 2-O-methyl modified nucleoside
modified_base      7
                   mod_base = OTHER
                   note = 2-fluoro-modified nucleoside
modified_base      8
                   mod_base = OTHER
                   note = 2-O-methyl modified nucleoside
modified_base      9
                   mod_base = OTHER
                   note = 2-fluoro-modified nucleoside
modified_base      10
                   mod_base = OTHER
                   note = 2-O-methyl modified nucleoside
modified_base      11
                   mod_base = OTHER
                   note = 2-fluoro-modified nucleoside
modified_base      12
                   mod_base = OTHER
                   note = 2-O-methyl modified nucleoside
modified_base      13
                   mod_base = OTHER
                   note = 2-O-methyl modified nucleoside
modified_base      14
                   mod_base = OTHER
                   note = 2-O-methyl modified nucleoside
modified_base      15
                   mod_base = OTHER
                   note = 2-O-methyl modified nucleoside
modified_base      16
                   mod_base = OTHER
                   note = 2-O-methyl modified nucleoside
modified_base      17
                   mod_base = OTHER
                   note = 2-O-methyl modified nucleoside
modified_base      18
                   mod_base = OTHER
                   note = 2-O-methyl modified nucleoside
modified_base      19
                   mod_base = OTHER
                   note = 2-O-methyl modified nucleoside
modified_base      20
                   mod_base = OTHER
                   note = 2-O-methyl modified nucleoside
modified_base      21
                   mod_base = OTHER
                   note = 2-O-methyl modified nucleoside
modified_base      19^20
                   mod_base = OTHER
                   note = phosphorothioate linkage
modified_base      20^21
                   mod_base = OTHER
                   note = phosphorothioate linkage
SEQUENCE: 4
ttgacacatt cttagcacat t                                              21

SEQ ID NO: 5       moltype = RNA   length = 21
FEATURE            Location/Qualifiers
source             1..21
                   mol_type = other RNA
                   note = GalNAc moiety-ETL17
                   organism = synthetic construct
modified_base      1
                   mod_base = OTHER
                   note = 2-O-methyl modified nucleoside
                   note = phosphorothioate linkage
```

| | |
|---|---|
| modified_base | 2<br>mod_base = OTHER<br>note = 2-O-methyl modified nucleoside |
| modified_base | 3<br>mod_base = OTHER<br>note = 2-O-methyl modified nucleoside |
| modified_base | 4<br>mod_base = OTHER<br>note = 2-O-methyl modified nucleoside |
| modified_base | 5<br>mod_base = OTHER<br>note = 2-O-methyl modified nucleoside |
| modified_base | 6<br>mod_base = OTHER<br>note = 2-O-methyl modified nucleoside |
| modified_base | 7<br>mod_base = OTHER<br>note = 2-O-methyl modified nucleoside |
| modified_base | 8<br>mod_base = OTHER<br>note = 2-O-methyl modified nucleoside |
| modified_base | 9<br>mod_base = OTHER<br>note = 2-fluoro-modified nucleoside |
| modified_base | 10<br>mod_base = OTHER<br>note = 2-fluoro-modified nucleoside |
| modified_base | 11<br>mod_base = OTHER<br>note = 2-O-methyl modified nucleoside |
| modified_base | 12<br>mod_base = OTHER<br>note = 2-O-methyl modified nucleoside |
| modified_base | 13<br>mod_base = OTHER<br>note = 2-O-methyl modified nucleoside |
| modified_base | 14<br>mod_base = OTHER<br>note = 2-O-methyl modified nucleoside |
| modified_base | 15<br>mod_base = OTHER<br>note = 2-O-methyl modified nucleoside |
| modified_base | 16<br>mod_base = OTHER<br>note = 2-O-methyl modified nucleoside |
| modified_base | 17<br>mod_base = OTHER<br>note = 2-O-methyl modified nucleoside |
| modified_base | 18<br>mod_base = OTHER<br>note = 2-O-methyl modified nucleoside |
| modified_base | 19<br>mod_base = OTHER<br>note = 2-O-methyl modified nucleoside |
| modified_base | 20<br>mod_base = OTHER<br>note = 2-O-methyl modified nucleoside |
| modified_base | 21<br>mod_base = OTHER<br>note = 2-O-methyl modified nucleoside |
| modified_base | 19^20<br>mod_base = OTHER<br>note = phosphorothioate linkage |
| modified_base | 20^21<br>mod_base = OTHER<br>note = phosphorothioate linkage |
| SEQUENCE: 5<br>acattcttag cactgaacat t | 21 |
| SEQ ID NO: 6<br>FEATURE<br>source | moltype = RNA  length = 21<br>Location/Qualifiers<br>1..21<br>mol_type = other RNA<br>note = GalNAc moiety-ETL17<br>organism = synthetic construct |
| modified_base | 1<br>mod_base = OTHER<br>note = phosphorothioate linkage<br>note = 2-O-methyl modified nucleoside |

```
modified_base       2
                    mod_base = OTHER
                    note = 2-O-methyl modified nucleoside
modified_base       3
                    mod_base = OTHER
                    note = 2-O-methyl modified nucleoside
modified_base       4
                    mod_base = OTHER
                    note = 2-O-methyl modified nucleoside
modified_base       5
                    mod_base = OTHER
                    note = 2-fluoro-modified nucleoside
modified_base       6
                    mod_base = OTHER
                    note = 2-O-methyl modified nucleoside
modified_base       7
                    mod_base = OTHER
                    note = 2-O-methyl modified nucleoside
modified_base       8
                    mod_base = OTHER
                    note = 2-fluoro-modified nucleoside
modified_base       9
                    mod_base = OTHER
                    note = 2-fluoro-modified nucleoside
modified_base       10
                    mod_base = OTHER
                    note = 2-O-methyl modified nucleoside
modified_base       11
                    mod_base = OTHER
                    note = 2-fluoro-modified nucleoside
modified_base       12
                    mod_base = OTHER
                    note = 2-O-methyl modified nucleoside
modified_base       13
                    mod_base = OTHER
                    note = 2-O-methyl modified nucleoside
modified_base       14
                    mod_base = OTHER
                    note = 2-O-methyl modified nucleoside
modified_base       15
                    mod_base = OTHER
                    note = 2-O-methyl modified nucleoside
modified_base       16
                    mod_base = OTHER
                    note = 2-O-methyl modified nucleoside
modified_base       17
                    mod_base = OTHER
                    note = 2-O-methyl modified nucleoside
modified_base       18
                    mod_base = OTHER
                    note = 2-O-methyl modified nucleoside
modified_base       19
                    mod_base = OTHER
                    note = 2-O-methyl modified nucleoside
modified_base       20
                    mod_base = OTHER
                    note = 2-O-methyl modified nucleoside
modified_base       21
                    mod_base = OTHER
                    note = 2-O-methyl modified nucleoside
modified_base       19^20
                    mod_base = OTHER
                    note = phosphorothioate linkage
modified_base       20^21
                    mod_base = OTHER
                    note = phosphorothioate linkage
SEQUENCE: 6
tgcatagtca ctcttttgat t                                         21

SEQ ID NO: 7        moltype = RNA  length = 21
FEATURE             Location/Qualifiers
source              1..21
                    mol_type = other RNA
                    note = GalNAc moiety-ETL17
                    organism = synthetic construct
modified_base       1
                    mod_base = OTHER
                    note = 2-O-methyl modified nucleoside
                    note = phosphorothioate linkage
```

| | |
|---|---|
| modified_base | 2<br>mod_base = OTHER<br>note = 2-O-methyl modified nucleoside |
| modified_base | 3<br>mod_base = OTHER<br>note = 2-O-methyl modified nucleoside |
| modified_base | 4<br>mod_base = OTHER<br>note = 2-O-methyl modified nucleoside |
| modified_base | 5<br>mod_base = OTHER<br>note = 2-O-methyl modified nucleoside |
| modified_base | 6<br>mod_base = OTHER<br>note = 2-fluoro-modified nucleoside |
| modified_base | 7<br>mod_base = OTHER<br>note = 2-fluoro-modified nucleoside |
| modified_base | 8<br>mod_base = OTHER<br>note = 2-O-methyl modified nucleoside |
| modified_base | 9<br>mod_base = OTHER<br>note = 2-fluoro-modified nucleoside |
| modified_base | 10<br>mod_base = OTHER<br>note = 2-O-methyl modified nucleoside |
| modified_base | 11<br>mod_base = OTHER<br>note = 2-fluoro-modified nucleoside |
| modified_base | 12<br>mod_base = OTHER<br>note = 2-O-methyl modified nucleoside |
| modified_base | 13<br>mod_base = OTHER<br>note = 2-O-methyl modified nucleoside |
| modified_base | 14<br>mod_base = OTHER<br>note = 2-O-methyl modified nucleoside |
| modified_base | 15<br>mod_base = OTHER<br>note = 2-O-methyl modified nucleoside |
| modified_base | 16<br>mod_base = OTHER<br>note = 2-O-methyl modified nucleoside |
| modified_base | 17<br>mod_base = OTHER<br>note = 2-O-methyl modified nucleoside |
| modified_base | 18<br>mod_base = OTHER<br>note = 2-O-methyl modified nucleoside |
| modified_base | 19<br>mod_base = OTHER<br>note = 2-O-methyl modified nucleoside |
| modified_base | 20<br>mod_base = OTHER<br>note = 2-O-methyl modified nucleoside |
| modified_base | 21<br>mod_base = OTHER<br>note = 2-O-methyl modified nucleoside |
| modified_base | 19^20<br>mod_base = OTHER<br>note = phosphorothioate linkage |
| modified_base | 20^21<br>mod_base = OTHER<br>note = phosphorothioate linkage |
| SEQUENCE: 7 | |
| aactactgca taatatggat t | 21 |
| SEQ ID NO: 8<br>FEATURE<br>source | moltype = RNA  length = 21<br>Location/Qualifiers<br>1..21<br>mol_type = other RNA<br>organism = synthetic construct |
| modified_base | 1^2<br>mod_base = OTHER<br>note = phosphorothioate linkage |
| modified_base | 1<br>mod_base = OTHER |

```
                        note = 2-O-methyl modified nucleoside
modified_base           2
                        mod_base = OTHER
                        note = 2-fluoro-modified nucleoside
modified_base           3
                        mod_base = OTHER
                        note = 2-O-methyl modified nucleoside
modified_base           4
                        mod_base = OTHER
                        note = 2-fluoro-modified nucleoside
modified_base           5
                        mod_base = OTHER
                        note = 2-O-methyl modified nucleoside
modified_base           6
                        mod_base = OTHER
                        note = 2-fluoro-modified nucleoside
modified_base           7
                        mod_base = OTHER
                        note = 2-O-methyl modified nucleoside
modified_base           8
                        mod_base = OTHER
                        note = 2-fluoro-modified nucleoside
modified_base           9
                        mod_base = OTHER
                        note = 2-O-methyl modified nucleoside
modified_base           10
                        mod_base = OTHER
                        note = 2-fluoro-modified nucleoside
modified_base           11
                        mod_base = OTHER
                        note = 2-O-methyl modified nucleoside
modified_base           12
                        mod_base = OTHER
                        note = 2-fluoro-modified nucleoside
modified_base           13
                        mod_base = OTHER
                        note = 2-O-methyl modified nucleoside
modified_base           14
                        mod_base = OTHER
                        note = 2-fluoro-modified nucleoside
modified_base           15
                        mod_base = OTHER
                        note = 2-O-methyl modified nucleoside
modified_base           16
                        mod_base = OTHER
                        note = 2-fluoro-modified nucleoside
modified_base           17
                        mod_base = OTHER
                        note = 2-O-methyl modified nucleoside
modified_base           18
                        mod_base = OTHER
                        note = 2-fluoro-modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 8
tggtgtccct taaaaactgt t                                        21

SEQ ID NO: 9            moltype = RNA   length = 21
FEATURE                 Location/Qualifiers
source                  1..21
                        mol_type = other RNA
                        organism = synthetic construct
modified_base           1^2
```

| | | |
|---|---|---|
| | | mod_base = OTHER |
| | | note = phosphorothioate linkage |
| modified_base | 1 | |
| | | mod_base = OTHER |
| | | note = 2-O-methyl modified nucleoside |
| modified_base | 3 | |
| | | mod_base = OTHER |
| | | note = 2-O-methyl modified nucleoside |
| modified_base | 5 | |
| | | mod_base = OTHER |
| | | note = 2-O-methyl modified nucleoside |
| modified_base | 7 | |
| | | mod_base = OTHER |
| | | note = 2-O-methyl modified nucleoside |
| modified_base | 9 | |
| | | mod_base = OTHER |
| | | note = 2-O-methyl modified nucleoside |
| modified_base | 11 | |
| | | mod_base = OTHER |
| | | note = 2-O-methyl modified nucleoside |
| modified_base | 13 | |
| | | mod_base = OTHER |
| | | note = 2-O-methyl modified nucleoside |
| modified_base | 15 | |
| | | mod_base = OTHER |
| | | note = 2-O-methyl modified nucleoside |
| modified_base | 17 | |
| | | mod_base = OTHER |
| | | note = 2-O-methyl modified nucleoside |
| modified_base | 19 | |
| | | mod_base = OTHER |
| | | note = 2-O-methyl modified nucleoside |
| modified_base | 20 | |
| | | mod_base = OTHER |
| | | note = 2-O-methyl modified nucleoside |
| modified_base | 21 | |
| | | mod_base = OTHER |
| | | note = 2-O-methyl modified nucleoside |
| modified_base | 2 | |
| | | mod_base = OTHER |
| | | note = 2-fluoro-modified nucleoside |
| modified_base | 4 | |
| | | mod_base = OTHER |
| | | note = 2-fluoro-modified nucleoside |
| modified_base | 6 | |
| | | mod_base = OTHER |
| | | note = 2-fluoro-modified nucleoside |
| modified_base | 8 | |
| | | mod_base = OTHER |
| | | note = 2-fluoro-modified nucleoside |
| modified_base | 10 | |
| | | mod_base = OTHER |
| | | note = 2-fluoro-modified nucleoside |
| modified_base | 12 | |
| | | mod_base = OTHER |
| | | note = 2-fluoro-modified nucleoside |
| modified_base | 14 | |
| | | mod_base = OTHER |
| | | note = 2-fluoro-modified nucleoside |
| modified_base | 16 | |
| | | mod_base = OTHER |
| | | note = 2-fluoro-modified nucleoside |
| modified_base | 18 | |
| | | mod_base = OTHER |
| | | note = 2-fluoro-modified nucleoside |
| modified_base | 19^20 | |
| | | mod_base = OTHER |
| | | note = phosphorothioate linkage |
| modified_base | 20^21 | |
| | | mod_base = OTHER |
| | | note = phosphorothioate linkage |
| modified_base | 2^3 | |
| | | mod_base = OTHER |
| | | note = phosphorothioate linkage |
| SEQUENCE: 9 | | |
| ttctggtgtc ccttaaaaat t | | 21 |
| | | |
| SEQ ID NO: 10 | moltype = RNA length = 21 | |
| FEATURE | Location/Qualifiers | |

| | | |
|---|---|---|
| source | 1..21<br>mol_type = other RNA<br>organism = synthetic construct | |
| modified_base | 1^2<br>mod_base = OTHER<br>note = phosphorothioate linkage | |
| modified_base | 1<br>mod_base = OTHER<br>note = 2-O-methyl modified nucleoside | |
| modified_base | 3<br>mod_base = OTHER<br>note = 2-O-methyl modified nucleoside | |
| modified_base | 5<br>mod_base = OTHER<br>note = 2-O-methyl modified nucleoside | |
| modified_base | 7<br>mod_base = OTHER<br>note = 2-O-methyl modified nucleoside | |
| modified_base | 9<br>mod_base = OTHER<br>note = 2-O-methyl modified nucleoside | |
| modified_base | 11<br>mod_base = OTHER<br>note = 2-O-methyl modified nucleoside | |
| modified_base | 13<br>mod_base = OTHER<br>note = 2-O-methyl modified nucleoside | |
| modified_base | 15<br>mod_base = OTHER<br>note = 2-O-methyl modified nucleoside | |
| modified_base | 17<br>mod_base = OTHER<br>note = 2-O-methyl modified nucleoside | |
| modified_base | 19<br>mod_base = OTHER<br>note = 2-O-methyl modified nucleoside | |
| modified_base | 20<br>mod_base = OTHER<br>note = 2-O-methyl modified nucleoside | |
| modified_base | 21<br>mod_base = OTHER<br>note = 2-O-methyl modified nucleoside | |
| modified_base | 2<br>mod_base = OTHER<br>note = 2-fluoro-modified nucleoside | |
| modified_base | 4<br>mod_base = OTHER<br>note = 2-fluoro-modified nucleoside | |
| modified_base | 6<br>mod_base = OTHER<br>note = 2-fluoro-modified nucleoside | |
| modified_base | 8<br>mod_base = OTHER<br>note = 2-fluoro-modified nucleoside | |
| modified_base | 10<br>mod_base = OTHER<br>note = 2-fluoro-modified nucleoside | |
| modified_base | 12<br>mod_base = OTHER<br>note = 2-fluoro-modified nucleoside | |
| modified_base | 14<br>mod_base = OTHER<br>note = 2-fluoro-modified nucleoside | |
| modified_base | 16<br>mod_base = OTHER<br>note = 2-fluoro-modified nucleoside | |
| modified_base | 18<br>mod_base = OTHER<br>note = 2-fluoro-modified nucleoside | |
| modified_base | 19^20<br>mod_base = OTHER<br>note = phosphorothioate linkage | |
| modified_base | 20^21<br>mod_base = OTHER<br>note = phosphorothioate linkage | |
| modified_base | 2^3<br>mod_base = OTHER<br>note = phosphorothioate linkage | |
| SEQUENCE: 10 | | |

```
tgctaagaat gtgtcaaaat t                                                    21
```

| | | |
|---|---|---|
| SEQ ID NO: 11 | moltype = RNA length = 21 | |
| FEATURE | Location/Qualifiers | |
| source | 1..21 | |
| | mol_type = other RNA | |
| | organism = synthetic construct | |
| modified_base | 1^2 | |
| | mod_base = OTHER | |
| | note = phosphorothioate linkage | |
| modified_base | 1 | |
| | mod_base = OTHER | |
| | note = 2-O-methyl modified nucleoside | |
| modified_base | 3 | |
| | mod_base = OTHER | |
| | note = 2-O-methyl modified nucleoside | |
| modified_base | 5 | |
| | mod_base = OTHER | |
| | note = 2-O-methyl modified nucleoside | |
| modified_base | 7 | |
| | mod_base = OTHER | |
| | note = 2-O-methyl modified nucleoside | |
| modified_base | 9 | |
| | mod_base = OTHER | |
| | note = 2-O-methyl modified nucleoside | |
| modified_base | 11 | |
| | mod_base = OTHER | |
| | note = 2-O-methyl modified nucleoside | |
| modified_base | 13 | |
| | mod_base = OTHER | |
| | note = 2-O-methyl modified nucleoside | |
| modified_base | 15 | |
| | mod_base = OTHER | |
| | note = 2-O-methyl modified nucleoside | |
| modified_base | 17 | |
| | mod_base = OTHER | |
| | note = 2-O-methyl modified nucleoside | |
| modified_base | 19 | |
| | mod_base = OTHER | |
| | note = 2-O-methyl modified nucleoside | |
| modified_base | 20 | |
| | mod_base = OTHER | |
| | note = 2-O-methyl modified nucleoside | |
| modified_base | 21 | |
| | mod_base = OTHER | |
| | note = 2-O-methyl modified nucleoside | |
| modified_base | 2 | |
| | mod_base = OTHER | |
| | note = 2-fluoro-modified nucleoside | |
| modified_base | 4 | |
| | mod_base = OTHER | |
| | note = 2-fluoro-modified nucleoside | |
| modified_base | 6 | |
| | mod_base = OTHER | |
| | note = 2-fluoro-modified nucleoside | |
| modified_base | 8 | |
| | mod_base = OTHER | |
| | note = 2-fluoro-modified nucleoside | |
| modified_base | 10 | |
| | mod_base = OTHER | |
| | note = 2-fluoro-modified nucleoside | |
| modified_base | 12 | |
| | mod_base = OTHER | |
| | note = 2-fluoro-modified nucleoside | |
| modified_base | 14 | |
| | mod_base = OTHER | |
| | note = 2-fluoro-modified nucleoside | |
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |
| modified_base | 19^20 | |
| | mod_base = OTHER | |
| | note = phosphorothioate linkage | |
| modified_base | 20^21 | |
| | mod_base = OTHER | |
| | note = phosphorothioate linkage | |

```
modified_base            2^3
                         mod_base = OTHER
                         note = phosphorothioate linkage
SEQUENCE: 11
tgtgctaaga atgtgtcaat t                                              21

SEQ ID NO: 12            moltype = RNA   length = 21
FEATURE                  Location/Qualifiers
source                   1..21
                         mol_type = other RNA
                         organism = synthetic construct
modified_base            1^2
                         mod_base = OTHER
                         note = phosphorothioate linkage
modified_base            1
                         mod_base = OTHER
                         note = 2-O-methyl modified nucleoside
modified_base            3
                         mod_base = OTHER
                         note = 2-O-methyl modified nucleoside
modified_base            5
                         mod_base = OTHER
                         note = 2-O-methyl modified nucleoside
modified_base            7
                         mod_base = OTHER
                         note = 2-O-methyl modified nucleoside
modified_base            9
                         mod_base = OTHER
                         note = 2-O-methyl modified nucleoside
modified_base            11
                         mod_base = OTHER
                         note = 2-O-methyl modified nucleoside
modified_base            13
                         mod_base = OTHER
                         note = 2-O-methyl modified nucleoside
modified_base            15
                         mod_base = OTHER
                         note = 2-O-methyl modified nucleoside
modified_base            17
                         mod_base = OTHER
                         note = 2-O-methyl modified nucleoside
modified_base            19
                         mod_base = OTHER
                         note = 2-O-methyl modified nucleoside
modified_base            20
                         mod_base = OTHER
                         note = 2-O-methyl modified nucleoside
modified_base            21
                         mod_base = OTHER
                         note = 2-O-methyl modified nucleoside
modified_base            2
                         mod_base = OTHER
                         note = 2-fluoro-modified nucleoside
modified_base            4
                         mod_base = OTHER
                         note = 2-fluoro-modified nucleoside
modified_base            6
                         mod_base = OTHER
                         note = 2-fluoro-modified nucleoside
modified_base            8
                         mod_base = OTHER
                         note = 2-fluoro-modified nucleoside
modified_base            10
                         mod_base = OTHER
                         note = 2-fluoro-modified nucleoside
modified_base            12
                         mod_base = OTHER
                         note = 2-fluoro-modified nucleoside
modified_base            14
                         mod_base = OTHER
                         note = 2-fluoro-modified nucleoside
modified_base            16
                         mod_base = OTHER
                         note = 2-fluoro-modified nucleoside
modified_base            18
                         mod_base = OTHER
                         note = 2-fluoro-modified nucleoside
modified_base            20^21
                         mod_base = OTHER
```

```
                            note = phosphorothioate linkage
modified_base               19^20
                            mod_base = OTHER
                            note = phosphorothioate linkage
modified_base               2^3
                            mod_base = OTHER
                            note = phosphorothioate linkage
SEQUENCE: 12
tgttcagtgc taagaatgtt t                                              21

SEQ ID NO: 13               moltype = RNA   length = 21
FEATURE                     Location/Qualifiers
source                      1..21
                            mol_type = other RNA
                            organism = synthetic construct
modified_base               1^2
                            mod_base = OTHER
                            note = phosphorothioate linkage
modified_base               1
                            mod_base = OTHER
                            note = 2-O-methyl modified nucleoside
modified_base               3
                            mod_base = OTHER
                            note = 2-O-methyl modified nucleoside
modified_base               5
                            mod_base = OTHER
                            note = 2-O-methyl modified nucleoside
modified_base               7
                            mod_base = OTHER
                            note = 2-O-methyl modified nucleoside
modified_base               9
                            mod_base = OTHER
                            note = 2-O-methyl modified nucleoside
modified_base               11
                            mod_base = OTHER
                            note = 2-O-methyl modified nucleoside
modified_base               13
                            mod_base = OTHER
                            note = 2-O-methyl modified nucleoside
modified_base               15
                            mod_base = OTHER
                            note = 2-O-methyl modified nucleoside
modified_base               17
                            mod_base = OTHER
                            note = 2-O-methyl modified nucleoside
modified_base               19
                            mod_base = OTHER
                            note = 2-O-methyl modified nucleoside
modified_base               21
                            mod_base = OTHER
                            note = 2-O-methyl modified nucleoside
modified_base               20
                            mod_base = OTHER
                            note = 2-O-methyl modified nucleoside
modified_base               19^20
                            mod_base = OTHER
                            note = phosphorothioate linkage
modified_base               20^21
                            mod_base = OTHER
                            note = phosphorothioate linkage
modified_base               2
                            mod_base = OTHER
                            note = 2-fluoro-modified nucleoside
modified_base               4
                            mod_base = OTHER
                            note = 2-fluoro-modified nucleoside
modified_base               6
                            mod_base = OTHER
                            note = 2-fluoro-modified nucleoside
modified_base               8
                            mod_base = OTHER
                            note = 2-fluoro-modified nucleoside
modified_base               10
                            mod_base = OTHER
                            note = 2-fluoro-modified nucleoside
modified_base               12
                            mod_base = OTHER
                            note = 2-fluoro-modified nucleoside
modified_base               14
```

```
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           2^3
                        mod_base = OTHER
                        note = phosphorothioate linkage
SEQUENCE: 13
tcaaaagagt gactatgcat t                                              21

SEQ ID NO: 14           moltype = RNA   length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
```

```
modified_base        16
                     mod_base = OTHER
                     note = 2-fluoro-modified nucleoside
modified_base        18
                     mod_base = OTHER
                     note = 2-fluoro-modified nucleoside
modified_base        19^20
                     mod_base = OTHER
                     note = phosphorothioate linkage
modified_base        20^21
                     mod_base = OTHER
                     note = phosphorothioate linkage
modified_base        2^3
                     mod_base = OTHER
                     note = phosphorothioate linkage
SEQUENCE: 14
tccatattat gcagtagttt t                                              21

SEQ ID NO: 15        moltype = RNA  length = 21
FEATURE              Location/Qualifiers
source               1..21
                     mol_type = other RNA
                     note = GalNAc moiety-ETL17
                     organism = synthetic construct
modified_base        1
                     mod_base = OTHER
                     note = 2-O-methyl modified nucleoside
                     note = phosphorothioate linkage
modified_base        2
                     mod_base = OTHER
                     note = 2-O-methyl modified nucleoside
modified_base        3
                     mod_base = OTHER
                     note = 2-O-methyl modified nucleoside
modified_base        4
                     mod_base = OTHER
                     note = 2-O-methyl modified nucleoside
modified_base        5
                     mod_base = OTHER
                     note = 2-O-methyl modified nucleoside
modified_base        6
                     mod_base = OTHER
                     note = 2-O-methyl modified nucleoside
modified_base        7
                     mod_base = OTHER
                     note = 2-fluoro-modified nucleoside
modified_base        8
                     mod_base = OTHER
                     note = 2-fluoro-modified nucleoside
modified_base        9
                     mod_base = OTHER
                     note = 2-fluoro-modified nucleoside
modified_base        10
                     mod_base = OTHER
                     note = 2-fluoro-modified nucleoside
modified_base        11
                     mod_base = OTHER
                     note = 2-fluoro-modified nucleoside
modified_base        12
                     mod_base = OTHER
                     note = 2-O-methyl modified nucleoside
modified_base        13
                     mod_base = OTHER
                     note = 2-O-methyl modified nucleoside
modified_base        14
                     mod_base = OTHER
                     note = 2-O-methyl modified nucleoside
modified_base        15
                     mod_base = OTHER
                     note = 2-O-methyl modified nucleoside
modified_base        16
                     mod_base = OTHER
                     note = 2-O-methyl modified nucleoside
modified_base        17
                     mod_base = OTHER
                     note = 2-O-methyl modified nucleoside
modified_base        18
                     mod_base = OTHER
                     note = 2-O-methyl modified nucleoside
```

```
modified_base       19
                    mod_base = OTHER
                    note = 2-O-methyl modified nucleoside
modified_base       20
                    mod_base = OTHER
                    note = 2-O-methyl modified nucleoside
modified_base       21
                    mod_base = OTHER
                    note = 2-O-methyl modified nucleoside
modified_base       19^20
                    mod_base = OTHER
                    note = phosphorothioate linkage
modified_base       20^21
                    mod_base = OTHER
                    note = phosphorothioate linkage
SEQUENCE: 15
ggtcctggaa ggaattatat t                                              21

SEQ ID NO: 16       moltype = RNA   length = 22
FEATURE             Location/Qualifiers
source              1..22
                    mol_type = other RNA
                    note = GalNAc moiety-ETL17
                    organism = synthetic construct
modified_base       1
                    mod_base = OTHER
                    note = 2-fluoro-modified nucleoside
                    note = phosphorothioate linkage
modified_base       3
                    mod_base = OTHER
                    note = 2-fluoro-modified nucleoside
modified_base       5
                    mod_base = OTHER
                    note = 2-fluoro-modified nucleoside
modified_base       7
                    mod_base = OTHER
                    note = 2-fluoro-modified nucleoside
modified_base       10
                    mod_base = OTHER
                    note = 2-fluoro-modified nucleoside
modified_base       12
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       2
                    mod_base = OTHER
                    note = 2-O-methyl modified nucleoside
modified_base       4
                    mod_base = OTHER
                    note = 2-O-methyl modified nucleoside
modified_base       6
                    mod_base = OTHER
                    note = 2-O-methyl modified nucleoside
modified_base       8
                    mod_base = OTHER
                    note = 2-O-methyl modified nucleoside
modified_base       11
                    mod_base = OTHER
                    note = 2-O-methyl modified nucleoside
modified_base       13
                    mod_base = OTHER
                    note = 2-O-methyl modified nucleoside
modified_base       14
                    mod_base = OTHER
                    note = 2-O-methyl modified nucleoside
modified_base       15
                    mod_base = OTHER
                    note = 2-O-methyl modified nucleoside
modified_base       17
                    mod_base = OTHER
                    note = 2-O-methyl modified nucleoside
modified_base       19
                    mod_base = OTHER
                    note = 2-O-methyl modified nucleoside
```

```
modified_base          20
                       mod_base = OTHER
                       note = 2-O-methyl modified nucleoside
modified_base          21
                       mod_base = OTHER
                       note = 2-O-methyl modified nucleoside
modified_base          22
                       mod_base = OTHER
                       note = 2-O-methyl modified nucleoside
modified_base          20^21
                       mod_base = OTHER
                       note = phosphorothioate linkage
modified_base          21^22
                       mod_base = OTHER
                       note = phosphorothioate linkage
SEQUENCE: 16
aacttcttdg tcagacataa tt                                                  22

SEQ ID NO: 17          moltype = RNA  length = 21
FEATURE                Location/Qualifiers
source                 1..21
                       mol_type = other RNA
                       note = GalNAc moiety-ETL17
                       organism = synthetic construct
modified_base          1
                       mod_base = OTHER
                       note = phosphorothioate linkage
                       note = 2-O-methyl modified nucleoside
modified_base          2
                       mod_base = OTHER
                       note = 2-O-methyl modified nucleoside
modified_base          3
                       mod_base = OTHER
                       note = 2-O-methyl modified nucleoside
modified_base          4
                       mod_base = OTHER
                       note = 2-O-methyl modified nucleoside
modified_base          5
                       mod_base = OTHER
                       note = 2-fluoro-modified nucleoside
modified_base          6
                       mod_base = OTHER
                       note = 2-fluoro-modified nucleoside
modified_base          7
                       mod_base = OTHER
                       note = 2-O-methyl modified nucleoside
modified_base          8
                       mod_base = OTHER
                       note = 2-fluoro-modified nucleoside
modified_base          9
                       mod_base = OTHER
                       note = 2-fluoro-modified nucleoside
modified_base          10
                       mod_base = OTHER
                       note = 2-O-methyl modified nucleoside
modified_base          11
                       mod_base = OTHER
                       note = 2-O-methyl modified nucleoside
modified_base          12
                       mod_base = OTHER
                       note = 2-O-methyl modified nucleoside
modified_base          13
                       mod_base = OTHER
                       note = 2-O-methyl modified nucleoside
modified_base          14
                       mod_base = OTHER
                       note = 2-O-methyl modified nucleoside
modified_base          15
                       mod_base = OTHER
                       note = 2-O-methyl modified nucleoside
modified_base          16
                       mod_base = OTHER
                       note = 2-O-methyl modified nucleoside
modified_base          17
                       mod_base = OTHER
                       note = 2-O-methyl modified nucleoside
modified_base          18
                       mod_base = OTHER
                       note = 2-O-methyl modified nucleoside
```

```
modified_base        19
                     mod_base = OTHER
                     note = 2-O-methyl modified nucleoside
modified_base        20
                     mod_base = OTHER
                     note = 2-O-methyl modified nucleoside
modified_base        21
                     mod_base = OTHER
                     note = 2-O-methyl modified nucleoside
modified_base        19^20
                     mod_base = OTHER
                     note = phosphorothioate linkage
modified_base        20^21
                     mod_base = OTHER
                     note = phosphorothioate linkage
SEQUENCE: 17
cttcttgtca gacataaaat t                                               21

SEQ ID NO: 18        moltype = RNA  length = 21
FEATURE              Location/Qualifiers
source               1..21
                     mol_type = other RNA
                     note = GalNAc moiety-ETL17
                     organism = synthetic construct
modified_base        1
                     mod_base = OTHER
                     note = phosphorothioate linkage
                     note = 2-O-methyl modified nucleoside
modified_base        2
                     mod_base = OTHER
                     note = 2-O-methyl modified nucleoside
modified_base        3
                     mod_base = OTHER
                     note = 2-O-methyl modified nucleoside
modified_base        4
                     mod_base = OTHER
                     note = 2-O-methyl modified nucleoside
modified_base        5
                     mod_base = OTHER
                     note = 2-O-methyl modified nucleoside
modified_base        6
                     mod_base = OTHER
                     note = 2-fluoro-modified nucleoside
modified_base        7
                     mod_base = OTHER
                     note = 2-fluoro-modified nucleoside
modified_base        8
                     mod_base = OTHER
                     note = 2-fluoro-modified nucleoside
modified_base        9
                     mod_base = OTHER
                     note = 2-fluoro-modified nucleoside
modified_base        10
                     mod_base = OTHER
                     note = 2-fluoro-modified nucleoside
modified_base        11
                     mod_base = OTHER
                     note = 2-O-methyl modified nucleoside
modified_base        12
                     mod_base = OTHER
                     note = 2-O-methyl modified nucleoside
modified_base        13
                     mod_base = OTHER
                     note = 2-O-methyl modified nucleoside
modified_base        14
                     mod_base = OTHER
                     note = 2-O-methyl modified nucleoside
modified_base        15
                     mod_base = OTHER
                     note = 2-O-methyl modified nucleoside
modified_base        16
                     mod_base = OTHER
                     note = 2-O-methyl modified nucleoside
modified_base        17
                     mod_base = OTHER
                     note = 2-O-methyl modified nucleoside
modified_base        18
                     mod_base = OTHER
                     note = 2-O-methyl modified nucleoside
```

```
modified_base      19
                   mod_base = OTHER
                   note = 2-O-methyl modified nucleoside
modified_base      20
                   mod_base = OTHER
                   note = 2-O-methyl modified nucleoside
modified_base      21
                   mod_base = OTHER
                   note = 2-O-methyl modified nucleoside
modified_base      19^20
                   mod_base = OTHER
                   note = 2-O-methyl modified nucleoside
modified_base      20^21
                   mod_base = OTHER
                   note = 2-O-methyl modified nucleoside
SEQUENCE: 18
caaccaggag tgtaacatat t                                              21

SEQ ID NO: 19      moltype = RNA  length = 21
FEATURE            Location/Qualifiers
source             1..21
                   mol_type = other RNA
                   organism = synthetic construct
modified_base      1^2
                   mod_base = OTHER
                   note = phosphorothioate linkage
modified_base      1
                   mod_base = OTHER
                   note = 2-O-methyl modified nucleoside
modified_base      3
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      9
                   mod_base = OTHER
                   note = 2-O-methyl modified nucleoside
modified_base      11
                   mod_base = OTHER
                   note = 2-O-methyl modified nucleoside
modified_base      13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
modified_base      19
                   mod_base = OTHER
                   note = 2-O-methyl modified nucleoside
modified_base      20
                   mod_base = OTHER
                   note = 2-O-methyl modified nucleoside
modified_base      21
                   mod_base = OTHER
                   note = 2-O-methyl modified nucleoside
modified_base      2
                   mod_base = OTHER
                   note = 2-fluoro-modified nucleoside
modified_base      4
                   mod_base = OTHER
                   note = 2-fluoro-modified nucleoside
modified_base      6
                   mod_base = OTHER
                   note = 2-fluoro-modified nucleoside
modified_base      8
                   mod_base = OTHER
                   note = 2-fluoro-modified nucleoside
modified_base      10
                   mod_base = OTHER
                   note = 2-fluoro-modified nucleoside
modified_base      12
                   mod_base = OTHER
```

```
                         note = 2-fluoro-modified nucleoside
modified_base            14
                         mod_base = OTHER
                         note = 2-fluoro-modified nucleoside
modified_base            16
                         mod_base = OTHER
                         note = 2-fluoro-modified nucleoside
modified_base            18
                         mod_base = OTHER
                         note = 2-fluoro-modified nucleoside
modified_base            19^20
                         mod_base = OTHER
                         note = phosphorothioate linkage
modified_base            20^21
                         mod_base = OTHER
                         note = phosphorothioate linkage
modified_base            2^3
                         mod_base = OTHER
                         note = phosphorothioate linkage
SEQUENCE: 19
tataattcct tccaggacct t                                            21

SEQ ID NO: 20            moltype = RNA  length = 21
FEATURE                  Location/Qualifiers
source                   1..21
                         mol_type = other RNA
                         organism = synthetic construct
modified_base            1^2
                         mod_base = OTHER
                         note = phosphorothioate linkage
modified_base            1
                         mod_base = OTHER
                         note = 2-O-methyl modified nucleoside
modified_base            3
                         mod_base = OTHER
                         note = 2-O-methyl modified nucleoside
modified_base            5
                         mod_base = OTHER
                         note = 2-O-methyl modified nucleoside
modified_base            7
                         mod_base = OTHER
                         note = 2-O-methyl modified nucleoside
modified_base            9
                         mod_base = OTHER
                         note = 2-O-methyl modified nucleoside
modified_base            11
                         mod_base = OTHER
                         note = 2-O-methyl modified nucleoside
modified_base            13
                         mod_base = OTHER
                         note = 2-O-methyl modified nucleoside
modified_base            15
                         mod_base = OTHER
                         note = 2-O-methyl modified nucleoside
modified_base            17
                         mod_base = OTHER
                         note = 2-O-methyl modified nucleoside
modified_base            19
                         mod_base = OTHER
                         note = 2-O-methyl modified nucleoside
modified_base            20
                         mod_base = OTHER
                         note = 2-O-methyl modified nucleoside
modified_base            21
                         mod_base = OTHER
                         note = 2-O-methyl modified nucleoside
modified_base            2
                         mod_base = OTHER
                         note = 2-fluoro-modified nucleoside
modified_base            4
                         mod_base = OTHER
                         note = 2-fluoro-modified nucleoside
modified_base            6
                         mod_base = OTHER
                         note = 2-fluoro-modified nucleoside
modified_base            8
                         mod_base = OTHER
                         note = 2-fluoro-modified nucleoside
modified_base            10
```

```
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 20
ttatgtctga caagaagttt t                                              21

SEQ ID NO: 21           moltype = RNA  length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
```

```
modified_base       8
                    mod_base = OTHER
                    note = 2-fluoro-modified nucleoside
modified_base       10
                    mod_base = OTHER
                    note = 2-fluoro-modified nucleoside
modified_base       12
                    mod_base = OTHER
                    note = 2-fluoro-modified nucleoside
modified_base       14
                    mod_base = OTHER
                    note = 2-fluoro-modified nucleoside
modified_base       16
                    mod_base = OTHER
                    note = 2-fluoro-modified nucleoside
modified_base       18
                    mod_base = OTHER
                    note = 2-fluoro-modified nucleoside
modified_base       19^20
                    mod_base = OTHER
                    note = phosphorothioate linkage
modified_base       20^21
                    mod_base = OTHER
                    note = phosphorothioate linkage
modified_base       2^3
                    mod_base = OTHER
                    note = phosphorothioate linkage
SEQUENCE: 21
tttatgtct gacaagaagt t                                      21

SEQ ID NO: 22       moltype = RNA  length = 21
FEATURE             Location/Qualifiers
source              1..21
                    mol_type = other RNA
                    organism = synthetic construct
modified_base       1^2
                    mod_base = OTHER
                    note = phosphorothioate linkage
modified_base       1
                    mod_base = OTHER
                    note = 2-O-methyl modified nucleoside
modified_base       3
                    mod_base = OTHER
                    note = 2-O-methyl modified nucleoside
modified_base       5
                    mod_base = OTHER
                    note = 2-O-methyl modified nucleoside
modified_base       7
                    mod_base = OTHER
                    note = 2-O-methyl modified nucleoside
modified_base       9
                    mod_base = OTHER
                    note = 2-O-methyl modified nucleoside
modified_base       11
                    mod_base = OTHER
                    note = 2-O-methyl modified nucleoside
modified_base       13
                    mod_base = OTHER
                    note = 2-O-methyl modified nucleoside
modified_base       15
                    mod_base = OTHER
                    note = 2-O-methyl modified nucleoside
modified_base       17
                    mod_base = OTHER
                    note = 2-O-methyl modified nucleoside
modified_base       19
                    mod_base = OTHER
                    note = 2-O-methyl modified nucleoside
modified_base       20
                    mod_base = OTHER
                    note = 2-O-methyl modified nucleoside
modified_base       21
                    mod_base = OTHER
                    note = 2-O-methyl modified nucleoside
modified_base       2
                    mod_base = OTHER
                    note = 2-fluoro-modified nucleoside
modified_base       4
                    mod_base = OTHER
```

```
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 22
tatgttacac tcctggttgt t                                                    21

SEQ ID NO: 23           moltype = RNA  length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = phosphorothioate linkage
                        note = 2-O-methyl modified nucleoside
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-O-methyl modified nucleoside
modified_base           6
                        mod_base = OTHER
                        note = 2-O-methyl modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
```

```
                              note = 2-O-methyl modified nucleoside
modified_base                 14
                              mod_base = OTHER
                              note = 2-O-methyl modified nucleoside
modified_base                 15
                              mod_base = OTHER
                              note = 2-O-methyl modified nucleoside
modified_base                 16
                              mod_base = OTHER
                              note = 2-O-methyl modified nucleoside
modified_base                 17
                              mod_base = OTHER
                              note = 2-O-methyl modified nucleoside
modified_base                 18
                              mod_base = OTHER
                              note = 2-O-methyl modified nucleoside
modified_base                 19
                              mod_base = OTHER
                              note = 2-O-methyl modified nucleoside
modified_base                 20
                              mod_base = OTHER
                              note = 2-O-methyl modified nucleoside
modified_base                 21
                              mod_base = OTHER
                              note = 2-O-methyl modified nucleoside
modified_base                 19^20
                              mod_base = OTHER
                              note = phosphorothioate linkage
modified_base                 20^21
                              mod_base = OTHER
                              note = phosphorothioate linkage
SEQUENCE: 23
gtatctccag aatgttatat t                                                     21

SEQ ID NO: 24              moltype = RNA   length = 21
FEATURE                    Location/Qualifiers
source                     1..21
                              mol_type = other RNA
                              note = GalNAc moiety-ETL17
                              organism = synthetic construct
modified_base              1
                              mod_base = OTHER
                              note = 2-O-methyl modified nucleoside
                              note = phosphorothioate linkage
modified_base              2
                              mod_base = OTHER
                              note = 2-O-methyl modified nucleoside
modified_base              3
                              mod_base = OTHER
                              note = 2-O-methyl modified nucleoside
modified_base              4
                              mod_base = OTHER
                              note = 2-O-methyl modified nucleoside
modified_base              5
                              mod_base = OTHER
                              note = 2-O-methyl modified nucleoside
modified_base              6
                              mod_base = OTHER
                              note = 2-O-methyl modified nucleoside
modified_base              7
                              mod_base = OTHER
                              note = 2-O-methyl modified nucleoside
modified_base              8
                              mod_base = OTHER
                              note = 2-fluoro-modified nucleoside
modified_base              9
                              mod_base = OTHER
                              note = 2-fluoro-modified nucleoside
modified_base              10
                              mod_base = OTHER
                              note = 2-fluoro-modified nucleoside
modified_base              11
                              mod_base = OTHER
                              note = 2-fluoro-modified nucleoside
modified_base              12
                              mod_base = OTHER
                              note = 2-O-methyl modified nucleoside
modified_base              13
                              mod_base = OTHER
```

```
                        note = 2-O-methyl modified nucleoside
modified_base           14
                        mod_base = OTHER
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 24
acttcctgga atcgatacat t                                             21

SEQ ID NO: 25           moltype = RNA   length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = 2-O-methyl modified nucleoside
                        note = phosphorothioate linkage
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-O-methyl modified nucleoside
modified_base           6
                        mod_base = OTHER
                        note = 2-O-methyl modified nucleoside
modified_base           7
                        mod_base = OTHER
                        note = 2-fluoro-modified nucleoside
modified_base           8
                        mod_base = OTHER
                        note = 2-fluoro-modified nucleoside
modified_base           9
                        mod_base = OTHER
                        note = 2-fluoro-modified nucleoside
modified_base           10
                        mod_base = OTHER
                        note = 2-fluoro-modified nucleoside
modified_base           11
                        mod_base = OTHER
                        note = 2-O-methyl modified nucleoside
modified_base           12
                        mod_base = OTHER
                        note = 2-O-methyl modified nucleoside
modified_base           13
                        mod_base = OTHER
```

|  |  |
|---|---|
| | note = 2-O-methyl modified nucleoside |
| modified_base | 14 |
| | mod_base = OTHER |
| | note = 2-O-methyl modified nucleoside |
| modified_base | 15 |
| | mod_base = OTHER |
| | note = 2-O-methyl modified nucleoside |
| modified_base | 16 |
| | mod_base = OTHER |
| | note = 2-O-methyl modified nucleoside |
| modified_base | 17 |
| | mod_base = OTHER |
| | note = 2-O-methyl modified nucleoside |
| modified_base | 18 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 19^20 |
| | mod_base = OTHER |
| | note = phosphorothioate linkage |
| modified_base | 20^21 |
| | mod_base = OTHER |
| | note = phosphorothioate linkage |
| SEQUENCE: 25 | |
| cttcctggaa tcgatactat t | 21 |
| | |
| SEQ ID NO: 26 | moltype = RNA  length = 21 |
| FEATURE | Location/Qualifiers |
| source | 1..21 |
| | mol_type = other RNA |
| | note = GalNAc moiety-ETL17 |
| | organism = synthetic construct |
| modified_base | 1 |
| | mod_base = OTHER |
| | note = phosphorothioate linkage |
| | note = 2-O-methyl modified nucleoside |
| modified_base | 2 |
| | mod_base = OTHER |
| | note = 2-O-methyl modified nucleoside |
| modified_base | 3 |
| | mod_base = OTHER |
| | note = 2-O-methyl modified nucleoside |
| modified_base | 4 |
| | mod_base = OTHER |
| | note = 2-O-methyl modified nucleoside |
| modified_base | 5 |
| | mod_base = OTHER |
| | note = 2-fluoro-modified nucleoside |
| modified_base | 6 |
| | mod_base = OTHER |
| | note = 2-fluoro-modified nucleoside |
| modified_base | 7 |
| | mod_base = OTHER |
| | note = 2-O-methyl modified nucleoside |
| modified_base | 8 |
| | mod_base = OTHER |
| | note = 2-O-methyl modified nucleoside |
| modified_base | 9 |
| | mod_base = OTHER |
| | note = 2-fluoro-modified nucleoside |
| modified_base | 10 |
| | mod_base = OTHER |
| | note = 2-fluoro-modified nucleoside |
| modified_base | 11 |
| | mod_base = OTHER |
| | note = 2-O-methyl modified nucleoside |
| modified_base | 12 |
| | mod_base = OTHER |
| | note = 2-O-methyl modified nucleoside |
| modified_base | 13 |
| | mod_base = OTHER |

```
                        note = 2-O-methyl modified nucleoside
modified_base           14
                        mod_base = OTHER
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 26
ctggaatcga tacttgtaat t                                            21

SEQ ID NO: 27           moltype = RNA  length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = 2-O-methyl modified nucleoside
                        note = phosphorothioate linkage
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-fluoro-modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
```

```
                        note = 2-O-methyl modified nucleoside
modified_base           14
                        mod_base = OTHER
                        note = 2-O-methyl modified nucleoside
modified_base           16
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 27
ggaatcgata cttgtattat t                                          21

SEQ ID NO: 28           moltype = RNA   length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = phosphorothioate linkage
                        note = 2-O-methyl modified nucleoside
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-fluoro-modified nucleoside
modified_base           7
                        mod_base = OTHER
                        note = 2-O-methyl modified nucleoside
modified_base           8
                        mod_base = OTHER
                        note = 2-fluoro-modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-O-methyl modified nucleoside
modified_base           12
                        mod_base = OTHER
                        note = 2-O-methyl modified nucleoside
modified_base           13
                        mod_base = OTHER
```

|                | |
|---|---|
| | note = 2-O-methyl modified nucleoside |
| modified_base | 14 |
| | mod_base = OTHER |
| | note = 2-O-methyl modified nucleoside |
| modified_base | 15 |
| | mod_base = OTHER |
| | note = 2-O-methyl modified nucleoside |
| modified_base | 16 |
| | mod_base = OTHER |
| | note = 2-O-methyl modified nucleoside |
| modified_base | 17 |
| | mod_base = OTHER |
| | note = 2-O-methyl modified nucleoside |
| modified_base | 18 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 19^20 |
| | mod_base = OTHER |
| | note = phosphorothioate linkage |
| modified_base | 20^21 |
| | mod_base = OTHER |
| | note = phosphorothioate linkage |
| SEQUENCE: 28 | |
| gatgctttct acaaaggtat t | 21 |
| | |
| SEQ ID NO: 29 | moltype = RNA  length = 21 |
| FEATURE | Location/Qualifiers |
| source | 1..21 |
| | mol_type = other RNA |
| | note = GalNAc moiety-ETL17 |
| | organism = synthetic construct |
| modified_base | 1 |
| | mod_base = OTHER |
| | note = phosphorothioate linkage |
| | note = 2-O-methyl modified nucleoside |
| modified_base | 2 |
| | mod_base = OTHER |
| | note = 2-O-methyl modified nucleoside |
| modified_base | 3 |
| | mod_base = OTHER |
| | note = 2-O-methyl modified nucleoside |
| modified_base | 4 |
| | mod_base = OTHER |
| | note = 2-O-methyl modified nucleoside |
| modified_base | 5 |
| | mod_base = OTHER |
| | note = 2-fluoro-modified nucleoside |
| modified_base | 6 |
| | mod_base = OTHER |
| | note = 2-fluoro-modified nucleoside |
| modified_base | 7 |
| | mod_base = OTHER |
| | note = 2-O-methyl modified nucleoside |
| modified_base | 8 |
| | mod_base = OTHER |
| | note = 2-O-methyl modified nucleoside |
| modified_base | 9 |
| | mod_base = OTHER |
| | note = 2-fluoro-modified nucleoside |
| modified_base | 10 |
| | mod_base = OTHER |
| | note = 2-fluoro-modified nucleoside |
| modified_base | 11 |
| | mod_base = OTHER |
| | note = 2-O-methyl modified nucleoside |
| modified_base | 12 |
| | mod_base = OTHER |
| | note = 2-O-methyl modified nucleoside |
| modified_base | 13 |
| | mod_base = OTHER |

|   |   |
|---|---|
| | note = 2-O-methyl modified nucleoside |
| modified_base | 14 |
| | mod_base = OTHER |
| | note = 2-O-methyl modified nucleoside |
| modified_base | 15 |
| | mod_base = OTHER |
| | note = 2-O-methyl modified nucleoside |
| modified_base | 16 |
| | mod_base = OTHER |
| | note = 2-O-methyl modified nucleoside |
| modified_base | 17 |
| | mod_base = OTHER |
| | note = 2-O-methyl modified nucleoside |
| modified_base | 18 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 19^20 |
| | mod_base = OTHER |
| | note = phosphorothioate linkage |
| modified_base | 20^21 |
| | mod_base = OTHER |
| | note = phosphorothioate linkage |
| SEQUENCE: 29 | |
| agaaaagcag aacggtgaat t | 21 |
| | |
| SEQ ID NO: 30 | moltype = RNA length = 22 |
| FEATURE | Location/Qualifiers |
| source | 1..22 |
| | mol_type = other RNA |
| | note = GalNAc moiety-ETL17 |
| | organism = synthetic construct |
| modified_base | 1 |
| | mod_base = OTHER |
| | note = phosphorothioate linkage |
| | note = 2-O-methyl modified nucleoside |
| modified_base | 2 |
| | mod_base = OTHER |
| | note = 2-O-methyl modified nucleoside |
| modified_base | 3 |
| | mod_base = OTHER |
| | note = 2-O-methyl modified nucleoside |
| modified_base | 4 |
| | mod_base = OTHER |
| | note = 2-O-methyl modified nucleoside |
| modified_base | 5 |
| | mod_base = OTHER |
| | note = 2-O-methyl modified nucleoside |
| modified_base | 6 |
| | mod_base = OTHER |
| | note = 2-O-methyl modified nucleoside |
| modified_base | 7 |
| | mod_base = OTHER |
| | note = 2-fluoro-modified nucleoside |
| modified_base | 8 |
| | mod_base = OTHER |
| | note = 2-fluoro-modified nucleoside |
| modified_base | 10 |
| | mod_base = OTHER |
| | note = 2-fluoro-modified nucleoside |
| modified_base | 11 |
| | mod_base = OTHER |
| | note = 2-fluoro-modified nucleoside |
| modified_base | 12 |
| | mod_base = OTHER |
| | note = 2-O-methyl modified nucleoside |
| modified_base | 13 |
| | mod_base = OTHER |
| | note = 2-O-methyl modified nucleoside |
| modified_base | 14 |
| | mod_base = OTHER |

```
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           21^22
                        mod_base = OTHER
                        note = phosphorothioate linkage
modified_base           20^21
                        mod_base = OTHER
                        note = phosphorothioate linkage
modified_base           22
                        mod_base = OTHER
                        note = 2-O-methyl modified nucleoside
SEQUENCE: 30
aagcagaaadc ggtgaaagta tt                                          22

SEQ ID NO: 31           moltype = RNA   length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = phosphorothioate linkage
                        note = 2-O-methyl modified nucleoside
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-fluoro-modified nucleoside
modified_base           7
                        mod_base = OTHER
                        note = 2-O-methyl modified nucleoside
modified_base           8
                        mod_base = OTHER
                        note = 2-fluoro-modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
```

```
                        note = 2-O-methyl modified nucleoside
modified_base           14
                        mod_base = OTHER
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 31
agtgggagat acattggaat t                                            21

SEQ ID NO: 32           moltype = RNA   length = 21
FEATURE                 Location/Qualifiers
source                  1..21
                        mol_type = other RNA
                        note = GalNAc moiety-ETL17
                        organism = synthetic construct
modified_base           1
                        mod_base = OTHER
                        note = 2-O-methyl modified nucleoside
                        note = phosphorothioate linkage
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-fluoro-modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
```

| | | |
|---|---|---|
| | note | = 2-O-methyl modified nucleoside |
| modified_base | 14 | |
| | mod_base | = OTHER |
| | note | = 2-O-methyl modified nucleoside |
| modified_base | 15 | |
| | mod_base | = OTHER |
| | note | = 2-O-methyl modified nucleoside |
| modified_base | 16 | |
| | mod_base | = OTHER |
| | note | = 2-O-methyl modified nucleoside |
| modified_base | 17 | |
| | mod_base | = OTHER |
| | note | = 2-O-methyl modified nucleoside |
| modified_base | 18 | |
| | mod_base | = OTHER |
| | note | = 2-O-methyl modified nucleoside |
| modified_base | 19 | |
| | mod_base | = OTHER |
| | note | = 2-O-methyl modified nucleoside |
| modified_base | 20 | |
| | mod_base | = OTHER |
| | note | = 2-O-methyl modified nucleoside |
| modified_base | 21 | |
| | mod_base | = OTHER |
| | note | = 2-O-methyl modified nucleoside |
| modified_base | 19^20 | |
| | mod_base | = OTHER |
| | note | = phosphorothioate linkage |
| modified_base | 20^21 | |
| | mod_base | = OTHER |
| | note | = phosphorothioate linkage |
| SEQUENCE: 32 | | |
| tgggagatac attggatcat t | | 21 |
| | | |
| SEQ ID NO: 33 | moltype = RNA  length = 21 | |
| FEATURE | Location/Qualifiers | |
| source | 1..21 | |
| | mol_type | = other RNA |
| | organism | = synthetic construct |
| modified_base | 1^2 | |
| | mod_base | = OTHER |
| | note | = phosphorothioate linkage |
| modified_base | 1 | |
| | mod_base | = OTHER |
| | note | = 2-O-methyl modified nucleoside |
| modified_base | 3 | |
| | mod_base | = OTHER |
| | note | = 2-O-methyl modified nucleoside |
| modified_base | 5 | |
| | mod_base | = OTHER |
| | note | = 2-O-methyl modified nucleoside |
| modified_base | 7 | |
| | mod_base | = OTHER |
| | note | = 2-O-methyl modified nucleoside |
| modified_base | 9 | |
| | mod_base | = OTHER |
| | note | = 2-O-methyl modified nucleoside |
| modified_base | 11 | |
| | mod_base | = OTHER |
| | note | = 2-O-methyl modified nucleoside |
| modified_base | 13 | |
| | mod_base | = OTHER |
| | note | = 2-O-methyl modified nucleoside |
| modified_base | 15 | |
| | mod_base | = OTHER |
| | note | = 2-O-methyl modified nucleoside |
| modified_base | 17 | |
| | mod_base | = OTHER |
| | note | = 2-O-methyl modified nucleoside |
| modified_base | 19 | |
| | mod_base | = OTHER |
| | note | = 2-O-methyl modified nucleoside |
| modified_base | 20 | |
| | mod_base | = OTHER |
| | note | = 2-O-methyl modified nucleoside |
| modified_base | 21 | |
| | mod_base | = OTHER |
| | note | = 2-O-methyl modified nucleoside |
| modified_base | 2 | |

```
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 33
tataacattc tggagatact t                                              21

SEQ ID NO: 34           moltype = RNA   length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
```

-continued

| | |
|---|---|
| modified_base | 21<br>mod_base = OTHER<br>note = 2-O-methyl modified nucleoside |
| modified_base | 2<br>mod_base = OTHER<br>note = 2-fluoro-modified nucleoside |
| modified_base | 4<br>mod_base = OTHER<br>note = 2-fluoro-modified nucleoside |
| modified_base | 6<br>mod_base = OTHER<br>note = 2-fluoro-modified nucleoside |
| modified_base | 8<br>mod_base = OTHER<br>note = 2-fluoro-modified nucleoside |
| modified_base | 10<br>mod_base = OTHER<br>note = 2-fluoro-modified nucleoside |
| modified_base | 12<br>mod_base = OTHER<br>note = 2-fluoro-modified nucleoside |
| modified_base | 14<br>mod_base = OTHER<br>note = 2-fluoro-modified nucleoside |
| modified_base | 16<br>mod_base = OTHER<br>note = 2-fluoro-modified nucleoside |
| modified_base | 18<br>mod_base = OTHER<br>note = 2-fluoro-modified nucleoside |
| modified_base | 19^20<br>mod_base = OTHER<br>note = phosphorothioate linkage |
| modified_base | 20^21<br>mod_base = OTHER<br>note = phosphorothioate linkage |
| modified_base | 2^3<br>mod_base = OTHER<br>note = phosphorothioate linkage |

SEQUENCE: 34
tgtatcgatt ccaggaagtt t                                         21

| | |
|---|---|
| SEQ ID NO: 35<br>FEATURE<br>source | moltype = RNA   length = 21<br>Location/Qualifiers<br>1..21<br>mol_type = other RNA<br>organism = synthetic construct |
| modified_base | 1^2<br>mod_base = OTHER<br>note = phosphorothioate linkage |
| modified_base | 1<br>mod_base = OTHER<br>note = 2-O-methyl modified nucleoside |
| modified_base | 3<br>mod_base = OTHER<br>note = 2-O-methyl modified nucleoside |
| modified_base | 5<br>mod_base = OTHER<br>note = 2-O-methyl modified nucleoside |
| modified_base | 7<br>mod_base = OTHER<br>note = 2-O-methyl modified nucleoside |
| modified_base | 9<br>mod_base = OTHER<br>note = 2-O-methyl modified nucleoside |
| modified_base | 11<br>mod_base = OTHER<br>note = 2-O-methyl modified nucleoside |
| modified_base | 13<br>mod_base = OTHER<br>note = 2-O-methyl modified nucleoside |
| modified_base | 15<br>mod_base = OTHER<br>note = 2-O-methyl modified nucleoside |
| modified_base | 17<br>mod_base = OTHER<br>note = 2-O-methyl modified nucleoside |
| modified_base | 19<br>mod_base = OTHER |

```
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 35
tagtatcgat tccaggaagt t                                                  21

SEQ ID NO: 36           moltype = RNA  length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
```

|  |  |  |
|---|---|---|
|  | mod_base = OTHER | |
|  | note = 2-O-methyl modified nucleoside | |
| modified_base | 19 | |
|  | mod_base = OTHER | |
|  | note = 2-O-methyl modified nucleoside | |
| modified_base | 20 | |
|  | mod_base = OTHER | |
|  | note = 2-O-methyl modified nucleoside | |
| modified_base | 21 | |
|  | mod_base = OTHER | |
|  | note = 2-O-methyl modified nucleoside | |
| modified_base | 2 | |
|  | mod_base = OTHER | |
|  | note = 2-fluoro-modified nucleoside | |
| modified_base | 4 | |
|  | mod_base = OTHER | |
|  | note = 2-fluoro-modified nucleoside | |
| modified_base | 6 | |
|  | mod_base = OTHER | |
|  | note = 2-fluoro-modified nucleoside | |
| modified_base | 8 | |
|  | mod_base = OTHER | |
|  | note = 2-fluoro-modified nucleoside | |
| modified_base | 10 | |
|  | mod_base = OTHER | |
|  | note = 2-fluoro-modified nucleoside | |
| modified_base | 12 | |
|  | mod_base = OTHER | |
|  | note = 2-fluoro-modified nucleoside | |
| modified_base | 14 | |
|  | mod_base = OTHER | |
|  | note = 2-fluoro-modified nucleoside | |
| modified_base | 16 | |
|  | mod_base = OTHER | |
|  | note = 2-fluoro-modified nucleoside | |
| modified_base | 18 | |
|  | mod_base = OTHER | |
|  | note = 2-fluoro-modified nucleoside | |
| modified_base | 19^20 | |
|  | mod_base = OTHER | |
|  | note = phosphorothioate linkage | |
| modified_base | 20^21 | |
|  | mod_base = OTHER | |
|  | note = phosphorothioate linkage | |
| modified_base | 2^3 | |
|  | mod_base = OTHER | |
|  | note = phosphorothioate linkage | |
| SEQUENCE: 36 | | |
| ttacaagtat cgattccagt t | | 21 |
|  |  |  |
| SEQ ID NO: 37 | moltype = RNA  length = 21 | |
| FEATURE | Location/Qualifiers | |
| source | 1..21 | |
|  | mol_type = other RNA | |
|  | organism = synthetic construct | |
| modified_base | 1^2 | |
|  | mod_base = OTHER | |
|  | note = phosphorothioate linkage | |
| modified_base | 1 | |
|  | mod_base = OTHER | |
|  | note = 2-O-methyl modified nucleoside | |
| modified_base | 3 | |
|  | mod_base = OTHER | |
|  | note = 2-O-methyl modified nucleoside | |
| modified_base | 5 | |
|  | mod_base = OTHER | |
|  | note = 2-O-methyl modified nucleoside | |
| modified_base | 7 | |
|  | mod_base = OTHER | |
|  | note = 2-O-methyl modified nucleoside | |
| modified_base | 9 | |
|  | mod_base = OTHER | |
|  | note = 2-O-methyl modified nucleoside | |
| modified_base | 11 | |
|  | mod_base = OTHER | |
|  | note = 2-O-methyl modified nucleoside | |
| modified_base | 13 | |
|  | mod_base = OTHER | |
|  | note = 2-O-methyl modified nucleoside | |

```
modified_base        15
                     mod_base = OTHER
                     note = 2-O-methyl modified nucleoside
modified_base        17
                     mod_base = OTHER
                     note = 2-O-methyl modified nucleoside
modified_base        19
                     mod_base = OTHER
                     note = 2-O-methyl modified nucleoside
modified_base        20
                     mod_base = OTHER
                     note = 2-O-methyl modified nucleoside
modified_base        21
                     mod_base = OTHER
                     note = 2-O-methyl modified nucleoside
modified_base        2
                     mod_base = OTHER
                     note = 2-fluoro-modified nucleoside
modified_base        4
                     mod_base = OTHER
                     note = 2-fluoro-modified nucleoside
modified_base        6
                     mod_base = OTHER
                     note = 2-fluoro-modified nucleoside
modified_base        8
                     mod_base = OTHER
                     note = 2-fluoro-modified nucleoside
modified_base        10
                     mod_base = OTHER
                     note = 2-fluoro-modified nucleoside
modified_base        12
                     mod_base = OTHER
                     note = 2-fluoro-modified nucleoside
modified_base        14
                     mod_base = OTHER
                     note = 2-fluoro-modified nucleoside
modified_base        16
                     mod_base = OTHER
                     note = 2-fluoro-modified nucleoside
modified_base        18
                     mod_base = OTHER
                     note = 2-fluoro-modified nucleoside
modified_base        19^20
                     mod_base = OTHER
                     note = phosphorothioate linkage
modified_base        20^21
                     mod_base = OTHER
                     note = phosphorothioate linkage
modified_base        2^3
                     mod_base = OTHER
                     note = phosphorothioate linkage
SEQUENCE: 37
taatacaagt atcgattcct t                                              21

SEQ ID NO: 38        moltype = RNA   length = 21
FEATURE              Location/Qualifiers
source               1..21
                     mol_type = other RNA
                     organism = synthetic construct
modified_base        1^2
                     mod_base = OTHER
                     note = phosphorothioate linkage
modified_base        1
                     mod_base = OTHER
                     note = 2-O-methyl modified nucleoside
modified_base        3
                     mod_base = OTHER
                     note = 2-O-methyl modified nucleoside
modified_base        5
                     mod_base = OTHER
                     note = 2-O-methyl modified nucleoside
modified_base        7
                     mod_base = OTHER
                     note = 2-O-methyl modified nucleoside
modified_base        9
                     mod_base = OTHER
                     note = 2-O-methyl modified nucleoside
modified_base        11
                     mod_base = OTHER
```

```
                          note = 2-O-methyl modified nucleoside
modified_base             13
                          mod_base = OTHER
                          note = 2-O-methyl modified nucleoside
modified_base             15
                          mod_base = OTHER
                          note = 2-O-methyl modified nucleoside
modified_base             17
                          mod_base = OTHER
                          note = 2-O-methyl modified nucleoside
modified_base             19
                          mod_base = OTHER
                          note = 2-O-methyl modified nucleoside
modified_base             21
                          mod_base = OTHER
                          note = 2-O-methyl modified nucleoside
modified_base             2
                          mod_base = OTHER
                          note = 2-fluoro-modified nucleoside
modified_base             4
                          mod_base = OTHER
                          note = 2-fluoro-modified nucleoside
modified_base             6
                          mod_base = OTHER
                          note = 2-fluoro-modified nucleoside
modified_base             8
                          mod_base = OTHER
                          note = 2-fluoro-modified nucleoside
modified_base             10
                          mod_base = OTHER
                          note = 2-fluoro-modified nucleoside
modified_base             12
                          mod_base = OTHER
                          note = 2-fluoro-modified nucleoside
modified_base             14
                          mod_base = OTHER
                          note = 2-fluoro-modified nucleoside
modified_base             16
                          mod_base = OTHER
                          note = 2-fluoro-modified nucleoside
modified_base             18
                          mod_base = OTHER
                          note = 2-fluoro-modified nucleoside
modified_base             20
                          mod_base = OTHER
                          note = 2-O-methyl modified nucleoside
modified_base             19^20
                          mod_base = OTHER
                          note = phosphorothioate linkage
modified_base             20^21
                          mod_base = OTHER
                          note = phosphorothioate linkage
modified_base             2^3
                          mod_base = OTHER
                          note = phosphorothioate linkage
SEQUENCE: 38
tacctttgta gaaagcatct t                                              21

SEQ ID NO: 39             moltype = RNA  length = 21
FEATURE                   Location/Qualifiers
source                    1..21
                          mol_type = other RNA
                          organism = synthetic construct
modified_base             1^2
                          mod_base = OTHER
                          note = phosphorothioate linkage
modified_base             1
                          mod_base = OTHER
                          note = 2-O-methyl modified nucleoside
modified_base             3
                          mod_base = OTHER
                          note = 2-O-methyl modified nucleoside
modified_base             5
                          mod_base = OTHER
                          note = 2-O-methyl modified nucleoside
modified_base             7
                          mod_base = OTHER
                          note = 2-O-methyl modified nucleoside
modified_base             9
```

-continued

|  |  |
|---|---|
|  | mod_base = OTHER |
|  | note = 2-O-methyl modified nucleoside |
| modified_base | 11 |
|  | mod_base = OTHER |
|  | note = 2-O-methyl modified nucleoside |
| modified_base | 13 |
|  | mod_base = OTHER |
|  | note = 2-O-methyl modified nucleoside |
| modified_base | 15 |
|  | mod_base = OTHER |
|  | note = 2-O-methyl modified nucleoside |
| modified_base | 17 |
|  | mod_base = OTHER |
|  | note = 2-O-methyl modified nucleoside |
| modified_base | 19 |
|  | mod_base = OTHER |
|  | note = 2-O-methyl modified nucleoside |
| modified_base | 20 |
|  | mod_base = OTHER |
|  | note = 2-O-methyl modified nucleoside |
| modified_base | 21 |
|  | mod_base = OTHER |
|  | note = 2-O-methyl modified nucleoside |
| modified_base | 2 |
|  | mod_base = OTHER |
|  | note = 2-fluoro-modified nucleoside |
| modified_base | 4 |
|  | mod_base = OTHER |
|  | note = 2-fluoro-modified nucleoside |
| modified_base | 6 |
|  | mod_base = OTHER |
|  | note = 2-fluoro-modified nucleoside |
| modified_base | 8 |
|  | mod_base = OTHER |
|  | note = 2-fluoro-modified nucleoside |
| modified_base | 10 |
|  | mod_base = OTHER |
|  | note = 2-fluoro-modified nucleoside |
| modified_base | 12 |
|  | mod_base = OTHER |
|  | note = 2-fluoro-modified nucleoside |
| modified_base | 14 |
|  | mod_base = OTHER |
|  | note = 2-fluoro-modified nucleoside |
| modified_base | 16 |
|  | mod_base = OTHER |
|  | note = 2-fluoro-modified nucleoside |
| modified_base | 18 |
|  | mod_base = OTHER |
|  | note = 2-fluoro-modified nucleoside |
| modified_base | 19^20 |
|  | mod_base = OTHER |
|  | note = phosphorothioate linkage |
| modified_base | 20^21 |
|  | mod_base = OTHER |
|  | note = phosphorothioate linkage |
| modified_base | 2^3 |
|  | mod_base = OTHER |
|  | note = phosphorothioate linkage |
| SEQUENCE: 39 |  |
| ttcaccgttc tgcttttctt t | 21 |
|  |  |
| SEQ ID NO: 40 | moltype = RNA  length = 21 |
| FEATURE | Location/Qualifiers |
| source | 1..21 |
|  | mol_type = other RNA |
|  | organism = synthetic construct |
| modified_base | 1^2 |
|  | mod_base = OTHER |
|  | note = phosphorothioate linkage |
| modified_base | 1 |
|  | mod_base = OTHER |
|  | note = 2-O-methyl modified nucleoside |
| modified_base | 3 |
|  | mod_base = OTHER |
|  | note = 2-O-methyl modified nucleoside |
| modified_base | 5 |
|  | mod_base = OTHER |
|  | note = 2-O-methyl modified nucleoside |

```
modified_base      7
                   mod_base = OTHER
                   note = 2-O-methyl modified nucleoside
modified_base      9
                   mod_base = OTHER
                   note = 2-O-methyl modified nucleoside
modified_base      11
                   mod_base = OTHER
                   note = 2-O-methyl modified nucleoside
modified_base      13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
modified_base      19
                   mod_base = OTHER
                   note = 2-O-methyl modified nucleoside
modified_base      21
                   mod_base = OTHER
                   note = 2-O-methyl modified nucleoside
modified_base      20
                   mod_base = OTHER
                   note = 2-O-methyl modified nucleoside
modified_base      2
                   mod_base = OTHER
                   note = 2-fluoro-modified nucleoside
modified_base      4
                   mod_base = OTHER
                   note = 2-fluoro-modified nucleoside
modified_base      6
                   mod_base = OTHER
                   note = 2-fluoro-modified nucleoside
modified_base      8
                   mod_base = OTHER
                   note = 2-fluoro-modified nucleoside
modified_base      10
                   mod_base = OTHER
                   note = 2-fluoro-modified nucleoside
modified_base      12
                   mod_base = OTHER
                   note = 2-fluoro-modified nucleoside
modified_base      14
                   mod_base = OTHER
                   note = 2-fluoro-modified nucleoside
modified_base      16
                   mod_base = OTHER
                   note = 2-fluoro-modified nucleoside
modified_base      18
                   mod_base = OTHER
                   note = 2-fluoro-modified nucleoside
modified_base      19^20
                   mod_base = OTHER
                   note = phosphorothioate linkage
modified_base      20^21
                   mod_base = OTHER
                   note = phosphorothioate linkage
modified_base      2^3
                   mod_base = OTHER
                   note = phosphorothioate linkage
SEQUENCE: 40
tactttcacc gttctgcttt t                                              21

SEQ ID NO: 41      moltype = RNA  length = 21
FEATURE            Location/Qualifiers
source             1..21
                   mol_type = other RNA
                   organism = synthetic construct
modified_base      1^2
                   mod_base = OTHER
                   note = phosphorothioate linkage
modified_base      1
                   mod_base = OTHER
                   note = 2-O-methyl modified nucleoside
modified_base      3
                   mod_base = OTHER
```

```
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 41
ttccaatgta tctcccactt t                                                  21

SEQ ID NO: 42           moltype = RNA   length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
```

-continued

|  |  |
|---|---|
| | mod_base = OTHER |
| | note = 2-O-methyl modified nucleoside |
| modified_base | 3 |
| | mod_base = OTHER |
| | note = 2-O-methyl modified nucleoside |
| modified_base | 5 |
| | mod_base = OTHER |
| | note = 2-O-methyl modified nucleoside |
| modified_base | 7 |
| | mod_base = OTHER |
| | note = 2-O-methyl modified nucleoside |
| modified_base | 9 |
| | mod_base = OTHER |
| | note = 2-O-methyl modified nucleoside |
| modified_base | 11 |
| | mod_base = OTHER |
| | note = 2-O-methyl modified nucleoside |
| modified_base | 13 |
| | mod_base = OTHER |
| | note = 2-O-methyl modified nucleoside |
| modified_base | 15 |
| | mod_base = OTHER |
| | note = 2-O-methyl modified nucleoside |
| modified_base | 17 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 2 |
| | mod_base = OTHER |
| | note = 2-fluoro-modified nucleoside |
| modified_base | 4 |
| | mod_base = OTHER |
| | note = 2-fluoro-modified nucleoside |
| modified_base | 6 |
| | mod_base = OTHER |
| | note = 2-fluoro-modified nucleoside |
| modified_base | 8 |
| | mod_base = OTHER |
| | note = 2-fluoro-modified nucleoside |
| modified_base | 10 |
| | mod_base = OTHER |
| | note = 2-fluoro-modified nucleoside |
| modified_base | 12 |
| | mod_base = OTHER |
| | note = 2-fluoro-modified nucleoside |
| modified_base | 14 |
| | mod_base = OTHER |
| | note = 2-fluoro-modified nucleoside |
| modified_base | 16 |
| | mod_base = OTHER |
| | note = 2-fluoro-modified nucleoside |
| modified_base | 18 |
| | mod_base = OTHER |
| | note = 2-fluoro-modified nucleoside |
| modified_base | 19^20 |
| | mod_base = OTHER |
| | note = phosphorothioate linkage |
| modified_base | 20^21 |
| | mod_base = OTHER |
| | note = phosphorothioate linkage |
| modified_base | 2^3 |
| | mod_base = OTHER |
| | note = phosphorothioate linkage |
| SEQUENCE: 42 | |
| tgatccaatg tatctcccat t | 21 |
| | |
| SEQ ID NO: 43 | moltype = RNA   length = 21 |
| FEATURE | Location/Qualifiers |
| source | 1..21 |
| | mol_type = other RNA |
| | note = GalNAc moiety-ETL17 |

|  | organism = synthetic construct |
| --- | --- |
| modified_base | 1 |
|  | mod_base = OTHER |
|  | note = 2-O-methyl modified nucleoside |
|  | note = phosphorothioate linkage |
| modified_base | 2 |
|  | mod_base = OTHER |
|  | note = 2-O-methyl modified nucleoside |
| modified_base | 3 |
|  | mod_base = OTHER |
|  | note = 2-O-methyl modified nucleoside |
| modified_base | 4 |
|  | mod_base = OTHER |
|  | note = 2-O-methyl modified nucleoside |
| modified_base | 5 |
|  | mod_base = OTHER |
|  | note = 2-fluoro-modified nucleoside |
| modified_base | 6 |
|  | mod_base = OTHER |
|  | note = 2-O-methyl modified nucleoside |
| modified_base | 7 |
|  | mod_base = OTHER |
|  | note = 2-O-methyl modified nucleoside |
| modified_base | 8 |
|  | mod_base = OTHER |
|  | note = 2-fluoro-modified nucleoside |
| modified_base | 9 |
|  | mod_base = OTHER |
|  | note = 2-fluoro-modified nucleoside |
| modified_base | 10 |
|  | mod_base = OTHER |
|  | note = 2-O-methyl modified nucleoside |
| modified_base | 11 |
|  | mod_base = OTHER |
|  | note = 2-O-methyl modified nucleoside |
| modified_base | 12 |
|  | mod_base = OTHER |
|  | note = 2-O-methyl modified nucleoside |
| modified_base | 13 |
|  | mod_base = OTHER |
|  | note = 2-O-methyl modified nucleoside |
| modified_base | 14 |
|  | mod_base = OTHER |
|  | note = 2-O-methyl modified nucleoside |
| modified_base | 15 |
|  | mod_base = OTHER |
|  | note = 2-O-methyl modified nucleoside |
| modified_base | 16 |
|  | mod_base = OTHER |
|  | note = 2-O-methyl modified nucleoside |
| modified_base | 17 |
|  | mod_base = OTHER |
|  | note = 2-O-methyl modified nucleoside |
| modified_base | 18 |
|  | mod_base = OTHER |
|  | note = 2-O-methyl modified nucleoside |
| modified_base | 19 |
|  | mod_base = OTHER |
|  | note = 2-O-methyl modified nucleoside |
| modified_base | 20 |
|  | mod_base = OTHER |
|  | note = 2-O-methyl modified nucleoside |
| modified_base | 21 |
|  | mod_base = OTHER |
|  | note = 2-O-methyl modified nucleoside |
| modified_base | 19^20 |
|  | mod_base = OTHER |
|  | note = phosphorothioate linkage |
| modified_base | 20^21 |
|  | mod_base = OTHER |
|  | note = phosphorothioate linkage |
| SEQUENCE: 43 |  | tcttgtcaga cataaagcat t           21

| SEQ ID NO: 44 | moltype = RNA  length = 21 |
| --- | --- |
| FEATURE | Location/Qualifiers |
| source | 1..21 |
|  | mol_type = other RNA |
|  | note = GalNAc moiety-ETL17 |

|                | organism = synthetic construct |
| --- | --- |
| modified_base  | 1 |
|                | mod_base = OTHER |
|                | note = phosphorothioate linkage |
|                | note = 2-O-methyl modified nucleoside |
| modified_base  | 2 |
|                | mod_base = OTHER |
|                | note = 2-O-methyl modified nucleoside |
| modified_base  | 3 |
|                | mod_base = OTHER |
|                | note = 2-O-methyl modified nucleoside |
| modified_base  | 4 |
|                | mod_base = OTHER |
|                | note = 2-O-methyl modified nucleoside |
| modified_base  | 5 |
|                | mod_base = OTHER |
|                | note = 2-fluoro-modified nucleoside |
| modified_base  | 6 |
|                | mod_base = OTHER |
|                | note = 2-O-methyl modified nucleoside |
| modified_base  | 7 |
|                | mod_base = OTHER |
|                | note = 2-O-methyl modified nucleoside |
| modified_base  | 8 |
|                | mod_base = OTHER |
|                | note = 2-fluoro-modified nucleoside |
| modified_base  | 9 |
|                | mod_base = OTHER |
|                | note = 2-fluoro-modified nucleoside |
| modified_base  | 10 |
|                | mod_base = OTHER |
|                | note = 2-O-methyl modified nucleoside |
| modified_base  | 11 |
|                | mod_base = OTHER |
|                | note = 2-O-methyl modified nucleoside |
| modified_base  | 12 |
|                | mod_base = OTHER |
|                | note = 2-O-methyl modified nucleoside |
| modified_base  | 13 |
|                | mod_base = OTHER |
|                | note = 2-O-methyl modified nucleoside |
| modified_base  | 14 |
|                | mod_base = OTHER |
|                | note = 2-O-methyl modified nucleoside |
| modified_base  | 15 |
|                | mod_base = OTHER |
|                | note = 2-O-methyl modified nucleoside |
| modified_base  | 16 |
|                | mod_base = OTHER |
|                | note = 2-O-methyl modified nucleoside |
| modified_base  | 17 |
|                | mod_base = OTHER |
|                | note = 2-O-methyl modified nucleoside |
| modified_base  | 18 |
|                | mod_base = OTHER |
|                | note = 2-O-methyl modified nucleoside |
| modified_base  | 19 |
|                | mod_base = OTHER |
|                | note = 2-O-methyl modified nucleoside |
| modified_base  | 20 |
|                | mod_base = OTHER |
|                | note = 2-O-methyl modified nucleoside |
| modified_base  | 21 |
|                | mod_base = OTHER |
|                | note = 2-O-methyl modified nucleoside |
| modified_base  | 19^20 |
|                | mod_base = OTHER |
|                | note = phosphorothioate linkage |
| modified_base  | 20^21 |
|                | mod_base = OTHER |
|                | note = phosphorothioate linkage |
| SEQUENCE: 44   | | tcttgtcaga cataaagcat t                                           21

| SEQ ID NO: 45 | moltype = RNA   length = 21 |
| --- | --- |
| FEATURE       | Location/Qualifiers |
| source        | 1..21 |
|               | mol_type = other RNA |
|               | note = GalNAc moiety-ETL17 |

|                | organism = synthetic construct |
| --- | --- |
| modified_base  | 1 |
|                | mod_base = OTHER |
|                | note = phosphorothioate linkage |
|                | note = 2-O-methyl modified nucleoside |
| modified_base  | 2 |
|                | mod_base = OTHER |
|                | note = 2-O-methyl modified nucleoside |
| modified_base  | 3 |
|                | mod_base = OTHER |
|                | note = 2-O-methyl modified nucleoside |
| modified_base  | 4 |
|                | mod_base = OTHER |
|                | note = 2-O-methyl modified nucleoside |
| modified_base  | 5 |
|                | mod_base = OTHER |
|                | note = 2-fluoro-modified nucleoside |
| modified_base  | 6 |
|                | mod_base = OTHER |
|                | note = 2-O-methyl modified nucleoside |
| modified_base  | 7 |
|                | mod_base = OTHER |
|                | note = 2-O-methyl modified nucleoside |
| modified_base  | 8 |
|                | mod_base = OTHER |
|                | note = 2-fluoro-modified nucleoside |
| modified_base  | 9 |
|                | mod_base = OTHER |
|                | note = 2-fluoro-modified nucleoside |
| modified_base  | 10 |
|                | mod_base = OTHER |
|                | note = 2-O-methyl modified nucleoside |
| modified_base  | 11 |
|                | mod_base = OTHER |
|                | note = 2-O-methyl modified nucleoside |
| modified_base  | 12 |
|                | mod_base = OTHER |
|                | note = 2-O-methyl modified nucleoside |
| modified_base  | 13 |
|                | mod_base = OTHER |
|                | note = 2-O-methyl modified nucleoside |
| modified_base  | 14 |
|                | mod_base = OTHER |
|                | note = 2-O-methyl modified nucleoside |
| modified_base  | 15 |
|                | mod_base = OTHER |
|                | note = 2-O-methyl modified nucleoside |
| modified_base  | 16 |
|                | mod_base = OTHER |
|                | note = 2-O-methyl modified nucleoside |
| modified_base  | 17 |
|                | mod_base = OTHER |
|                | note = 2-O-methyl modified nucleoside |
| modified_base  | 18 |
|                | mod_base = OTHER |
|                | note = 2-O-methyl modified nucleoside |
| modified_base  | 19 |
|                | mod_base = OTHER |
|                | note = 2-O-methyl modified nucleoside |
| modified_base  | 20 |
|                | mod_base = OTHER |
|                | note = 2-O-methyl modified nucleoside |
| modified_base  | 21 |
|                | mod_base = OTHER |
|                | note = 2-O-methyl modified nucleoside |
| modified_base  | 19^20 |
|                | mod_base = OTHER |
|                | note = phosphorothioate linkage |
| modified_base  | 20^21 |
|                | mod_base = OTHER |
|                | note = phosphorothioate linkage |
| SEQUENCE: 45   | | tcttgtcaga cataaagcat t                                        21

| SEQ ID NO: 46 | moltype = RNA  length = 21 |
| --- | --- |
| FEATURE       | Location/Qualifiers |
| source        | 1..21 |
|               | mol_type = other RNA |
|               | note = GalNAc moiety-ETL17 |

|  |  |
|---|---|
| modified_base | 1<br>mod_base = OTHER<br>note = 2-O-methyl modified nucleoside<br>note = phosphorothioate linkage |
| modified_base | 2<br>mod_base = OTHER<br>note = 2-O-methyl modified nucleoside |
| modified_base | 3<br>mod_base = OTHER<br>note = 2-O-methyl modified nucleoside |
| modified_base | 4<br>mod_base = OTHER<br>note = 2-O-methyl modified nucleoside |
| modified_base | 5<br>mod_base = OTHER<br>note = 2-fluoro-modified nucleoside |
| modified_base | 6<br>mod_base = OTHER<br>note = 2-O-methyl modified nucleoside |
| modified_base | 7<br>mod_base = OTHER<br>note = 2-O-methyl modified nucleoside |
| modified_base | 8<br>mod_base = OTHER<br>note = 2-fluoro-modified nucleoside |
| modified_base | 9<br>mod_base = OTHER<br>note = 2-fluoro-modified nucleoside |
| modified_base | 10<br>mod_base = OTHER<br>note = 2-O-methyl modified nucleoside |
| modified_base | 11<br>mod_base = OTHER<br>note = 2-O-methyl modified nucleoside |
| modified_base | 12<br>mod_base = OTHER<br>note = 2-O-methyl modified nucleoside |
| modified_base | 13<br>mod_base = OTHER<br>note = 2-O-methyl modified nucleoside |
| modified_base | 14<br>mod_base = OTHER<br>note = 2-O-methyl modified nucleoside |
| modified_base | 15<br>mod_base = OTHER<br>note = 2-O-methyl modified nucleoside |
| modified_base | 16<br>mod_base = OTHER<br>note = 2-O-methyl modified nucleoside |
| modified_base | 17<br>mod_base = OTHER<br>note = 2-O-methyl modified nucleoside |
| modified_base | 18<br>mod_base = OTHER<br>note = 2-O-methyl modified nucleoside |
| modified_base | 19<br>mod_base = OTHER<br>note = 2-O-methyl modified nucleoside |
| modified_base | 20<br>mod_base = OTHER<br>note = 2-O-methyl modified nucleoside |
| modified_base | 21<br>mod_base = OTHER<br>note = 2-O-methyl modified nucleoside |
| modified_base | 19^20<br>mod_base = OTHER<br>note = 2-O-methyl modified nucleoside |
| modified_base | 20^21<br>mod_base = OTHER<br>note = 2-O-methyl modified nucleoside |
| SEQUENCE: 46 | |
| tcttgtcaga cataaagcat t | 21 |
| SEQ ID NO: 47<br>FEATURE<br>source | moltype = RNA  length = 21<br>Location/Qualifiers<br>1..21<br>mol_type = other RNA<br>note = GalNAc moiety-ETL17 |

|              |                                              |
|--------------|----------------------------------------------|
|              | organism = synthetic construct               |
| modified_base | 1                                           |
|              | mod_base = OTHER                             |
|              | note = phosphorothioate linkage              |
|              | note = 2-O-methyl modified nucleoside        |
| modified_base | 2                                           |
|              | mod_base = OTHER                             |
|              | note = 2-O-methyl modified nucleoside        |
| modified_base | 3                                           |
|              | mod_base = OTHER                             |
|              | note = 2-O-methyl modified nucleoside        |
| modified_base | 4                                           |
|              | mod_base = OTHER                             |
|              | note = 2-O-methyl modified nucleoside        |
| modified_base | 5                                           |
|              | mod_base = OTHER                             |
|              | note = 2-fluoro-modified nucleoside          |
| modified_base | 6                                           |
|              | mod_base = OTHER                             |
|              | note = 2-O-methyl modified nucleoside        |
| modified_base | 7                                           |
|              | mod_base = OTHER                             |
|              | note = 2-O-methyl modified nucleoside        |
| modified_base | 8                                           |
|              | mod_base = OTHER                             |
|              | note = 2-fluoro-modified nucleoside          |
| modified_base | 9                                           |
|              | mod_base = OTHER                             |
|              | note = 2-fluoro-modified nucleoside          |
| modified_base | 10                                          |
|              | mod_base = OTHER                             |
|              | note = 2-O-methyl modified nucleoside        |
| modified_base | 11                                          |
|              | mod_base = OTHER                             |
|              | note = 2-O-methyl modified nucleoside        |
| modified_base | 12                                          |
|              | mod_base = OTHER                             |
|              | note = 2-O-methyl modified nucleoside        |
| modified_base | 13                                          |
|              | mod_base = OTHER                             |
|              | note = 2-O-methyl modified nucleoside        |
| modified_base | 14                                          |
|              | mod_base = OTHER                             |
|              | note = 2-O-methyl modified nucleoside        |
| modified_base | 15                                          |
|              | mod_base = OTHER                             |
|              | note = 2-O-methyl modified nucleoside        |
| modified_base | 16                                          |
|              | mod_base = OTHER                             |
|              | note = 2-O-methyl modified nucleoside        |
| modified_base | 17                                          |
|              | mod_base = OTHER                             |
|              | note = 2-O-methyl modified nucleoside        |
| modified_base | 18                                          |
|              | mod_base = OTHER                             |
|              | note = 2-O-methyl modified nucleoside        |
| modified_base | 19                                          |
|              | mod_base = OTHER                             |
|              | note = 2-O-methyl modified nucleoside        |
| modified_base | 20                                          |
|              | mod_base = OTHER                             |
|              | note = 2-O-methyl modified nucleoside        |
| modified_base | 21                                          |
|              | mod_base = OTHER                             |
|              | note = 2-O-methyl modified nucleoside        |
| modified_base | 19^20                                       |
|              | mod_base = OTHER                             |
|              | note = phosphorothioate linkage              |
| modified_base | 20^21                                       |
|              | mod_base = OTHER                             |
|              | note = phosphorothioate linkage              |
| SEQUENCE: 47 |                                              |
| tcttgtcaga cataaagcat t | 21                                 |
|              |                                              |
| SEQ ID NO: 48 | moltype = RNA   length = 22                |
| FEATURE      | Location/Qualifiers                          |
| source       | 1..22                                        |
|              | mol_type = other RNA                         |
|              | note = GalNAc moiety-ETL17                   |

| | |
|---|---|
| | organism = synthetic construct |
| modified_base | 1<br>mod_base = OTHER<br>note = 2-O-methyl modified nucleoside<br>note = phosphorothioate linkage |
| modified_base | 2<br>mod_base = OTHER<br>note = 2-O-methyl modified nucleoside |
| modified_base | 3<br>mod_base = OTHER<br>note = 2-O-methyl modified nucleoside |
| modified_base | 4<br>mod_base = OTHER<br>note = 2-O-methyl modified nucleoside |
| modified_base | 5<br>mod_base = OTHER<br>note = 2-fluoro-modified nucleoside |
| modified_base | 6<br>mod_base = OTHER<br>note = 2-O-methyl modified nucleoside |
| modified_base | 8<br>mod_base = OTHER<br>note = 2-fluoro-modified nucleoside |
| modified_base | 9<br>mod_base = OTHER<br>note = 2-O-methyl modified nucleoside |
| modified_base | 10<br>mod_base = OTHER<br>note = 2-fluoro-modified nucleoside |
| modified_base | 11<br>mod_base = OTHER<br>note = 2-O-methyl modified nucleoside |
| modified_base | 12<br>mod_base = OTHER<br>note = 2-fluoro-modified nucleoside |
| modified_base | 13<br>mod_base = OTHER<br>note = 2-O-methyl modified nucleoside |
| modified_base | 14<br>mod_base = OTHER<br>note = 2-O-methyl modified nucleoside |
| modified_base | 15<br>mod_base = OTHER<br>note = 2-O-methyl modified nucleoside |
| modified_base | 16<br>mod_base = OTHER<br>note = 2-O-methyl modified nucleoside |
| modified_base | 17<br>mod_base = OTHER<br>note = 2-O-methyl modified nucleoside |
| modified_base | 18<br>mod_base = OTHER<br>note = 2-O-methyl modified nucleoside |
| modified_base | 19<br>mod_base = OTHER<br>note = 2-O-methyl modified nucleoside |
| modified_base | 20<br>mod_base = OTHER<br>note = 2-O-methyl modified nucleoside |
| modified_base | 21<br>mod_base = OTHER<br>note = 2-O-methyl modified nucleoside |
| modified_base | 20^21<br>mod_base = OTHER<br>note = phosphorothioate linkage |
| modified_base | 21^22<br>mod_base = OTHER<br>note = phosphorothioate linkage |
| modified_base | 22<br>mod_base = OTHER<br>note = 2-O-methyl modified nucleoside |
| SEQUENCE: 48 | |
| ttgtcadgac ataaagccaa tt | 22 |
| SEQ ID NO: 49 | moltype = RNA  length = 22 |
| FEATURE | Location/Qualifiers |
| source | 1..22<br>mol_type = other RNA<br>note = GalNAc moiety-ETL17 |

| | |
|---|---|
| | organism = synthetic construct |
| modified_base | 1 |
| | mod_base = OTHER |
| | note = 2-O-methyl modified nucleoside |
| | note = phosphorothioate linkage |
| modified_base | 2 |
| | mod_base = OTHER |
| | note = 2-O-methyl modified nucleoside |
| modified_base | 3 |
| | mod_base = OTHER |
| | note = 2-O-methyl modified nucleoside |
| modified_base | 4 |
| | mod_base = OTHER |
| | note = 2-O-methyl modified nucleoside |
| modified_base | 5 |
| | mod_base = OTHER |
| | note = 2-O-methyl modified nucleoside |
| modified_base | 6 |
| | mod_base = OTHER |
| | note = 2-O-methyl modified nucleoside |
| modified_base | 7 |
| | mod_base = OTHER |
| | note = 2-O-methyl modified nucleoside |
| modified_base | 8 |
| | mod_base = OTHER |
| | note = 2-O-methyl modified nucleoside |
| modified_base | 9 |
| | mod_base = OTHER |
| | note = 2-fluoro-modified nucleoside |
| modified_base | 11 |
| | mod_base = OTHER |
| | note = 2-fluoro-modified nucleoside |
| modified_base | 12 |
| | mod_base = OTHER |
| | note = 2-fluoro-modified nucleoside |
| modified_base | 13 |
| | mod_base = OTHER |
| | note = 2-O-methyl modified nucleoside |
| modified_base | 14 |
| | mod_base = OTHER |
| | note = 2-O-methyl modified nucleoside |
| modified_base | 15 |
| | mod_base = OTHER |
| | note = 2-O-methyl modified nucleoside |
| modified_base | 16 |
| | mod_base = OTHER |
| | note = 2-O-methyl modified nucleoside |
| modified_base | 17 |
| | mod_base = OTHER |
| | note = 2-O-methyl modified nucleoside |
| modified_base | 18 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 22 |
| | mod_base = OTHER |
| | note = 2-O-methyl modified nucleoside |
| modified_base | 20^21 |
| | mod_base = OTHER |
| | note = phosphorothioate linkage |
| modified_base | 21^22 |
| | mod_base = OTHER |
| | note = phosphorothioate linkage |
| SEQUENCE: 49 | |
| ttgtcagacd ataaagccaa tt | 22 |
| | |
| SEQ ID NO: 50 | moltype = RNA  length = 21 |
| FEATURE | Location/Qualifiers |
| source | 1..21 |
| | mol_type = other RNA |
| | note = GalNAc moiety-ETL17 |

```
                        organism = synthetic construct
modified_base           1
                        mod_base = OTHER
                        note = phosphorothioate linkage
                        note = 2-O-methyl modified nucleoside
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-O-methyl modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
                        note = 2-O-methyl modified nucleoside
modified_base           14
                        mod_base = OTHER
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 50
ttgtcagaca taaagccaat t                                              21

SEQ ID NO: 51           moltype = RNA   length = 21
FEATURE                 Location/Qualifiers
source                  1..21
                        mol_type = other RNA
                        note = GalNAc moiety-ETL17
```

| | | |
|---|---|---|
| modified_base | 1 | |
| | mod_base = OTHER | |
| | note = phosphorothioate linkage | |
| | note = 2-O-methyl modified nucleoside | |
| modified_base | 2 | |
| | mod_base = OTHER | |
| | note = 2-O-methyl modified nucleoside | |
| modified_base | 3 | |
| | mod_base = OTHER | |
| | note = 2-O-methyl modified nucleoside | |
| modified_base | 4 | |
| | mod_base = OTHER | |
| | note = 2-O-methyl modified nucleoside | |
| modified_base | 5 | |
| | mod_base = OTHER | |
| | note = 2-fluoro-modified nucleoside | |
| modified_base | 6 | |
| | mod_base = OTHER | |
| | note = 2-O-methyl modified nucleoside | |
| modified_base | 7 | |
| | mod_base = OTHER | |
| | note = 2-O-methyl modified nucleoside | |
| modified_base | 8 | |
| | mod_base = OTHER | |
| | note = 2-O-methyl modified nucleoside | |
| modified_base | 9 | |
| | mod_base = OTHER | |
| | note = 2-fluoro-modified nucleoside | |
| modified_base | 10 | |
| | mod_base = OTHER | |
| | note = 2-O-methyl modified nucleoside | |
| modified_base | 11 | |
| | mod_base = OTHER | |
| | note = 2-fluoro-modified nucleoside | |
| modified_base | 12 | |
| | mod_base = OTHER | |
| | note = 2-O-methyl modified nucleoside | |
| modified_base | 13 | |
| | mod_base = OTHER | |
| | note = 2-O-methyl modified nucleoside | |
| modified_base | 14 | |
| | mod_base = OTHER | |
| | note = 2-O-methyl modified nucleoside | |
| modified_base | 15 | |
| | mod_base = OTHER | |
| | note = 2-O-methyl modified nucleoside | |
| modified_base | 16 | |
| | mod_base = OTHER | |
| | note = 2-O-methyl modified nucleoside | |
| modified_base | 17 | |
| | mod_base = OTHER | |
| | note = 2-O-methyl modified nucleoside | |
| modified_base | 18 | |
| | mod_base = OTHER | |
| | note = 2-O-methyl modified nucleoside | |
| modified_base | 19 | |
| | mod_base = OTHER | |
| | note = 2-O-methyl modified nucleoside | |
| modified_base | 20 | |
| | mod_base = OTHER | |
| | note = 2-O-methyl modified nucleoside | |
| modified_base | 21 | |
| | mod_base = OTHER | |
| | note = 2-O-methyl modified nucleoside | |
| modified_base | 19^20 | |
| | mod_base = OTHER | |
| | note = phosphorothioate linkage | |
| modified_base | 20^21 | |
| | mod_base = OTHER | |
| | note = phosphorothioate linkage | |
| SEQUENCE: 51 | | |
| ttgtcagaca taaagccaat t | | 21 |
| | | |
| SEQ ID NO: 52 | moltype = RNA   length = 21 | |
| FEATURE | Location/Qualifiers | |
| source | 1..21 | |
| | mol_type = other RNA | |
| | note = GalNAc moiety-ETL17 | |

-continued

```
                        organism = synthetic construct
modified_base           1
                        mod_base = OTHER
                        note = phosphorothioate linkage
                        note = 2-O-methyl modified nucleoside
modified_base           2
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-fluoro-modified nucleoside
modified_base           6
                        mod_base = OTHER
                        note = 2-O-methyl modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-fluoro-modified nucleoside
modified_base           10
                        mod_base = OTHER
                        note = 2-O-methyl modified nucleoside
modified_base           11
                        mod_base = OTHER
                        note = 2-fluoro-modified nucleoside
modified_base           12
                        mod_base = OTHER
                        note = 2-O-methyl modified nucleoside
modified_base           13
                        mod_base = OTHER
                        note = 2-O-methyl modified nucleoside
modified_base           14
                        mod_base = OTHER
                        note = 2-O-methyl modified nucleoside
modified_base           15
                        mod_base = OTHER
                        note = 2-O-methyl modified nucleoside
modified_base           16
                        mod_base = OTHER
                        note = 2-O-methyl modified nucleoside
modified_base           17
                        mod_base = OTHER
                        note = 2-O-methyl modified nucleoside
modified_base           18
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           19^20
                        mod_base = OTHER
                        note = phosphorothioate linkage
modified_base           20^21
                        mod_base = OTHER
                        note = phosphorothioate linkage
SEQUENCE: 52
ttgtcagaca taaagccaat t                                               21

SEQ ID NO: 53           moltype = RNA   length = 21
FEATURE                 Location/Qualifiers
source                  1..21
                        mol_type = other RNA
                        note = GalNAc moiety-ETL17
```

| | |
|---|---|
| | organism = synthetic construct |
| modified_base | 1<br>mod_base = OTHER<br>note = 2-O-methyl modified nucleoside<br>note = phosphorothioate linkage |
| modified_base | 2<br>mod_base = OTHER<br>note = 2-O-methyl modified nucleoside |
| modified_base | 3<br>mod_base = OTHER<br>note = 2-O-methyl modified nucleoside |
| modified_base | 4<br>mod_base = OTHER<br>note = 2-O-methyl modified nucleoside |
| modified_base | 5<br>mod_base = OTHER<br>note = 2-fluoro-modified nucleoside |
| modified_base | 6<br>mod_base = OTHER<br>note = 2-O-methyl modified nucleoside |
| modified_base | 7<br>mod_base = OTHER<br>note = 2-O-methyl modified nucleoside |
| modified_base | 8<br>mod_base = OTHER<br>note = 2-O-methyl modified nucleoside |
| modified_base | 9<br>mod_base = OTHER<br>note = 2-fluoro-modified nucleoside |
| modified_base | 10<br>mod_base = OTHER<br>note = 2-O-methyl modified nucleoside |
| modified_base | 11<br>mod_base = OTHER<br>note = 2-fluoro-modified nucleoside |
| modified_base | 12<br>mod_base = OTHER<br>note = 2-O-methyl modified nucleoside |
| modified_base | 13<br>mod_base = OTHER<br>note = 2-O-methyl modified nucleoside |
| modified_base | 14<br>mod_base = OTHER<br>note = 2-O-methyl modified nucleoside |
| modified_base | 15<br>mod_base = OTHER<br>note = 2-O-methyl modified nucleoside |
| modified_base | 16<br>mod_base = OTHER<br>note = 2-O-methyl modified nucleoside |
| modified_base | 17<br>mod_base = OTHER<br>note = 2-O-methyl modified nucleoside |
| modified_base | 18<br>mod_base = OTHER<br>note = 2-O-methyl modified nucleoside |
| modified_base | 19<br>mod_base = OTHER<br>note = 2-O-methyl modified nucleoside |
| modified_base | 20<br>mod_base = OTHER<br>note = 2-O-methyl modified nucleoside |
| modified_base | 21<br>mod_base = OTHER<br>note = 2-O-methyl modified nucleoside |
| modified_base | 19^20<br>mod_base = OTHER<br>note = phosphorothioate linkage |
| modified_base | 20^21<br>mod_base = OTHER<br>note = phosphorothioate linkage |
| SEQUENCE: 53 | |
| ttgtcagaca taaagccaat t | 21 |
| | |
| SEQ ID NO: 54<br>FEATURE<br>source | moltype = RNA length = 21<br>Location/Qualifiers<br>1..21<br>mol_type = other RNA<br>organism = synthetic construct |

| | | |
|---|---|---|
| modified_base | 1^2 | |
| | mod_base = OTHER | |
| | note = phosphorothioate linkage | |
| modified_base | 1 | |
| | mod_base = OTHER | |
| | note = 2-O-methyl modified nucleoside | |
| modified_base | 3 | |
| | mod_base = OTHER | |
| | note = 2-O-methyl modified nucleoside | |
| modified_base | 5 | |
| | mod_base = OTHER | |
| | note = 2-O-methyl modified nucleoside | |
| modified_base | 7 | |
| | mod_base = OTHER | |
| | note = 2-O-methyl modified nucleoside | |
| modified_base | 9 | |
| | mod_base = OTHER | |
| | note = 2-O-methyl modified nucleoside | |
| modified_base | 11 | |
| | mod_base = OTHER | |
| | note = 2-O-methyl modified nucleoside | |
| modified_base | 13 | |
| | mod_base = OTHER | |
| | note = 2-O-methyl modified nucleoside | |
| modified_base | 15 | |
| | mod_base = OTHER | |
| | note = 2-O-methyl modified nucleoside | |
| modified_base | 17 | |
| | mod_base = OTHER | |
| | note = 2-O-methyl modified nucleoside | |
| modified_base | 19 | |
| | mod_base = OTHER | |
| | note = 2-O-methyl modified nucleoside | |
| modified_base | 20 | |
| | mod_base = OTHER | |
| | note = 2-O-methyl modified nucleoside | |
| modified_base | 21 | |
| | mod_base = OTHER | |
| | note = 2-O-methyl modified nucleoside | |
| modified_base | 2 | |
| | mod_base = OTHER | |
| | note = 2-fluoro-modified nucleoside | |
| modified_base | 4 | |
| | mod_base = OTHER | |
| | note = 2-fluoro-modified nucleoside | |
| modified_base | 6 | |
| | mod_base = OTHER | |
| | note = 2-fluoro-modified nucleoside | |
| modified_base | 8 | |
| | mod_base = OTHER | |
| | note = 2-fluoro-modified nucleoside | |
| modified_base | 10 | |
| | mod_base = OTHER | |
| | note = 2-fluoro-modified nucleoside | |
| modified_base | 12 | |
| | mod_base = OTHER | |
| | note = 2-fluoro-modified nucleoside | |
| modified_base | 14 | |
| | mod_base = OTHER | |
| | note = 2-fluoro-modified nucleoside | |
| modified_base | 16 | |
| | mod_base = OTHER | |
| | note = 2-fluoro-modified nucleoside | |
| modified_base | 18 | |
| | mod_base = OTHER | |
| | note = 2-fluoro-modified nucleoside | |
| modified_base | 19^20 | |
| | mod_base = OTHER | |
| | note = phosphorothioate linkage | |
| modified_base | 20^21 | |
| | mod_base = OTHER | |
| | note = phosphorothioate linkage | |
| modified_base | 2^3 | |
| | mod_base = OTHER | |
| | note = phosphorothioate linkage | |
| SEQUENCE: 54 | | |
| tgctttatgt ctgacaagat t | | 21 |
| | | |
| SEQ ID NO: 55 | moltype = RNA  length = 21 | |

| FEATURE | Location/Qualifiers |
|---|---|
| source | 1..21 |
| | mol_type = other RNA |
| | organism = synthetic construct |
| modified_base | 1^2 |
| | mod_base = OTHER |
| | note = phosphorothioate linkage |
| modified_base | 1 |
| | mod_base = OTHER |
| | note = 2-O-methyl modified nucleoside |
| modified_base | 3 |
| | mod_base = OTHER |
| | note = 2-O-methyl modified nucleoside |
| modified_base | 4 |
| | mod_base = OTHER |
| | note = 2-O-methyl modified nucleoside |
| modified_base | 5 |
| | mod_base = OTHER |
| | note = 2-O-methyl modified nucleoside |
| modified_base | 7 |
| | mod_base = OTHER |
| | note = 2-O-methyl modified nucleoside |
| modified_base | 9 |
| | mod_base = OTHER |
| | note = 2-O-methyl modified nucleoside |
| modified_base | 11 |
| | mod_base = OTHER |
| | note = 2-O-methyl modified nucleoside |
| modified_base | 13 |
| | mod_base = OTHER |
| | note = 2-O-methyl modified nucleoside |
| modified_base | 15 |
| | mod_base = OTHER |
| | note = 2-O-methyl modified nucleoside |
| modified_base | 17 |
| | mod_base = OTHER |
| | note = 2-O-methyl modified nucleoside |
| modified_base | 19 |
| | mod_base = OTHER |
| | note = 2-O-methyl modified nucleoside |
| modified_base | 20 |
| | mod_base = OTHER |
| | note = 2-O-methyl modified nucleoside |
| modified_base | 21 |
| | mod_base = OTHER |
| | note = 2-O-methyl modified nucleoside |
| modified_base | 2 |
| | mod_base = OTHER |
| | note = 2-fluoro-modified nucleoside |
| modified_base | 6 |
| | mod_base = OTHER |
| | note = 2-fluoro-modified nucleoside |
| modified_base | 8 |
| | mod_base = OTHER |
| | note = 2-fluoro-modified nucleoside |
| modified_base | 10 |
| | mod_base = OTHER |
| | note = 2-fluoro-modified nucleoside |
| modified_base | 12 |
| | mod_base = OTHER |
| | note = 2-fluoro-modified nucleoside |
| modified_base | 14 |
| | mod_base = OTHER |
| | note = 2-fluoro-modified nucleoside |
| modified_base | 16 |
| | mod_base = OTHER |
| | note = 2-fluoro-modified nucleoside |
| modified_base | 18 |
| | mod_base = OTHER |
| | note = 2-fluoro-modified nucleoside |
| modified_base | 19^20 |
| | mod_base = OTHER |
| | note = phosphorothioate linkage |
| modified_base | 20^21 |
| | mod_base = OTHER |
| | note = phosphorothioate linkage |
| modified_base | 2^3 |
| | mod_base = OTHER |
| | note = phosphorothioate linkage |

```
SEQUENCE: 55
tgctttatgt ctgacaagat t                                              21

SEQ ID NO: 56           moltype = RNA  length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           6
                        mod_base = OTHER
                        note = 2-fluoro-modified nucleoside
modified_base           10
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
```

```
                       note = phosphorothioate linkage
modified_base          2^3
                       mod_base = OTHER
                       note = phosphorothioate linkage
SEQUENCE: 56
tgctttatgt ctgacaagat t                                             21

SEQ ID NO: 57          moltype = RNA  length = 21
FEATURE                Location/Qualifiers
source                 1..21
                       mol_type = other RNA
                       organism = synthetic construct
modified_base          1^2
                       mod_base = OTHER
                       note = phosphorothioate linkage
modified_base          1
                       mod_base = OTHER
                       note = 2-O-methyl modified nucleoside
modified_base          3
                       mod_base = OTHER
                       note = 2-O-methyl modified nucleoside
modified_base          5
                       mod_base = OTHER
                       note = 2-O-methyl modified nucleoside
modified_base          7
                       mod_base = OTHER
                       note = 2-O-methyl modified nucleoside
modified_base          9
                       mod_base = OTHER
                       note = 2-O-methyl modified nucleoside
modified_base          11
                       mod_base = OTHER
                       note = 2-O-methyl modified nucleoside
modified_base          13
                       mod_base = OTHER
                       note = 2-O-methyl modified nucleoside
modified_base          10
                       mod_base = OTHER
                       note = 2-O-methyl modified nucleoside
modified_base          13
                       mod_base = OTHER
                       note = 2-O-methyl modified nucleoside
modified_base          15
                       mod_base = OTHER
                       note = 2-O-methyl modified nucleoside
modified_base          17
                       mod_base = OTHER
                       note = 2-O-methyl modified nucleoside
modified_base          19
                       mod_base = OTHER
                       note = 2-O-methyl modified nucleoside
modified_base          20
                       mod_base = OTHER
                       note = 2-O-methyl modified nucleoside
modified_base          21
                       mod_base = OTHER
                       note = 2-O-methyl modified nucleoside
modified_base          2
                       mod_base = OTHER
                       note = 2-fluoro-modified nucleoside
modified_base          4
                       mod_base = OTHER
                       note = 2-fluoro-modified nucleoside
modified_base          6
                       mod_base = OTHER
                       note = 2-fluoro-modified nucleoside
modified_base          8
                       mod_base = OTHER
                       note = 2-fluoro-modified nucleoside
modified_base          12
                       mod_base = OTHER
                       note = 2-fluoro-modified nucleoside
modified_base          14
                       mod_base = OTHER
                       note = 2-fluoro-modified nucleoside
modified_base          16
                       mod_base = OTHER
                       note = 2-fluoro-modified nucleoside
modified_base          18
```

|  |  |
|---|---|
|  | mod_base = OTHER |
|  | note = 2-fluoro-modified nucleoside |
| modified_base | 19^20 |
|  | mod_base = OTHER |
|  | note = phosphorothioate linkage |
| modified_base | 20^21 |
|  | mod_base = OTHER |
|  | note = phosphorothioate linkage |
| modified_base | 2^3 |
|  | mod_base = OTHER |
|  | note = phosphorothioate linkage |
| SEQUENCE: 57 |  |
| tgctttatgt ctgacaagat t | 21 |
|  |  |
| SEQ ID NO: 58 | moltype = RNA   length = 21 |
| FEATURE | Location/Qualifiers |
| source | 1..21 |
|  | mol_type = other RNA |
|  | organism = synthetic construct |
| modified_base | 1^2 |
|  | mod_base = OTHER |
|  | note = phosphorothioate linkage |
| modified_base | 1 |
|  | mod_base = OTHER |
|  | note = 2-O-methyl modified nucleoside |
| modified_base | 3 |
|  | mod_base = OTHER |
|  | note = 2-O-methyl modified nucleoside |
| modified_base | 5 |
|  | mod_base = OTHER |
|  | note = 2-O-methyl modified nucleoside |
| modified_base | 6 |
|  | mod_base = OTHER |
|  | note = 2-O-methyl modified nucleoside |
| modified_base | 8 |
|  | mod_base = OTHER |
|  | note = 2-O-methyl modified nucleoside |
| modified_base | 9 |
|  | mod_base = OTHER |
|  | note = 2-O-methyl modified nucleoside |
| modified_base | 11 |
|  | mod_base = OTHER |
|  | note = 2-O-methyl modified nucleoside |
| modified_base | 13 |
|  | mod_base = OTHER |
|  | note = 2-O-methyl modified nucleoside |
| modified_base | 15 |
|  | mod_base = OTHER |
|  | note = 2-O-methyl modified nucleoside |
| modified_base | 17 |
|  | mod_base = OTHER |
|  | note = 2-O-methyl modified nucleoside |
| modified_base | 19 |
|  | mod_base = OTHER |
|  | note = 2-O-methyl modified nucleoside |
| modified_base | 20 |
|  | mod_base = OTHER |
|  | note = 2-O-methyl modified nucleoside |
| modified_base | 21 |
|  | mod_base = OTHER |
|  | note = 2-O-methyl modified nucleoside |
| modified_base | 2 |
|  | mod_base = OTHER |
|  | note = 2-fluoro-modified nucleoside |
| modified_base | 4 |
|  | mod_base = OTHER |
|  | note = 2-fluoro-modified nucleoside |
| modified_base | 7 |
|  | mod_base = OTHER |
|  | note = 2-fluoro-modified nucleoside |
| modified_base | 10 |
|  | mod_base = OTHER |
|  | note = 2-fluoro-modified nucleoside |
| modified_base | 12 |
|  | mod_base = OTHER |
|  | note = 2-fluoro-modified nucleoside |
| modified_base | 14 |
|  | mod_base = OTHER |
|  | note = 2-fluoro-modified nucleoside |

```
modified_base      16
                   mod_base = OTHER
                   note = 2-fluoro-modified nucleoside
modified_base      18
                   mod_base = OTHER
                   note = 2-fluoro-modified nucleoside
modified_base      19^20
                   mod_base = OTHER
                   note = phosphorothioate linkage
modified_base      20^21
                   mod_base = OTHER
                   note = phosphorothioate linkage
modified_base      2^3
                   mod_base = OTHER
                   note = phosphorothioate linkage
SEQUENCE: 58
tgctttatgt ctgacaagat t                                           21

SEQ ID NO: 59      moltype = RNA  length = 21
FEATURE            Location/Qualifiers
source             1..21
                   mol_type = other RNA
                   organism = synthetic construct
modified_base      1^2
                   mod_base = OTHER
                   note = phosphorothioate linkage
modified_base      1
                   mod_base = OTHER
                   note = 2-O-methyl modified nucleoside
modified_base      3
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      9
                   mod_base = OTHER
                   note = 2-O-methyl modified nucleoside
modified_base      11
                   mod_base = OTHER
                   note = 2-O-methyl modified nucleoside
modified_base      13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
modified_base      19
                   mod_base = OTHER
                   note = 2-O-methyl modified nucleoside
modified_base      20
                   mod_base = OTHER
                   note = 2-O-methyl modified nucleoside
modified_base      21
                   mod_base = OTHER
                   note = 2-O-methyl modified nucleoside
modified_base      2
                   mod_base = OTHER
                   note = 2-fluoro-modified nucleoside
modified_base      4
                   mod_base = OTHER
                   note = 2-fluoro-modified nucleoside
modified_base      6
                   mod_base = OTHER
                   note = 2-fluoro-modified nucleoside
modified_base      8
                   mod_base = OTHER
                   note = 2-fluoro-modified nucleoside
modified_base      10
                   mod_base = OTHER
                   note = 2-fluoro-modified nucleoside
modified_base      12
                   mod_base = OTHER
```

```
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 59
ttggctttat gtctgacaat t                                              21

SEQ ID NO: 60           moltype = RNA   length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           5
                        mod_base = OTHER
                        note = 2-O-methyl modified nucleoside
modified_base           7
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
modified_base           19
                        mod_base = OTHER
                        note = 2-O-methyl modified nucleoside
modified_base           20
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           4
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           10
```

```
                          mod_base = OTHER
                          note = 2-fluoro-modified nucleoside
modified_base             12
                          mod_base = OTHER
                          note = 2-fluoro-modified nucleoside
modified_base             14
                          mod_base = OTHER
                          note = 2-fluoro-modified nucleoside
modified_base             16
                          mod_base = OTHER
                          note = 2-fluoro-modified nucleoside
modified_base             18
                          mod_base = OTHER
                          note = 2-fluoro-modified nucleoside
modified_base             19^20
                          mod_base = OTHER
                          note = phosphorothioate linkage
modified_base             20^21
                          mod_base = OTHER
                          note = phosphorothioate linkage
modified_base             2^3
                          mod_base = OTHER
                          note = phosphorothioate linkage
SEQUENCE: 60
ttggctttat gtctgacaat t                                                  21

SEQ ID NO: 61             moltype = RNA  length = 21
FEATURE                   Location/Qualifiers
source                    1..21
                          mol_type = other RNA
                          organism = synthetic construct
modified_base             1^2
                          mod_base = OTHER
                          note = phosphorothioate linkage
modified_base             1
                          mod_base = OTHER
                          note = 2-O-methyl modified nucleoside
modified_base             3
                          mod_base = OTHER
                          note = 2-O-methyl modified nucleoside
modified_base             4
                          mod_base = OTHER
                          note = 2-O-methyl modified nucleoside
modified_base             5
                          mod_base = OTHER
                          note = 2-O-methyl modified nucleoside
modified_base             7
                          mod_base = OTHER
                          note = 2-O-methyl modified nucleoside
modified_base             9
                          mod_base = OTHER
                          note = 2-O-methyl modified nucleoside
modified_base             11
                          mod_base = OTHER
                          note = 2-O-methyl modified nucleoside
modified_base             13
                          mod_base = OTHER
                          note = 2-O-methyl modified nucleoside
modified_base             15
                          mod_base = OTHER
                          note = 2-O-methyl modified nucleoside
modified_base             17
                          mod_base = OTHER
                          note = 2-O-methyl modified nucleoside
modified_base             19
                          mod_base = OTHER
                          note = 2-O-methyl modified nucleoside
modified_base             21
                          mod_base = OTHER
                          note = 2-O-methyl modified nucleoside
modified_base             2
                          mod_base = OTHER
                          note = 2-fluoro-modified nucleoside
modified_base             6
                          mod_base = OTHER
                          note = 2-fluoro-modified nucleoside
modified_base             8
                          mod_base = OTHER
                          note = 2-fluoro-modified nucleoside
```

```
modified_base     10
                  mod_base = OTHER
                  note = 2-fluoro-modified nucleoside
modified_base     12
                  mod_base = OTHER
                  note = 2-fluoro-modified nucleoside
modified_base     14
                  mod_base = OTHER
                  note = 2-fluoro-modified nucleoside
modified_base     18
                  mod_base = OTHER
                  note = 2-fluoro-modified nucleoside
modified_base     16
                  mod_base = OTHER
                  note = 2-fluoro-modified nucleoside
modified_base     20
                  mod_base = OTHER
                  note = 2-O-methyl modified nucleoside
modified_base     19^20
                  mod_base = OTHER
                  note = phosphorothioate linkage
modified_base     20^21
                  mod_base = OTHER
                  note = phosphorothioate linkage
modified_base     2^3
                  mod_base = OTHER
                  note = phosphorothioate linkage
SEQUENCE: 61
ttggctttat gtctgacaat t                                              21

SEQ ID NO: 62      moltype = RNA   length = 21
FEATURE            Location/Qualifiers
source             1..21
                   mol_type = other RNA
                   organism = synthetic construct
modified_base      1^2
                   mod_base = OTHER
                   note = phosphorothioate linkage
modified_base      1
                   mod_base = OTHER
                   note = 2-O-methyl modified nucleoside
modified_base      3
                   mod_base = OTHER
                   note = 2-O-methyl modified nucleoside
modified_base      5
                   mod_base = OTHER
                   note = 2-O-methyl modified nucleoside
modified_base      7
                   mod_base = OTHER
                   note = 2-O-methyl modified nucleoside
modified_base      9
                   mod_base = OTHER
                   note = 2-O-methyl modified nucleoside
modified_base      10
                   mod_base = OTHER
                   note = 2-O-methyl modified nucleoside
modified_base      11
                   mod_base = OTHER
                   note = 2-O-methyl modified nucleoside
modified_base      13
                   mod_base = OTHER
                   note = 2-O-methyl modified nucleoside
modified_base      15
                   mod_base = OTHER
                   note = 2-O-methyl modified nucleoside
modified_base      17
                   mod_base = OTHER
                   note = 2-O-methyl modified nucleoside
modified_base      20
                   mod_base = OTHER
                   note = 2-O-methyl modified nucleoside
modified_base      21
                   mod_base = OTHER
                   note = 2-O-methyl modified nucleoside
modified_base      20
                   mod_base = OTHER
                   note = 2-O-methyl modified nucleoside
modified_base      2
                   mod_base = OTHER
```

|  |  |
|---|---|
|  | note = 2-fluoro-modified nucleoside |
| modified_base | 4 |
|  | mod_base = OTHER |
|  | note = 2-fluoro-modified nucleoside |
| modified_base | 6 |
|  | mod_base = OTHER |
|  | note = 2-fluoro-modified nucleoside |
| modified_base | 8 |
|  | mod_base = OTHER |
|  | note = 2-fluoro-modified nucleoside |
| modified_base | 12 |
|  | mod_base = OTHER |
|  | note = 2-fluoro-modified nucleoside |
| modified_base | 14 |
|  | mod_base = OTHER |
|  | note = 2-fluoro-modified nucleoside |
| modified_base | 16 |
|  | mod_base = OTHER |
|  | note = 2-fluoro-modified nucleoside |
| modified_base | 18 |
|  | mod_base = OTHER |
|  | note = 2-fluoro-modified nucleoside |
| modified_base | 19^20 |
|  | mod_base = OTHER |
|  | note = phosphorothioate linkage |
| modified_base | 20^21 |
|  | mod_base = OTHER |
|  | note = phosphorothioate linkage |
| modified_base | 2^3 |
|  | mod_base = OTHER |
|  | note = phosphorothioate linkage |
| SEQUENCE: 62 |  |
| ttggctttat gtctgacaat t | 21 |
| SEQ ID NO: 63 | moltype = RNA  length = 21 |
| FEATURE | Location/Qualifiers |
| source | 1..21 |
|  | mol_type = other RNA |
|  | organism = synthetic construct |
| modified_base | 1^2 |
|  | mod_base = OTHER |
|  | note = phosphorothioate linkage |
| modified_base | 1 |
|  | mod_base = OTHER |
|  | note = 2-O-methyl modified nucleoside |
| modified_base | 3 |
|  | mod_base = OTHER |
|  | note = 2-O-methyl modified nucleoside |
| modified_base | 4 |
|  | mod_base = OTHER |
|  | note = 2-O-methyl modified nucleoside |
| modified_base | 5 |
|  | mod_base = OTHER |
|  | note = 2-O-methyl modified nucleoside |
| modified_base | 7 |
|  | mod_base = OTHER |
|  | note = 2-O-methyl modified nucleoside |
| modified_base | 9 |
|  | mod_base = OTHER |
|  | note = 2-O-methyl modified nucleoside |
| modified_base | 10 |
|  | mod_base = OTHER |
|  | note = 2-O-methyl modified nucleoside |
| modified_base | 11 |
|  | mod_base = OTHER |
|  | note = 2-O-methyl modified nucleoside |
| modified_base | 13 |
|  | mod_base = OTHER |
|  | note = 2-O-methyl modified nucleoside |
| modified_base | 15 |
|  | mod_base = OTHER |
|  | note = 2-O-methyl modified nucleoside |
| modified_base | 17 |
|  | mod_base = OTHER |
|  | note = 2-O-methyl modified nucleoside |
| modified_base | 19 |
|  | mod_base = OTHER |
|  | note = 2-O-methyl modified nucleoside |
| modified_base | 20 |

```
                        mod_base = OTHER
                        note = 2-O-methyl modified nucleoside
modified_base           21
                        mod_base = OTHER
                        note = 2-O-methyl modified nucleoside
modified_base           2
                        mod_base = OTHER
                        note = 2-fluoro-modified nucleoside
modified_base           6
                        mod_base = OTHER
                        note = 2-fluoro-modified nucleoside
modified_base           8
                        mod_base = OTHER
                        note = 2-fluoro-modified nucleoside
modified_base           12
                        mod_base = OTHER
                        note = 2-fluoro-modified nucleoside
modified_base           14
                        mod_base = OTHER
                        note = 2-fluoro-modified nucleoside
modified_base           16
                        mod_base = OTHER
                        note = 2-fluoro-modified nucleoside
modified_base           18
                        mod_base = OTHER
                        note = 2-fluoro-modified nucleoside
modified_base           19^20
                        mod_base = OTHER
                        note = phosphorothioate linkage
modified_base           20^21
                        mod_base = OTHER
                        note = phosphorothioate linkage
modified_base           2^3
                        mod_base = OTHER
                        note = phosphorothioate linkage
SEQUENCE: 63
ttggctttat gtctgacaat t                                              21

SEQ ID NO: 64           moltype = RNA   length = 21
FEATURE                 Location/Qualifiers
source                  1..21
                        mol_type = other RNA
                        organism = synthetic construct
modified_base           1^2
                        mod_base = OTHER
                        note = phosphorothioate linkage
modified_base           1
                        mod_base = OTHER
                        note = 2-O-methyl modified nucleoside
modified_base           3
                        mod_base = OTHER
                        note = 2-O-methyl modified nucleoside
modified_base           4
                        mod_base = OTHER
                        note = 2-O-methyl modified nucleoside
modified_base           6
                        mod_base = OTHER
                        note = 2-O-methyl modified nucleoside
modified_base           7
                        mod_base = OTHER
                        note = 2-O-methyl modified nucleoside
modified_base           8
                        mod_base = OTHER
                        note = 2-O-methyl modified nucleoside
modified_base           9
                        mod_base = OTHER
                        note = 2-O-methyl modified nucleoside
modified_base           11
                        mod_base = OTHER
                        note = 2-O-methyl modified nucleoside
modified_base           13
                        mod_base = OTHER
                        note = 2-O-methyl modified nucleoside
modified_base           15
                        mod_base = OTHER
                        note = 2-O-methyl modified nucleoside
modified_base           17
                        mod_base = OTHER
                        note = 2-O-methyl modified nucleoside
```

```
modified_base    19
                 mod_base = OTHER
                 note = 2-O-methyl modified nucleoside
modified_base    2
                 mod_base = OTHER
                 note = 2-fluoro-modified nucleoside
modified_base    5
                 mod_base = OTHER
                 note = 2-fluoro-modified nucleoside
modified_base    10
                 mod_base = OTHER
                 note = 2-fluoro-modified nucleoside
modified_base    12
                 mod_base = OTHER
                 note = 2-fluoro-modified nucleoside
modified_base    14
                 mod_base = OTHER
                 note = 2-fluoro-modified nucleoside
modified_base    16
                 mod_base = OTHER
                 note = 2-fluoro-modified nucleoside
modified_base    18
                 mod_base = OTHER
                 note = 2-fluoro-modified nucleoside
modified_base    20
                 mod_base = OTHER
                 note = 2-O-methyl modified nucleoside
modified_base    21
                 mod_base = OTHER
                 note = 2-O-methyl modified nucleoside
modified_base    19^20
                 mod_base = OTHER
                 note = phosphorothioate linkage
modified_base    20^21
                 mod_base = OTHER
                 note = phosphorothioate linkage
modified_base    2^3
                 mod_base = OTHER
                 note = phosphorothioate linkage
SEQUENCE: 64
ttggctttat gtctgacaat t                                        21
```